US008071625B2

(12) United States Patent
Qian et al.

(10) Patent No.: US 8,071,625 B2
(45) Date of Patent: *Dec. 6, 2011

(54) CERTAIN CHEMICAL ENTITIES, COMPOSITIONS, AND METHODS

(75) Inventors: Xiangping Qian, Foster City, CA (US); Pu-Ping Lu, Foster City, CA (US); Chihyuan (Grace) Chuang, San Mateo, CA (US); Bradley P. Morgan, Moraga, CA (US); David J. Morgans, Jr., Los Altos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 1089 days.

This patent is subject to a terminal disclaimer.

(21) Appl. No.: 11/888,892

(22) Filed: Aug. 1, 2007

(65) Prior Publication Data

US 2008/0194633 A1 Aug. 14, 2008

Related U.S. Application Data

(60) Provisional application No. 60/835,251, filed on Aug. 2, 2006.

(51) Int. Cl.
*A61K 31/445* (2006.01)
*C07D 211/06* (2006.01)
*C07D 309/02* (2006.01)

(52) U.S. Cl. ......... 514/330; 514/451; 546/226; 549/425

(58) Field of Classification Search .................. 514/330, 514/451; 546/226; 549/425
See application file for complete search history.

(56) References Cited

U.S. PATENT DOCUMENTS

| | | | |
|---|---|---|---|
| 5,328,819 A | | 7/1994 | Ohno et al. |
| 5,602,161 A | | 2/1997 | Naito et al. |
| 5,958,944 A | * | 9/1999 | Arita et al. ............... 514/300 |
| 7,294,642 B2 | | 11/2007 | Fobian et al. |
| 2003/0232826 A1 | | 12/2003 | Bekkali et al. |
| 2005/0137230 A1 | | 6/2005 | Dorsch et al. |
| 2007/0135435 A1 | | 6/2007 | Qian et al. |
| 2007/0207991 A1 | | 9/2007 | Schwink et al. |
| 2007/0293530 A1 | | 12/2007 | Smil et al. |
| 2009/0275537 A1 | * | 11/2009 | Qian et al. ............... 514/82 |

FOREIGN PATENT DOCUMENTS

WO WO-2005/016870 2/2005

OTHER PUBLICATIONS

Database CAPLUS on STN (Columbus, OH, USA) No. 177:58747, 'silver halide color photographic material containing gcyan coupler' abstract, Tsukahara et al (1992) RN 142050-83-7.
Database CAS on STN (Columbus, OH, USA) No. 119:82805, Silver halide color reversal image formation method' abstract, Oono et al (1993) RN 149125-96-2.
Database CAS on STN (Columbus, OH, USA) No. 139:369336, Cosmetic compositions containing tetrzoles for increasing hair growth abstract, See RN 337503-04-5, 337503-17-0, 618453-22-8, (2003).
Database CAS on STN (Columbus, OH, USA) No. 143:7654, 'Acylation of amines with 5-phenyltetraol-2-ylacetyl chloride' abstract, Putis et al, see RN 329933-13-3, 329933-14-4, 337498-87-0, 337503-04-5, 694500-81-7, 852312-44-8, (2005).
International Search Report and Written Opinion for international application No. PCT/US2008/09636 mailed Nov. 5, 2008.
International Search Report dated Jun. 3, 2008 in PCT application PCT/US2007/017231.
International Search Report dated Sep. 23, 2008 in PCT application PCT/US2007/071246.
US Office Action dated Oct. 22, 2010 in U.S. Appl. No. 11/888,903.
US Office Action dated Jul. 13, 2010 in U.S. Appl. No. 11/888,903.

\* cited by examiner

*Primary Examiner* — Celia Chang
(74) *Attorney, Agent, or Firm* — Foley & Lardner LLP

(57) ABSTRACT

Chemical entities that modulate smooth muscle myosin and/or non-muscle myosin, pharmaceutical compositions and methods of treatment of diseases and conditions associated with smooth muscle myosin and/or non-muscle myosin are described.

67 Claims, No Drawings

CERTAIN CHEMICAL ENTITIES, COMPOSITIONS, AND METHODS

This application claims the benefit of U.S. Provisional Patent Application No. 60/835,251, filed Aug. 2, 2006, which is incorporated herein by reference for all purposes.

Provided are certain chemical entities that modulate smooth muscle myosin and/or non-muscle myosin, pharmaceutical compositions and methods of treatment of diseases and conditions associated with smooth muscle myosin and/or non-muscle myosin.

Myosin is present in all muscle and non-muscle cells. Of the ten distinct classes of myosin in human cells, myosin-II is thought to be the form responsible for contraction of skeletal, cardiac, and smooth muscle. Myosin-II is also the isoform present in non-muscle myosins, also known as cytoplasmic myosins. The non-muscle myosins are ubiquitously present in eukaryotic cells, where the smooth muscle myosins are generally present in smooth muscle cells.

Myosin-II is significantly different in amino acid composition and in overall structure from myosins in the other nine distinct classes. Myosin-II consists of two globular head domains, called Subfragment-1 or S1, linked together by a long alpha-helical coiled-coiled tail. Proteolysis of myosin generates either S1 or heavy meromyosin (HMM, a two-headed form with a truncated tail), depending on the proteolysis conditions. S1 contains the ATPase and actin-binding properties of the molecule. S1 has been shown to be sufficient to move actin filaments in vitro, and is therefore likely to be the motor domain of the molecule.

Although myosin-II isoforms from various tissues differ in a number of biological properties, they share the same basic molecular structure as a dimer of two heavy chains (approximately 200 kDa) which are noncovalently associated with two pairs of light chains (approximately 20 and 17 kDa). The two globular amino-terminal heads are tethered together by the carboxy-terminal alpha-helical coiled-coil that forms a tail. The tails are believed to be involved in the assembly of myosin molecules into filaments, whereas the heads are thought to have an actin-activated $Mg^{2+}$-ATPase activity. Each myosin head can be divided by three protease-sensitive regions into peptides of approximately 25, 50, and 20 kDa. The more amino-terminal 25 kDa-50 kDa junction is close to the ATP binding region, whereas the actin-binding domain is near the 50 kDa-20 kDa junction.

S1 consists of a globular actin binding and nucleotide binding region known as the catalytic domain. This domain is attached at its carboxy-terminus to an alpha-helix that has two light chains of about 20 kDa each wrapped around it. This light-chain binding domain of S1 is known as the lever arm. Upon transitioning from the pre-stroke to the post-stroke state, the lever arm is believed to swing through an angle of about 90 degrees about a fulcrum point in the catalytic domain near the nucleotide-binding site. The "power stroke" is driven by the hydrolysis of ATP.

The other end of the myosin molecule is an alpha-helical coiled-coiled tail involved in self assembly of myosin molecules into bipolar thick filaments. These thick filaments interdigitate between thinner actin filaments, and the two filament systems slide past one another during contraction of the muscle. This filament sliding mechanism is thought to involve conformational changes in the myosin heads causing them to walk along the thin actin filaments at the expense of ATP hydrolysis. While non-muscle myosins act in a similar manner, they are understood to slide at a slower velocity than the smooth muscle myosins.

The complete cDNA of the human smooth muscle myosin has been described. The sequence of human smooth muscle myosin is 52% identical to human cardiac myosin in the catalytic S1 region. See, for example, PCT publication No. WO 03/14323.

Provided is at least one chemical entity selected from compounds of Formula I

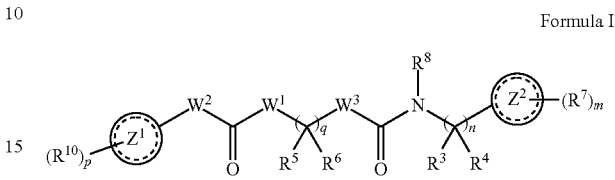

Formula I and pharmaceutically acceptable salts thereof, wherein $W^1$ and $W^2$ are independently selected from $CR^{11}R^{12}$, $NR^{13}$, and O; provided at least one of $W^1$ and $W^2$ is $NR^{13}$;

$W^3$ is selected from $CR^1R^2$, $NR^{14}$ and O;

$Z^1$ is aryl;

$Z^2$ is aryl;

$R^8$ is selected from hydrogen, optionally substituted alkyl, optionally substituted cycloalkyl, optionally substituted aryl, optionally substituted heteroaryl, and optionally substituted heterocycloalkyl;

$R^1$, $R^2$, $R^{11}$, and $R^{12}$ are independently selected from hydrogen, hydroxy, carboxy, optionally substituted alkyl, optionally substituted cycloalkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, optionally substituted alkoxycarbonyl, optionally substituted amino, optionally substituted aryl, optionally substituted heteroaryl, optionally substituted heterocycloalkyl, optionally substituted aminocarbonyl, and optionally substituted aminosulfonyl;

or $R^1$ and $R^2$ may together with any intervening atoms to which they are attached, form a group selected from optionally substituted cycloalkyl and optionally substituted heterocycloalkyl;

$R^{13}$ and $R^{14}$ are independently selected from hydrogen, optionally substituted alkyl, optionally substituted cycloalkyl, optionally substituted aryl, optionally substituted heteroaryl, and optionally substituted heterocycloalkyl;

for each occurrence, $R^3$, $R^4$, $R^5$, and $R^6$ are independently selected from hydrogen, hydroxyl, optionally substituted alkyl, optionally substituted cycloalkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, optionally substituted acyl, optionally substituted alkoxycarbonyl, optionally substituted amino, optionally substituted aryl, optionally substituted heteroaryl, optionally substituted heterocycloalkyl, optionally substituted aminocarbonyl, and optionally substituted aminosulfonyl;

or $R^1$ and one occurrence of $R^5$ may optionally be joined together with any intervening atoms to form a group selected from optionally substituted cycloalkyl and optionally substituted heterocycloalkyl;

or $R^{14}$ and one occurrence of $R^5$ may optionally be joined together with any intervening atoms to form an optionally substituted heterocycloalkyl ring;

or if $W^1$ is $NR^{13}$, then $R^{13}$ and $R^1$ may optionally be joined together with any intervening atoms to form an optionally substituted heterocycloalkyl ring;

or if $W^1$ is $NR^{13}$, then $R^{13}$ and one occurrence of $R^5$ may optionally be joined together with any intervening atoms to form an optionally substituted heterocycloalkyl ring;

$R^7$ and $R^{10}$ are independently selected from hydrogen, cyano, halo, hydroxy, carboxy, azido, nitro, sulfonyl, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted aminocarbonyl, optionally substituted aminosulfonyl, optionally substituted carbaminodoyl;

m is selected from 0, 1, 2 and 3;
n is selected from 0, 1, 2, 3, and 4;
p is selected from 0, 1, 2, and 3; and
q is selected from 0, 1, 2, 3, and 4.

Also provided is a pharmaceutical composition comprising at least one chemical entity described herein, together with at least one pharmaceutically acceptable vehicle selected from carriers, adjuvants, and excipients.

Also provided are methods of treatment of one or more diseases associated with smooth muscle myosin or non-muscle myosin. The methods of treatment comprise administering a therapeutically effective amount of at least one chemical entity provided herein or a pharmaceutical composition comprising at least one chemical entity described herein, together with at least one pharmaceutically acceptable vehicle selected from carriers, adjuvants, and excipients.

Other aspects and embodiments will be apparent to those skilled in the art from the following detailed description.

As used herein, the following words and phrases are generally intended to have the meanings as set forth below, except to the extent that the context in which they are used indicates otherwise.

The following abbreviations and terms have the indicated meanings throughout:
PIPES=1,4-piperazinediethanesulfonic acid
ATP=adenosine 5'-triphosphate
DTT=DL-dithiothreitol
BSA=bovine serum albumin
NADH=nicotinamide adenine dinucleotide
PEP=phosphoenolpyruvic acid
EGTA=ethylene glycol-bis(2-aminoethylether)-N,N,N',N'-tetraacetic acid
Ac=acetyl
APCI=atmospheric pressure chemical ionization
atm=atomosphere
Boc=tert-butoxycarbonyl
c-=cyclo
CBZ=carbobenzyloxy=benzyloxycarbonyl
CDI=carbonyldiimidazole
DCM=dichloromethane=methylene chloride=$CH_2Cl_2$
DIAD=diisopropyl azodicarboxylate
DIEA=DIPEA=N,N-diisopropylethylamine
DMAP=4-(dimethylamino)pyridine
DMF=N,N-dimethylformamide
DMSO=dimethyl sulfoxide
(DPPF)$PdCl_2$=[1,1'-bis(diphenylphosphino)ferrocene] dichloropalladium(II)
Et=ethyl
EtOAc=ethyl acetate
EtOH=ethanol
g=gram
GC=gas chromatography
h or hr=hour
HATU=O-(7-azabenzotriazol-1-yl)-N,N,N',N'-tetramethyluronium hexafluorophosphate
HBTU=O-(benzotriazol-1-yl)-N,N,N',N'-tetramethyluronium hexafluorophosphate
HOBT=1-hydroxybenzotriazole
HPLC=high pressure liquid chromatography
i-=iso
kg or Kg=kilogram
L or l=liter
LC/MS=LCMS=liquid chromatography-mass spectrometry
LDA=lithium diisopropylamide
LRMS=low resolution mass spectrometry
m/z=mass-to-charge ratio
Me=methyl
NMP=N-Methyl-2-pyrrolidone
NMR=nuclear magnetic resonance
MPLC=medium pressure liquid chromatography
min=minute
mL=milliliter
MW=microwave
n-=normal
Ph=phenyl
$(Ph_3P)_4Pd$=tetrakis(triphenylphosphine)palladium(0)
$(Ph_3P)_2PdCl_2$=dichlorobis(triphenylphosphine)palladium(II)
RP-HPLC=reverse phase-high pressure liquid chromatography
rt or RT=room temperature
s-=sec-=secondary
t-=tert-=tertiary
TBAF=tetrabutylammonium fluoride
TBS=TBDMS=tert-butyldimethylsilyl
TES=triethylsilyl or triethylsilane
TMS=trimethylsilyl or trimethylsilane
TFA=trifluoroacetic acid
THF=tetrahydrofuran
TLC=thin layer chromatography
UV=ultraviolet
vol=volume equivalent in mL/g or L/Kg or the limiting reagent unless otherwise specified As used herein, when any variable occurs more than one time in a chemical formula, its definition on each occurrence is independent of its definition at every other occurrence.

As used herein, a dash ("-") that is not between two letters or symbols is used to indicate a point of attachment for a substituent. For example, —$CONH_2$ is attached through the carbon atom.

As used herein, "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "ATPase" refers to an enzyme that is capable of hydrolyzing ATP. ATPases include proteins comprising molecular motors such as myosins.

As used herein, "alkyl" refers to straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

As used herein, "alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

As used herein, "alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

As used herein, "cycloalkyl" refers to a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to six carbons.

As used herein, "mono- and di-alkylcarboxamide" refers to a group of the formula —(C=O)NR$_a$R$_b$ where R$_a$ and R$_b$ are independently selected from hydrogen and alkyl groups of the indicated number of carbon atoms, provided that R$_a$ and R$_b$ are not both hydrogen.

As used herein, "acyl" refers to the groups H—C(O)—; (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)$—.

As used herein, "formyl" refers to the group —C(O)H.

As used herein, "carboxy" and/or "carboxyl" refer to the group —C(O)OH.

As used herein, "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

As used herein, "azido" refers to the group —$N_3$.

As used herein, "amino" refers to the group —$NH_2$.

As used herein, "mono- and di-(alkyl)amino" refers to secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

As used herein, "aminocarbonyl" refers to the group —CONR$^b$R$^c$, where

R$^b$ is selected from H, optionally substituted $C_1$-$C_6$ alkyl, optionally substituted cycloalkyl, optionally substituted heterocycloalkyl, optionally substituted aryl, and optionally substituted heteroaryl, optionally substituted alkoxy; and R$^c$ is independently selected from hydrogen and optionally substituted $C_1$-$C_4$ alkyl; or R$^b$ and R$^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl).

As used herein, "aryl" refers to: 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms selected from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g. a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

As used herein, "aryloxy" refers to the group —O-aryl.

As used herein, "aralkyl" refers to the group -alkyl-aryl.

As used herein, "carbamimidoyl" refers to the group —C(=NH)—NH2.

As used herein, "substituted carbamimidoyl" refers to the group —C(=NR$^e$)—NR$^f$R$^g$ where R$^e$ is selected from hydrogen, cyano, optionally substituted alkyl, optionally substituted cycloalkyl, optionally substituted aryl, optionally substituted heteroaryl, and optionally substituted heterocycloalkyl; and R$^f$ and R$^g$ are independently selected from hydrogen optionally substituted alkyl, optionally substituted cycloalkyl, optionally substituted aryl, optionally substituted heteroaryl, and optionally substituted heterocycloalkyl, provided that at least one of R$^e$, R$^f$, and R$^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently selected from —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is selected from optionally substituted C1-C6 alkyl, optionally substituted aryl, and optionally substituted heteroaryl;

R$^b$ is selected from H, optionally substituted C1-C6 alkyl, optionally substituted aryl, and optionally substituted heteroaryl; and R$^c$ is independently selected from hydrogen and optionally substituted C1-C4 alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO2($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

As used herein, "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

As used herein, "heteroaryl" refers to:

5- to 7-membered aromatic, monocyclic rings containing one or more, for example, from 1 to 4, or in certain embodiments, from 1 to 3, heteroatoms selected from N, O, and S, with the remaining ring atoms being carbon;

bicyclic heterocycloalkyl rings containing one or more, for example, from 1 to 4, or in certain embodiments, from 1 to 3, heteroatoms selected from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms selected from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridazinyl, triazolyl, quinolinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g. a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—O⁻) substituents, such as pyridinyl N-oxides.

As used herein, "heterocycloalkyl" refers to a single, non-aromatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, and 2,5-piperizinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—O⁻) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

As used herein, "sulfanyl" refers to the groups: —S-(optionally substituted ($C_1$-$C_6$)alkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

As used herein, "sulfinyl" refers to the groups: —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

As used herein, "sulfonyl" refers to the groups: —S($O_2$)-(optionally substituted ($C_1$-$C_6$)alkyl), —S($O_2$)-optionally substituted aryl), —S($O_2$)-optionally substituted heteroaryl), —S($O_2$)-(optionally substituted heterocycloalkyl), and —S($O_2$)-(optionally substituted amino).

As used herein, "substituted" refers to any one or more hydrogens on the designated atom or group is replaced with a selection from the indicated group, provided that the designated atom's normal valence is not exceeded. When a substituent is oxo (i.e. =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

As used herein, the terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently selected from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, azido, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is selected from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl;

$R^b$ is selected from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is independently selected from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl or heterocycloalkyl), —$CO_2H$, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

As used herein, "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently selected from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, $OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is selected from optionally substituted $C_1$-$C_6$ alkyl, optionally substituted alkenyl, optionally substituted alkynyl, optionally substituted aryl, and optionally substituted heteroaryl;

$R^b$ is selected from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently selected from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

As used herein, "substituted alkoxy" refers to alkoxy wherein the alkyl constituent is substituted (i.e. —O-(substituted alkyl)) wherein "substituted alkyl" refers to alkyl wherein one or more (such as up to 5, for example, up to 3) hydrogen atoms are replaced by a substituent independently selected from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, $OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is selected from optionally substituted $C_1$-$C_6$ alkyl, optionally substituted alkenyl, optionally substituted alkynyl, optionally substituted aryl, and optionally substituted heteroaryl;

$R^b$ is selected from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently selected from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

In some embodiments, a substituted alkoxy group is "polyalkoxy" or —O-(optionally substituted alkylene)-(optionally substituted alkoxy), and includes groups such as —OCH2CH2OCH3, and residues of glycol ethers such as polyethyleneglycol, and —O(CH2CH2O)xCH3, where x is an integer of 2-20, such as 2-10, and for example, 2-5. Another substituted alkoxy group is hydroxyalkoxy or —OCH2(CH2)yOH, where y is an integer of 1-10, such as 1-4.

As used herein, "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently selected from —$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl or heterocycloalkyl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, $OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is selected from optionally substituted $C_1$-$C_6$ alkyl, optionally substituted alkenyl, optionally substituted alkynyl, optionally substituted aryl, and optionally substituted heteroaryl;

$R^b$ is selected from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently selected from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl or heterocycloalkyl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

As used herein, "substituted amino" refers to the group —NHR$^d$ or —NR$^d$R$^e$ wherein R$^d$ is selected from hydroxy, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein R$^e$ is selected from optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently selected from —R$^a$, —OR$^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl or heterocycloalkyl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, OCONR$^b$R$^c$, —OP(O)(OR$^b$)OR$^c$, sulfanyl (such as SR$^b$), sulfinyl (such as —SOR$^a$), and sulfonyl (such as —SO$_2$R$^a$ and —SO$_2$NR$^b$R$^c$), where R$^a$ is selected from optionally substituted C$_1$-C$_6$ alkyl, optionally substituted alkenyl, optionally substituted alkynyl, optionally substituted aryl, and optionally substituted heteroaryl;

R$^b$ is selected from H, optionally substituted C$_1$-C$_6$ alkyl, optionally substituted cycloalkyl, optionally substituted heterocycloalkyl, optionally substituted aryl, and optionally substituted heteroaryl; and R$^c$ is independently selected from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substituent for cycloalkyl or heterocycloalkyl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ alkylphenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl); and wherein optionally substituted acyl, optionally substituted alkoxycarbonyl, sulfinyl and sulfonyl are as defined herein.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds of Formula I include, but are not limited to, optical isomers of compounds of Formula I, racemates, and other mixtures thereof. In those situations, the single enantiomers or diastereomers, i.e. optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with carbon-carbon double bonds. Where compounds of Formula I exists in various tautomeric forms, chemical entities described herein include all tautomeric forms of the compound.

Chemical entities described herein include, but are not limited to compounds of Formula I and all pharmaceutically acceptable forms thereof. Pharmaceutically acceptable forms of the chemical entities recited herein include pharmaceutically acceptable salts, solvates, crystal forms (including polymorphs and clathrates), chelates, non-covalent complexes, prodrugs, and mixtures thereof. In certain embodiments, the chemical entities described herein are in the form of pharmaceutically acceptable salts. Hence, the terms "chemical entity" and "chemical entities" also encompass pharmaceutically acceptable salts, solvates, chelates, non-covalent complexes, prodrugs, and mixtures.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium.

In addition, if the compound of Formula I is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula I. The term "prodrugs" includes any chemical entities that become compounds of Formula I when administered to a patient, e.g. upon metabolic processing of the prodrug. Examples of prodrugs include, but are not limited to, acetate, formate, phosphate, and benzoate and like derivatives of functional groups (such as alcohol or amine groups) in the compounds of Formula I.

As used herein, "solvate" refers to the chemical entity formed by the interaction of a solvent and a compound. Suitable solvates are pharmaceutically acceptable solvates, such as hydrates, including monohydrates and hemi-hydrates.

As used herein, "chelate" refers to the chemical entity formed by the coordination of a compound to a metal ion at two (or more) points.

As used herein, "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

As used herein, "active agent" is used to indicate a chemical entity which has biological activity. In certain embodiments, an "active agent" is a compound having pharmaceutical utility. For example an active agent may be an anticancer therapeutic.

As used herein, "significant" refers to any detectable change that is statistically significant in a standard parametric test of statistical significance such as Student's T-test, where $p<0.05$.

As used herein, "therapeutically effective amount" of a chemical entity described herein refers to an amount effective, when administered to a human or non-human patient, to provide a therapeutic benefit such as amelioration of symptoms, slowing of disease progression, or prevention of disease.

As used herein, "treatment" or "treating" refers to any treatment of a disease in a patient, including:
  a) preventing the disease, that is, causing the clinical symptoms of the disease not to develop;
  b) inhibiting the disease;
  c) slowing or arresting the development of clinical symptoms; and/or
  d) relieving the disease, that is, causing the regression of clinical symptoms.

As used herein, "patient" refers to an animal, such as a mammal, that has been or will be the object of treatment, observation or experiment. The methods described herein can be useful in both human therapy and veterinary applications. In some embodiments, the patient is a mammal; in some embodiments the patient is human; and in some embodiments the patient is selected from cats and dogs.

Provided is at least one chemical entity selected from compounds of Formula I

Formula I and pharmaceutically acceptable salts thereof, wherein
  $W^1$ and $W^2$ are independently selected from $CR^{11}R^{12}$, $NR^{13}$, and O; provided at least one of $W^1$ and $W^2$ is $NR^{13}$;
  $W^3$ is selected from $CR^1R^2$, $NR^{14}$ and O;
  $Z^1$ is aryl;
  $Z^2$ is aryl;

$R^8$ is selected from hydrogen, optionally substituted alkyl, optionally substituted cycloalkyl, optionally substituted aryl, optionally substituted heteroaryl, and optionally substituted heterocycloalkyl;
  $R^1$, $R^2$, $R^{11}$, and $R^{12}$ are independently selected from hydrogen, hydroxy, carboxy, optionally substituted alkyl, optionally substituted cycloalkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, optionally substituted alkoxycarbonyl, optionally substituted amino, optionally substituted aryl, optionally substituted heteroaryl, optionally substituted heterocycloalkyl, optionally substituted aminocarbonyl, and optionally substituted aminosulfonyl;
  or $R^1$ and $R^2$ may together with any intervening atoms to which they are attached, form a group selected from optionally substituted cycloalkyl and optionally substituted heterocycloalkyl;
  $R^{13}$ and $R^{14}$ are independently selected from hydrogen, optionally substituted alkyl, optionally substituted cycloalkyl, optionally substituted aryl, optionally substituted heteroaryl, and optionally substituted heterocycloalkyl;
    for each occurrence, $R^3$, $R^4$, $R^5$, and $R^6$ are independently selected from hydrogen, hydroxyl, optionally substituted alkyl, optionally substituted cycloalkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, optionally substituted acyl, optionally substituted alkoxycarbonyl, optionally substituted amino, optionally substituted aryl, optionally substituted heteroaryl, optionally substituted heterocycloalkyl, optionally substituted aminocarbonyl, and optionally substituted aminosulfonyl;
  or $R^1$ and one occurrence of $R^5$ may optionally be joined together with any intervening atoms to form a group selected from optionally substituted cycloalkyl and optionally substituted heterocycloalkyl;
  or $R^{14}$ and one occurrence of $R^5$ may optionally be joined together with any intervening atoms to form an optionally substituted heterocycloalkyl ring;
  or if $W^1$ is $NR^{13}$, then $R^{13}$ and $R^1$ may optionally be joined together with any intervening atoms to form an optionally substituted heterocycloalkyl ring;
  or if $W^1$ is $NR^{13}$, then $R^{13}$ and one occurrence of $R^5$ may optionally be joined together with any intervening atoms to form an optionally substituted heterocycloalkyl ring;
  $R^7$ and $R^{10}$ are independently selected from hydrogen, cyano, halo, hydroxy, carboxy, azido, nitro, sulfonyl, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted aminocarbonyl, optionally substituted aminosulfonyl, optionally substituted carbaminodoyl;
  m is selected from 0, 1, 2 and 3;
  n is selected from 0, 1, 2, 3, and 4;
  p is selected from 0, 1, 2, and 3; and q is selected from 0, 1, 2, 3, and 4.

In some embodiments, $Z^1$ is chosen from phenyl, naphthyl, and indanyl.

In some embodiments of compounds of Formula I, $Z^1$ is phenyl.

In some embodiments, $Z^2$ is chosen from phenyl, naphthyl, and indanyl.

In some embodiments of compounds of Formula I, $Z^2$ is phenyl.

In some embodiments, $W^1$ is $CR^{11}R^{12}$.

In some embodiments, $W^1$ is $NR^{13}$.

In some embodiments, $W^1$ is O.

In some embodiments, $W^2$ is $CR^{11}R^{12}$.

In some embodiments, $W^2$ is $NR^{13}$.

In some embodiments, $W^2$ is O.

In some embodiments, $W^3$ is $CR^1R^2$.

In some embodiments, $W^3$ is $NR^{14}$.

In some embodiments, $R^8$ is selected from hydrogen and optionally substituted lower alkyl.

In some embodiments, $R^8$ is selected from hydrogen and lower alkyl.

In some embodiments, $R^8$ is selected from hydrogen and methyl.

In some embodiments, $R^8$ is hydrogen.

In some embodiments, $R^{11}$ and $R^{12}$ are independently selected from hydrogen and optionally substituted lower alkyl.

In some embodiments, $R^{11}$ and $R^{12}$ are independently selected from hydrogen and lower alkyl.

In some embodiments, $R^{11}$ and $R^{12}$ are independently selected from hydrogen and methyl.

In some embodiments, $R^{11}$ is hydrogen and $R^{12}$ is methyl.

In some embodiments, $R^{13}$ is selected from hydrogen and optionally substituted lower alkyl.

In some embodiments, $R^{13}$ is selected from hydrogen and lower alkyl.

In some embodiments, $R^{13}$ is selected from hydrogen and methyl.

In some embodiments, $R^{13}$ is methyl.

In some embodiments, q is 2.

In some embodiments, q is 1.

In some embodiments, q is 0.

In some embodiments, each $R^5$ and $R^6$ is independently selected from hydrogen, optionally substituted lower alkyl, and lower alkoxycarbonyl.

In some embodiments, each $R^5$ and $R^6$ is independently selected from hydrogen, methyl, ethyl, isopropyl, hydroxymethyl, and methoxycarbonyl.

In some embodiments, each $R^5$ and $R^6$ is hydrogen.

In some embodiments, m is selected from 1 and 2.

In some embodiments, $R^7$ is selected from halo, lower alkyl, and optionally substituted lower alkyl.

In some embodiments, $R^7$ is selected from chloro, fluoro, methyl, and trifluoromethyl.

In some embodiments, $R^7$ is chloro.

In some embodiments, $R^7$ is at position 2 or 3 relative to the point of attachment of the phenyl ring.

In some embodiments, n is selected from 1 and 2.

In some embodiments, n is 1.

In some embodiments, each $R^3$ and $R^4$ is independently selected from hydrogen, optionally substituted lower alkyl, and lower alkoxycarbonyl.

In some embodiments, each $R^3$ and $R^4$ is independently selected from hydrogen, methyl, ethyl, isopropyl, hydroxymethyl, and methoxycarbonyl.

In some embodiments, each $R^3$ and $R^4$ is hydrogen.

In some embodiments, p is selected from 1 and 2.

In some embodiments of compounds of Formula I, p is 1.

In some embodiments of compounds of Formula I, p is 0.

In some embodiments of compounds of Formula I, each $R^{10}$ is independently selected from cyano, halo, optionally substituted lower alkyl, optionally substituted lower alkenyl, and optionally substituted phenyl.

In some embodiments of compounds of Formula I, each $R^{10}$ is independently selected from cyano, chloro, bromo, methyl, ethyl, isopropyl, t-butyl, hydroxymethyl, trifluoromethyl, methoxycarbonyl, phenoxy, phenyl, trifluoromethoxy, methoxy, N,N-dimethylamino, and 1H-imidazolyl.

In some embodiments of compounds of Formula I, each $R^{10}$ is independently selected from cyano, chloro, fluoro, bromo, trifluoromethyl, methyl, ethyl, vinyl, and phenyl.

In some embodiments of compounds of Formula I, each $R^{10}$ is selected from methyl, ethyl, isopropyl, and trifluoromethyl.

In some embodiments of compounds of Formula I, p is selected from 1 and 2, and each $R^{10}$ is independently selected from cyano, halo, optionally substituted alkyl, optionally substituted alkenyl, and optionally substituted aryl.

In some embodiments of compounds of Formula I, $(R^{10})_p$, together with $Z^1$ to which is attached, forms a group selected from 2-naphthyl, 5-indanyl, 4-ethylphenyl, 4-methylphenyl, 4-isopropylphenyl, 4-trifluoromethylphenyl, 4-chlorophenyl, 4-phenylphenyl, 4-methyl-2-chlorophenyl, 4-methyl-3-fluorophenyl, 4-ethyl-3-fluorophenyl, and 4-ethyl-2-chlorophenyl.

In some embodiments of compounds of Formula I, p is 1 and $R^{10}$ is selected from ethyl and isopropyl.

In some embodiments, $R^{14}$ is selected from hydrogen and optionally substituted lower alkyl.

In some embodiments, $R^{14}$ is selected from hydrogen and lower alkyl.

In some embodiments, $R^{14}$ is hydrogen.

In some embodiments, each $R^1$ and $R^2$ is independently selected from hydrogen, lower alkyl, and substituted alkyl.

In some embodiments, each $R^1$ and $R^2$ is independently selected from hydrogen and methyl.

In some embodiments, $R^1$ and $R^2$ are hydrogen.

In some embodiments, $R^1$ and $R^2$ are methyl.

In some embodiments, $R^1$ is hydrogen and $R^2$ is methyl.

In some embodiments, $R^1$ and $R^2$, together with the carbon to which they are attached, form a group selected from optionally substituted cycloalkyl and optionally substituted heterocycloalkyl.

In some embodiments, $R^1$ and $R^2$, together with the carbon to which they are attached, form a group selected from cyclopropyl, cyclobutyl, cyclopentyl, cyclohexyl, piperidinyl, and 2H-3,4,5,6-tetrahydropyranyl, each of which is optionally substituted.

In some embodiments, $R^1$ and $R^2$, together with the carbon to which they are attached, form a group selected from cyclopentyl, cyclohexyl, piperidinyl, and 2H-3,4,5,6-tetrahydropyranyl, each of which is optionally substituted.

Also provided is at least one chemical entity selected from compounds of Formula Ia Formula Ia

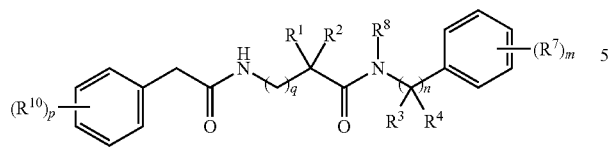

and pharmaceutically acceptable salts thereof, wherein $R^1$, $R^2$, n, $R^3$, $R^4$, q, m, $R^7$, $R^8$, p, and $R^{10}$ are as described for compounds of Formula I.

Also provided is at least one chemical entity selected from compounds of Formula Ib Formula Ib

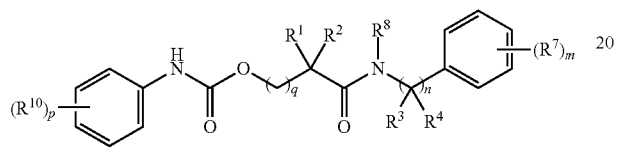

and pharmaceutically acceptable salts thereof, wherein $R^1$, $R^2$, n, $R^3$, $R^4$, q, m, $R^7$, $R^8$, p, and $R^{10}$ are as described for compounds of Formula I.

Also provided is at least one chemical entity selected from compounds of Ic

Formula Ic and pharmaceutically acceptable salts thereof, wherein $R^1$, $R^2$, n, $R^3$, $R^4$, q, m, $R^7$, $R^8$, p, and $R^{10}$ are as described for compounds of Formula I.

Also provided is at least one chemical entity selected from compounds of Formula Id Formula Id and pharmaceutically acceptable salts thereof, wherein $R^{14}$, n, $R^3$, $R^4$, q, $R^5$, $R^6$, m, $R^7$, $R^8$, p, and $R^{10}$ are as described for compounds of Formula I.

In some embodiments, the compound of Formula I is selected from

| Structure | Chemical Name |
|---|---|
| 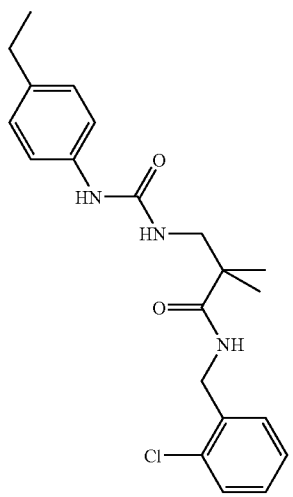 | N-[(2-chlorophenyl)methyl]-3-{[(4-ethylphenyl)amino]carbonylamino}-2,2-dimethylpropanamide |
| 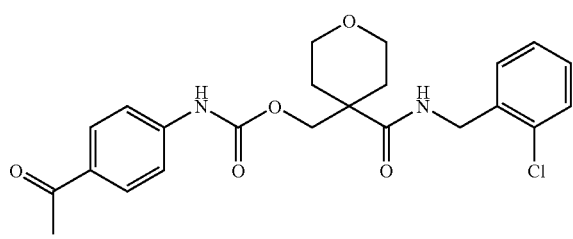 | (4-{[N-(4-acetylphenyl)carbamoyloxy]methyl}(2H-3,4,5,6-tetrahydropyran-4-yl))-N-[(2-chlorophenyl)methyl]carboxamide |

-continued

| Structure | Chemical Name |
|---|---|
| 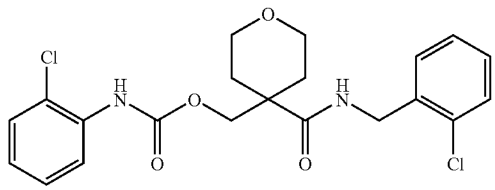 | (4-{[N-(2-chlorophenyl)carbamoyloxy]methyl}(2H-3,4,5,6-tetrahydropyran-4-yl))-N-[(2-chlorophenyl)methyl]carboxamide |
| 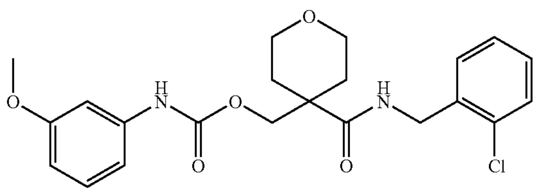 | N-[(2-chlorophenyl)methyl](4-{[N-(3-methoxyphenyl)carbamoyloxy]methyl}(2H-3,4,5,6-tetrahydropyran-4-yl))carboxamide |
| 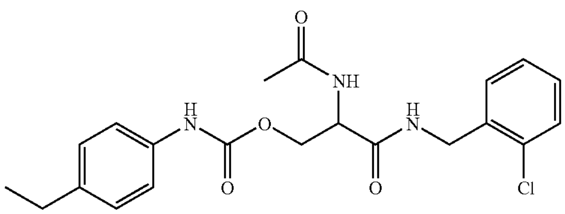 | 2-(acetylamino)-N-[(2-chlorophenyl)methyl]-3-[N-(4-ethylphenyl)carbamoyloxy]propanamide |
| 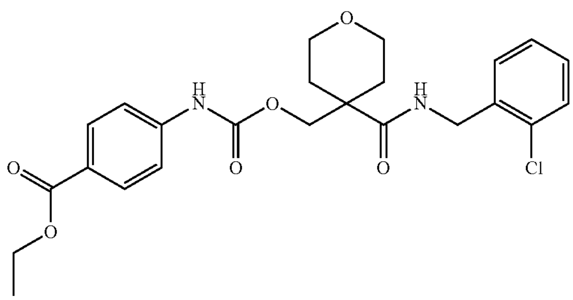 | ethyl 4-{[(4-{N-[(2-chlorophenyl)methyl]carbamoyl}-2H-3,4,5,6-tetrahydropyran-4-yl)methoxy]carbonylamino}benzoate |
| 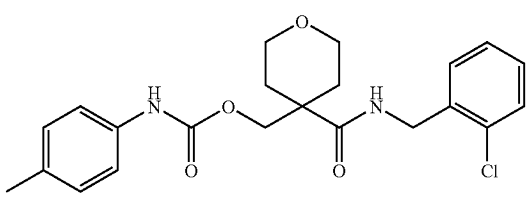 | N-[(2-chlorophenyl)methyl](4-{[N-(4-methylphenyl)carbamoyloxy]methyl}(2H-3,4,5,6-tetrahydropyran-4-yl))carboxamide |
| 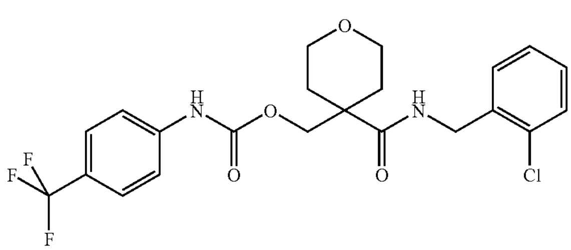 | N-[(2-chlorophenyl)methyl][4-({N-[4-(trifluoromethyl)phenyl]carbamoyloxylmethyl)(2H-3,4,5,6-tetrahydropyran-4-yl)]carboxamide |
| 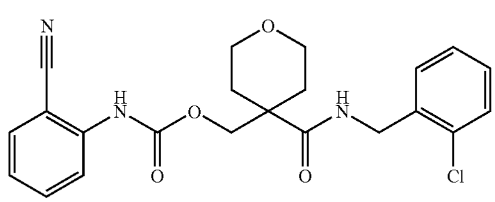 | N-[(2-chlorophenyl)methyl](4-{[N-(2-cyanophenyl)carbamoyloxy]methyl}(2H-3,4,5,6-tetrahydropyran-4-yl))carboxamide |

-continued

| Structure | Chemical Name |
|---|---|
| 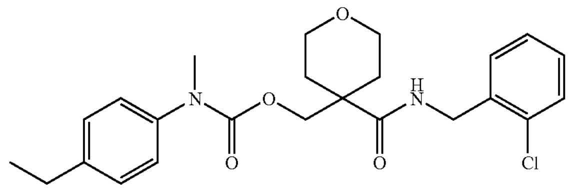 | N-[(2-chlorophenyl)methyl](4-{[N-(4-ethylphenyl)-N-methylcarbamoyloxy]methyl}(2H-3,4,5,6-tetrahydropyran-4-yl))carboxamide |
| 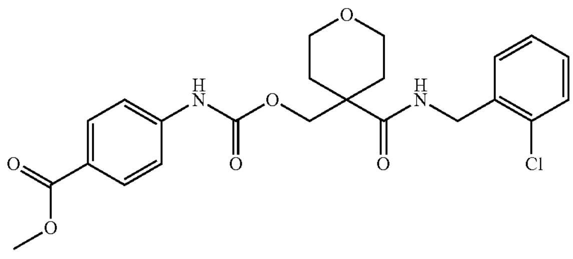 | methyl 4-{[(4-{N-[(2-chlorophenyl)methyl]carbamoyl}-2H-3,4,5,6-tetrahydropyran-4-yl)methoxy]carbonylamino}benzoate |
| 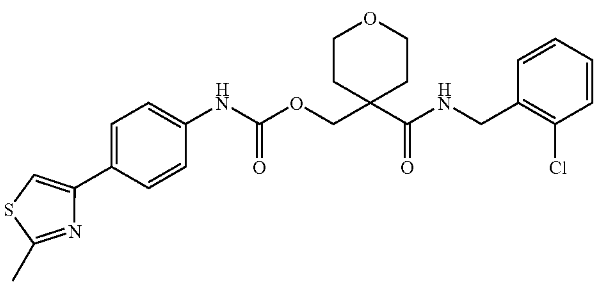 | N-[(2-chlorophenyl)methyl][4-({N-[4-(2-methyl(1,3-thiazol-4-yl))phenyl]carbamoyloxy}methyl)(2H-3,4,5,6-tetrahydropyran-4-yl)]carboxamide |
| 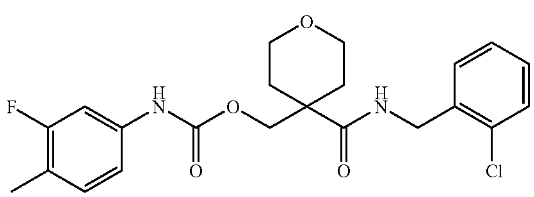 | N-[(2-chlorophenyl)methyl](4-{[N-(3-fluoro-4-methylphenyl)carbamoyloxy]methyl}(2H-3,4,5,6-tetrahydropyran-4-yl))carboxamide |
| 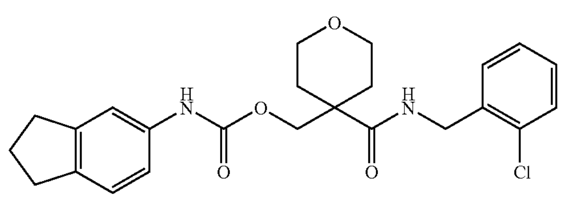 | N-[(2-chlorophenyl)methyl]{4-[(N-indan-5-ylcarbamoyloxy)methyl](2H-3,4,5,6-tetrahydropyran-4-yl)}carboxamide |
| 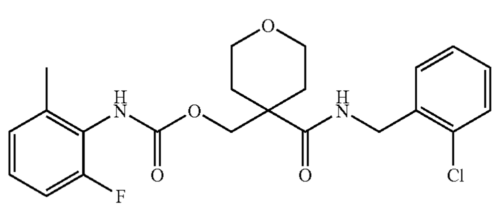 | N-[(2-chlorophenyl)methyl](4-{[N-(6-fluoro-2-methylphenyl)carbamoyloxy]methyl}(2H-3,4,5,6-tetrahydropyran-4-yl))carboxamide |
| 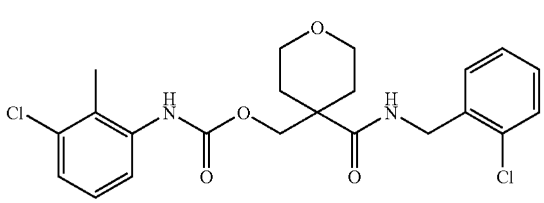 | (4-{[N-(3-chloro-2-methylphenyl)carbamoyloxy]methyl}(2H-3,4,5,6-tetrahydropyran-4-yl))-N-[(2-chlorophenyl)methyl]carboxamide |

| Structure | Chemical Name |
|---|---|
| 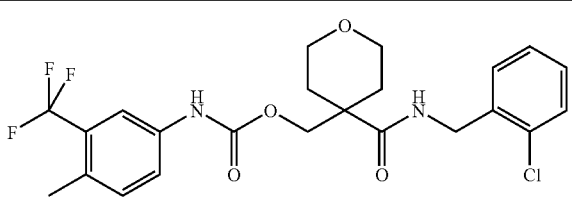 | N-[(2-chlorophenyl)methyl][4-({N-[4-methyl-3-(trifluoromethyl)phenyl]carbamoyloxy}methyl)(2H-3,4,5,6-tetrahydropyran-4-yl)]carboxamide |
| 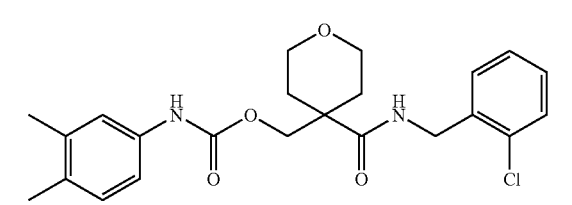 | (4-{[N-(3,4-dimethylphenyl)carbamoyloxy]methyl}(2H-3,4,5,6-tetrahydropyran-4-yl))-N-[(2-chlorophenyl)methyl]carboxamide |
| 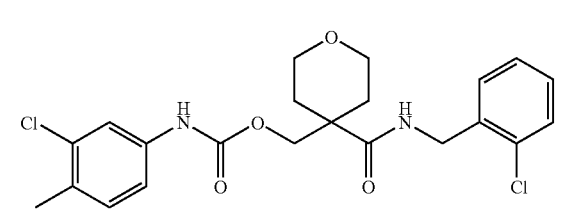 | (4-{[N-(3-chloro-4-methylphenyl)carbamoyloxy]methyl}(2H-3,4,5,6-tetrahydropyran-4-yl))-N-[(2-chlorophenyl)methyl]carboxamide |
| 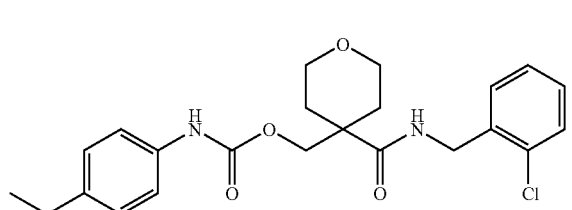 | N-[(2-chlorophenyl)methyl][4-({N-[4-(methylethyl)phenyl]carbamoyloxy}methyl)(2H-3,4,5,6-tetrahydropyran-4-yl)]carboxamide |
| 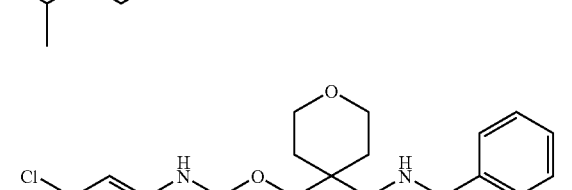 | (4-{[N-(3,5-dichlorophenyl)carbamoyloxy]methyl}(2H-3,4,5,6-tetrahydropyran-4-yl))-N-[(2-chlorophenyl)methyl]carboxamide |
| 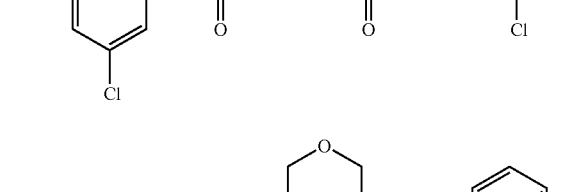 | (4-{[N-(2,4-dimethylphenyl)carbamoyloxy]methyl}(2H-3,4,5,6-tetrahydropyran-4-yl))-N-[(2-chlorophenyl)methyl]carboxamide |
| 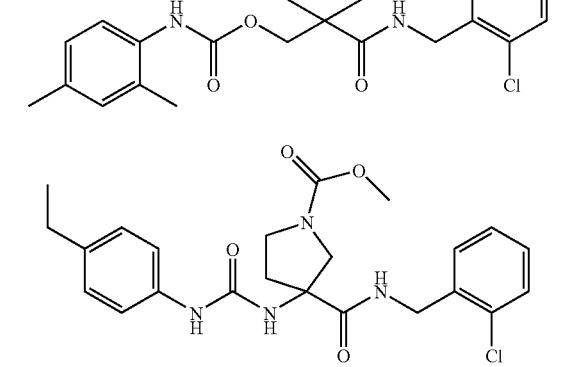 | methyl 3-{N-[(2-chlorophenyl)methyl]carbamoyl}-3-{[(4-ethylphenyl)amino]carbonylamino}pyrrolidine-carboxylate |

-continued

| Structure | Chemical Name |
|---|---|
| 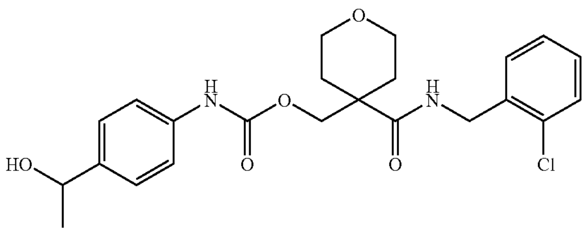 | N-[(2-chlorophenyl)methyl][4-({N-[4-(hydroxyethyl)phenyl]carbamoyloxy}methyl)(2H-3,4,5,6-tetrahydropyran-4-yl)]carboxamide |
| 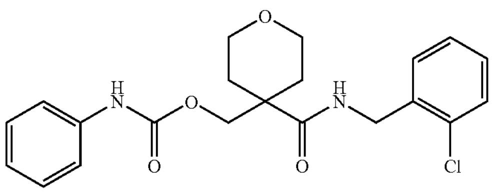 | N-[(2-chlorophenyl)methyl]{4-[(N-phenylcarbamoyloxy)methyl](2H-3,4,5,6-tetrahydropyran-4-yl)}carboxamide |
| 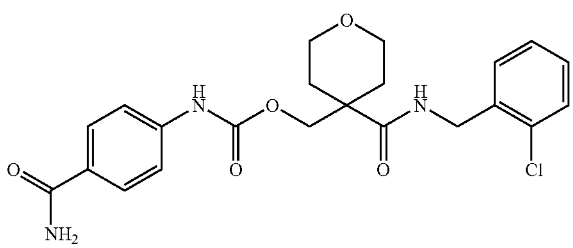 | 4-{[(4-{N-[(2-chlorophenyl)methyl]carbamoyl}-2H-3,4,5,6-tetrahydropyran-4-yl)methoxy]carbonylamino}benzamide |
| | N-[(2-chlorophenyl)methyl][4-({[(4-ethylphenyl)amino]carbonylamino}methyl)(4-piperidyl)]carboxamide |
| 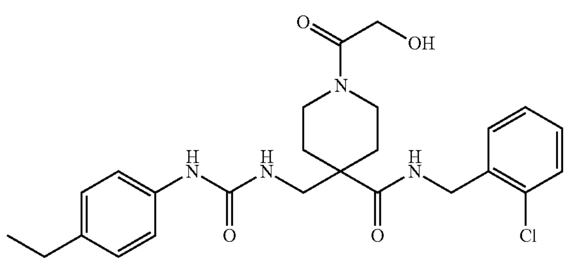 | N-[(2-chlorophenyl)methyl][4-({[(4-ethylphenyl)amino]carbonylamino}methyl)-1-(2-hydroxyacetyl)(4-piperidyl)]carboxamide |
| 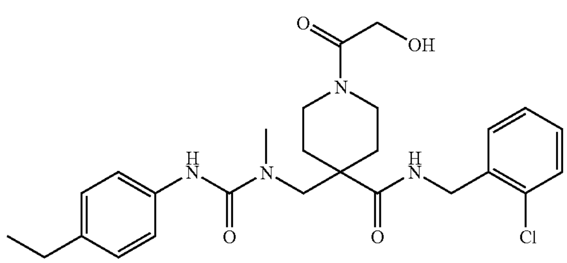 | N-[(2-chlorophenyl)methyl][4-({[(4-ethylphenyl)amino]-N-methylcarbonylamino}methyl)-1-(2-hydroxyacetyl)(4-piperidyl)]carboxamide |

| Structure | Chemical Name |
|---|---|
| 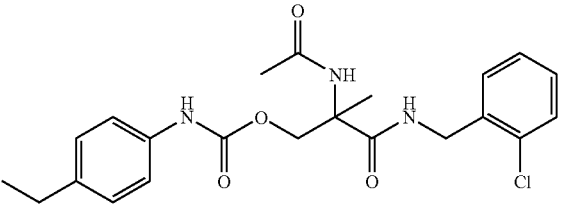 | 2-(acetylamino)-N-[(2-chlorophenyl)methyl]-3-[N-(4-ethylphenyl)carbamoyloxy]-2-methylpropanamide |
| 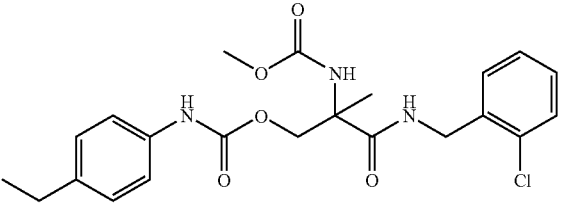 | N-[(2-chlorophenyl)methyl]-3-[N-(4-ethylphenyl)carbamoyloxy]-2-(methoxycarbonylamino)-2-methylpropanamide |
| 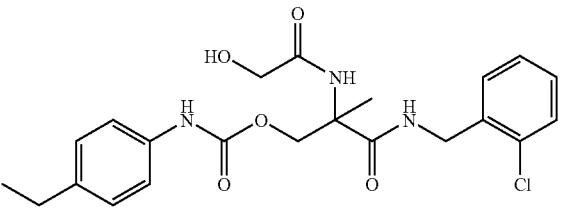 | N-[(2-chlorophenyl)methyl]-3-[N-(4-ethylphenyl)carbamoyloxy]-2-(2-hydroxyacetylamino)-2-methylpropanamide |
| 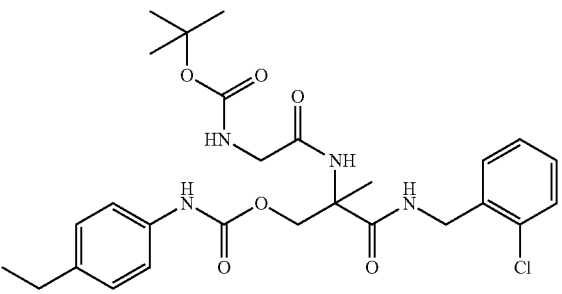 | 2-{2-[(tert-butoxy)carbonylamino]acetylamino}-N-[(2-chlorophenyl)methyl]-3-[N-(4-ethylphenyl)carbamoyloxy]-2-methylpropanamide |
| 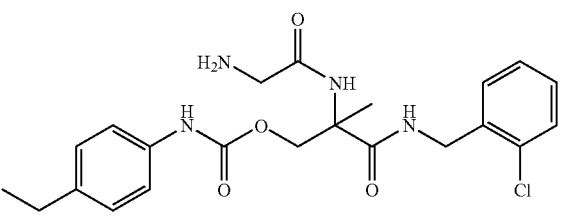 | 2-(2-aminoacetylamino)-N-[(2-chlorophenyl)methyl]-3-[N-(4-ethylphenyl)carbamoyloxy]-2-methylpropanamide |
| 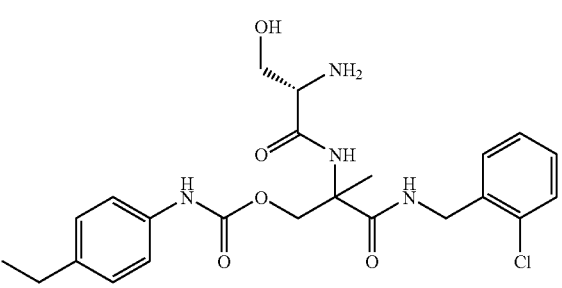 | 2-((2S)-2-amino-3-hydroxypropanoylamino)-N-[(2-chlorophenyl)methyl]-3-[N-(4-ethylphenyl)carbamoyloxy]-2-methylpropanamide |

| Structure | Chemical Name |
|---|---|
| 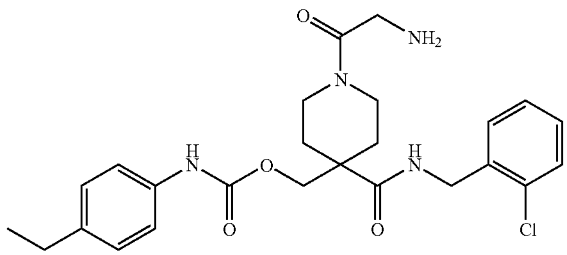 | {[1-(2-aminoacetyl)-4-({[(2-chlorophenyl)methyl]amino}methyl)(4-piperidyl)]methoxy}-N-(4-ethylphenyl)carboxamide |
| 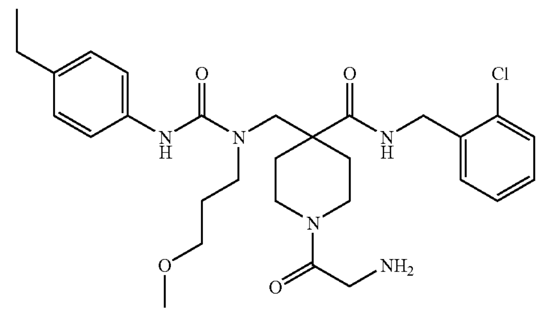 | N-[(1-(2-aminoacetyl)-4-(N-[(2-chlorophenyl)methyl]carbamoyl}(4-piperidyl))methyl][(4-ethylphenyl)amino]-N-(3-methoxypropyl)carboxamide |
| 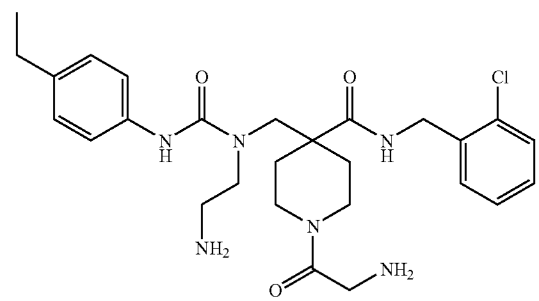 | N-[(1-(2-aminoacetyl)-4-{N-[(2-chlorophenyl)methyl]carbamoyl}(4-piperidyl))methyl]-N-(2-aminoethyl)[(4-ethylphenyl)amino]carboxamide |
|  | (tert-butoxy)-N-(2-{N-[(1-{2-[(tert-butoxy)carbonylamino]acetyl}-4-{N-[(2-chlorophenyl)methyl]carbamoyl}(4-piperidyl))methyl][(4-ethylphenyl)amino]carbonylamino}ethyl)carboxamide |
| 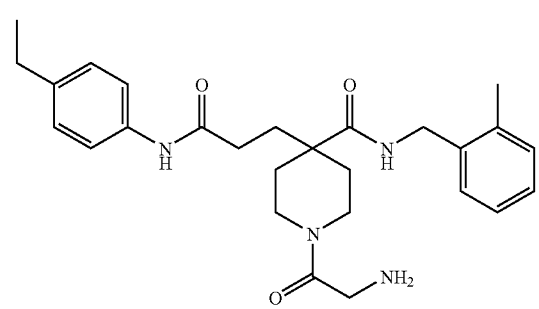 | 3-(1-(2-aminoacetyl)-4-{N-[(2-methylphenyl)methyl]carbamoyl}(4-piperidyl))-N-(4-ethylphenyl)propanamide |

-continued

| Structure | Chemical Name |
|---|---|
| 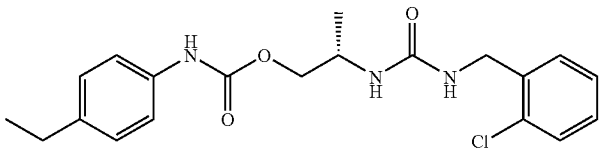 | N-{(1S)-2-[N-(4-ethylphenyl)carbamoyloxy]-isopropyl}{[(2-chlorophenyl)methyl]amino}carboxamide |
| 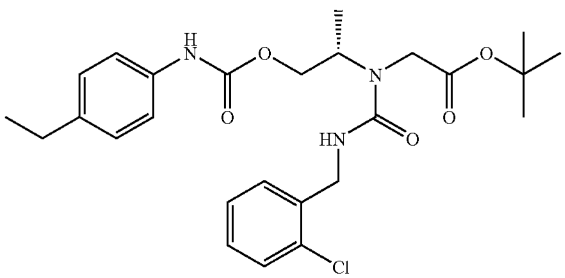 | tert-butyl 2-(N-{(1S)-2-[N-(4-ethylphenyl)carbamoyloxy]-isopropyl}{[(2-chlorophenyl)methyl]amino}carbonylamino)acetate |
| 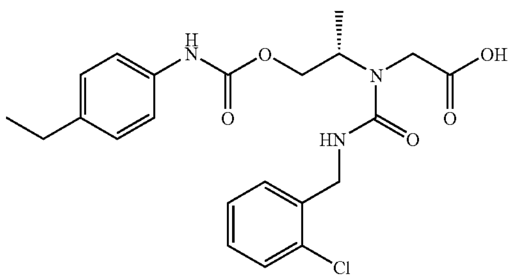 | 2-(N-{(1S)-2-[N-(4-ethylphenyl)carbamoyloxy]-isopropyl}{[(2-chlorophenyl)methyl]amino}carbonylamino)acetic acid |
| 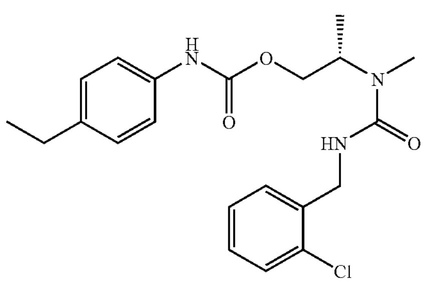 | N-{(1S)-2-[N-(4-ethylphenyl)carbamoyloxy]-isopropyl}{[(2-chlorophenyl)methyl]amino}-N-methylcarboxamide |
| 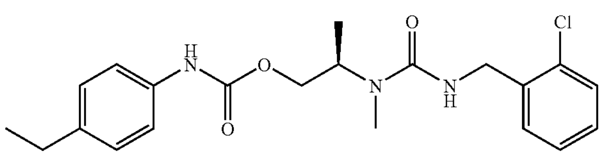 | [(2R)-2-({[(2-chlorophenyl)methyl]amino}-N-methylcarbonylamino)propoxy]-N-(4-ethylphenyl)carboxamide |
| 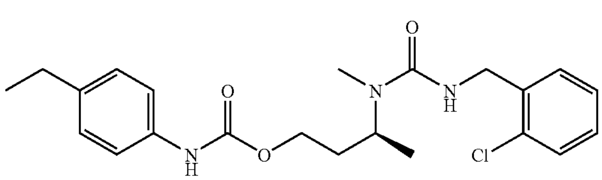 | N-{(1S)-3-[N-(4-ethylphenyl)carbamoyloxy]-1-methylpropyl}{[(2-chlorophenyl)methyl]amino}-N-methylcarboxamide |

| Structure | Chemical Name |
|---|---|
| 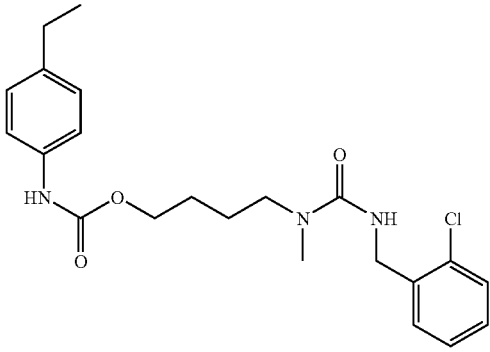 | {[(2-chlorophenyl)methyl]amino}-N-{4-[N-(4-ethylphenyl)carbamoyloxy]butyl}-N-methylcarboxamide |
| 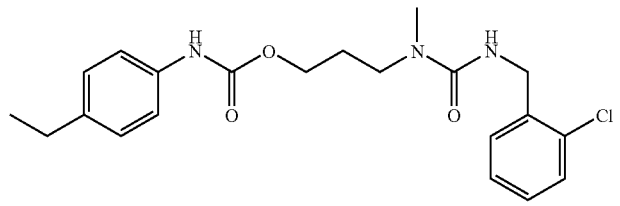 | {[(2-chlorophenyl)methyl]amino}-N-{3-[N-(4-ethylphenyl)carbamoyloxy]propyl}-N-methylcarboxamide |
| 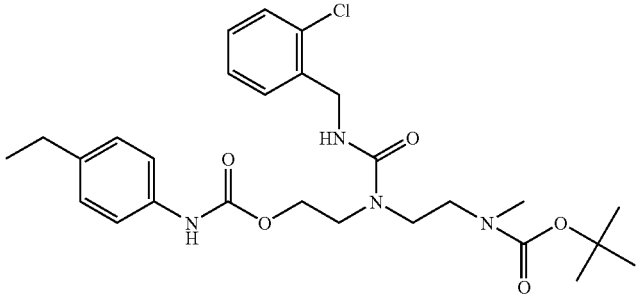 | (tert-butoxy)-N-[2-({[(2-chlorophenyl)methyl]amino}-N-{2-[N-(4-ethylphenyl)carbamoyloxy]ethyl}carbonylamino)ethyl]-N-methylcarboxamide |
| 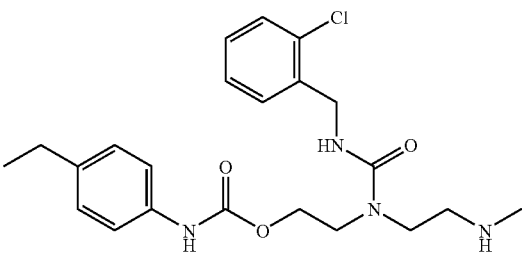 | {[(2-chlorophenyl)methyl]amino}-N-[2-[N-(4-ethylphenyl)carbamoyloxy]ethyl}-N-[2-(methylamino)ethyl]carboxamide |
| 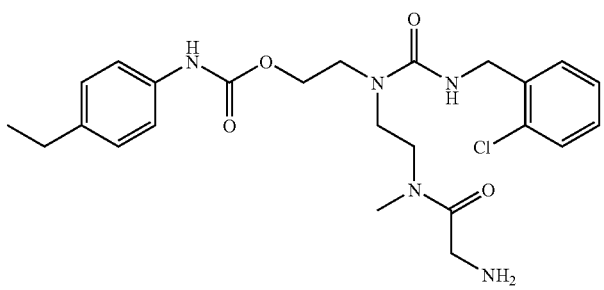 | 2-amino-N-[2-({[(2-chlorophenyl)methyl]amino}-N-{2-[N-(4-ethylphenyl)carbamoyloxy]ethyl}carbonylamino)ethyl]-N-methylacetamide |

-continued

| Structure | Chemical Name |
|---|---|
| 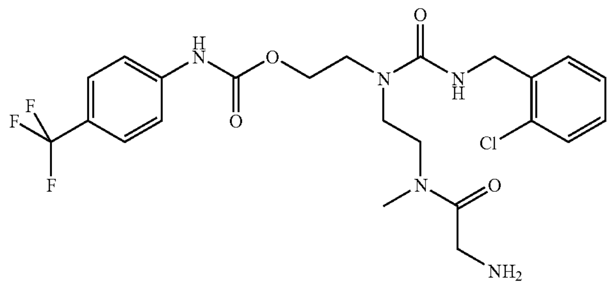 | 2-amino-N-{2-[{[(2-chlorophenyl)methyl]amino}-N-(2-{N-[4-(trifluoromethyl)phenyl]carbamoyloxy}ethyl)carbonylamino]ethyl}-N-methylacetamide |
| 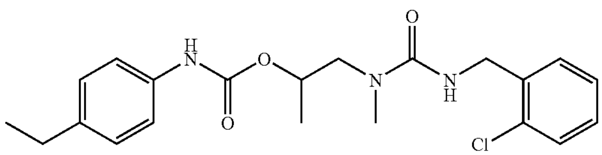 | [2-({[(2-chlorophenyl)methyl]amino}-N-methylcarbonylamino)-isopropoxy]-N-(4-ethylphenyl)carboxamide |
| 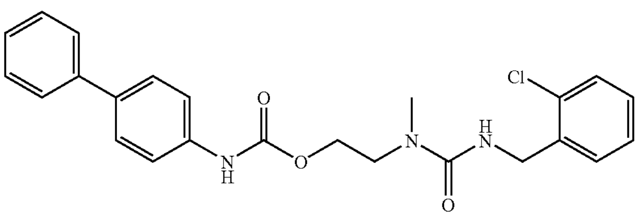 | {[(2-chlorophenyl)methyl]amino}-N-methyl-N-{2-[N-(4-phenylphenyl)carbamoyloxy]ethyl}carboxamide |
| 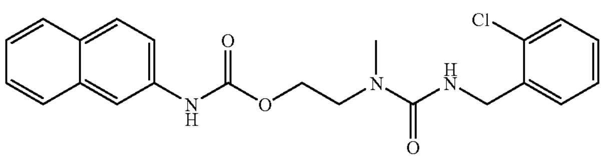 | {[(2-chlorophenyl)methyl]amino}-N-methyl-N-[2-(N-(2-naphthyl)carbamoyloxy)ethyl]carboxamide |
| 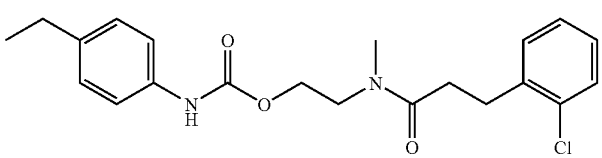 | 3-(2-chlorophenyl)-N-{2-[N-(4-ethylphenyl)carbamoyloxy]ethyl}-N-methylpropanamide |
| | N-{2-[N-(4-ethylphenyl)carbamoyloxy]ethyl}-2-hydroxy-N-methyl-3-[2-(trifluoromethyl)phenyl]propanamide |
| 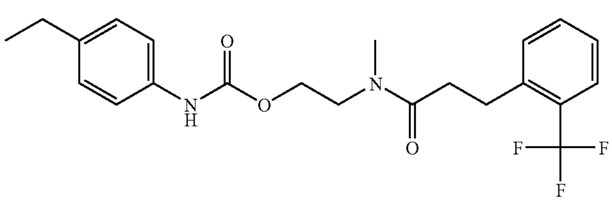 | N-(2-[N-(4-ethylphenyl)carbamoyloxy]ethyl}-N-methyl-3-[2-(trifluoromethyl)phenyl]propanamide |
| 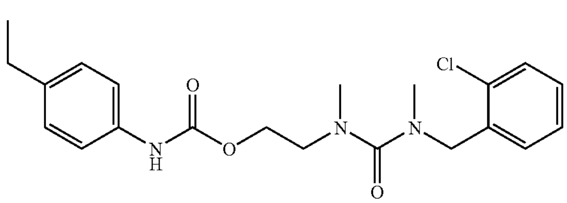 | {[(2-chlorophenyl)methyl]methylamino}-N-(2-[N-(4-ethylphenyl)carbamoyloxy]ethyl}-N-methylcarboxamide |

| Structure | Chemical Name |
|---|---|
| 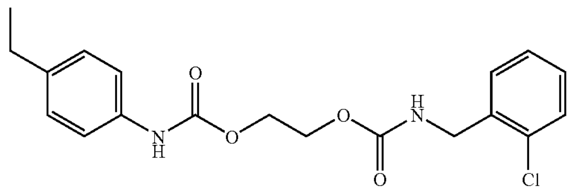 | (2-{N-[(2-chlorophenyl)methyl]carbamoyloxy}ethoxy)-N-(4-ethylphenyl)carboxamide |
| 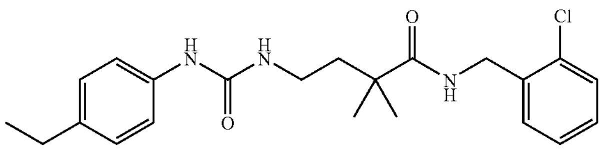 | N-[(2-chlorophenyl)methyl]-4-{[N-(4-ethylphenyl)carbamoyl]amino}-2,2-dimethylbutanamide |
| 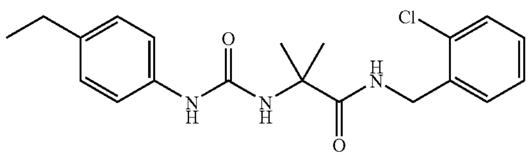 | [(2-chlorophenyl)methyl]-2-{[(4-ethylphenyl)amino]carbonylamino}-2-methylpropanamide |
| 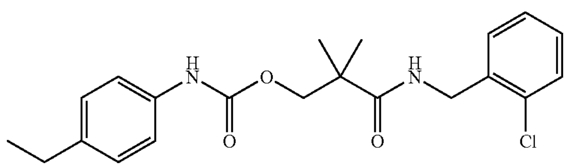 | N-[(2-chlorophenyl)methyl]-3-[N-(4-ethylphenyl)carbamoyloxy]-2,2-dimethylpropanamide |
| 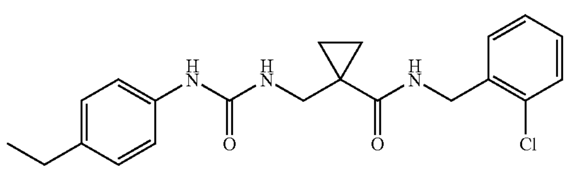 | N-[({N-[(2-chlorophenyl)methyl]carbamoyl}cyclopropyl)methyl](4-ethylphenyl)amino]carboxamide |
| 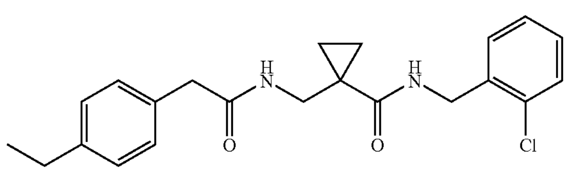 | N-[({N-[(2-chlorophenyl)methyl]carbamoyl}cyclopropyl)methyl]-2-(4-ethylphenyl)acetamide |
| 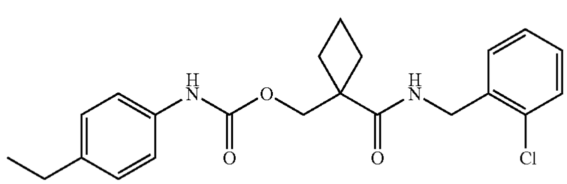 | [({N-[2-(chlorophenyl)methyl]carbamoyl}cyclobutyl)methoxy]-N-(4-ethylphenyl)carboxamide |
| 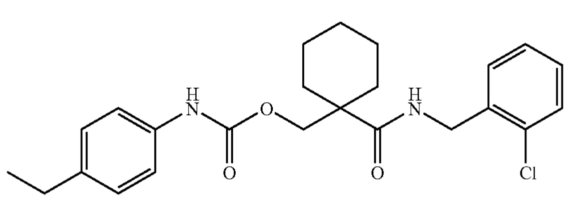 | N-[(2-chlorophenyl)methyl]({[N-(4-ethylphenyl)carbamoyloxy]methyl}cyclohexyl)carboxamide |

-continued

| Structure | Chemical Name |
|---|---|
| 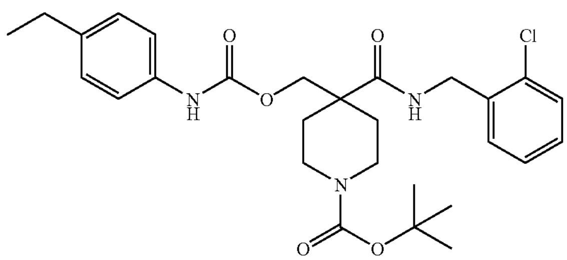 | tert-butyl 4-(N-[(2-chlorophenyl)methyl]carbamoyl}-4-{[N-(4-ethylphenyl)carbamoyloxy]methyl}piperidinecarboxylate |
| 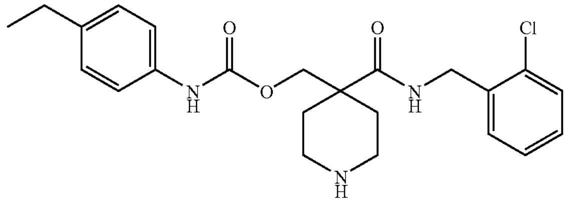 | N-[(2-chlorophenyl)methyl](4-{[N-(4-ethylphenyl)carbamoyloxy]methyl}(4-piperidyl))carboxamide |
| 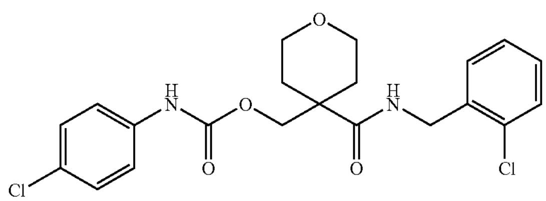 | (4-{[N-(4-chlorophenyl)carbamoyloxy]methyl}(2H-3,4,5,6-tetrahydropyran-4-yl))-N-[(2-chlorophenyl)methyl]carboxamide |
| | N-[(2-chlorophenyl)methyl](1-{[N-(4-ethylphenyl)carbamoyloxy]methyl}cyclopent-3-enyl)carboxamide |
| 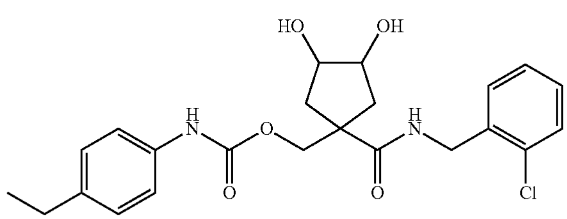 | N-[(2-chlorophenyl)methyl](1-{[N-(4-ethylphenyl)carbamoyloxy]methyl}-3,4-dihydroxycyclopentyl)carboxamide |
| | methyl 4-{N-[(2-chlorophenyl)methyl]carbamoyl}-4-{[N-(4-ethylphenyl)carbamoyloxymethyl}piperidinecarboxylate |
| 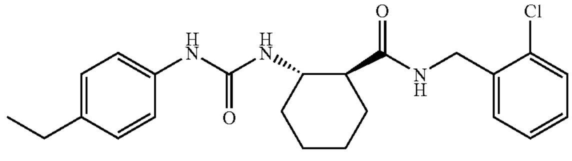 | ((1S,2S)-2-{[(4-ethylphenyl)amino]carbonylamino}cyclohexyl)-N-[(2-chlorophenyl)methyl]carboxamide |

| Structure | Chemical Name |
|---|---|
| 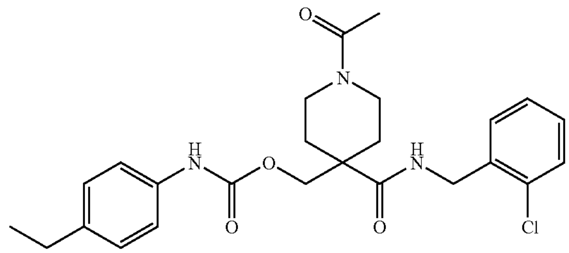 | (1-acetyl-4-{[N-(4-ethylphenyl)carbamoyloxy]methyl}(4-piperidyl))-N-[(2-chlorophenyl)methyl]carboxamide |
| 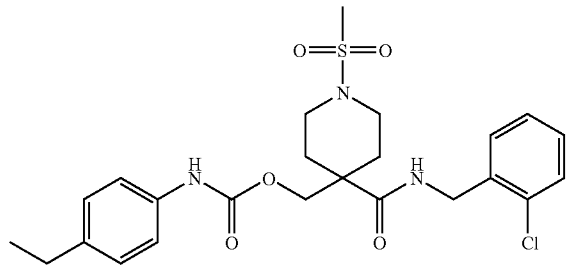 | N-[(2-chlorophenyl)methyl](4-{[N-(4-ethylphenyl)carbamoyloxy]methyl}-1-(methylsulfonyl)(4-piperidyl))carboxamide |
| 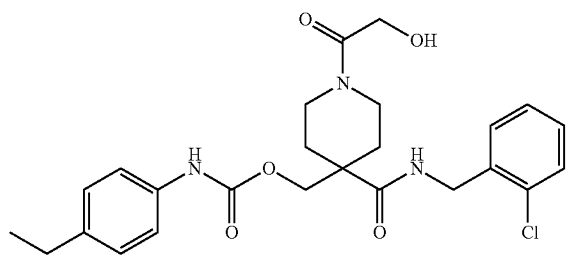 | N-[(2-chlorophenyl)methyl](4-{[N-(4-ethylphenyl)carbamoyloxy]methyl}-1-(2-hydroxyacetyl)(4-piperidyl))carboxamide |
| 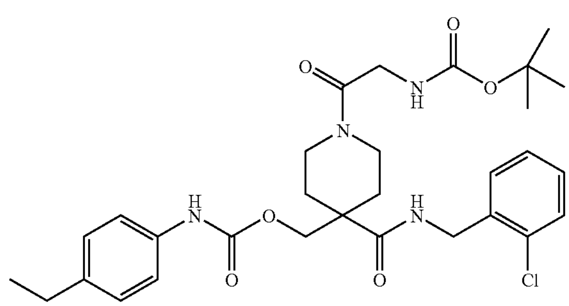 | (tert-butoxy)-N-[2-(4-{N-[(2-chlorophenyl)methyl]carbamoyl}-4-{[N-(4-ethylphenyl)carbamoyloxy]methyl}piperidyl)-2-oxoethyl]carboxamide |
| 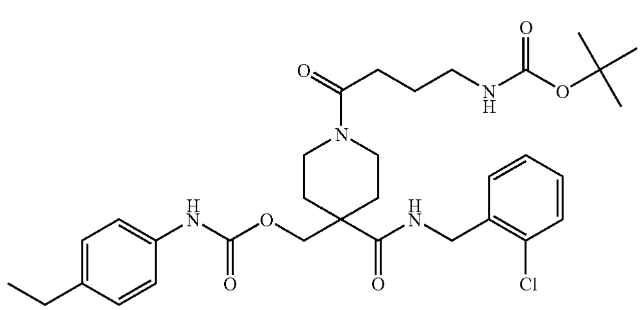 | (tert-butoxy)-N-[4-(4-{N-[(2-chlorophenyl)methyl]carbamoyl}-4-{[N-(4-ethylphenyl)carbamoyloxy]methyl}piperidyl)-4-oxobutyl]carboxamide |

| Structure | Chemical Name |
|---|---|
| 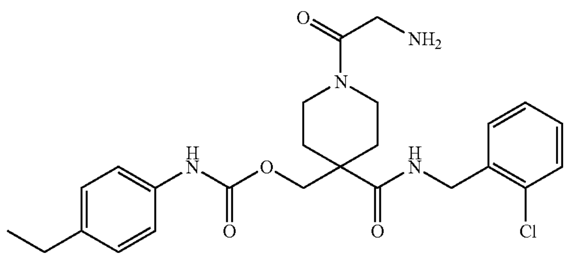 | (1-(2-aminoacetyl)-4-{[N-(4-ethylphenyl)carbamoyl-oxy]methyl}(4-piperidyl))-N-[(2-chlorophenyl)methyl]carboxamide |
| 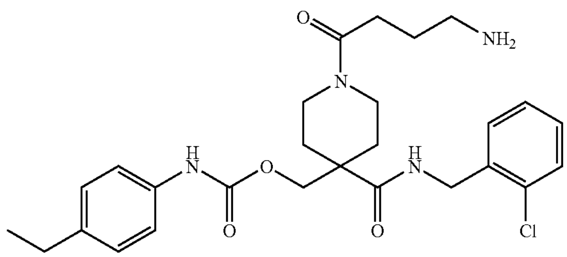 | (1-(4-aminobutanoyl)-4-([N-(4-ethylphenyl)carbamoyloxy]methyl}(4-piperidyl))-N-[(2-chlorophenyl)methyl]carboxamide |
| 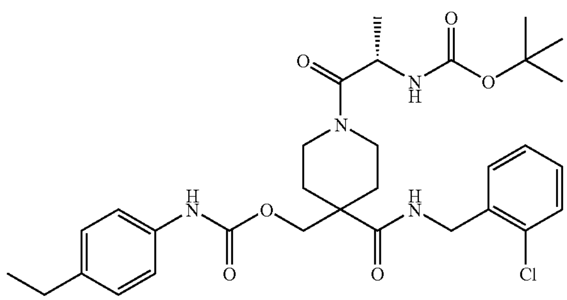 | N-[(1S)-2-(4-{N-[(2-chlorophenyl)methyl]carbamoyl}-4-{[N-(4-ethylphenyl)carbamoyloxy]methyl}piperidyl)-1-methyl-2-oxoethyl](tert-butoxy)carboxamide |
| 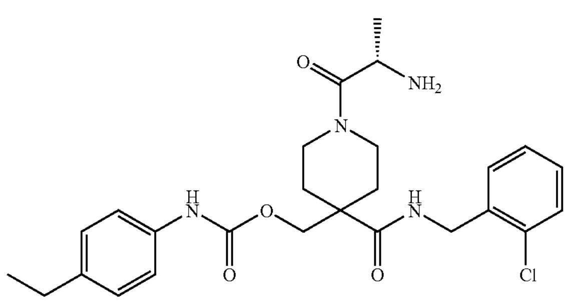 | (1-((2S)-2-aminopropanoyl)-4-{[N-(4-ethylphenyl)carbamoyloxy]methyl}(4-piperidyl))-N-[(2-chlorophenyl)methyl]carboxamide |
| 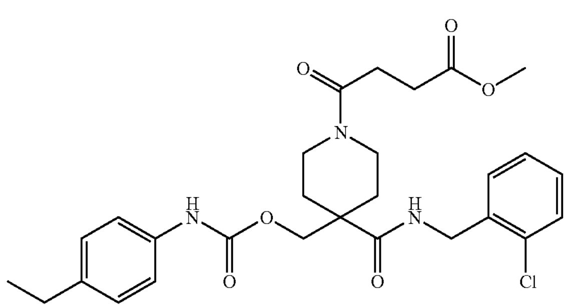 | methyl 4-(4-{N-[(2-chlorophenyl)methyl]carbamoyl}-4-{[N-(4-ethylphenyl)carbamoyloxy]methyl)piperidyl)-4-oxobutanoate |

-continued

| Structure | Chemical Name |
|---|---|
| 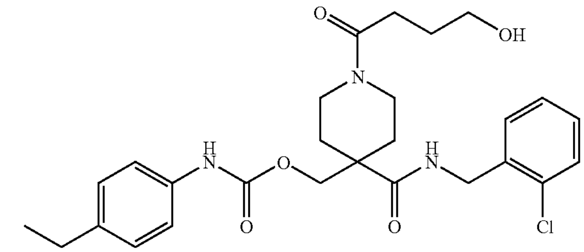 | N-[(2-chlorophenyl)methyl](4-{[N-(4-ethylphenyl)carbamoyloxy]methyl}-1-(4-hydroxybutanoyl)(4-piperidyl))carboxamide |
| 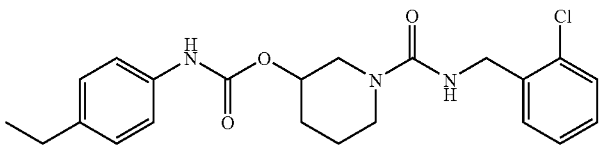 | N-[(2-chlorophenyl)methyl]{3-[N-(4-ethylphenyl)carbamoyl-oxy]piperidyl}carboxamide |
| 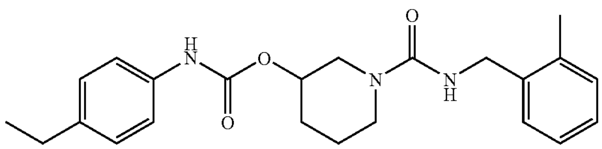 | {3-[N-(4-ethylphenyl)carbamoyloxy]piperidyl}-N-[(2-methylphenyl)methyl]carboxamide |
| 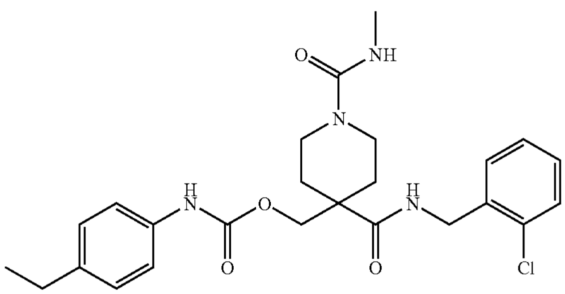 | N-[(2-chlorophenyl)methyl](4-{[N-(4-ethylphenyl)carbamoyloxy]methyl}-1-N-methylcarbamoyl)(4-piperidyl))carboxamide |
| 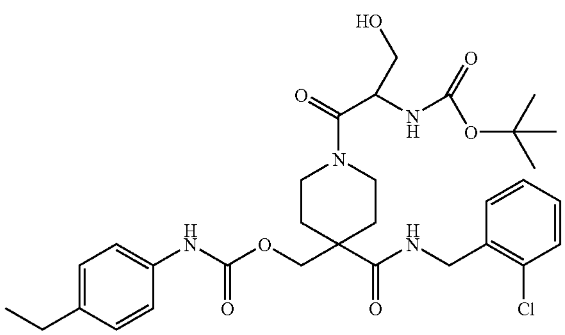 | (tert-butoxy)-N-[2-(4-(N-[(2-chlorophenyl)methyl]carbamoyl}-4-{[N-(4-ethylphenyl)carbamoyloxy]methyl}piperidyl)-1-(hydroxymethyl)-2-oxoethyl]carboxamide |
| 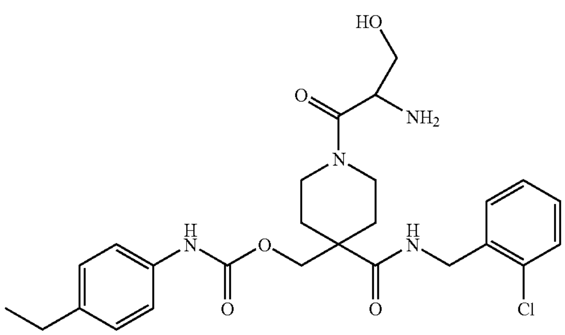 | (1-(2-amino-3-hydroxypropanoyl)-4-{[N-(4-ethylphenyl)carbamoyloxy]methyl}(4-piperidyl))-N-[(2-chlorophenyl)methyl]carboxamide |

| Structure | Chemical Name |
|---|---|
| 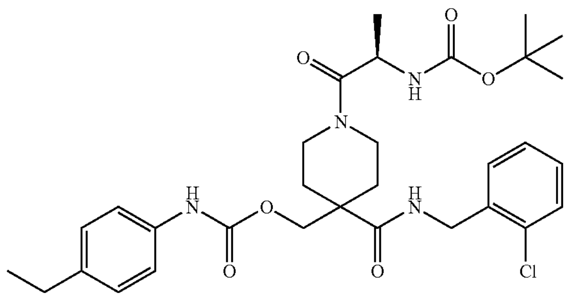 | N-[(1R)-2-(4-{N-[(2-chlorophenyl)methyl]carbamoyl}-4-{[N-(4-ethylphenyl)carbamoyloxy]methyl}piperidyl)-1-methyl-2-oxoethyl](tert-butoxy)carboxamide |
| 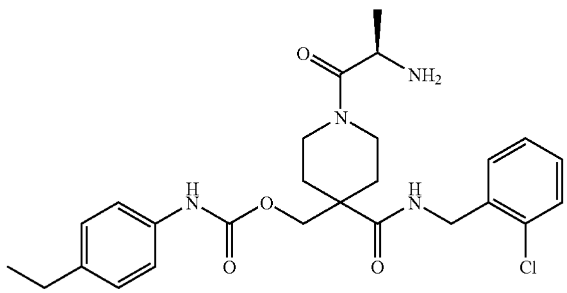 | (1-((2R)-2-aminopropanoyl)-4-([N-(4-ethylphenyl)carbamoyloxylmethyl}(4-piperidyl))-N-[(2-chlorophenyl)methyl]carboxamide |
| 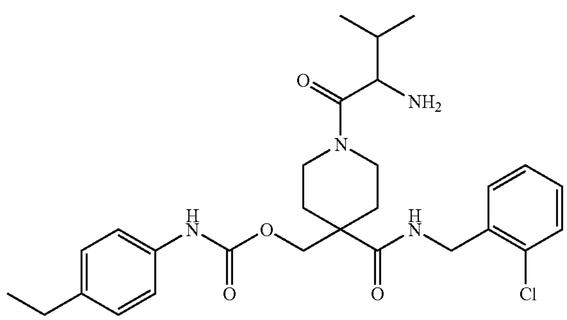 | (1-(2-amino-3-methylbutanoyl)-4-{[N-(4-ethylphenyl)carbamoyloxy]methyl}(4-piperidyl))-N-[(2-chlorophenyl)methyl]carboxamide |
| | tert-butyl 4-[(4-{N-[(2-chlorophenyl)methyl]carbamoyl}-4-{[N-(4-ethylphenyl)carbamoyloxy]methyl}piperidyl)carbonyl]piperidinecarboxylate |
| 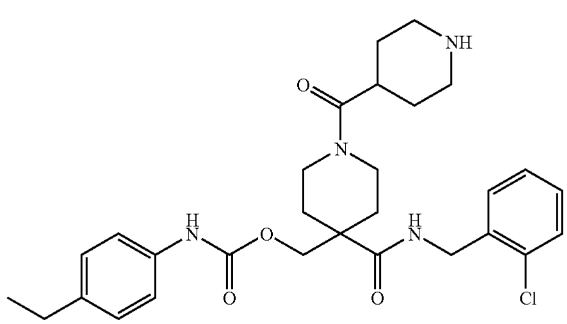 | N-[(2-chlorophenyl)methyl](4-{[N-(4-ethylphenyl)carbamoyloxy]methyl}-1-(4-piperidylcarbonyl)(4-piperidyl))carboxamide |

-continued

| Structure | Chemical Name |
|---|---|
| 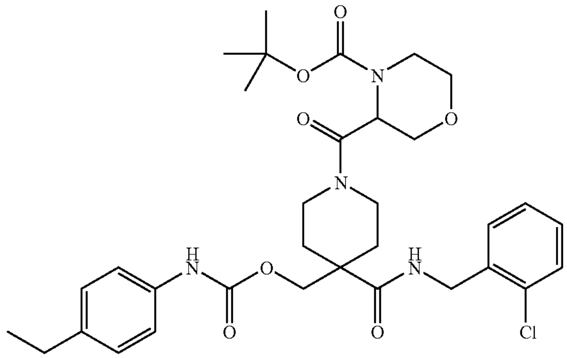 | tert-butyl 3-[(4-(N-[(2-chlorophenyl)methyl]carbamoyl}-4-{[N-(4-ethylphenyl)carbamoyloxy]methyl}piperidyl)carbonyl]morpholine-4-carboxylate |
| 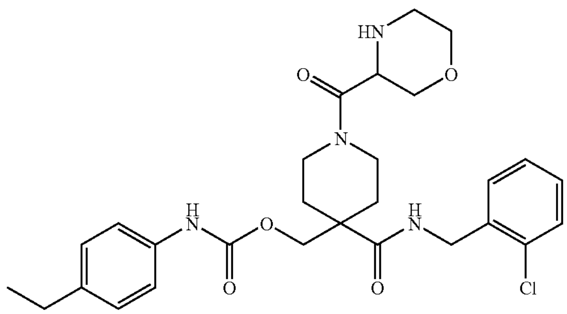 | N-[(2-chlorophenyl)methyl](4-{[N-(4-ethylphenyl)carbamoyloxy]methyl}-1-(morpholin-3-ylcarbonyl)(4-piperidyl))carboxamide |
| 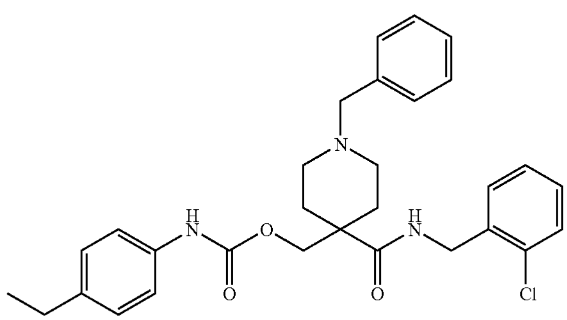 | N-[(2-chlorophenyl)methyl](4-{[N-(4-ethylphenyl)carbamoyloxy]methyl}-1-benzyl(4-piperidyl))carboxamide |
| 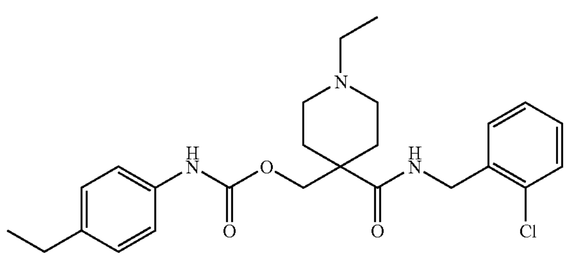 | N-[(2-chlorophenyl)methyl](1-ethyl-4-{[N-(4-ethylphenyl)carbamoyloxy]methyl}(4-piperidyl))carboxamide |
| 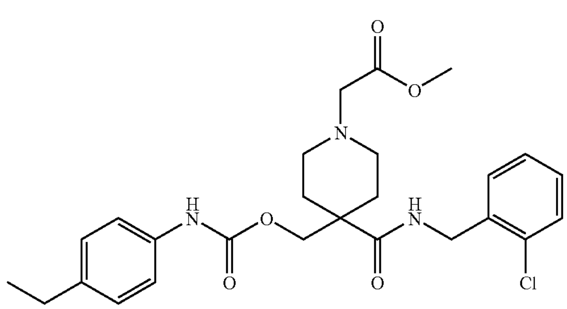 | methyl 2-(4-{N-[(2-chlorophenyl)methyl]carbamoyl}-4-{[N-(4-ethylphenyl)carbamoyloxy]methyl}piperidyl)acetate |

-continued

| Structure | Chemical Name |
|---|---|
| 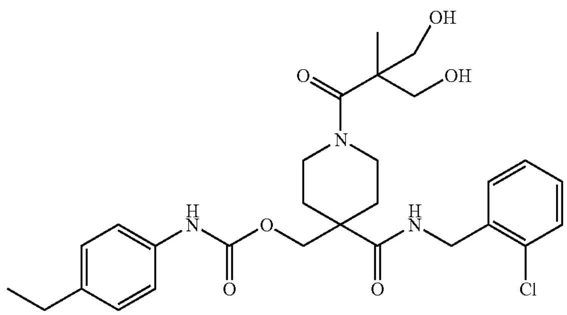 | N-[(2-chlorophenyl)methyl](4-{[N-(4-ethylphenyl)carbamoyloxy]methyl}-1-[3-hydroxy-2-(hydroxymethyl)-2-methylpropanoyl](4-piperidyl))carboxamide |
| 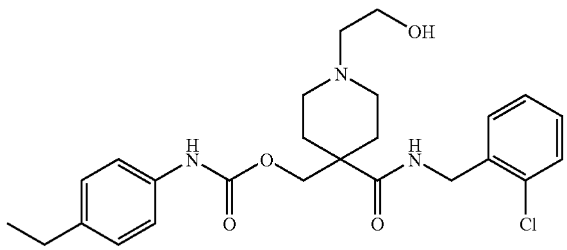 | N-[(2-chlorophenyl)methyl](4-([N-(4-ethylphenyl)carbamoyloxy]methyl}-1-(2-hydroxyethyl)(4-piperidyl))carboxamide |
| 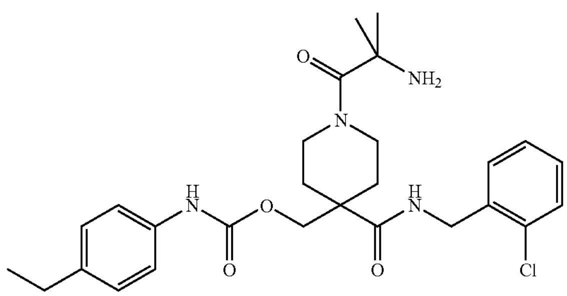 | (1-(2-amino-2-methylpropanoyl)-4-{[N-(4-ethylphenyl)carbamoyloxy]methyl}(4-piperidyl))-N-[(2-chlorophenyl)methyl]carboxamide |
| 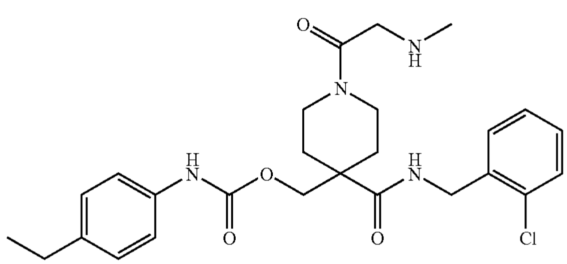 | N-[(2-chlorophenyl)methyl](4-{[N-(4-ethylphenyl)carbamoyloxy]methyl}-1-[2-(methylamino)acetyl](4-piperidyl))carboxamide |
| 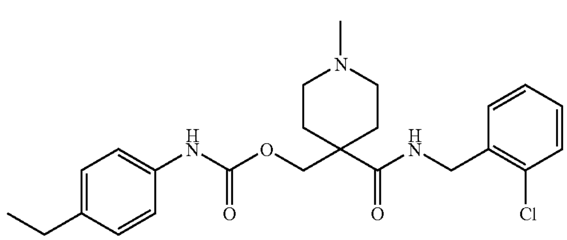 | N-[(2-chlorophenyl)methyl](4-{[N-(4-ethylphenyl)carbamoyloxy]methyl}-1-methyl(4-piperidyl))carboxamide |

-continued

| Structure | Chemical Name |
|---|---|
| 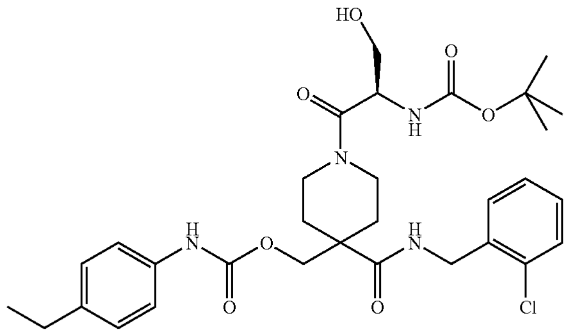 | N-[(1R)-2-(4-{N-[(2-chlorophenyl)methyl]carbamoyl}-4-{[N-(4-ethylphenyl)carbamoyloxy]methyl}piperidyl)-1-(hydroxymethyl)-2-oxoethyl](tert-butoxy)carboxamide |
| 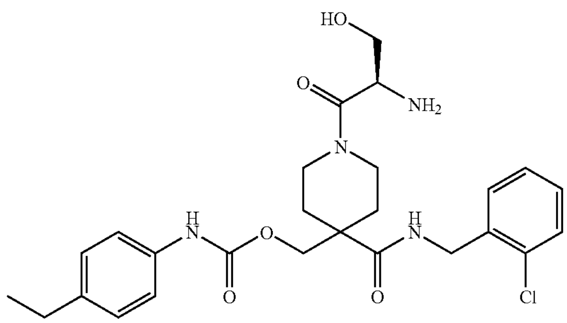 | (1-((2R)-2-amino-3-hydroxypropanoyl)-4-{[N-(4-ethylphenyl)carbamoyloxy]methyl}(4-piperidyl))-N-[(2-chlorophenyl)methyl]carboxamide |
| 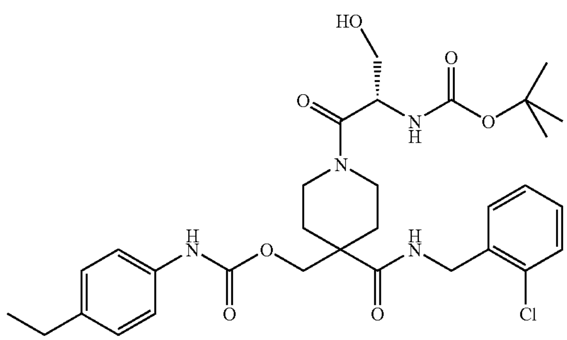 | N-[(1S)-2-(4-{N-[(2-chlorophenyl)methyl]carbamoyl}-4-{[N-(4-ethylphenyl)carbamoyloxy]methyl}piperidyl)-1-(hydroxymethyl)-2-oxoethyl](tert-butoxy)carboxamide |
| 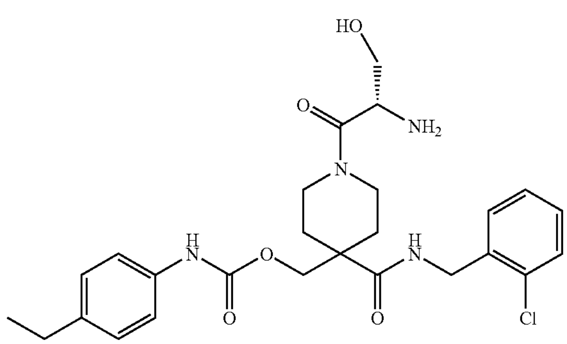 | (1-((2S)-2-amino-3-hydroxypropanoyl)-4-{[N-(4-ethylphenyl)carbamoyloxy]methyl}(4-piperidyl))-N-[(2-chlorophenyl)methyl]carboxamide |
| 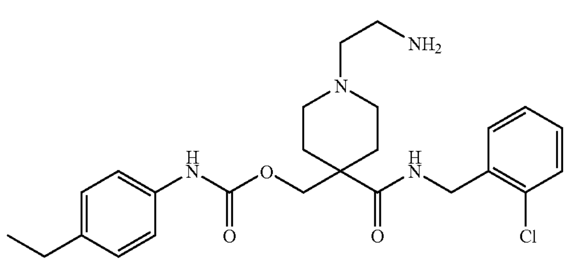 | (1-(2-aminoethyl)-4-{[N-(4-ethylphenyl)carbamoyloxy]methyl}(4-piperidyl))-N-[(2-chlorophenyl)methyl]carboxamide |

-continued

| Structure | Chemical Name |
|---|---|
| 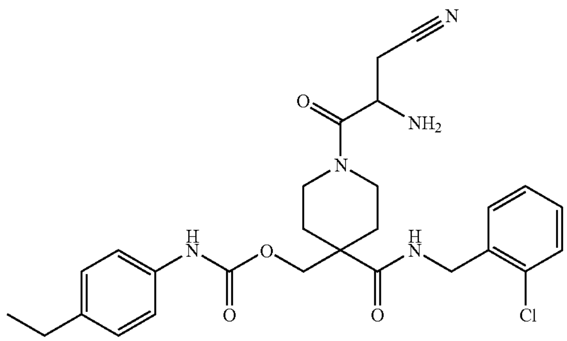 | (1-(2-amino-3-cyanopropanoyl)-4-{[N-(4-ethylphenyl)carbamoyloxy]methyl}(4-piperidyl))-N-[(2-chlorophenyl)methyl]carboxamide |
| 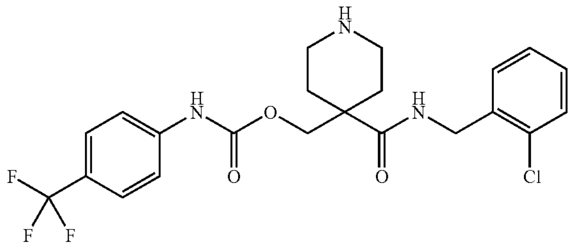 | N-[(2-chlorophenyl)methyl][4-({N-[4-(trifluoromethyl)phenyl]carbamoyl-oxy}methyl)(4-piperidyl)]carboxamide |
| 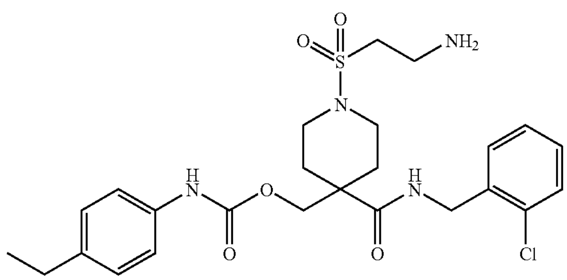 | (1-[(2-aminoethyl)sulfonyl]-4-{[N-(4-ethylphenyl)carbamoyloxy]methyl}(4-piperidyl))-N-[(2-chlorophenyl)methyl]carboxamide |
| 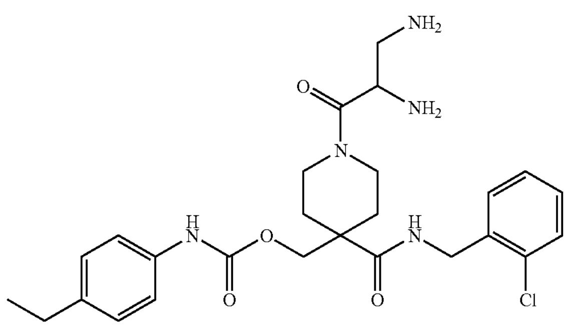 | (1-(2,3-diaminopropanoyl)-4-{[N-(4-ethylphenyl)carbamoyloxy]methyl}(4-piperidyl))-N-[(2-chlorophenyl)methyl]carboxamide |
| 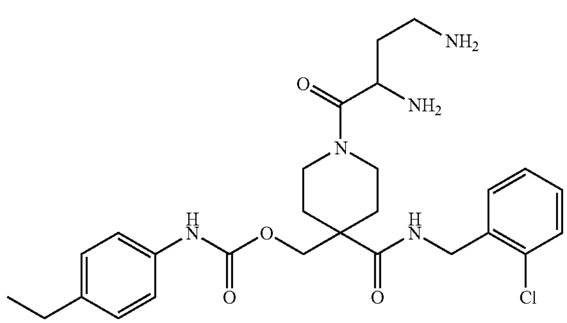 | (1-(2,4-diaminobutanoyl)-4-{[N-(4-ethylphenyl)carbamoyloxy]methyl}(4-piperidyl))-N-[(2-chlorophenyl)methyl]carboxamide |

-continued

| Structure | Chemical Name |
|---|---|
| 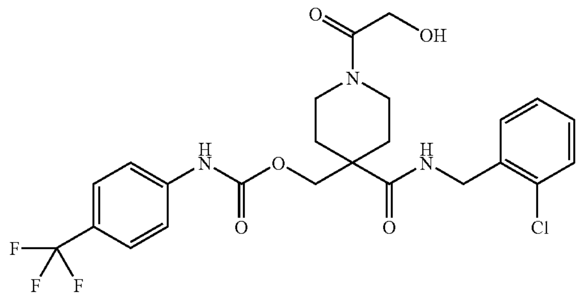 | N-[(2-chlorophenyl)methyl][1-(2-hydroxyacetyl)-4-({N-[4-(trifluoromethyl)phenyl]carbamoyloxy}methyl)(4-piperidyl)]carboxamide |
| 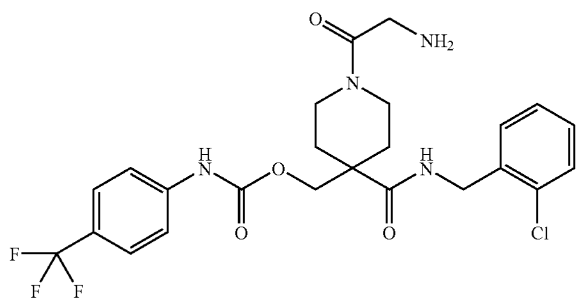 | [1-(2-aminoacetyl)-4-((N-[4-(trifluoromethyl)phenyl]carbamoyloxy}methyl)(4-piperidyl)]-N-[(2-chlorophenyl)methyl]carboxamide |
| | [1-((2S)-2-amino-3-hydroxy-propanoyl)-4-({N-[4-(trifluoromethyl)phenyl]carbamoyloxy}methyl)(4-piperidyl)]-N-[(2-chlorophenyl)methyl]carboxamide |
| 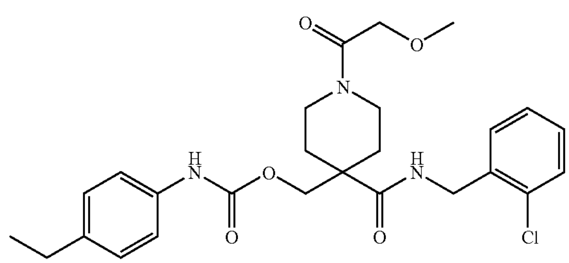 | N-[(2-chlorophenyl)methyl](4-{[N-(4-ethylphenyl)carbamoyloxy]methyl}-1-(2-methoxyacetyl)(4-piperidyl))carboxamide |
| 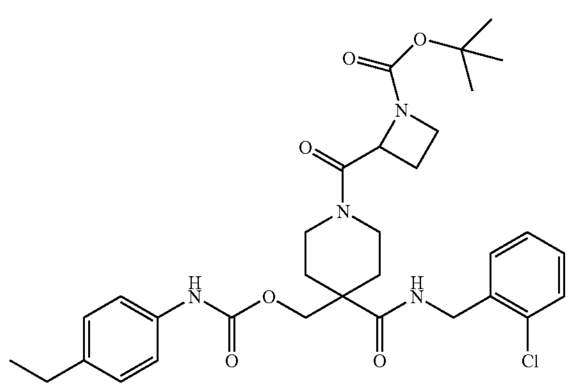 | tert-butyl 2-[(4-{N-[(2-chlorophenyl)methyl]carbamoyl}-4-{[N-(4-ethylphenyl)carbamoyloxy]methyl}piperidyl)carbonyl]azetidinecarboxylate |

-continued

| Structure | Chemical Name |
|---|---|
| 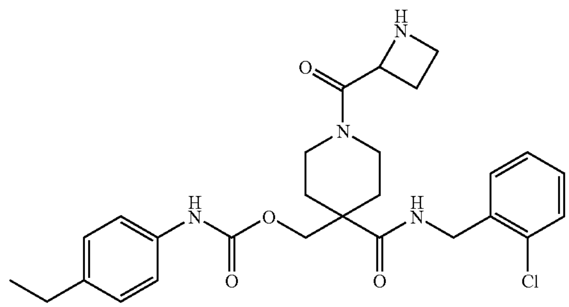 | (1-(azetidin-2-ylcarbonyl)-4-{[N-(4-ethylphenyl)carbamoyloxy]methyl}(4-piperidyl))-N-[(2-chlorophenyl)methyl]carboxamide |
| 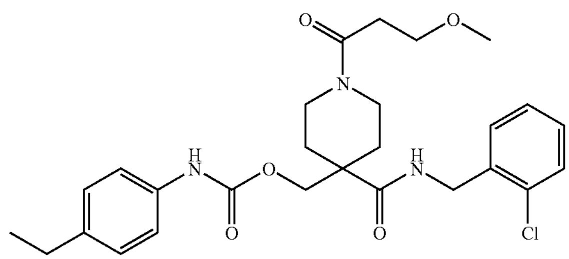 | N-[(2-chlorophenyl)methyl](4-{[N-(4-ethylphenyl)carbamoyloxy]methyl}-1-(3-methoxypropanoyl)(4-piperidyl))carboxamide |
| 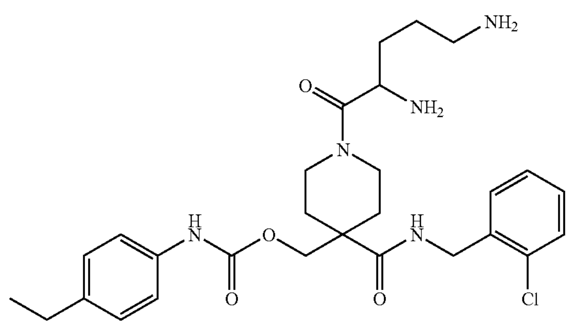 | (1-(2,5-diaminopentanoyl)-4-([N-(4-ethylphenyl)carbamoyloxy]methyl}(4-piperidyl))-N-[(2-chlorophenyl)methyl]carboxamide |
| 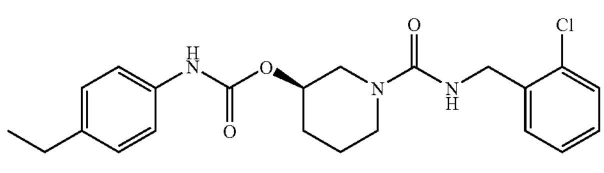 | {(3R)-3-[N-(4-ethylphenyl)carbamoyloxy]piperidyl}-N-[(2-chlorophenyl)methyl]carboxamide |
| 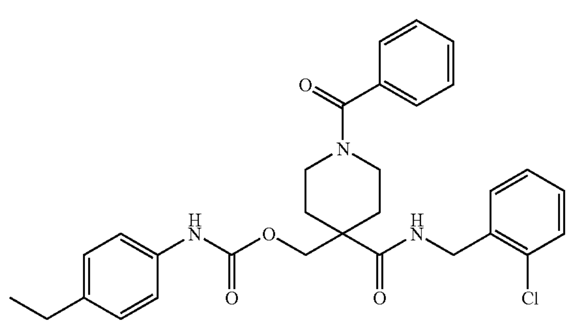 | N-[(2-chlorophenyl)methyl](4-{[N-(4-ethylphenyl)carbamoyloxy]methyl}-1-(phenylcarbonyl)(4-piperidyl))carboxamide |

| Structure | Chemical Name |
|---|---|
| 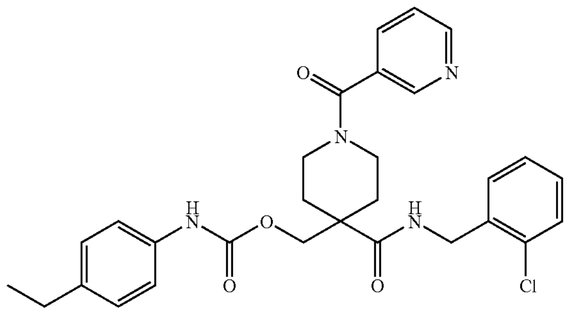 | N-[(2-chlorophenyl)methyl](4-{[N-(4-ethylphenyl)carbamoyloxy]methyl}-1-(3-pyridylcarbonyl)(4-piperidyl))carboxamide |
| 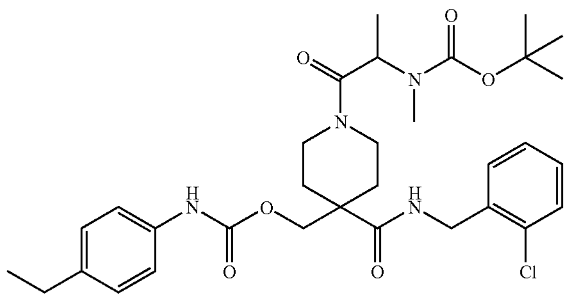 | (tert-butoxy)-N-[2-(4-{N-[(2-chlorophenyl)methyl]carbamoyl}-4-{[N-(4-ethylphenyl)carbamoyloxy]methyl}piperidyl)-1-methyl-2-oxoethyl]-N-methylcarboxamide |
| 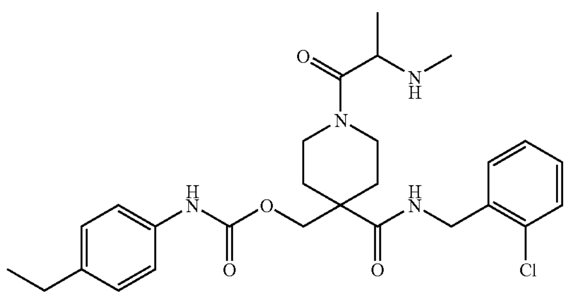 | N-[(2-chlorophenyl)methyl](4-{[N-(4-ethylphenyl)carbamoyloxy]methyl}-1-[2-(methylamino)propanoyl](4-piperidyl))carboxamide |
| 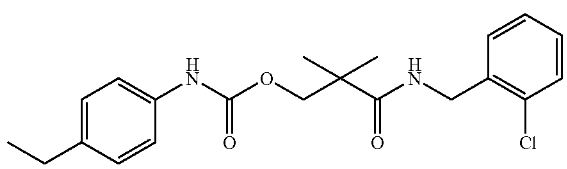 | N-[(2-chlorophenyl)methyl]-N'-(4-ethylphenyl)-2,2-dimethylpentane-1,5-diamide |
| | methyl (3S)-3-amino-4-(4-{N-[(2-chlorophenyl)methyl]carbamoyl}-4-{[N-(4-ethylphenyl)carbamoyloxy]methyl}piperidyl)-4-oxobutanoate |

| Structure | Chemical Name |
|---|---|
| 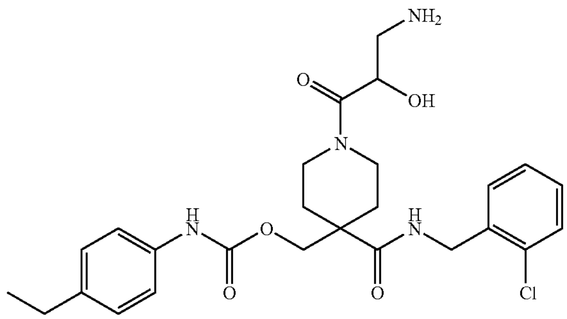 | (1-(3-amino-2-hydroxypropanoyl)-4-{[N-(4-ethylphenyl)carbamoyloxy]methyl}(4-piperidyl))-N-[(2-chlorophenyl)methyl]carboxamide |
| 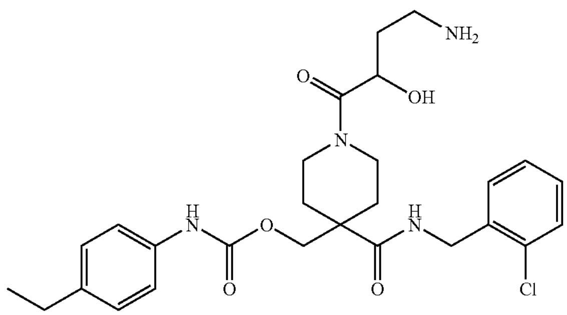 | (1-(4-amino-2-hydroxybutanoyl)-4-{[N-(4-ethylphenyl)carbamoyloxy]methyl}(4-piperidyl))-N-[(2-chlorophenyl)methyl]carboxamide |
| 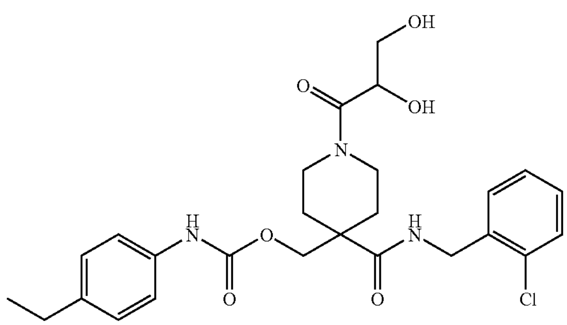 | (1-(2,3-dihydroxypropanoyl)-4-{[N-(4-ethylphenyl)carbamoyloxy]methyl}(4-piperidyl))-N-[(2-chlorophenyl)methyl]carboxamide |
| 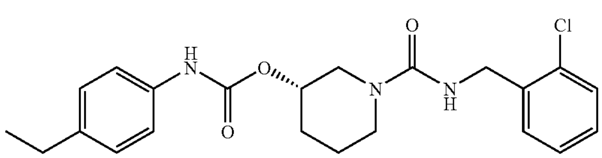 | {(3S)-3-[N-(4-ethylphenyl)carbamoyloxy]piperidyl}-N-[(2-chlorophenyl)methyl]carboxamide |
| 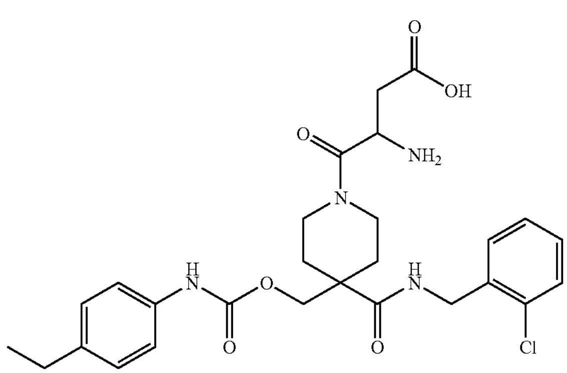 | 3-amino-4-(4-{N-[(2-chlorophenyl)methyl]carbamoyl}-4-{[N-(4-ethylphenyl)carbamoyloxy]methyl}piperidyl)-4-oxobutanoic acid |

| Structure | Chemical Name |
|---|---|
| 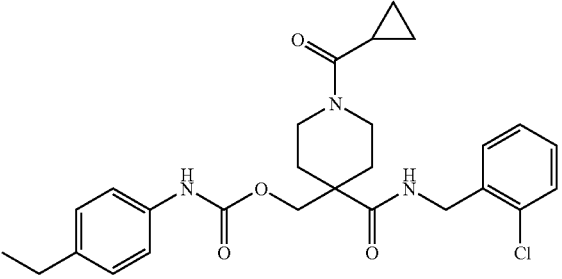 | N-[(2-chlorophenyl)methyl](1-(cyclopropylcarbonyl)-4-{[N-(4-ethylphenyl)carbamoyloxy]methyl}(4-piperidyl))carboxamide |
| 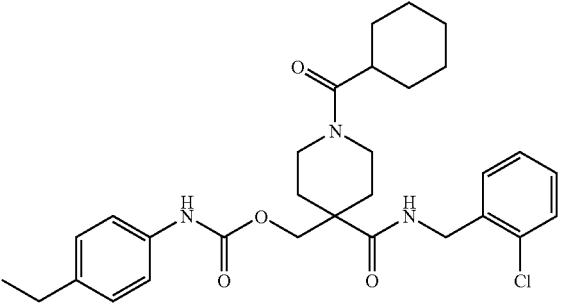 | N-[(2-chlorophenyl)methyl](1-(cyclohexylcarbonyl)-4-{[N-(4-ethylphenyl)carbamoyloxy]methyl}(4-piperidyl))carboxamide |
| 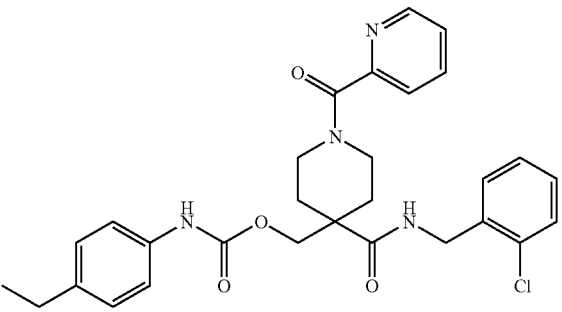 | N-[(2-chlorophenyl)methyl](4-{[N-(4-ethylphenyl)carbamoyloxy]methyl}-1-(2-pyridylcarbonyl)(4-piperidyl))carboxamide |
| 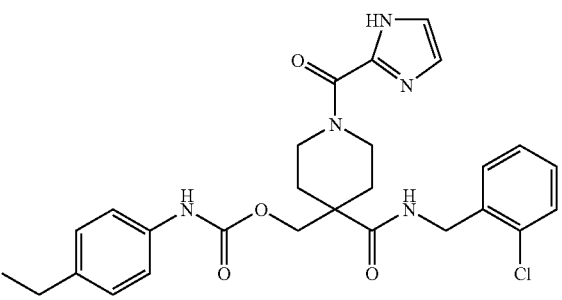 | N-[(2-chlorophenyl)methyl](4-{[N-(4-ethylphenyl)carbamoyloxy]methyl}-1-(imidazol-2-ylcarbonyl)(4-piperidyl))carboxamide |
| 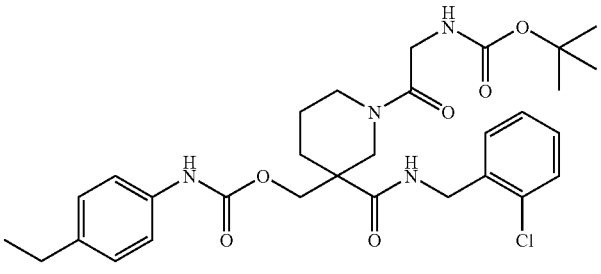 | (tert-butoxy)-N-[2-(3-(N-[(2-chlorophenyl)methyl]carbamoyl}-3-{[N-(4-ethylphenyl)carbamoyloxy]methyl}piperidyl)-2-oxoethyl]carboxamide |

-continued

| Structure | Chemical Name |
|---|---|
| 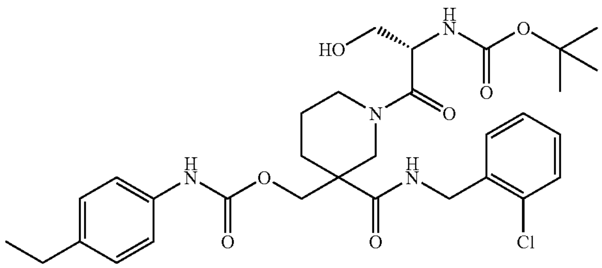 | N-[(1S)-2-(3-{N-[(2-chlorophenyl)methyl]carbamoyl}-3-{[N-(4-ethylphenyl)carbamoyloxy]methyl}piperidyl)-1-(hydroxymethyl)-2-oxoethyl](tert-butoxy)carboxamide |
| | (1-(2-aminoacetyl)-3-{[N-(4-ethylphenyl)carbamoyloxymethyl}(3-piperidyl))-N-[(2-chlorophenyl)methyl]carboxamide |
| 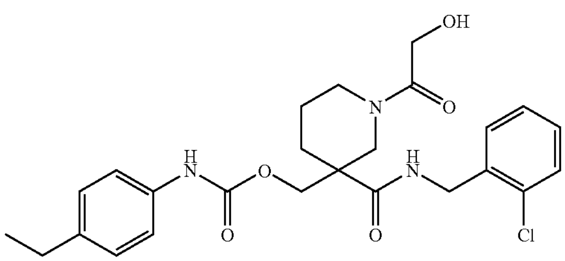 | N-[(2-chlorophenyl)methyl](3-{[N-(4-ethylphenyl)carbamoyloxy]methyl}-1-(2-hydroxyacetyl)(3-piperidyl))carboxamide |
| 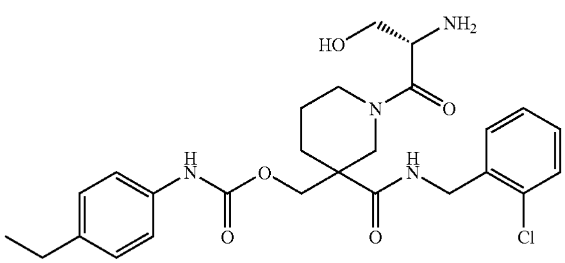 | (1-((2S)-2-amino-3-hydroxypropanoyl)-3-{[N-(4-ethylphenyl)carbamoyloxy]methyl}(3-piperidyl))-N-[(2-chlorophenyl)methyl]carboxamide |
| 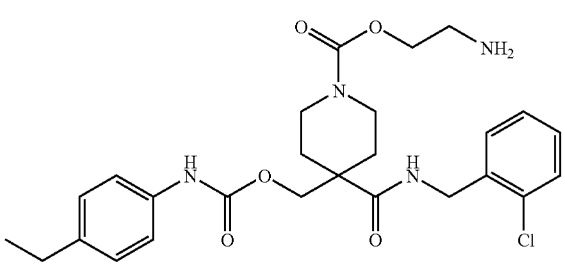 | 2-aminoethyl 4-{N-[(2-chlorophenyl)methyl]carbamoyl}-4-{[N-(4-ethylphenyl)carbamoyloxy]methyl}piperidinecarboxylate |
| 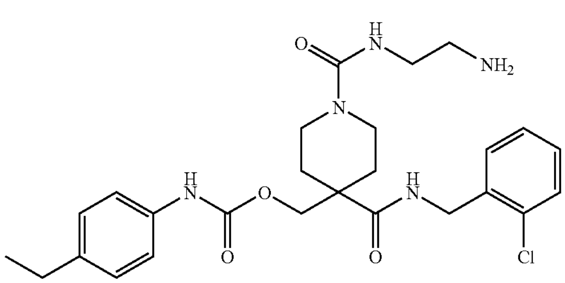 | N-(2-aminoethyl)(4-{N-[(2-chlorophenyl)methyl]carbamoyl}-4-([N-(4-ethylphenyl)carbamoyloxy]methyl}piperidyl)carboxamide |

| Structure | Chemical Name |
|---|---|
| 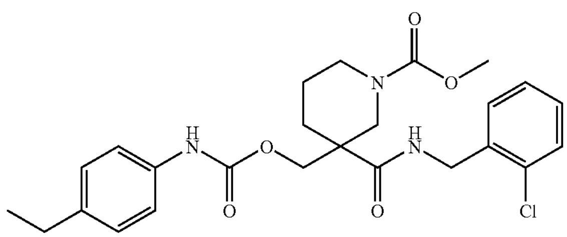 | methyl 3-{N-[(2-chlorophenyl)methyl]carbamoyl}-3-{[N-(4-ethylphenyl)carbamoyloxy]methyl}piperidinecarboxylate |
| 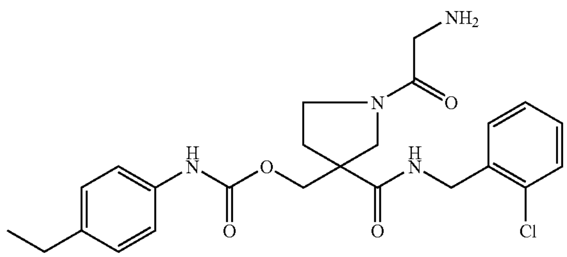 | (1-(2-aminoacetyl)-3-{[N-(4-ethylphenyl)carbamoyloxy]methyl}pyrrolidin-3-yl)-N-[(2-chlorophenyl)methyl]carboxamide |
| 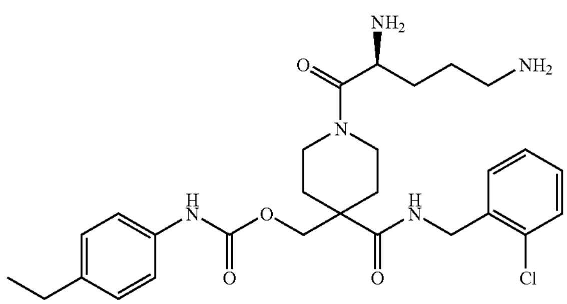 | (1-((2S)-2,5-diaminopentanoyl)-4-{[N-(4-ethylphenyl)carbamoyloxy]methyl}(4-piperidyl))-N-[(2-chlorophenyl)methyl]carboxamide |
| 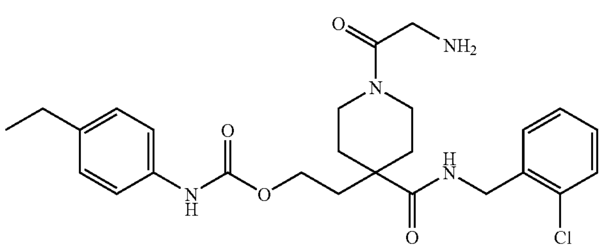 | (1-(2-aminoacetyl)-4-{2-[N-(4-ethylphenyl)carbamoyloxy]ethyl}(4-piperidyl))-N-[(2-chlorophenyl)methyl]carboxamide |
| 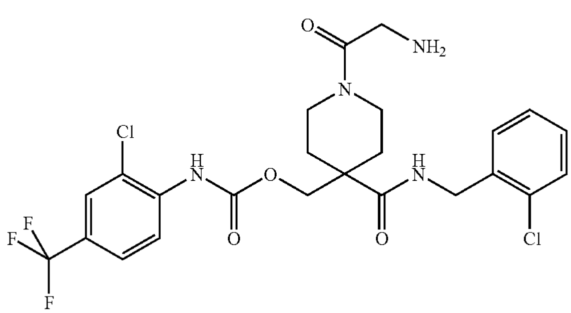 | [1-(2-aminoacetyl)-4-({N-[2-chloro-4-(trifluoromethyl)phenyl]carbamoyloxy}methyl)(4-piperidyl)]-N-[(2-chlorophenyl)methyl]carboxamide |
| 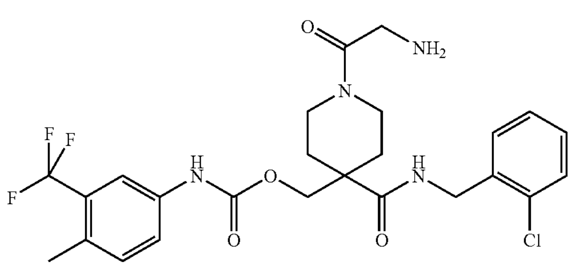 | [1-(2-aminoacetyl)-4-({N-[4-methyl-3-(trifluoromethyl)phenyl]carbamoyloxy}methyl)(4-piperidyl)]-N-[(2-chlorophenyl)methyl]carboxamide |

-continued

| Structure | Chemical Name |
|---|---|
| 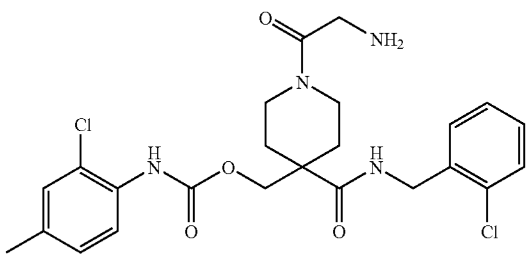 | (1-(2-aminoacetyl)-4-{[N-(2-chloro-4-methylphenyl)carbamoyloxy]methyl}(4-piperidyl))-N-[(2-chlorophenyl)methyl]carboxamide |
| 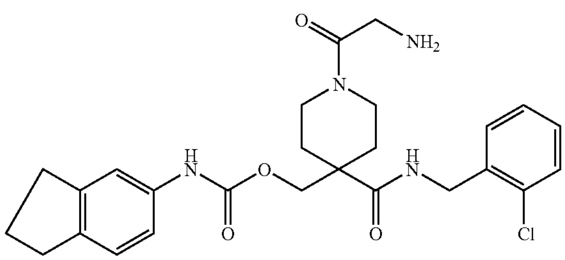 | {1-(2-aminoacetyl)-4-[(N-indan-5-ylcarbamoyloxy)methyl](4-piperidyl)}-N-[(2-chlorophenyl)methyl]carboxamide |
| 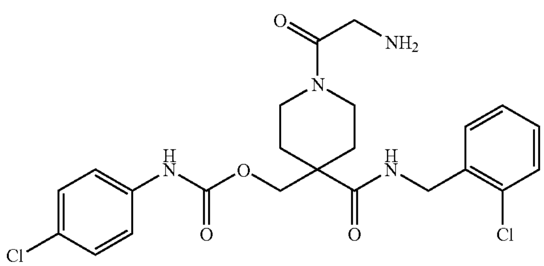 | (1-(2-aminoacetyl)-4-{[N-(4-chlorophenyl)carbamoyloxy]methyl}(4-piperidyl))-N-[(2-chlorophenyl)methyl]carboxamide |
| 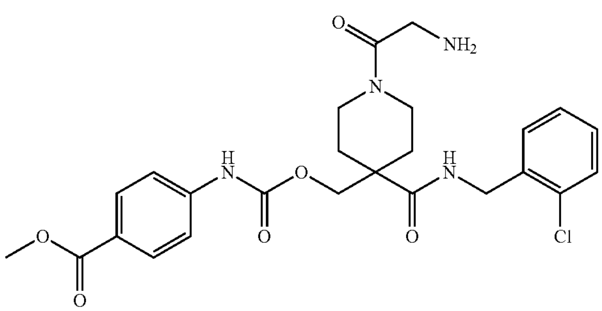 | methyl 4-{[(1-(2-aminoacetyl)-4-{N-[(2-chlorophenyl)methyl]carbamoyl}-4-piperidyl)methoxy]carbonylamino}benzoate |
| 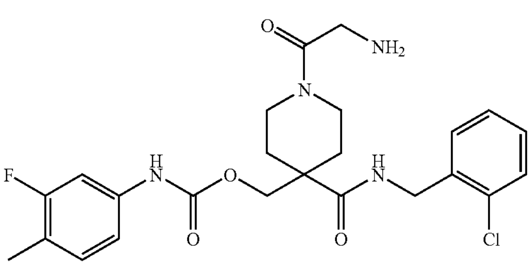 | (1-(2-aminoacetyl)-4-{[N-(3-fluoro-4-methylphenyl)carbamoyloxy]methyl}(4-piperidyl))-N-[(2-chlorophenyl)methyl]carboxamide |

-continued

| Structure | Chemical Name |
|---|---|
| 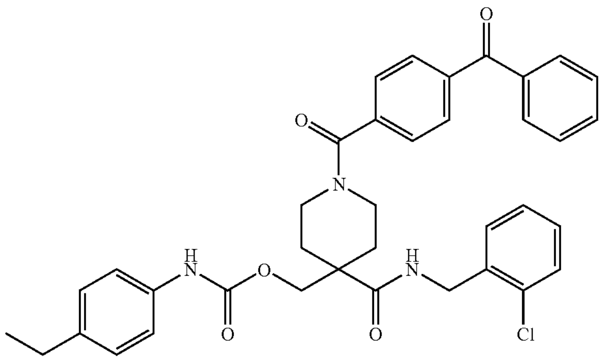 | N-[(2-chlorophenyl)methyl](4-{[N-(4-ethylphenyl)carbamoyloxy]methyl}-1-([4-(phenylcarbonyl)phenyl]carbonyl}(4-piperidyl))carboxamide |
| 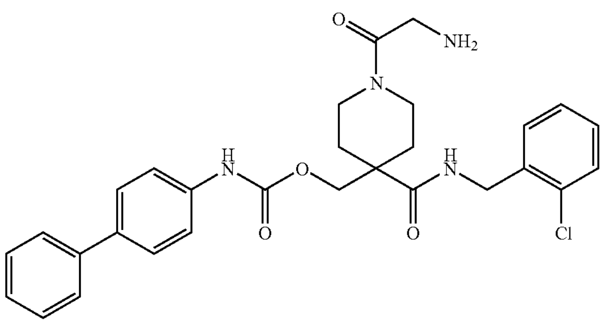 | (1-(2-aminoacetyl)-4-{[N-(4-phenylphenyl)carbamoyloxy]methyl}(4-piperidyl))-N-[(2-chlorophenyl)methyl]carboxamide |
| 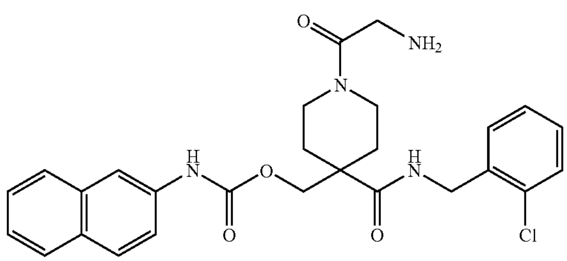 | (1-(2-aminoacetyl)-4-[(N-(2-naphthyl)carbamoyloxy)methyl](4-piperidyl)}-N-[(2-chlorophenyl)methyl]carboxamide |
| 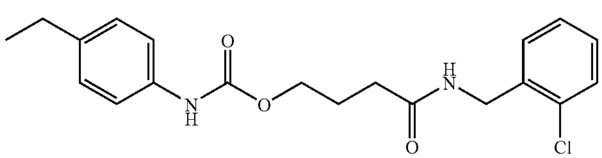 | N-[(2-chlorophenyl)methyl]-4-[N-(4-ethylphenyl)carbamoyloxy]butanamide |
| 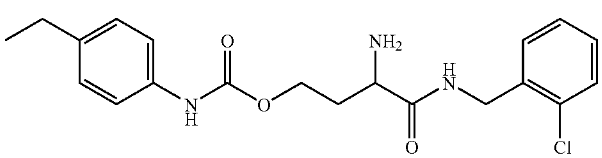 | 2-amino-N-[(2-chlorophenyl)methyl]-4-[N-(4-ethylphenyl)carbamoyloxy]butanamide |
| 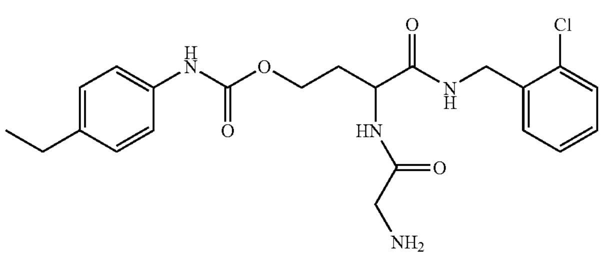 | 2-(2-aminoacetylamino)-N-[(2-chlorophenyl)methyl]-4-[N-(4-ethylphenyl)carbamoyloxy]butanamide |

-continued

| Structure | Chemical Name |
|---|---|
| 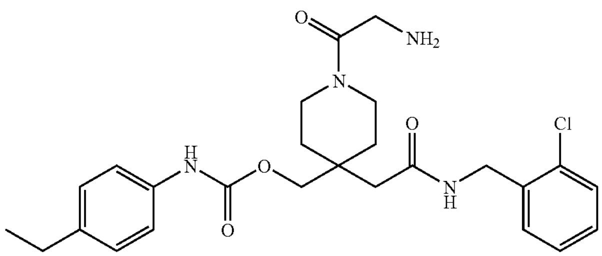 | 2-(1-(2-aminoacetyl)-4-{[N-(4-ethylphenyl)carbamoyloxy]methyl}(4-piperidyl))-N-[(2-chlorophenyl)methyl]acetamide |
| 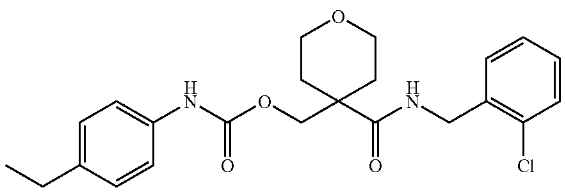 | N-[(2-chlorophenyl)methyl](4-{[N-(4-ethylphenyl)carbamoyloxy]methyl}(2H-3,4,5,6-tetrahydropyran-4-yl))carboxamide |
| 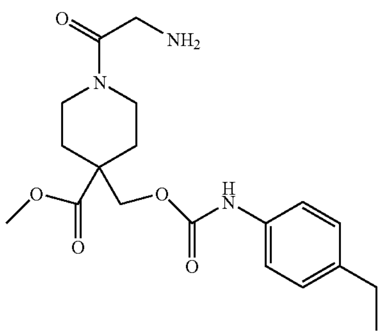 | methyl 1-(2-aminoacetyl)-4-([N-(4-ethylphenyl)carbamoyloxy]methyl}piperidine-4-carboxylate |
| 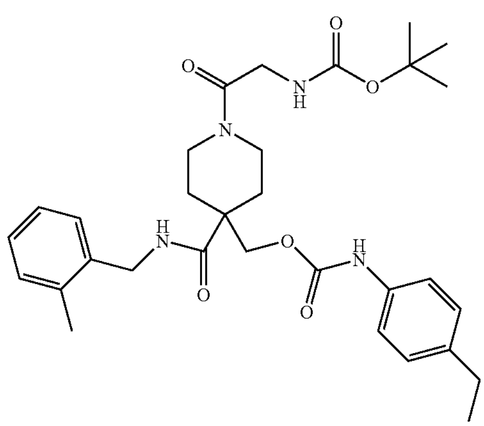 | (tert-butoxy)-N-[2-(4-{[N-(4-ethylphenyl)carbamoyloxy]methyl}-4-{N-[(2-methylphenyl)methyl]carbamoyl}piperidyl)-2-oxoethyl]carboxamide |

| Structure | Chemical Name |
|---|---|
| 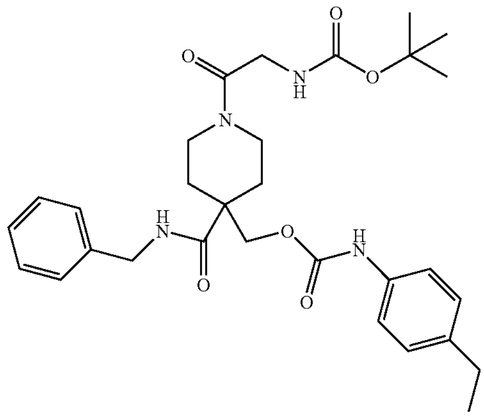 | (tert-butoxy)-N-[2-(4-{[N-(4-ethylphenyl)carbamoyloxy]methyl}-4-[N-benzylcarbamoyl]piperidyl)-2-oxoethyl]carboxamide |
| 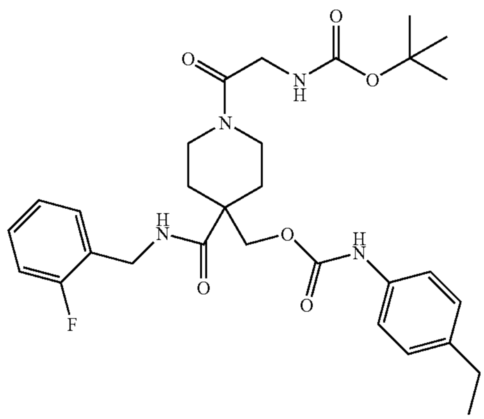 | (tert-butoxy)-N-[2-(4-{[N-(4-ethylphenyl)carbamoyloxy]methyl}-4-{N-[(2-fluorophenyl)methyl]carbamoyl}piperidyl)-2-oxoethyl]carboxamide |
| 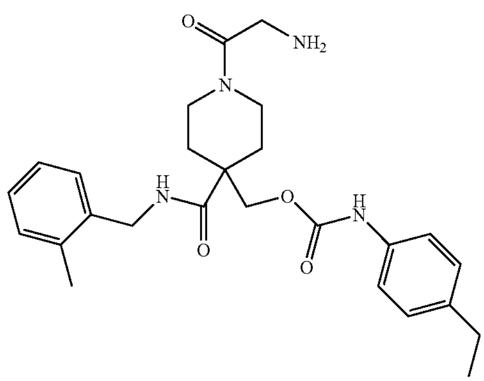 | (1-(2-aminoacetyl)-4-{[N-(4-ethylphenyl)carbamoyloxy]methyl}(4-piperidyl))-N-[(2-methylphenyl)methyl]carboxamide |
| 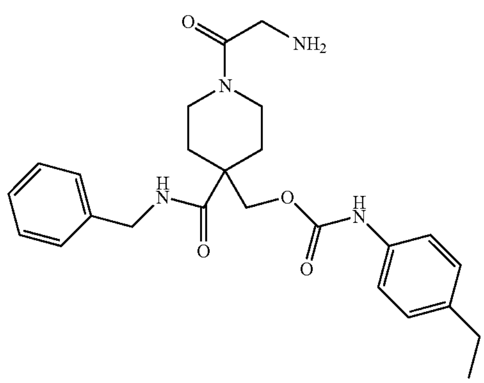 | (1-(2-aminoacetyl)-4-{[N-(4-ethylphenyl)carbamoyloxy]methyl}(4-piperidyl))-N-benzylcarboxamide |

-continued

| Structure | Chemical Name |
|---|---|
| 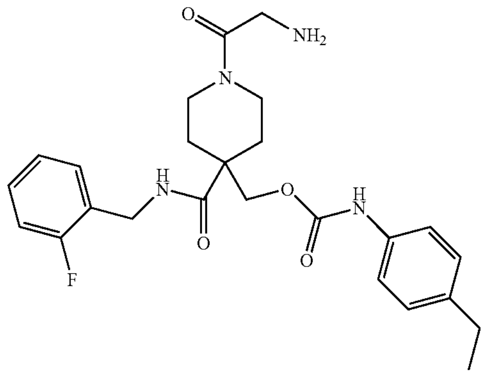 | (1-(2-aminoacetyl)-4-{[N-(4-ethylphenyl)carbamoyloxy]methyl}(4-piperidyl))-N-[(2-fluorophenyl)methyl]carboxamide |
| 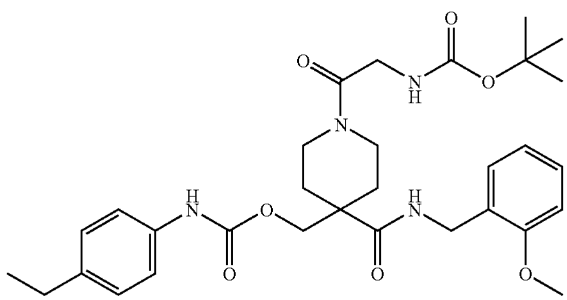 | (1-{2-[(tert-butoxy)carbonylamino]acetyl}-4-{[N-(4-ethylphenyl)carbamoyloxy]methyl}(4-piperidyl))-N-[(2-methoxyphenyl)methyl]carboxamide |
| 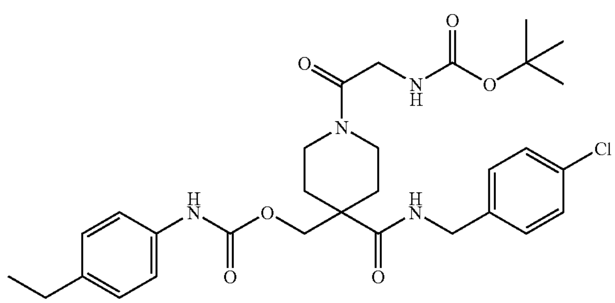 | [(1-{2-[(tert-butoxy)carbonylamino]acetyl}-4-{N-[(4-chlorophenyl)methyl]carbamoyl}(4-piperidyl))methoxy]-N-(4-ethylphenyl)carboxamide |
| 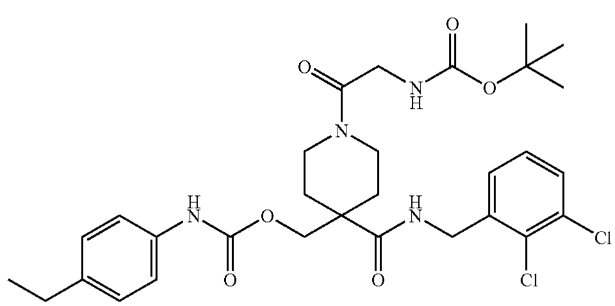 | [(4-{N-[(2,3-dichlorophenyl)methyl]carbamoyl}-1-{2-[(tert-butoxy)carbonylamino]acetyl}(4-piperidyl))methoxy]-N-(4-ethylphenyl)carboxamide |
| 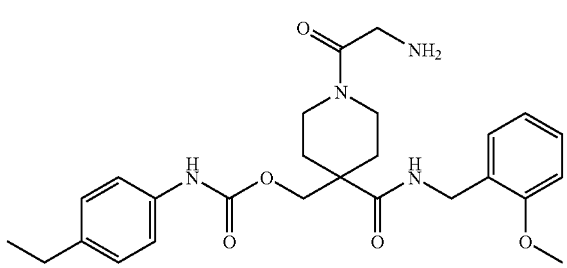 | (1-(2-aminoacetyl)-4-([N-(4-ethylphenyl)carbamoyloxy]methyl}(4-piperidyl))-N-[(2-methoxyphenyl)methyl]carboxamide |

-continued

| Structure | Chemical Name |
|---|---|
| 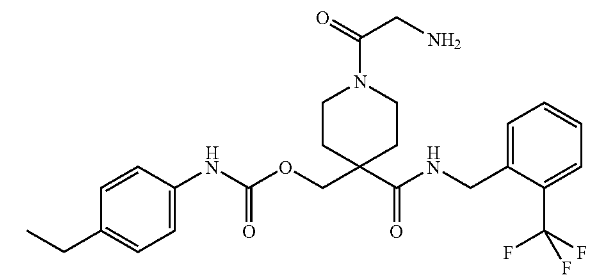 | {[1-(2-aminoacetyl)-4-(N-{[2-(trifluoromethyl)phenyl]methyl}carbamoyl)(4-piperidyl)]methoxy}-N-(4-ethylphenyl)carboxamide |
| 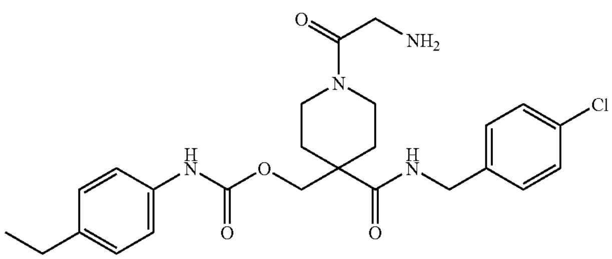 | [(1-(2-aminoacetyl)-4-{N-[(4-chlorophenyl)methyl]carbamoyl}(4-piperidyl))methoxy]-N-(4-ethylphenyl)carboxamide |
| 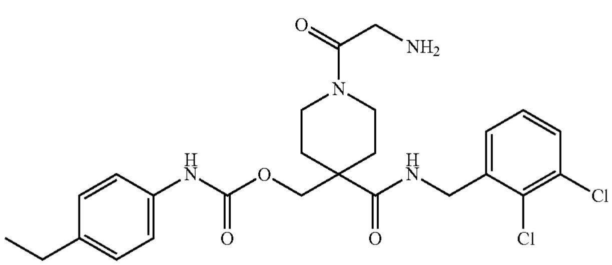 | [(1-(2-aminoacetyl)-4-{N-[(2,3-dichlorophenyl)methyl]carbamoyl}(4-piperidyl))methoxy]-N-(4-ethylphenyl)carboxamide |
| 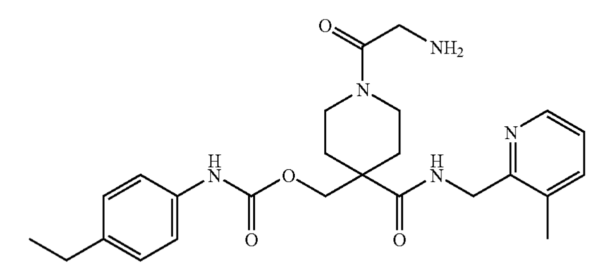 | [(1-(2-aminoacetyl)-4-{N-[(3-methyl(2-pyridyl))methyl]carbamoyl}(4-piperidyl))methoxy]-N-(4-ethylphenyl)carboxamide |
| 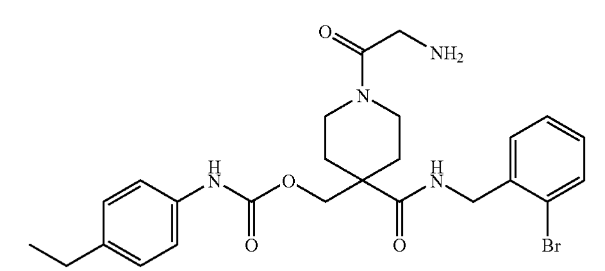 | [(1-(2-aminoacetyl)-4-(N-[(2-bromophenyl)methyl]carbamoyl}(4-piperidyl))methoxy]-N-(4-ethylphenyl)carboxamide |
| 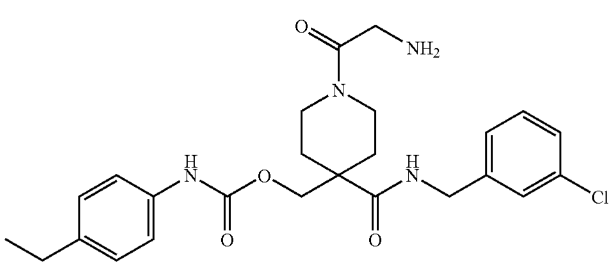 | [(1-(2-aminoacetyl)-4-{N-[(3-chlorophenyl)methyl]carbamoyl}(4-piperidyl))methoxy]-N-(4-ethylphenyl)carboxamide |

| Structure | Chemical Name |
|---|---|
| 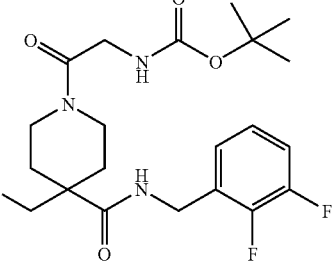 | [(4-{N-[(2,3-difluorophenyl)methyl]carbamoyl}-1-{2-[(tert-butoxy)carbonylamino]acetyl}(4-piperidyl))methoxy]-N-(4-ethylphenyl)carboxamide |
| 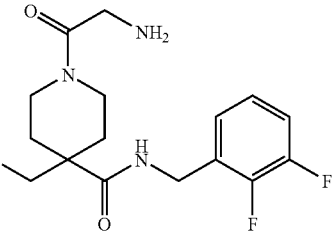 | [(1-(2-aminoacetyl)-4-{N-[(2,3-difluorophenyl)methyl]carbamoyl}(4-piperidyl))methoxy]-N-(4-ethylphenyl)carboxamide |
| 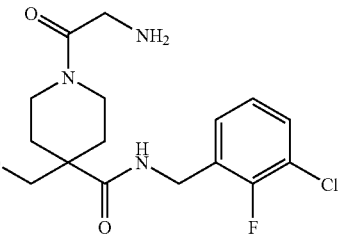 | [(1-(2-aminoacetyl)-4-(N-[(3-chloro-2-fluorophenyl)methyl]carbamoyl}(4-piperidyl))methoxy]-N-(4-ethylphenyl)carboxamide |
| 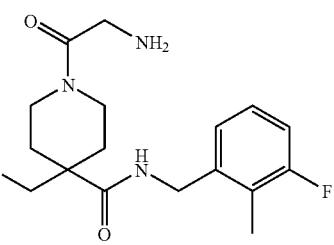 | [(1-(2-aminoacetyl)-4-{N-[(3-fluoro-2-methylphenyl)methyl]carbamoyl}(4-piperidyl))methoxy]-N-(4-ethylphenyl)carboxamide |
| 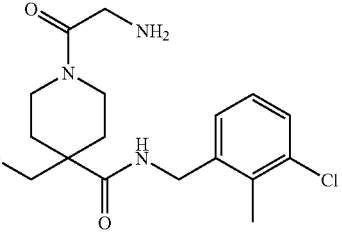 | [(1-(2-aminoacetyl)-4-{N-[(3-chloro-2-methylphenyl)methyl]carbamoyl}(4-piperidyl))methoxy]-N-(4-ethylphenyl)carboxamide |

| Structure | Chemical Name |
|---|---|
| 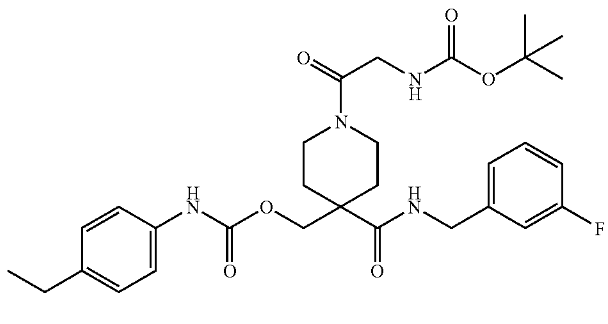 | [(1-{2-[(tert-butoxy)carbonyl-amino]acetyl}-4-{N-[(3-fluorophenyl)methyl]carbamoyl}(4-piperidyl))methoxy]-N-(4-ethylphenyl)carboxamide |
| 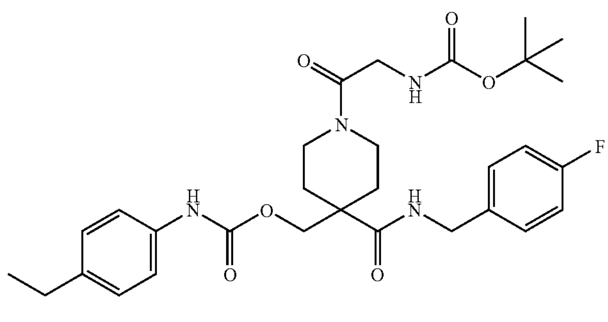 | [(1-(2-[(tert-butoxy)carbonyl-amino]acetyl}-4-{N-[(4-fluorophenyl)methyl]carbamoyl}(4-piperidyl))methoxy]-N-(4-ethylphenyl)carboxamide |
| 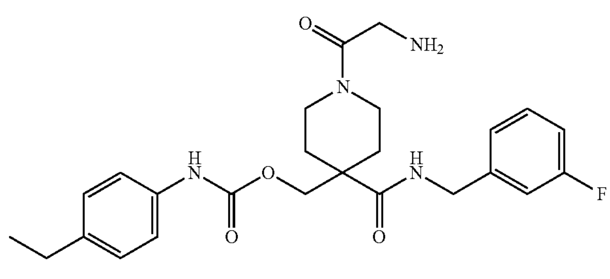 | [(1-(2-aminoacetyl)-4-{N-[(3-fluorophenyl)methyl]carbamoyl}(4-piperidyl))methoxy]-N-(4-ethylphenyl)carboxamide |
| 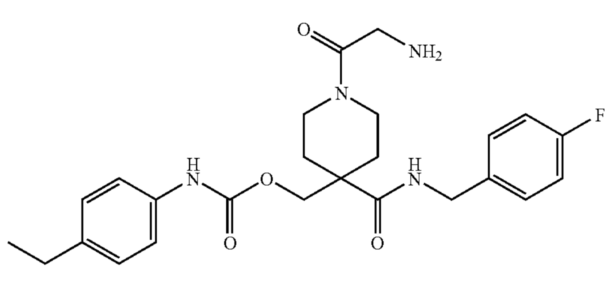 | [(1-(2-aminoacetyl)-4-(N-[(4-fluorophenyl)methyl]carbamoyl}(4-piperidyl))methoxy]-N-(4-ethylphenyl)carboxamide |
| 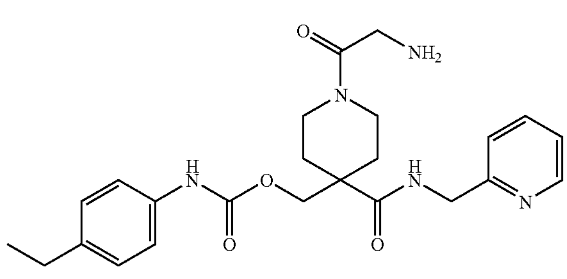 | ({1-(2-aminoacetyl)-4-[N-(2-pyridylmethyl)carbamoyl](4-piperidyl)}methoxy)-N-(4-ethylphenyl)carboxamide |

| Structure | Chemical Name |
|---|---|
| 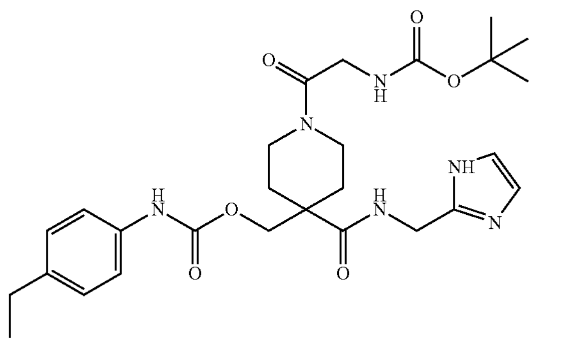 | [(1-{2-[(tert-butoxy)carbonylamino]acetyl}-4-[N-(imidazol-2-ylmethyl)carbamoyl](4-piperidyl))methoxy]-N-(4-ethylphenyl)carboxamide |
| 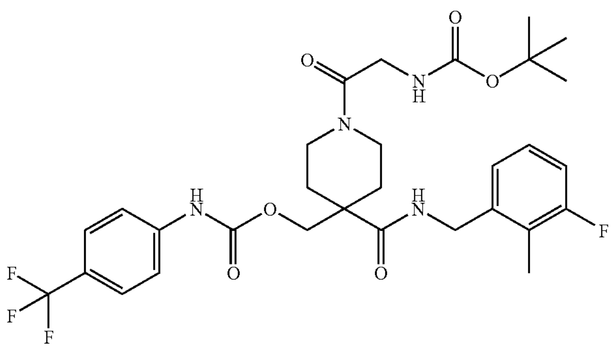 | [(1-{2-[(tert-butoxy)carbonylamino]acetyl}-4-{N-[(3-fluoro-2-methylphenyl)methyl]carbamoyl}(4-piperidyl))methoxy]-N-[4-(trifluoromethyl)phenyl]carboxamide |
| 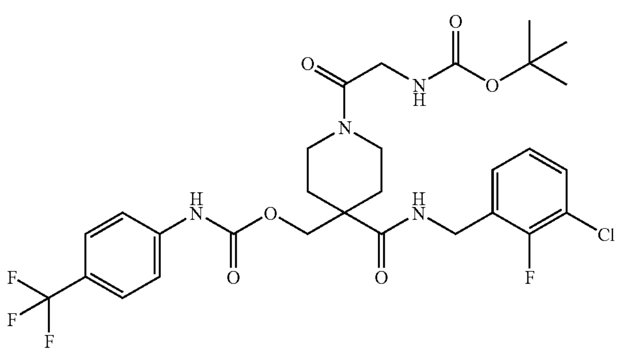 | [(1-(2-[(tert-butoxy)carbonylamino]acetyl}-4-{N-[(3-chloro-2-fluorophenyl)methyl]carbamoyl}(4-piperidyl))methoxy]-N-[4-(trifluoromethyl)phenyl]carboxamide |
| 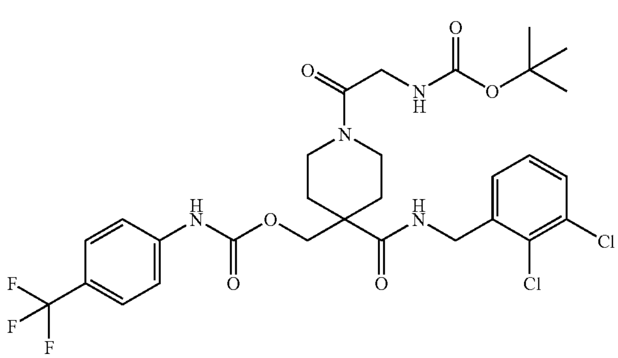 | [(4-(N-[(2,3-dichlorophenyl)methyl]carbamoyl}-1-(2-[(tert-butoxy)carbonylamino]acetyl}(4-piperidyl))methoxy]-N-[4-(trifluoromethyl)phenyl]carboxamide |

| Structure | Chemical Name |
|---|---|
| 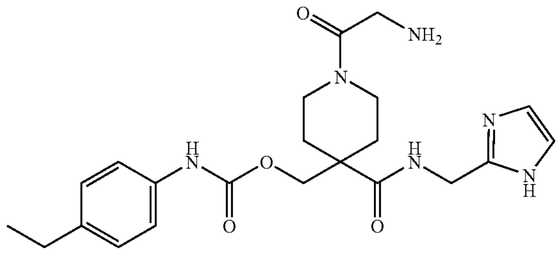 | ({1-(2-aminoacetyl)-4-[N-(imidazol-2-ylmethyl)carbamoyl](4-piperidyl)}methoxy)-N-(4-ethylphenyl)carboxamide |
| 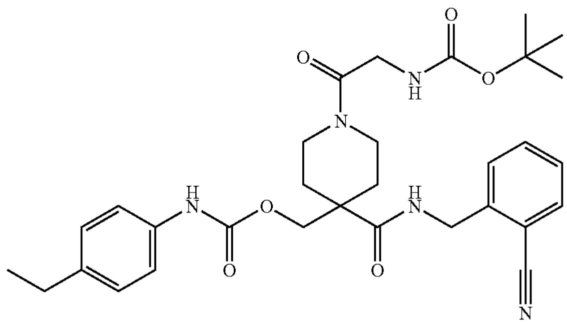 | (1-{2-[(tert-butoxy)carbonyl-amino]acetyl}-4-{[N-(4-ethylphenyl)carbamoyloxy]methyl}(4-piperidyl))-N-[(2-cyanophenyl)methyl]carboxamide |
| | [(1-(2-aminoacetyl)-4-{N-[(3-fluoro-2-methylphenyl)methyl]carbamoyl}(4-piperidyl)methoxy]-N-[4-(trifluoromethyl)phenyl]carboxamide |
| 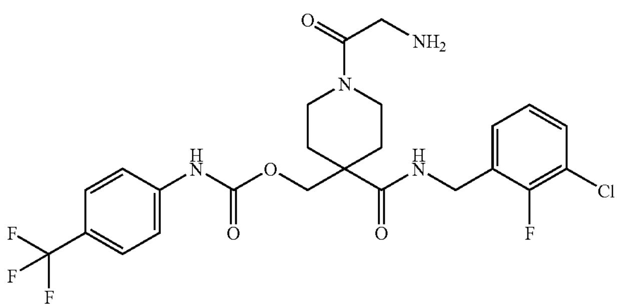 | [(1-(2-aminoacetyl)-4-(N-[(3-fluoro-2-fluorophenyl)methyl]carbamoyl}(4-piperidyl))methoxy]-N-[4-(trifluoromethyl)phenyl]carboxamide |
| 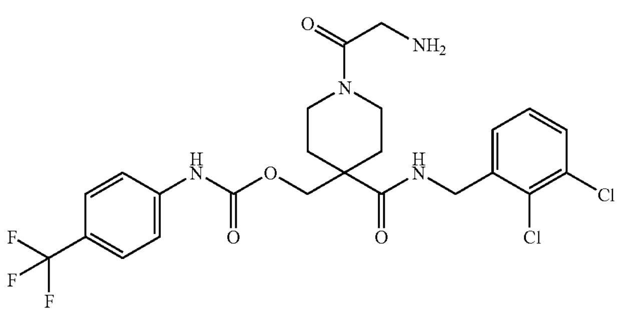 | [(1-(2-aminoacetyl)-4-{N-[(2,3-dichlorophenyl)methyl]carbamoyl}(4-piperidyl))methoxy]-N-[4-(trifluoromethyl)phenyl]carboxamide |

| Structure | Chemical Name |
|---|---|
| | [(1-{2-[(tert-butoxy)carbonylamino]acetyl}-4-{N-[(3-chloro-2-methylphenyl)methyl]carbamoyl}(4-piperidyl)))methoxy]-N-[4-(trifluoromethyl)phenyl]carboxamide |
| 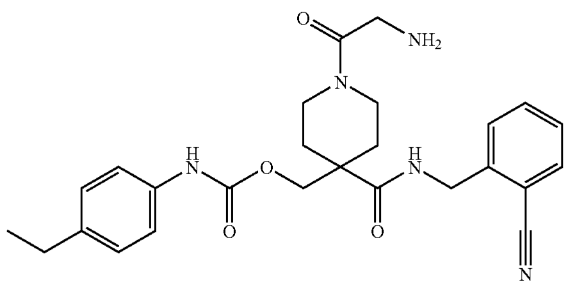 | [(1-(2-aminoacetyl)-4-{N-[(2,3-ethylphenyl)carbamoyloxy]methyl}(4-piperidyl))-N-[(2-cyanophenyl)methyl]carboxamide |
| 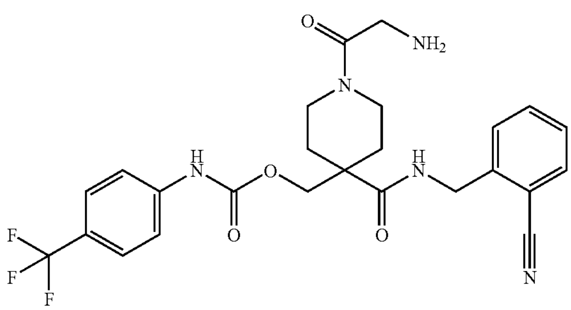 | [1-(2-aminoacetyl)-4-({N-[4-(trifluoromethyl)phenyl]carbamoyloxy}methyl)(4-piperidyl)]-N-[(2-cyanophenyl)methyl]carboxamide |
| | [(1-(2-aminoacetyl)-4-{N-[(3-chloro-2-methylphenyl)methyl]carbamoyl}(4-piperidyl)))methoxy]-N-[4-(trifluoromethyl)phenyl]carboxamide |
| 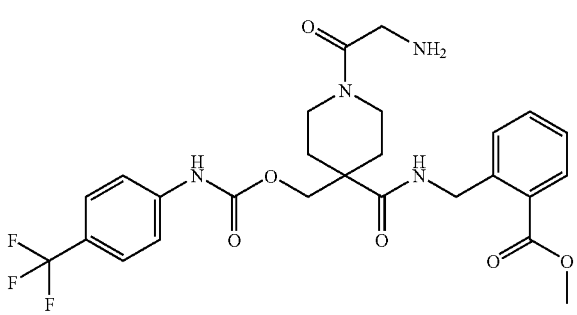 | methyl 2-({[1-(2-aminoacetyl)-4-({N-[4-(trifluoromethyl)phenyl]carbamoyloxy}methyl)-4-piperidyl]carbonylamino}methyl)benzoate |

-continued

| Structure | Chemical Name |
|---|---|
| 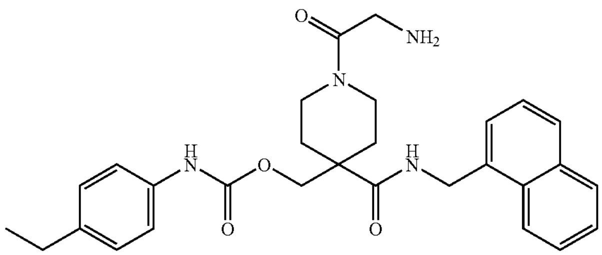 | ({1-(2-aminoacetyl)-4-[N-(4-(naphthylmethyl)carbamoyl](4-piperidyl)}methoxy)-N-(4-ethylphenyl)carboxamide |
| 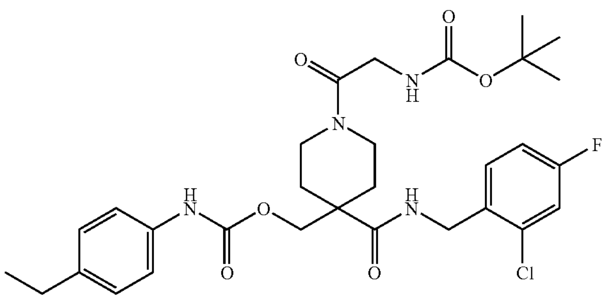 | [(1-{2-[(tert-butoxy)carbonylamino]acetyl}-4-{N-[(2-chloro-4-fluorophenyl)methyl]carbamoyl}(4-piperidyl))methoxy]-N-(4-ethylphenyl)carboxamide |
| 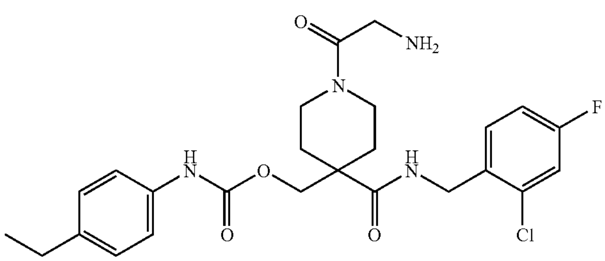 | [(1-(2-aminoacetyl)-4-{N-[(2-chloro-4-fluorophenyl)methyl]carbamoyl}(4-piperidyl))methoxy]-N-(4-ethylphenyl)carboxamide |
| 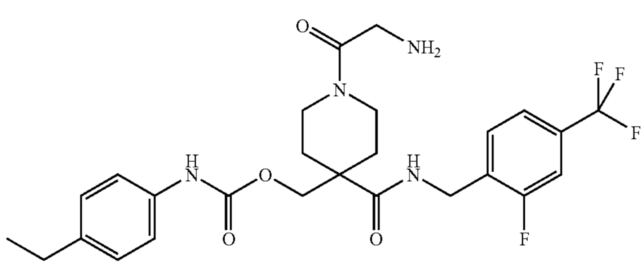 | {[1-(2-aminoacetyl)-4-(N-([2-fluoro-4-(trifluoromethyl)phenyl]methyl}carbamoyl)(4-piperidyl)]methoxy}-N-(4-ethylphenyl)carboxamide |
| 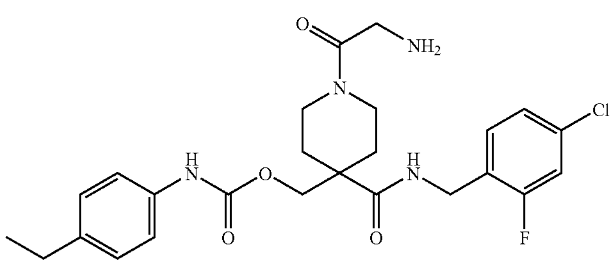 | [(1-(2-aminoacetyl)-4-{N-[(4-chloro-2-fluorophenyl)methyl]carbamoyl}(4-piperidyl))methoxy]-N-(4-ethylphenyl)carboxamide |
| 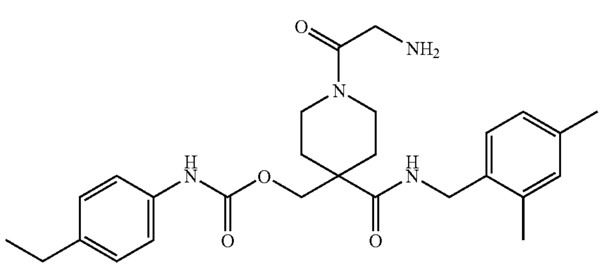 | [(1-(2-aminoacetyl)-4-{N-[(2,4-dimethylphenyl)methyl]carbamoyl}(4-piperidyl))methoxy]-N-(4-ethylphenyl)carboxamide |

-continued

| Structure | Chemical Name |
|---|---|
| 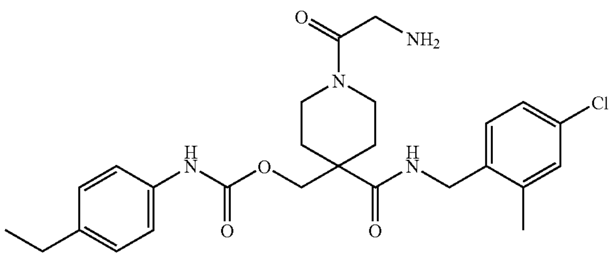 | [(1-(2-aminoacetyl)-4-{N-[(4-chloro-2-methylphenyl)methyl]carbamoyl}(4-piperidyl))methoxy]-N-(4-ethylphenyl)carboxamide |
| 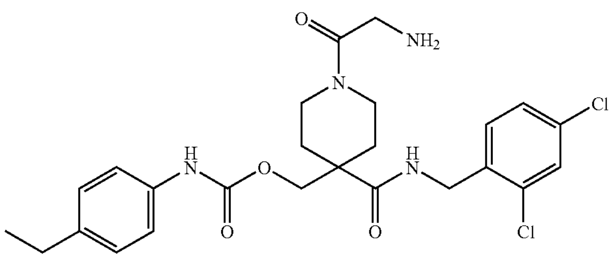 | [(1-(2-aminoacetyl)-4-{N-[(2,4-dichlorophenyl)methyl]carbamoyl}(4-piperidyl))methoxy]-N-(4-ethylphenyl)carboxamide |
| 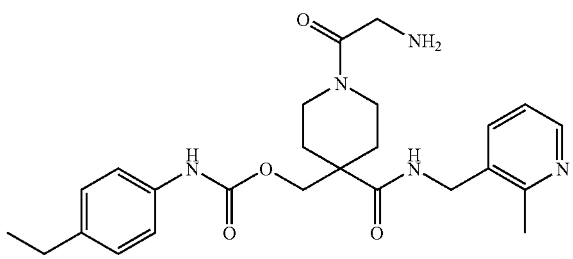 | [(1-(2-aminoacetyl)-4-{N-[(2-methyl(3-pyridyl))methyl]carbamoyl}(4-piperidyl))methoxy]-N-(4-ethylphenyl)carboxamide |
| 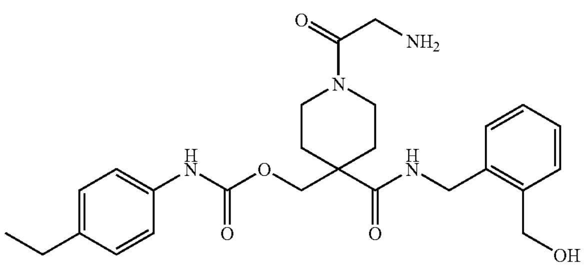 | (1-(2-aminoacetyl)-4-{[N-(4-ethylphenyl)carbamoyl-oxy]methyl}(4-piperidyl))-N-{[2-(hydroxymethyl)phenyl]-methyl)carboxamide |
| 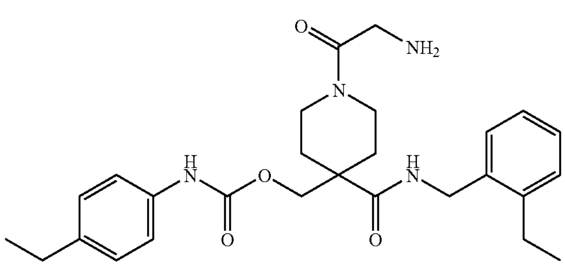 | [(1-(2-aminoacetyl)-4-{N-[(2-ethylphenyl)methyl]carbamoyl}(4-piperidyl))methoxy]-N-(4-ethylphenyl)carboxamide |
| 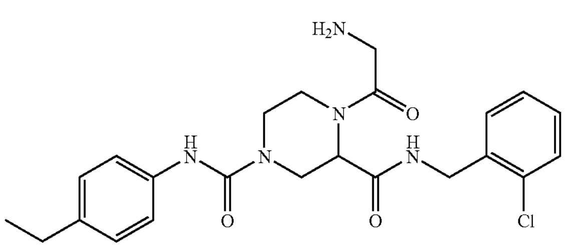 | (4-(2-aminoacetyl)-3-{N-[(2-chlorophenyl)methyl]carbamoyl}piperazinyl)-N-(4-ethylphenyl)carboxamide |

| Structure | Chemical Name |
|---|---|
| 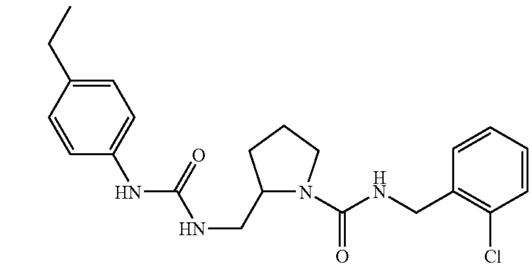 | N-[(2-chlorophenyl)methyl][2-({[(4-ethylphenyl)amino]carbonyl-amino}methyl)pyrrolidinyl]carboxamide |
| 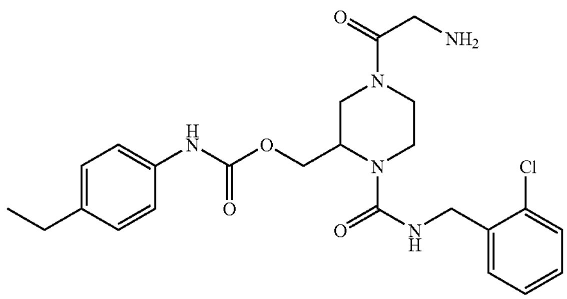 | (4-(2-aminoacetyl)-2-{[N-(4-ethylphenyl)carbamoyl-oxy]methyl}piperazinyl)-N-[(2-chlorophenyl)methyl]carboxamide |
| 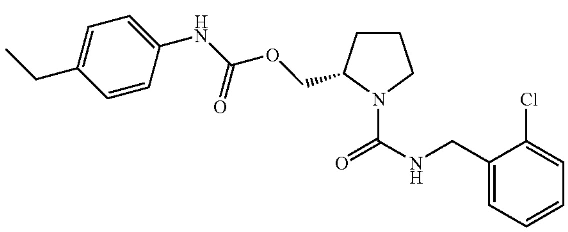 | ((2S)-2-{[N-(4-ethylphenyl)carbamoyl-oxy]methyl}pyrrolidinyl)-N-[(2-chlorophenyl)methyl]carboxamide |
| 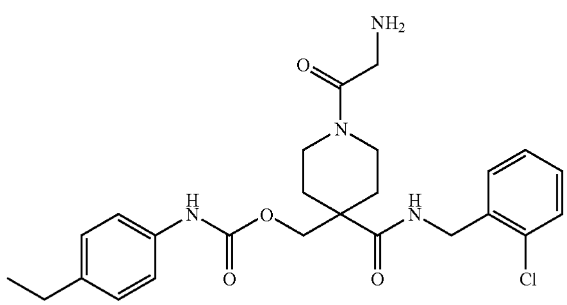 | N-[(1-(2-aminoacetyl)-4-{N-[(2-chlorophenyl)methyl]carbamoyl}(4-piperidyl))methyl]-2-(4-ethylphenyl)acetamide |
| 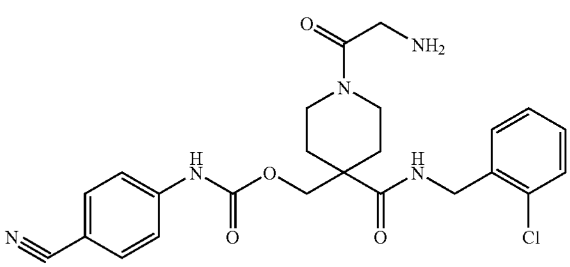 | (1-(2-aminoacetyl)-4-{[N-(4-cyanophenyl)carbamoyloxy]methyl}(4-piperidyl))-N-[(2-chlorophenyl)methyl]carboxamide |

| Structure | Chemical Name |
|---|---|
| 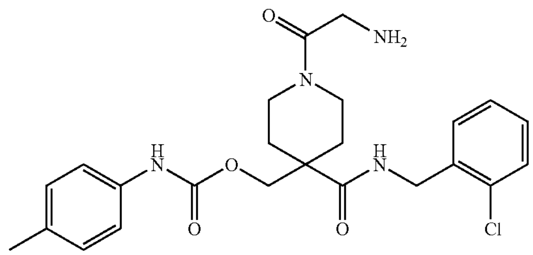 | (1-(2-aminoacetyl)-4-{[N-(4-methylphenyl)carbamoyloxy]methyl}(4-piperidyl))-N-[(2-chlorophenyl)methyl]carboxamide |
| 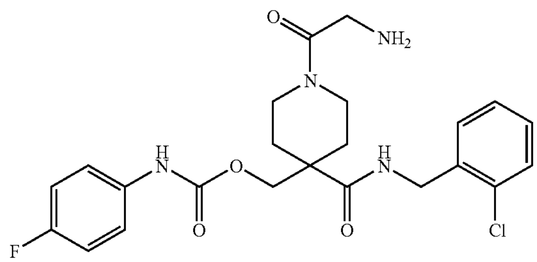 | (1-(2-aminoacetyl)-4-{[N-(4-fluorophenyl)carbamoyloxy]methyl}(4-piperidyl))-N-[(2-chlorophenyl)methyl]carboxamide |
| 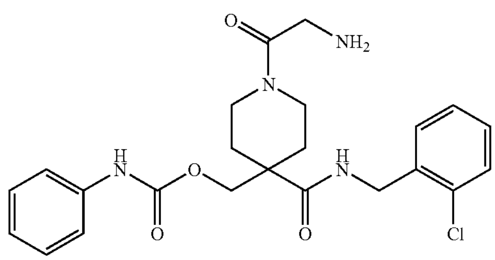 | {1-(2-aminoacetyl)-4-[(N-phenylcarbamoyloxy)methyl](4-piperidyl)}-N-[(2-chlorophenyl)methyl]carboxamide |
| 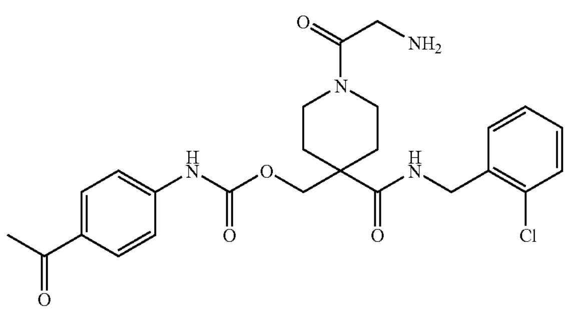 | (4-{[N-(4-acetylphenyl)carbamoyloxy]methyl}-1-(2-aminoacetyl)(4-piperidyl))-N-[(2-chlorophenyl)methyl]carboxamide |
| 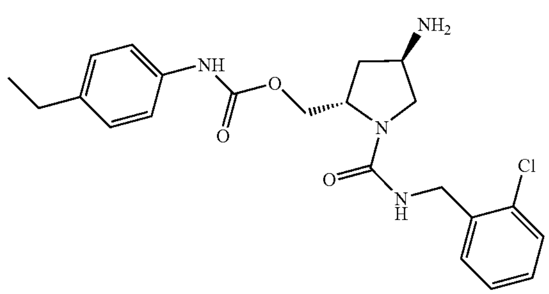 | ((5S,3R)-3-amino-5-{[N-(4-ethylphenyl)carbamoyloxy]methyl}pyrrolidinyl)-N-[(2-chlorophenyl)methyl]carboxamide |

| Structure | Chemical Name |
|---|---|
| 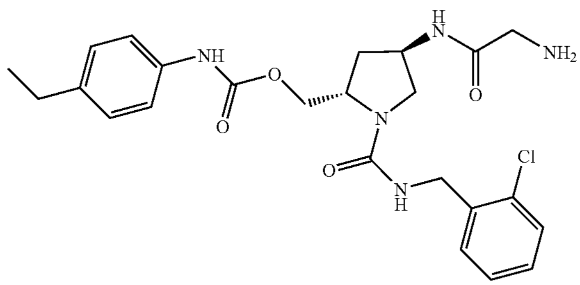 | N-((5S,3R)-1-{N-[(2-chlorophenyl)methyl]carbamoyl}-5-{[N-(4-ethylphenyl)carbamoyloxy]methyl}pyrrolidin-3-yl)-2-aminoacetamide |
| 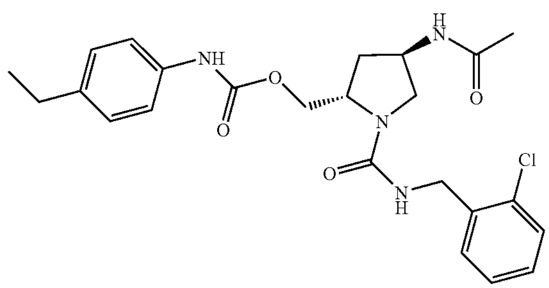 | N-((5S,3R)-1-{N-[(2-chlorophenyl)methyl]carbamoyl}-5-{[N-(4-ethylphenyl)carbamoyloxy]methyl}pyrrolidin-3-yl)acetamide |
| | {[(2-chlorophenyl)methyl]amino}-N-(2-[N-(4-ethylphenyl)carbamoyloxy]ethyl}-N-methylcarboxamide |
| 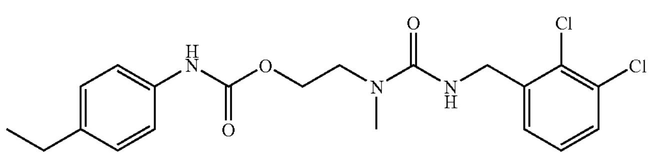 | {[(2,3-dichlorophenyl)methyl]amino}-N-(2-[N-(4-ethylphenyl)carbamoyloxy]ethyl}-N-methylcarboxamide |
| 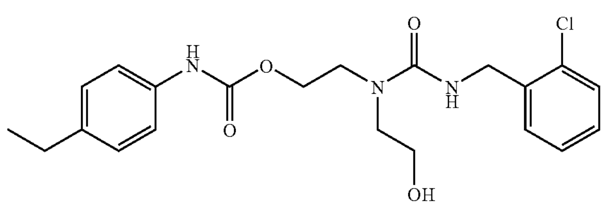 | [2-({[(2-chlorophenyl)methyl]amino}-N-(2-hydroxyethyl)carbonylamino)ethoxy]-N-(4-ethylphenyl)carboxamide |
| 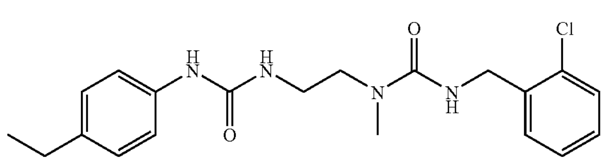 | N-[2-({[(2-chlorophenyl)methyl]amino}-N-methylcarbonylamino)ethyl][(4-ethylphenyl)amino]carboxamide |
| 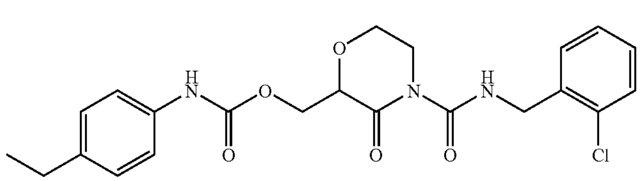 | [(4-{N-[(2-chlorophenyl)methyl]carbamoyl}morpholin-2-yl)methoxy]-N-(4-ethylphenyl)carboxamide |

| Structure | Chemical Name |
|---|---|
| 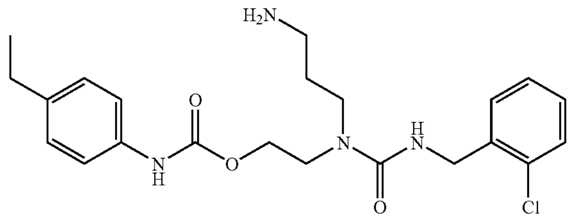 | N-(3-aminopropyl){[(2-chlorophenyl)methyl]amino}-N-{2-[N-(4-ethylphenyl)carbamoyloxy]ethyl}carboxamide |
| 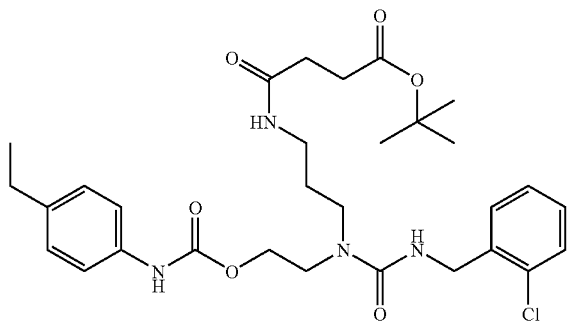 | 2-[(tert-butoxy)carbonylamino]-N-[3-({[(2-chlorophenyl)methyl]amino}-N-{2-[N-(4-ethylphenyl)carbamoyloxy]ethyl}carbonylamino)propyl]acetamide |
| 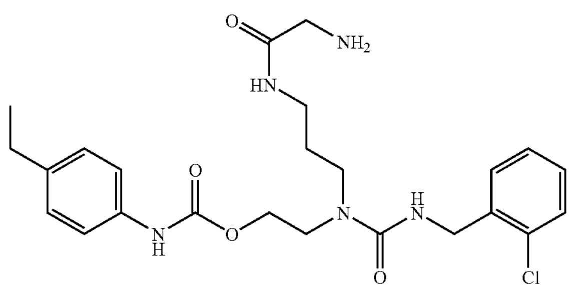 | 2-amino-N-[3-({[(2-chlorophenyl)methyl]amino]-N-{2-[N-(4-ethylphenyl)carbamoyloxy]ethyl}carbonylamino)propyl]acetamide |
| 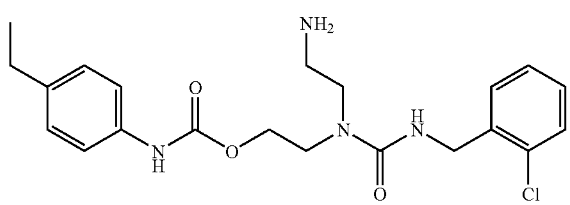 | N-(2-aminoethyl){[(2-chlorophenyl)methyl]amino}-N-{2-[N-(4-ethylphenyl)carbamoyloxy]ethyl}carboxamide |
| 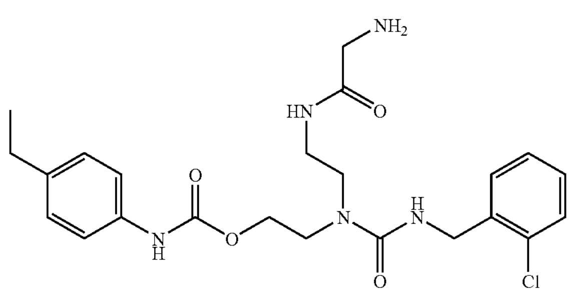 | 2-amino-N-[2-({[(2-chlorophenyl)methyl]amino}-N-{2-[N-(4-ethylphenyl)carbamoyloxy]ethyl}carbonylamino)ethyl]acetamide |
| 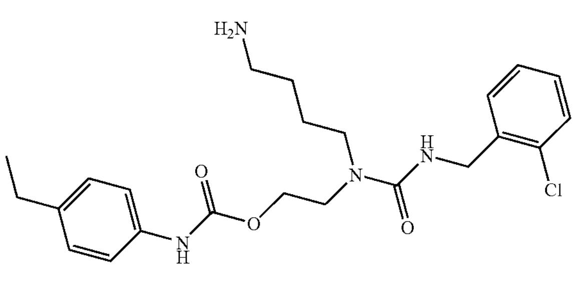 | [2-(N-(4-aminobutyl){[(2-chlorophenyl)methyl]amino}carbonylamino)-ethoxy]-N-(4-ethylphenyl)carboxamide |

| Structure | Chemical Name |
|---|---|
| 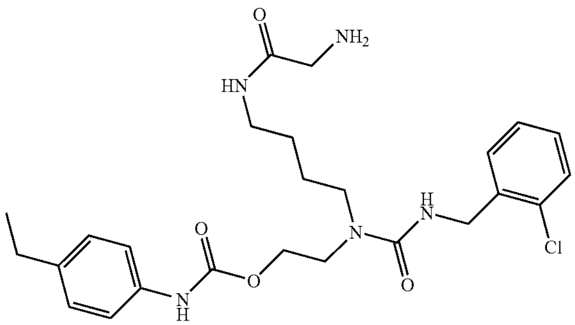 | 2-amino-N-[4-({[(2-chlorophenyl)methyl]amino}-N-{2-[N-(4-ethylphenyl)carbamoyloxy]ethyl}carbonylamino)butyl]acetamide |
| 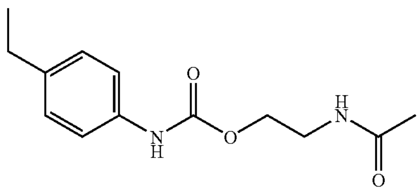 | N-{2-[N-(4-ethylphenyl)carbamoyloxy]ethyl}acetamide |
| 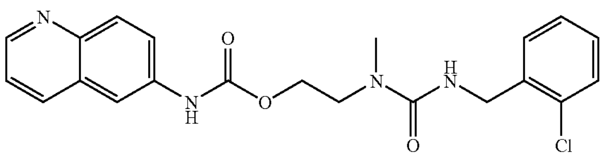 | {[(2-chlorophenyl)methyl]amino}-N-methyl-N-[2-(N-(6-quinolyl)carbamoyloxy)ethyl]carboxamide |
| | N-(5-aminopentyl){[(2-chlorophenyl)methyl]amino}-N-{2-[N-(4-ethylphenyl)carbamoyloxy]ethyl}carboxamlde |
| 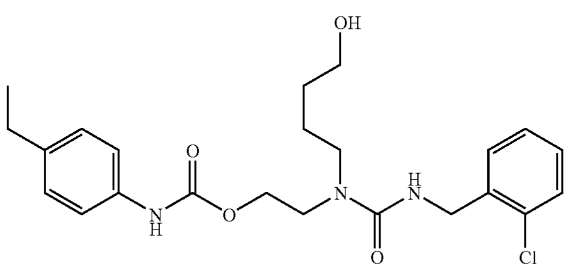 | {[(2-chlorophenyl)methyl]amino}-N-(2-[N-(4-ethylphenyl)carbamoyloxy]ethyl}-N-(4-hydroxybutyl)carboxamide |
| 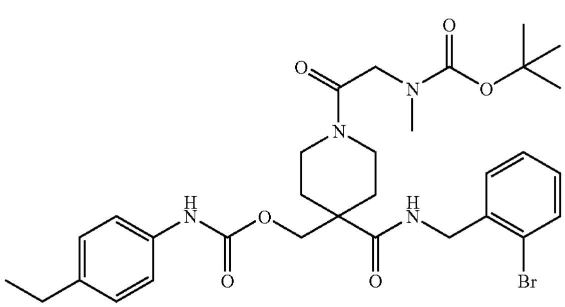 | (tert-butoxy)-N-[2-(4-{N-[(2-bromophenyl)methyl]carbamoyl}-4-{[N-(4-ethylphenyl)carbamoyloxy]methyl}piperidyl)-2-oxoethyl]-N-methylcarboxamide |

| Structure | Chemical Name |
|---|---|
| 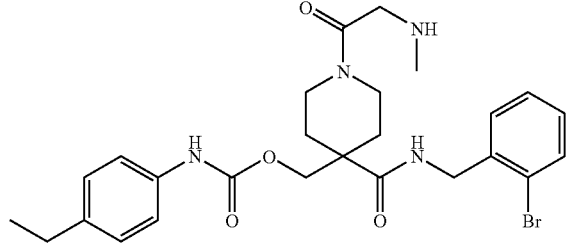 | [(4-{N-[(2-bromophenyl)methyl]carbamoyl}-1-[2-(methylamino)acetyl](4-piperidyl))methoxy]-N-(4-ethylphenyl)carboxamide |
| 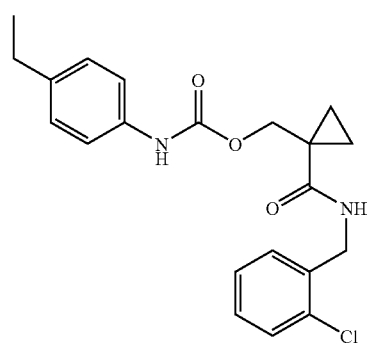 | N-[(2-chlorophenyl)methyl]({[N-(4-ethylphenyl)carbamoyloxy]methyl}cyclopropyl)-carboxamide |
| 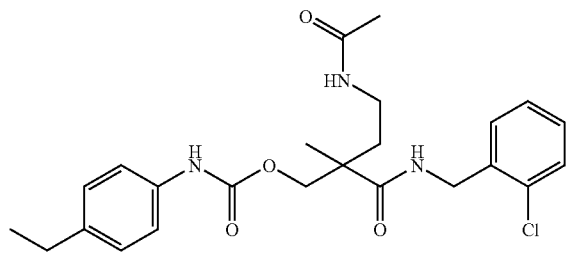 | 4-(acetylamino)-N-[(2-chlorophenyl)methyl]-2-{[N-(4-ethylphenyl)carbamoyloxy]methyl}-2-methylbutanamide |
| 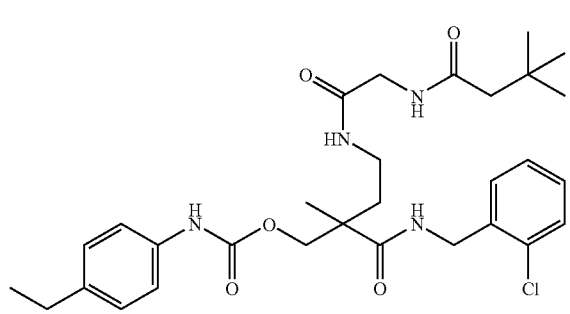 | 4-{2-[(tert-butoxy)carbonylamino]acetylamino}-N-[(2-chlorophenyl)methyl]-2-{[N-(4-ethylphenyl)carbamoyloxy]methyl}-2-methylbutanamide |
| 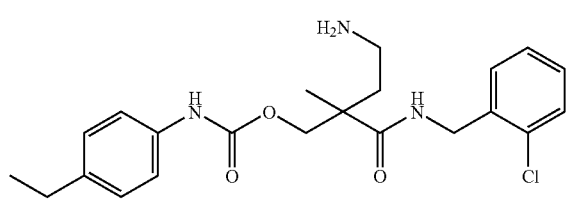 | 4-amino-N-[(2-chlorophenyl)methyl]-2-{[N-(4-ethylphenyl)carbamoyloxy]methyl}-2-methylbutanamide |

| Structure | Chemical Name |
|---|---|
| 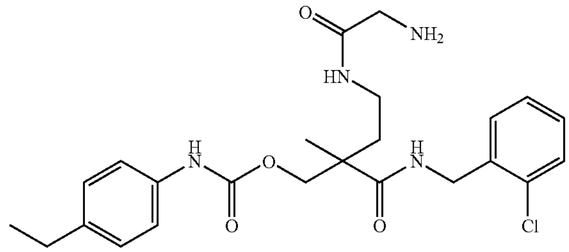 | 4-(2-aminoacetylamino)-N-[(2-chlorophenyl)methyl]-2-{[N-(4-ethylphenyl)carbamoyloxy]methyl}-2-methylbutanamide |
| 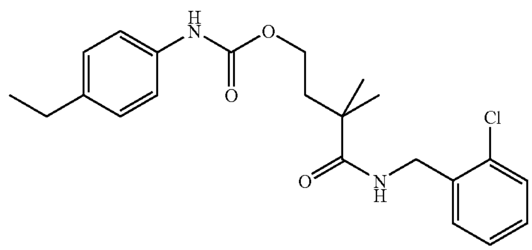 | N-[(2-chlorophenyl)methyl]-4-[N-(4-ethylphenyl)carbamoyloxy]-2,2-dimethylbutanamide |
| 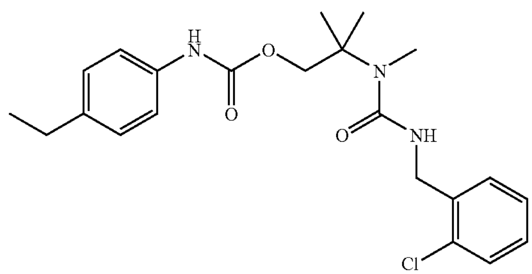 | {[(2-chlorophenyl)methyl]amino}-N-{2-[N-(4-ethylphenyl)carbamoyloxy]-tert-butyl}-N-methylcarboxamide |
| 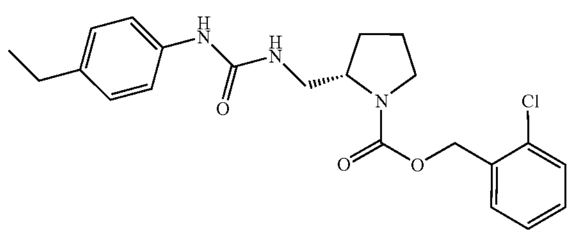 | (2-chlorophenyl)methyl (2S)-2-({[(4-ethylphenyl)amino]carbonylamino}methyl)-pyrrolidinecarboxylate |

The compounds described herein can be named and numbered (e.g. using NamExpert™ available from Cheminnovation Software, Inc. or the struct <=> name feature of ChemDraw Ultra version 10.0 from CambridgeSoft Corporation) as described below. For example, the compound:

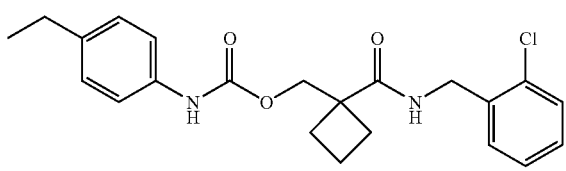

i.e. the compound according to Formula I where $R^{10}$ is ethyl, $W^2$ is $NR^{13}$, $R^{13}$ is hydrogen, $W^1$ is O, $R^5$ is hydrogen, $R^6$ is hydrogen, $W^3$ is $CR^1R^2$, $R^1$ and $R^2$ form a cyclobutyl group with the carbon atom to which they are bound, $R^8$ is hydrogen, $R^3$ is hydrogen, $R^4$ is hydrogen, and $R^7$ is chloro, can be named [({N-[(2-chlorophenyl)methyl]carbamoyl} cyclobutyl)methoxy]-N-(4-ethylphenyl)carboxamide or (1-(2-chlorobenzylcarbamoyl)cyclobutyl)methyl 4-ethylphenylcarbamate. Also, a chemical name generated for a structure drawn in a certain software environment may or may not give the same structure when that name is converted into a structure in a different software environment.

Many of the optionally substituted starting compounds and other reactants are commercially available, e.g. from Aldrich Chemical Company (Milwaukee, Wis.) or can be readily prepared by those skilled in the art using commonly employed synthetic methodology.

The chemical entities described herein can be synthesized utilizing techniques well known in the art from commercially available starting materials and reagents. For example, the chemical entities described herein can be prepared as illustrated below with reference to the examples and reaction schemes.

Reaction Scheme 1

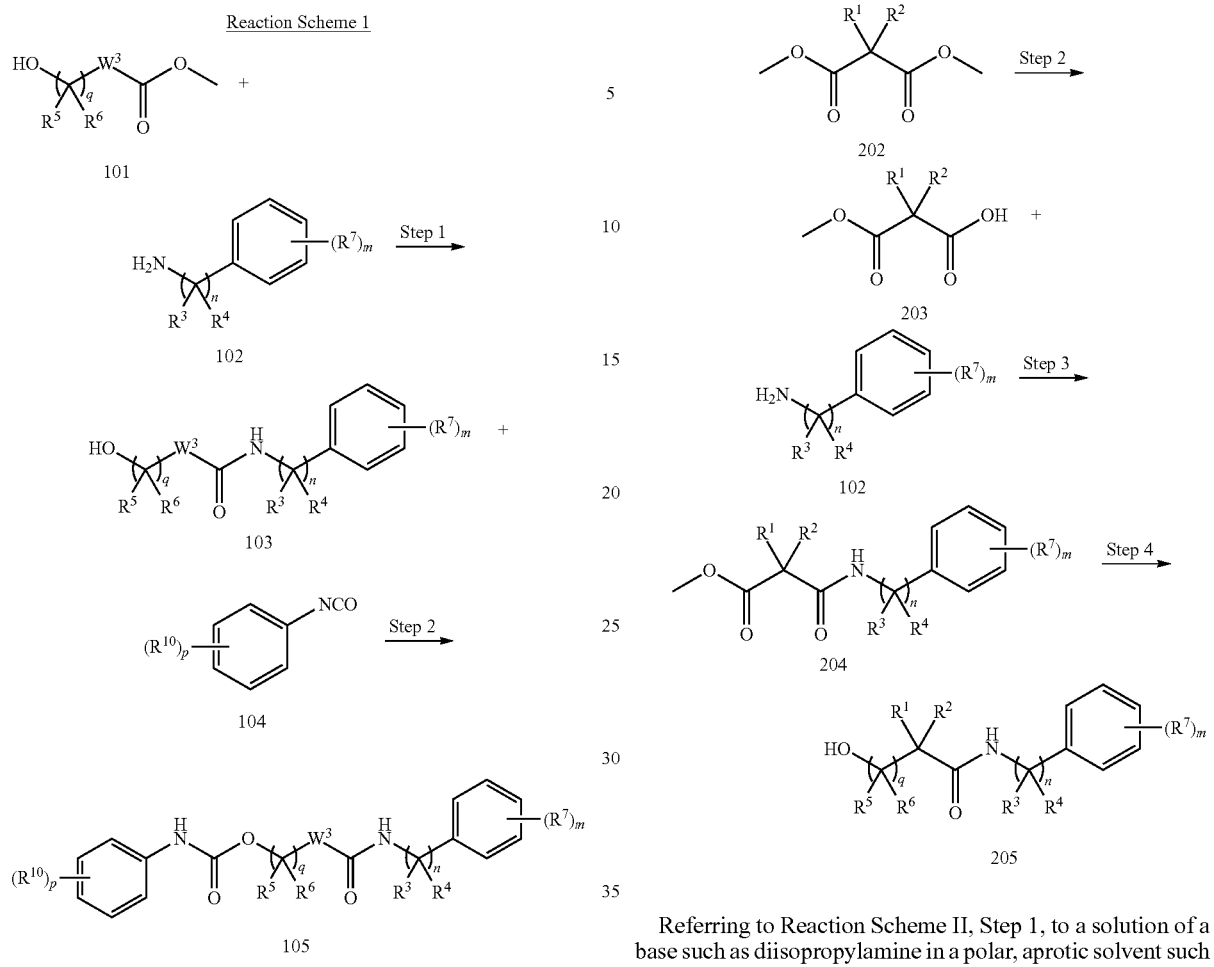

Referring to Reaction Scheme I, Step 1, to a solution of a compound of Formula 101 and an excess (such as about 1.2 equivalents) of a compound of Formula 102 in a non-polar solvent such as toluene is added an excess (such as about 1.5 equivalents) of trialkylaluminum (for example, 2M trimethylaluminum in hexanes). The reaction mixture is stirred at about rt to 150° C. for about 1 h to 24 h. The product, a compound of Formula 103, is isolated and optionally purified.

Referring to Reaction Scheme I, Step 2, to a solution of a compound of Formula 103 in a non-polar solvent such as dichloromethane is added a catalytic amount of 4-dimethylaminopyridine and an excess (such as about 1.5 equivalents) of a compound of Formula 104. The reaction mixture is stirred for about 1 h to 24 h. The product, a compound of Formula 105, is isolated and optionally purified.

Reaction Scheme II

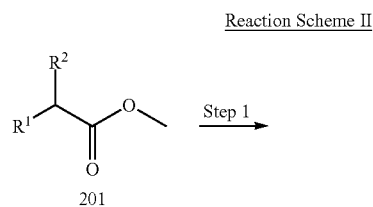

Referring to Reaction Scheme II, Step 1, to a solution of a base such as diisopropylamine in a polar, aprotic solvent such as tetrahydrofuran at about −78° C. to rt is added an excess (such as about 1.2 equivalents) of an organometallic reagent such as n-butyllithium (for example, 2M n-butyllithium in hexane). The reaction mixture is stirred for about 1 h to 24 h. A solution of a compound of Formula 201 in a polar, aprotic solvent such as tetrahydrofuran is then added dropwise at about −78° C. to rt. The reaction mixture is stirred for about 1 h to 24 h and then an excess (such as about 1.1 equivalents) of methyl chloroformate is added. The product, a compound of Formula of 202, is isolated and optionally purified.

Referring to Reaction Scheme II, Step 2, to a solution of a compound of Formula 202 in a polar solvent system such as a 1:1 mixture of tetrahydrofuran and methanol is added an aqueous solution of an excess (such as about 1.1 equivalents) of a base such as lithium hydroxide (for example, 2N lithium hydroxide in water). The reaction mixture is stirred at about rt to 150° C. for about 1 h to 24 h. The product, a compound of Formula 203, is isolated and optionally purified.

Referring to Reaction Scheme II, Step 3, to a solution of a compound of Formula 203 in a polar, aprotic solvent such as dimethylformamide is added an excess (such as about 1.2 equivalents) of a peptide coupling reagent such as N,N,N′,N′-tetramethyl-O-(7-azabenzotriazol-1-yl)uronium hexafluorophosphate, an excess (such as about 1.2 equivalents) of a compound of Formula 102, and about 0.1 equivalents of a base such as diisopropylethylamine. The reaction mixture is stirred for about 1 h to 24 h. The product, a compound of Formula 204, is isolated and optionally purified.

Referring to Reaction Scheme II, Step 4, to a solution of a compound of Formula 204 in a polar solvent system such as a 1:1 mixture of tetrahydrofuran and methanol is added an excess of a reducing agent such as lithium borohydride. The reaction mixture is stirred for about 1 h to 24 h. The product, a compound of Formula 205, is isolated and optionally purified.

Reaction Scheme III

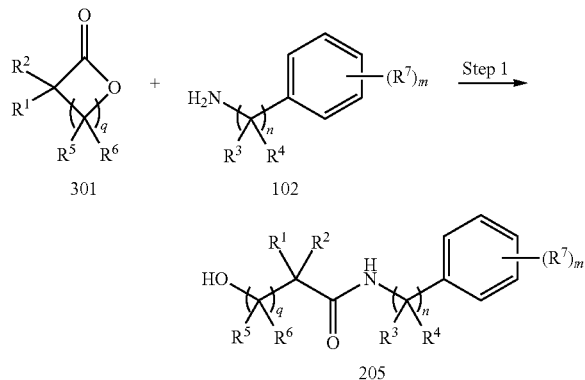

Referring to Reaction Scheme III, Step 1, to a solution of a compound of Formula 301 in a polar, aprotic solvent such as tetrahydrofuran is added an excess (such as about 1.1 equivalents) of a compound of Formula 102 and about 0.5 equivalents of trialkylaluminum (for example, 2M trimethylaluminum in toluene). The reaction mixture is stirred for about 1 day to 7 days. The product, a compound of Formula 205, is isolated and optionally purified.

Reaction Scheme IV

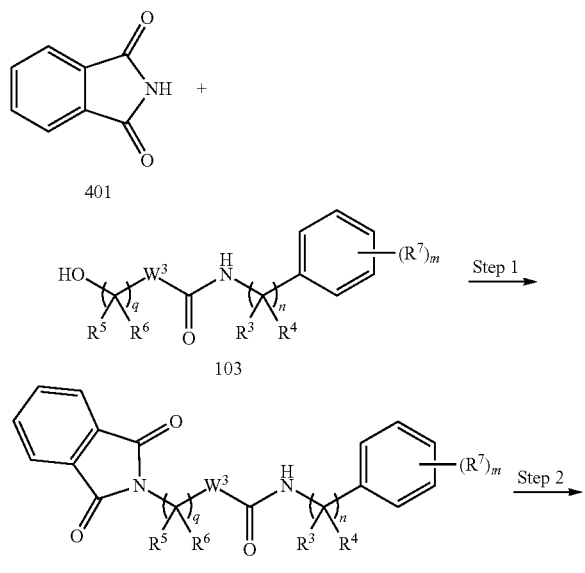

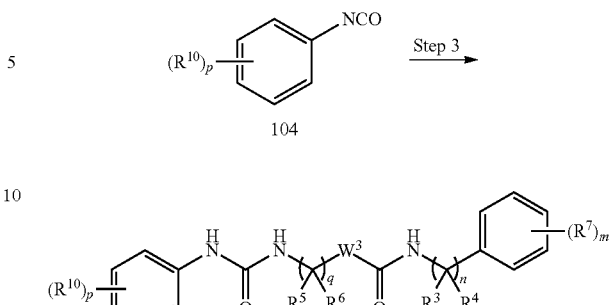

Referring to Reaction Scheme IV, Step 1, to a solution of a compound of Formula 103 in a polar, aprotic solvent such as tetrahydrofuran is added an excess (such as about 1.5 equivalents) of phthalimide (Formula 401) and an excess (such as about 1.5 equivalents) of a phosphine such as triphenylphosphine. An excess (such as about 1.5 equivalents) of a dialkyl azodicarboxylate such as diisopropyl azodicarboxylate is then added dropwise into the reaction mixture. The resulting mixture is stirred from 1 h to 48 h. The product, a compound of Formula 402, is isolated and optionally purified.

Referring to Reaction Scheme IV, Step 2, to a solution of a compound of Formula 402 in a polar, protic solvent such as methanol is added an excess of hydrazine. The reaction mixture is stirred from 1 h to 48 h. The product, a compound of Formula 403, is isolated and optionally purified.

Referring to Reaction Scheme IV, Step 3, to a solution of a compound of Formula 403 in a non-polar solvent such as dichloromethane is added an excess (such as about 2.0 equivalents of) a base such as diisopropylethylamine and an excess (such as about 1.5 equivalents) of a compound of Formula 104. The reaction mixture is stirred for about 0.1 h to 24 h. The product, a compound of Formula 404, is isolated and optionally purified.

Reaction Scheme V

-continued

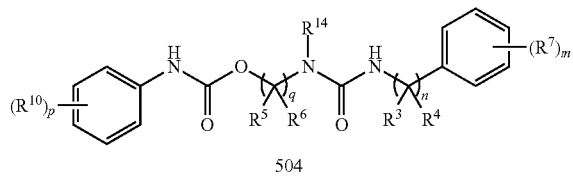

504

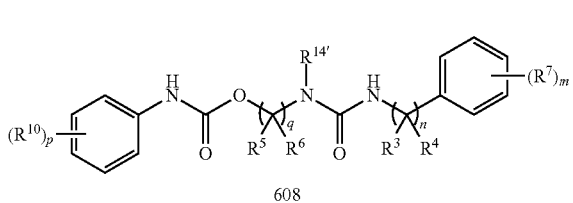

608

Referring to Reaction Scheme V, Step 1, to a solution of an excess (such as about 1.1 equivalents) of a compound of Formula 501 in a polar, aprotic solvent such as tetrahydrofuran is added a compound of Formula 502. The reaction mixture is stirred for about 1 h to 24 h. The product, a compound of Formula 503, is isolated and optionally purified.

Referring to Reaction Scheme V, Step 2, to a solution of a compound of Formula 503 in a polar, aprotic solvent such as tetrahydrofuran is added an excess (such as about 1.5 equivalents) of a compound of Formula 104. The reaction mixture is stirred for about 1 h to 24 h. The product, a compound of Formula 504, is isolated and optionally purified.

Reaction Scheme VI

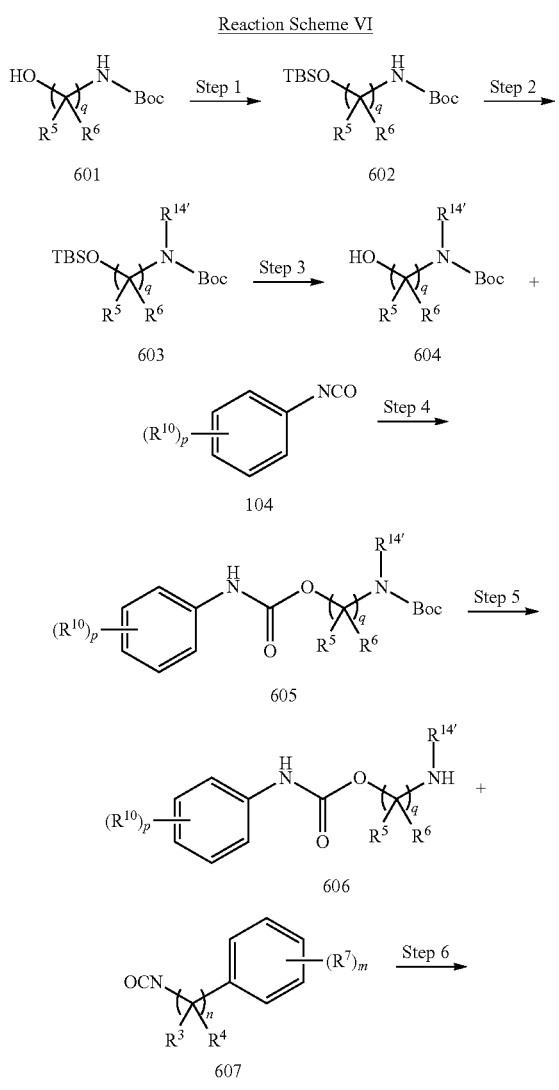

Referring to Reaction Scheme VI, Step 1, to a solution of a compound of Formula 601 in a non-polar solvent such as dichloromethane is added an excess (such as about 1.1 equivalents) of a silyl protecting group reagent such as tert-butyldimethylsilyl chloride and an excess (such as about 1.5 equivalents) of a base such as diisopropylethylamine. The reaction is stirred for about 1 h to 24 h. The product, a compound of Formula 602, is isolated and optionally purified.

Referring to Reaction Scheme VI, Step 2, to a solution of an excess (such as about 1.2 equivalents) of a base such as sodium hydride (for example, 60% sodium hydride in mineral oil) in a polar, aprotic solvent such as dimethylformamide is added a compound of Formula 602. The reaction mixture is stirred for about 0.1 h to 24 h and then an excess (such as about 1.2 equivalents) of $R^{14i}$, —X, wherein $R^{14i}$, is optionally substituted alkyl and X is halo, is added. The reaction mixture is then stirred for about an 1 h to 24 h more. The product, a compound of Formula 603, is isolated and optionally purified.

Referring to Reaction Scheme VI, Step 3, to a solution of a compound of Formula 603 in a polar, aprotic solvent such as tetrahydrofuran is added an excess (such as about 1.5 equivalents) of fluoride-releasing reagent such as tetrabutylammonium fluoride (for example, 1M tetrabutylammonium fluoride in tetrahydrofuran). The reaction mixture is stirred for about 0.1 h to 24 h. The product, a compound of Formula 604, is isolated and optionally purified.

Referring to Reaction Scheme VI, Step 4, to a solution of a compound of Formula 604 in a polar, aprotic solvent such as tetrahydrofuran is added a catalytic amount of 4-dimethylaminopyridine and an excess of equivalents (such as about 1.1 equivalents) of a compound of Formula 104. The reaction mixture is stirred for about 0.1 h to 24 h. The product, a compound of Formula 605, was isolated and optionally purified.

Referring to Reaction Scheme VI, Step 5, to a solution of a compound of Formula 605 in a polar, protic solvent such as methanol is added an excess (such as about 3.0 equivalents) of an acid such as hydrogen chloride (for example, 4M hydrogen chloride in dioxane). The resulting reaction mixture is stirred for about 1 h to 24 h. The product, a compound of Formula 606, is isolated and optionally purified.

Referring to Reaction Scheme VI, Step 5, to a solution of a compound of Formula 606 in a polar, aprotic solvent such as tetrahydrofuran is added about 1 equivalents of a compound of Formula 607 and an excess (such as about 2.5 equivalents) of a base such as diisopropylethylamine. The reaction mixture is stirred for about 1 h to 24 h. The product, a compound of Formula 608, is isolated and optionally purified.

Reaction Scheme VII

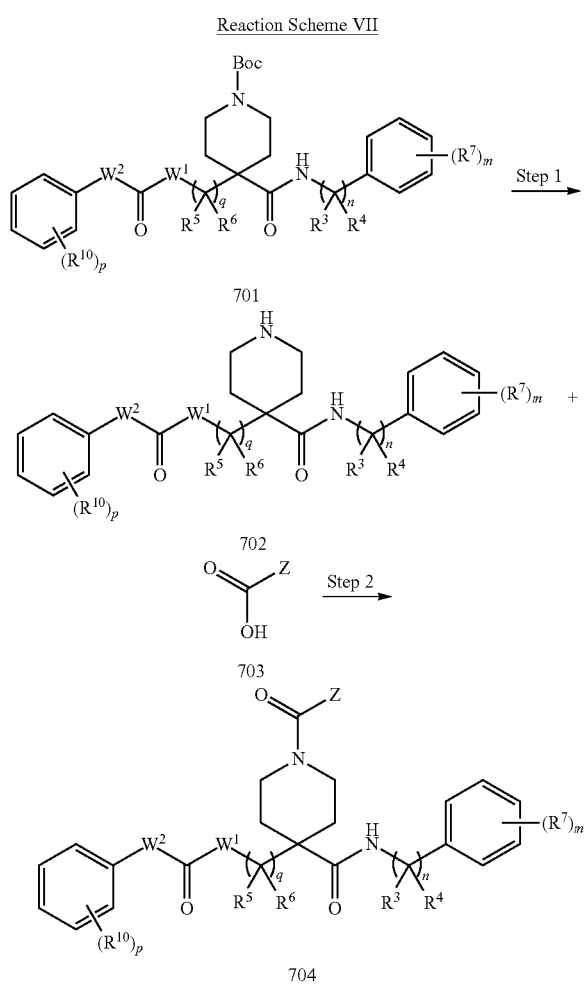

Referring to Reaction Scheme VII, Step 1, to a solution of a compound of Formula 701 in a polar, protic solvent such as methanol is added an excess (such as about 3.0 equivalents) of an acid such as hydrogen chloride (for example, 4M hydrogen chloride in dioxane). The resulting reaction mixture is stirred about 1 h to 48 h. The product, a compound of Formula 702, is isolated and optionally purified.

Referring to Reaction Scheme VII, Step 2, to an excess (such as about 1.2 equivalents) of a compound of Formula 703, wherein Z is optionally substituted alkyl, optionally substituted alkenyl, optionally substituted alkynyl, optionally substituted cycloalkyl, optionally substituted aryl, optionally substituted heteroaryl, and optionally substituted heterocycloalkyl, in a polar, aprotic solvent such as dimethylformamide is added an excess (such as about 1.2 equivalents) of N,N,N',N'-tetramethyl-O-(7-azabenzotriazol-1-yl)uronium hexafluorophosphate, a compound of Formula 702, and an excess (such as about 2.0 equivalents) of a base such as diisopropylethylamine. The reaction mixture is stirred for about 1 h to 24 h. The product, a compound of Formula 704, is isolated and optionally purified.

Unless specified to the contrary, the reactions described herein take place at atmospheric pressure, generally within a temperature range from −10° C. to 200° C. Further, except as employed in the examples or as otherwise specified, reaction times and conditions are intended to be approximate, e.g. taking place at about atmospheric pressure within a temperature range of about −10° C. to about 110° C. over a period of about 1 to about 24 hours; reactions left to run overnight average a period of about 16 hours. For each gram of the limiting reagent, one cc (or mL) of solvent constitutes a volume equivalent.

The terms "solvent," "organic solvent," and "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like]. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R) and (S) isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that when the desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts and/or solvents, or by converting one enantiomer to the other by asymmetric transformation.

The chemical entities described herein may be useful in a variety of applications involving smooth muscle cells and/or non-muscle cells. In certain embodiments, the chemical entities may be used to inhibit smooth muscle myosin. The chemical entities may be useful to bind to, and/or inhibit the activity of, smooth muscle myosin. In certain embodiments, the smooth muscle myosin is human, although the chemical entities may be used to bind to or inhibit the activity of smooth muscle myosin from other organisms, such as other mammals.

In certain embodiments, the chemical entities may be used to inhibit non-muscle myosin. The chemical entities may be useful to bind to, and/or inhibit the activity of, non-muscle myosin. In certain embodiments, the non-muscle myosin is human, although the chemical entities may be used to bind to or inhibit the activity of non-muscle myosin from other organisms, such as other mammals.

The chemical entities described herein may be used to treat disease states associated with smooth muscle and/or non-muscle myosin. Such disease states which can be treated by the chemical entities described herein include, but are not limited to, hypertension, asthma, incontinence, chronic obstructive pulmonary disorder, pre-term labor, and the like. It is appreciated that in some cases the cells may not be in an abnormal state and still require treatment. Thus, in certain embodiments, the chemical entities described herein are applied to cells or administered to individuals afflicted or subject to impending affliction with any one of these disorders or states.

More specifically, the chemical entities described herein may be useful for the treatment of diseases or symptoms related to abnormal increased muscle tone or excessive contraction, or spasm of vascular smooth muscle in systemic, coronary, pulmonary circulation, and micro-circulatory smooth muscle as well, such as systemic hypertension, malignant hypertension, hypertension crisis, symptomatic hypertension, pulmonary hypertension, pulmonary infarction, angina pectoris, cardiac infarction, micro-circulation malfunction under shock condition, and infarction occurred in other location or organs of the human or animal body. Other diseases or symptoms that can be treated with the chemical entities described herein include:

spasm of gastro-intestine smooth muscle, including sphincters, such as gastric spasm, pylorospasm, and spasms of biliary tract, pancreatic tract, urinary tract, caused by inflammation, stimulation of stones or parasites;

spasm of other visceral organs such as uterus, Fallopian tube, and so on;

spasm of trachea-bronchial tree smooth muscle, diaphragm muscle, such as various asthma, breathlessness, dyspnea, diaphragmatic convulsion, and so on; spasm of alimentary canal smooth muscle, including stomach, intestine and colons, biliary and pancreatic duct etc.; and spasm of urinary tract smooth muscle.

In addition, the chemical entities described herein can be used for control, management and manipulation of labor during pregnancy. The method is particularly useful for inhibition of spontaneous preterm labor which would, if untreated, result in premature delivery or abortion and for inhibition of surgically induced labor during transuterine fetal surgery. The method is also useful for inducing the labor in overterm pregnancies where the labor does not occur on term and when it is necessary to induce labor in order to assure the normal delivery.

Further, the chemical entities described herein can be used for the treatment of "airway wall remodeling", which is a condition associated with diseases or conditions characterized by airway wall thickening and air obstruction, which may, for example occur in the small airways of patients with certain respiratory disease conditions, such as, chronic obstructive pulmonary disease (COPD).

Other disease states which can be treated by the chemical entities, compositions and methods provided herein also include, but are not limited to glaucoma and other ocular indications. More specifically, chemical entities described herein may be useful for the treatment of diseases or symptoms related to glaucoma, including increased intraocular pressure, reduced flow of intraocular aqueous humor, and optical nerve damage. Other diseases or symptoms that can be treated with the chemical entities, compositions, and methods described herein including intraocular hypertension.

ATP hydrolysis is employed by myosin to produce force. An increase in ATP hydrolysis would correspond to an increase in the force or velocity of muscle contraction. In the presence of actin, myosin ATPase activity is stimulated more than 100-fold. Thus, the measurement of ATP hydrolysis not only measures myosin enzymatic activity but also its interaction with the actin filament. Assays for such activity may employ smooth muscle myosin from a human source, although myosin from other organisms can also be used. Systems that model the regulatory role of calcium in myosin binding may also be used.

The in vitro rate of ATP hydrolysis correlates to smooth muscle myosin potentiating activity, which can be determined by monitoring the production of either ADP or phosphate, for example as described in U.S. Pat. No. 6,410,254. ADP production can also be monitored by coupling the ADP production to NADH oxidation (using, for example, the enzymes pyruvate kinase and lactate dehydrogenase) and monitoring the NADH level, by example, either by absorbance or fluorescence (Greengard, P., *Nature* 178 (Part 4534): 632-634 (1956); *Mol Pharmacol* 1970 January; 6 (1):31-40). Phosphate production can be monitored using purine nucleoside phosphorylase to couple phosphate production to the cleavage of a purine analog, which results in either a change in absorbance (*Proc Natl Acad Sci USA* 1992 June 1; 89 (11):4884-7) or fluorescence (*Biochem J* 1990 March 1; 266 (2):611-4). While a single measurement is employed, multiple measurements of the same sample at different times in order may be used to determine the absolute rate of the protein activity; such measurements have higher specificity particularly in the presence of test compounds that have similar absorbance or fluorescence properties with those of the enzymatic readout.

Test compounds may be assayed in a highly parallel fashion using multiwell plates by placing the compounds either individually in wells or testing them in mixtures. Assay components including the target protein complex, coupling enzymes and substrates, and ATP may then be added to the wells and the absorbance or fluorescence of each well of the plate can be measured with a plate reader.

One method uses a 384 well plate format and a 25 µL reaction volume. A pyruvate kinase/lactate dehydrogenase coupled enzyme system (Huang T G and Hackney D D. (1994) J Biol Chem 269 (23):16493-16501) is used to measure the rate of ATP hydrolysis in each well. As will be appreciated by those of skill in the art, the assay components are added in buffers and reagents. Since the methods outlined herein allow kinetic measurements, incubation periods may be optimized to give adequate detection signals over the background. The assay is performed in real time to give the kinetics of ATP hydrolysis to increase the signal-to-noise ratio of the assay.

Selectivity for smooth muscle myosin may be determined by substituting other myosins in one or more of the above-described assays and comparing the results obtained against those obtained using the cardiac equivalents.

Chemical entities identified by the methods described herein as smooth muscle myosin modulators may be further tested in an efficacy screen, such as a screen using strips of permeabilized smooth muscle from, e.g., chicken gizzard. Calcium-sensitive smooth muscle strips are prepared by dissecting chicken gizzard tissue, followed by treatment with 1% Triton X-100 to make the strips permeable to exogenous compounds (Barsotti, R J, et al., Am J. Physiol. 1987 May; 252 (5 Pt 1):C543-54). These strips can be stored in 50% glycerol for several weeks at −20° C., allowing multiple experiments to be performed with each batch of muscle strips. Experiments are performed using a solution of 20 mM imidazole pH 7.0, 5.5 mM ATP, 7 mM $MgCl_2$, 55 mM KCl, 1 µM Calmodulin, and 10 mM EGTA. Free calcium will be controlled by addition of various amounts of $CaCl_2$, according to the calculations of MAXChelator (Patton, et al. Cell Calcium. 35/5 pp. 427-431, 2004). An isometric muscle fiber apparatus is used to measure isometric tension, for example using an Aurora Scientific 400A transducer with National Instruments PCI-MIO-16E-4, 16 channels, 12 bit A/D board for data acquisition. The chemically skinned gizzard fibers are relaxed when bathed in low calcium solutions (pCa 8), but develop isometric tension when the free calcium of the bathing solution is increased to pCa 5. These fibers can be repeatedly contracted and relaxed by switching between high and low calcium bathing solutions.

Compounds are first tested for their ability to prevent contraction of gizzard strips, by preincubating relaxed fibers with a compound, followed by transfer to high calcium solution containing the compound. Next, compounds are tested for their ability to cause relaxation of contracting fibers by adding the compound to fibers already incubating in high calcium solution. Washout experiments are performed to ensure that the inhibitory effects are reversible, so that the compounds do not cause denaturation or other irreparable damage to the smooth muscle myosin.

The chemical entities are administered at a therapeutically effective dosage, e.g., a dosage sufficient to provide treatment of the disease states previously described. Generally, a daily dose is from about 0.05 to about 100 mg/kg of body weight, such as from about 0.10 to about 10 mg/kg of body weight or from about 0.15 to about 1 mg/kg of body weight. Thus, for administration to a 70 kg person, the dosage range is from about 3.5 to about 7000 mg per day, such as from about 7 to about 700 mg per day or from about 10 to about 100 mg per day. The amount of active chemical entity administered will, of course, be dependent on the subject and disease state being treated, the severity of the affliction, the manner and schedule of administration and the judgment of the prescribing physician; for example, a dose range for oral administration may be from about 70 to about 700 mg per day, whereas for intravenous administration the dose range may be from about 700 to about 7000 mg per day. The active agents may be selected for longer or shorter plasma half-lives, respectively.

Administration of the chemical entities described herein can be via any of the accepted modes of administration for agents that serve similar utilities including, but not limited to, orally, subcutaneously, intravenously, intranasally, topically, transdermally, sublingually, intramucosally, intraperitoneally, intramuscularly, intrapulmonarily, vaginally, rectally, and intraocularly (including intraocular injection). Oral, topical, parenteral, and intraocular administration are customary in treating many of the indications recited herein.

Pharmaceutical compositions include solid, semi-solid, liquid and aerosol dosage forms, such as, e.g., tablets, capsules, powders, liquids, suspensions, suppositories, aerosols, and the like. The chemical entities can also be administered in sustained- or controlled-release dosage forms, including depot injections, osmotic pumps, pills, transdermal (including electrotransport) patches, drops and the like, for prolonged and/or timed, pulsed administration at a predetermined rate. The compositions may be provided in unit dosage forms suitable for single administration of a precise dose.

The chemical entities may be administered either alone or in combination with a conventional pharmaceutical carrier or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition may also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate. Generally, depending on the intended mode of administration, the pharmaceutical composition may contain from about 0.005% to about 95%, for example, from about 0.5% to about 50%, by weight of at least one chemical entity described herein. Actual methods of preparing such dosage forms are known or will be apparent, to those skilled in this art; for example, see *Remington's Pharmaceutical Sciences*, Mack Publishing Company, Easton, Pa.

In addition, the chemical entities may be co-administered with, and the pharmaceutical compositions can include, other medicinal agents, pharmaceutical agents, adjuvants, and the like.

In certain embodiments, the compositions are in the form of a pill or tablet and contain, along with the active ingredient, one or more of a diluent such as lactose, sucrose, dicalcium phosphate, and the like; a lubricant such as magnesium stearate or the like; and a binder such as starch, gum acacia, polyvinylpyrrolidine, gelatin, cellulose, cellulose derivatives and the like. In another solid dosage form, a powder, marume, solution or suspension (e.g., in propylene carbonate, vegetable oils or triglycerides) may be encapsulated in a gelatin capsule.

Liquid pharmaceutical compositions may, for example, be prepared by dissolving, dispersing, etc. at least one chemical entity and one or more optional pharmaceutical adjuvants in a carrier (e.g., water, saline, aqueous dextrose, glycerol, glycols, ethanol and the like) to form a solution or suspension. Injectables may be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient ranging from about 0.01% to about 10% in solution may be used, and may be higher if the composition is a solid which will be subsequently diluted to the above percentages. In certain embodiments, the composition has from about 0.2% to about 2% of the active agent in solution.

Compositions comprising at least one chemical entity may be administered intraocularly (including intraocular, periocular, and retrobulbar injection and perfusion). When administered intraocularly the sterile composition is typically aqueous. An appropriate buffer system may be added to prevent pH drift under storage conditions. When administered during intraocular surgical procedures, such as retrobulbar or periocular injection and intraocular perfusion or injection, the use of balanced salt irrigating solutions may be necessary. When used in a multidose form, preservatives may be required to prevent microbial contamination during use.

Compositions comprising at least one chemical entity may also be administered topically as eye drops, eye wash, creams, ointments, gels, and sprays. When administered as eye drops or eye wash, the active ingredients are typically dissolved or suspended in suitable carrier, typically a sterile aqueous solvent. An appropriate buffer system may be added to prevent pH drift under storage conditions. When used in a multidose form, preservatives may be required to prevent microbial contamination during use.

Compositions comprising at least one chemical entity may also be administered to the respiratory tract as an aerosol or in a solution for a nebulizer, or as a microfine powder for insufflation, alone or in combination with an inert carrier such as lactose. The particles of the composition typically have diameters of less than 50 microns, for example, less than 10 microns.

EXAMPLES

The following examples serve to more fully describe the manner of using the invention. These examples are presented for illustrative purposes and should not serve to limit the true scope of the invention.

Example I

Preparation of 3-(2-chlorobenzylamino)-2,2-dimethyl-3-oxopropyl 4-ethylphenylcarbamate

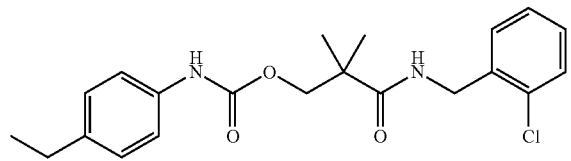

3-(2-chlorobenzylamino)-2,2-dimethyl-3-oxopropyl 4-ethylphenylcarbamate

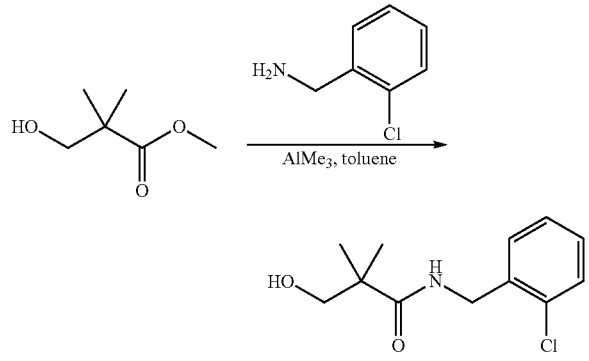

To a solution of methyl 3-hydroxy-2,2-dimethylpropanoate (1 g, 7.31 mmol) and 2-chlorobenzylamine (1 mL, 8.75 mmol, 1.2 equiv.) in toluene (7 mL) was added trimethylaluminum (2 M in hexane, 5.4 mL, 10.8 mmol, 1.5 equiv.). The reaction mixture was stirred at 80° C. for 2 h. The reaction mixture was quenched with saturated NaHCO$_3$. The resulting mixture was extracted with EtOAc. The organic layer was dried over Na$_2$SO$_4$ and concentrated to give N-(2-chlorobenzyl)-3-hydroxy-2,2-dimethylpropanamide (1.5 g, 85%), which was used without further purification. LRMS (M+H$^+$) m/z 242.1.

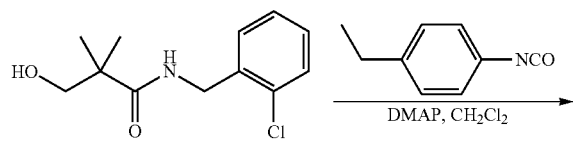

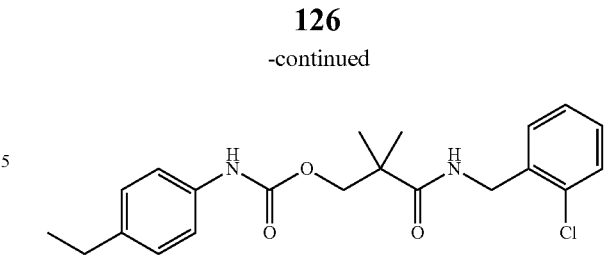

To a solution of N-(2-chlorobenzyl)-3-hydroxy-2,2-dimethylpropanamide (30 mg, 0.12 mmol), in CH$_2$Cl$_2$ were added DMAP and 4-ethylphenylisocyanate (21 µL, 0.15 mmol, 1.5 equiv.). The reaction mixture was stirred for 1 h. The reaction mixture was concentrated. The resulting residue was to purify on RP-HPLC to give 3-(2-chlorobenzylamino)-2,2-dimethyl-3-oxopropyl 4-ethylphenylcarbamate (10 mg, 17%). LRMS (M+H$^+$) m/z 389.1.

Example II

Preparation of (1-(2-aminoacetyl)-4-(2-chlorobenzylcarbamoyl)piperidin-4-yl)methyl 4-ethylphenylcarbamate

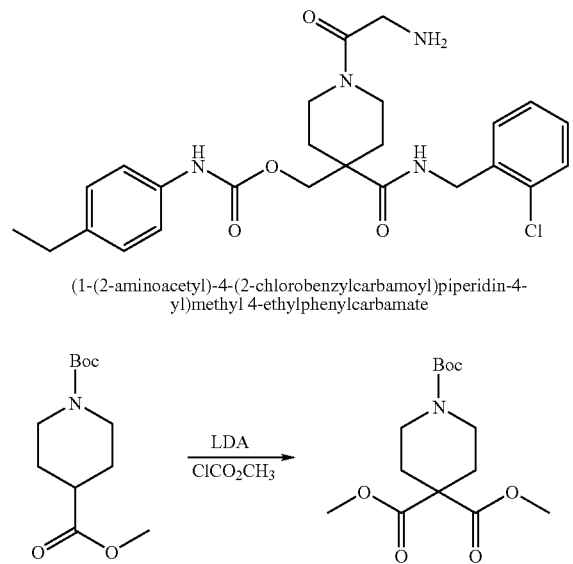

(1-(2-aminoacetyl)-4-(2-chlorobenzylcarbamoyl)piperidin-4-yl)methyl 4-ethylphenylcarbamate To a chilled solution of diisopropylamine (3.5 mL, 24.7 mmol) in THF (20 mL) at −78° C. was added n-BuLi (2M in hexane, 14.8 mL, 1.2 equiv.). The reaction mixture was stirred for 1 h. A solution of 1-tert-butyl 4-methyl piperidine-1,4-dicarboxylate (5 g, 20.6 mmol, 1 equiv.) in THF (15 mL) was added dropwise at −78° C. The reaction mixture was stirred for 1 h. Methyl chloroformate (1.7 mL, 22.6 mmol, 1.1 equiv.) was added to the above mixture. The reaction mixture was warmed to rt slowly while stirring. After 3 h, the reaction mixture was quenched with saturated NH$_4$Cl and extracted with ethyl acetate. The organic layer was dried over Na$_2$SO$_4$ and concentrated to give 1-tert-butyl 4,4-dimethyl piperidine-1,4,4-tricarboxylate (6.2 g, quant.), which was used without further purification. LRMS (M+H$^+$-Boc) m/z 202.1.

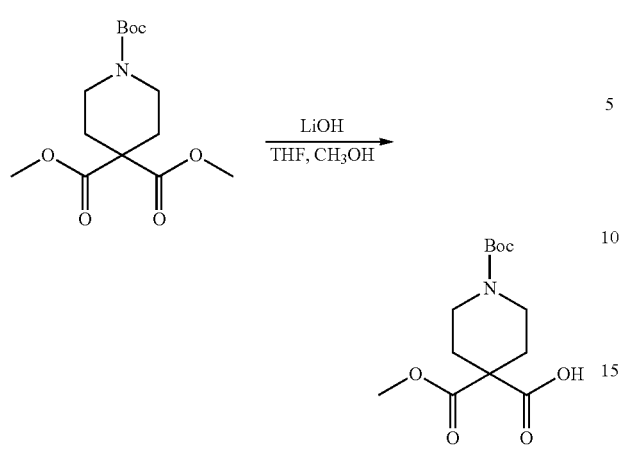

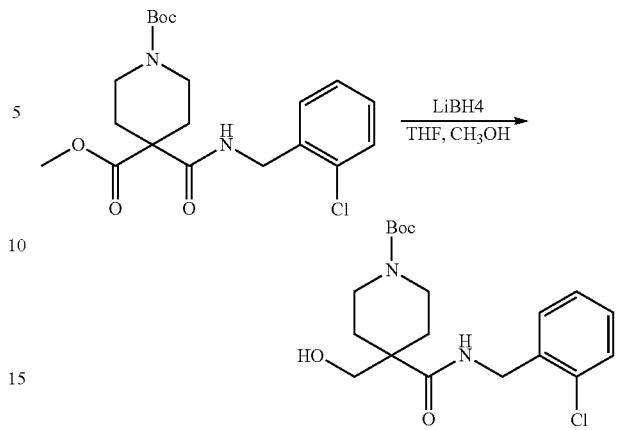

To a solution of 1-tert-butyl 4,4-dimethyl piperidine-1,4,4-tricarboxylate (6.2 g, 20.5 mmol) in THF (11 mL) and CH₃OH (11 mL) was added aqueous LiOH (2 N, 11 mL, 22 mmol, 1.1 equiv.). The reaction mixture was stirred at 80° C. for 1 h. The reaction mixture was neutralized with HCl (1N) and was concentrated to dryness. The residue was dissolved in ethyl acetate and dried over Na₂SO₄ and concentrated to give 1-(tert-butoxycarbonyl)-4-(methoxycarbonyl)piperidine-4-carboxylic acid (4.7 g, 80%), which was used without further purification. LRMS (M+H⁺-Boc) m/z 188.0.

To a solution of 1-tert-butyl 4-methyl 4-(2-chlorobenzylcarbamoyl)piperidine-1,4-dicarboxylate (2.8 g, 6.8 mmol) in THF (20 mL) and CH₃OH (10 mL) was added lithium borohydride (1.4 g, 68 mmol, 10 equiv.). The reaction mixture was stirred for 3 h and neutralized with HCl (1N). The residue was partitioned between EtOAc and H₂O. The organic layer was dried over Na₂SO₄ and concentrated to purify on RP-HPLC using a mixture of acetonitrile and H₂O to give tert-butyl 4-(2-chlorobenzylcarbamoyl)-4-(hydroxymethyl)piperidine-1-carboxylate (2.2 g, 84%). LRMS (M-ᵗBu+H⁺) m/z 327.0.

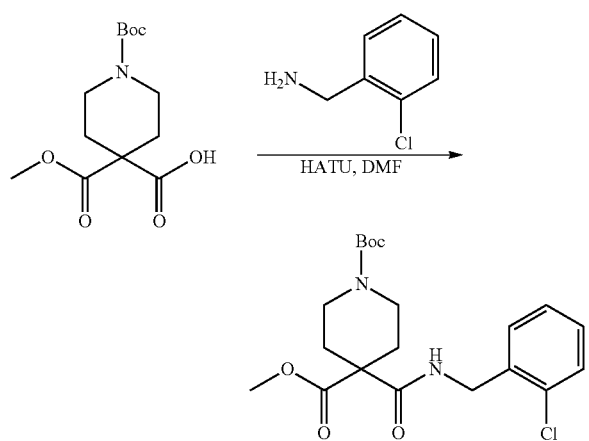

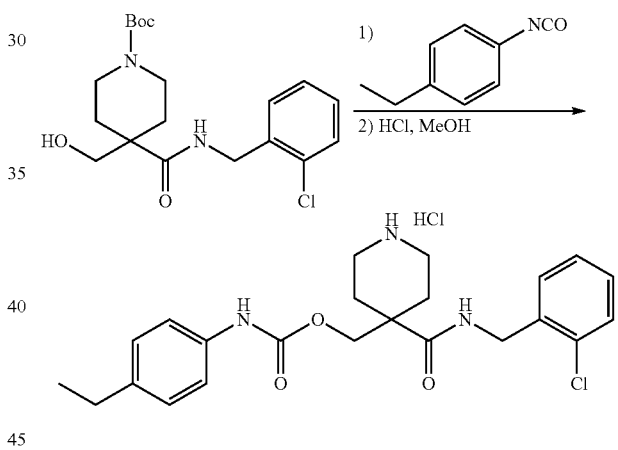

To a solution of 1-(tert-butoxycarbonyl)-4-(methoxycarbonyl)piperidine-4-carboxylic acid (3.7 g, 13.2 mmol) in DMF (30 mL) were added HATU (6.0 g, 15.8 mmol, 1.2 equiv.), 2-chlorobenzylamine (1.9 mL, 15.8 mmol, 1.2 equiv.) and DIEA (228 µL, 1.31 mmol, 0.1 equiv.). The reaction mixture was stirred for 3 h and purified on RP-HPLC using a mixture of acetonitrile and H₂O to give 1-tert-butyl 4-methyl 4-(2-chlorobenzylcarbamoyl)piperidine-1,4-dicarboxylate (2.8 g, 52%). LRMS (M+H⁺-Boc) m/z 311.0.

To a solution of tert-butyl 4-(2-chlorobenzylcarbamoyl)-4-(hydroxymethyl)piperidine-1-carboxylate (1.8 g, 4.8 mmol) in THF were added DMAP (118 mg, 0.9 mmol, 0.1 equiv.) and 4-ethylphenylisocyanate (1.1 mL, 7.3 mmol, 1.5 equiv.) at r. t. The reaction mixture was stirred for 1 h. The reaction mixture was concentrated to dryness. To a solution of the above product in CH₃OH was added 4M HCl in dioxane (3.6 mL, 3 equiv.), which was stirred overnight. The white solid was filtered and dried to give (4-(2-chlorobenzylcarbamoyl)piperidin-4-yl)methyl 4-ethylphenylcarbamate hydrochloride (1.7 g, 81%). LRMS (M-Boc+H⁺) m/z 430.1.

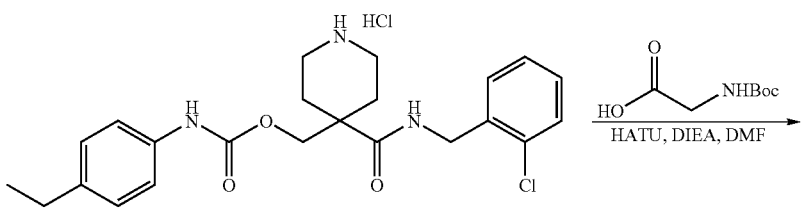

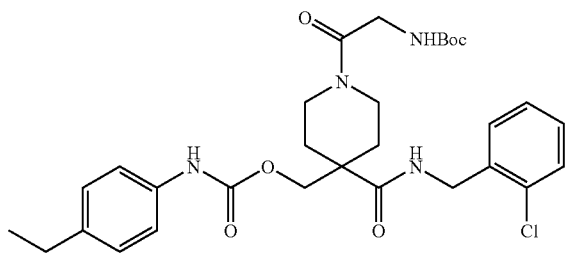

To a solution of Boc-Gly-OH (54 mg, 0.31 mmol, 1.2 equiv.) in DMF (1 mL) were added HATU (120 mg, 0.31 mmol, 1.2 equiv.), followed by addition of (4-(2-chlorobenzylcarbamoyl)piperidin-4-yl)methyl 4-ethylphenylcarbamate hydrochloride (120 mg, 0.26 mmol, 1 equiv.) and DIEA (89 µL, 0.51 mmol, 2 equiv.) at rt The reaction mixture was stirred for 3 h and purified on RP-HPLC using a mixture of acetonitrile and H$_2$O to give (1-(2-(tert-butoxycarbonyl)aminoacetyl)-4-(2-chlorobenzylcarbamoyl)piperidin-4-yl)methyl 4-ethylphenylcarbamate (127 mg, 84%). LRMS (M-Boc+H$^+$) m/z 487.1.

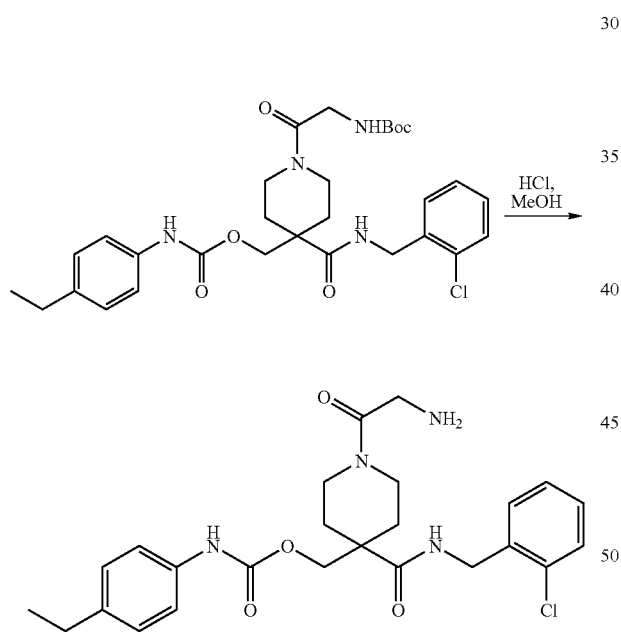

To a solution of (1-(2-(tert-butoxycarbonyl)aminoacetyl)-4-(2-chlorobenzylcarbamoyl)piperidin-4-yl)methyl 4-ethylphenylcarbamate (87 mg, 0.15 mmol) in CH$_3$OH (1 mL) was added HCl (4M in dioxane, 100 µL, 0.4 mmol, 2.6 equiv.), which was stirred for 2 h. The reaction mixture was concentrated to dryness by co-evaporating with toluene to give (1-(2-aminoacetyl)-4-(2-chlorobenzylcarbamoyl)piperidin-4-yl)methyl 4-ethylphenylcarbamate (81 mg, quant.). LRMS (M+H$^+$) m/z 487.1.

Example III

Preparation of (S)-(1-(2-amino-3-hydroxypropanoyl)-4-(2-chlorobenzylcarbamoyl)piperidin-4-yl) methyl 4-(trifluoromethyl)phenylcarbamate

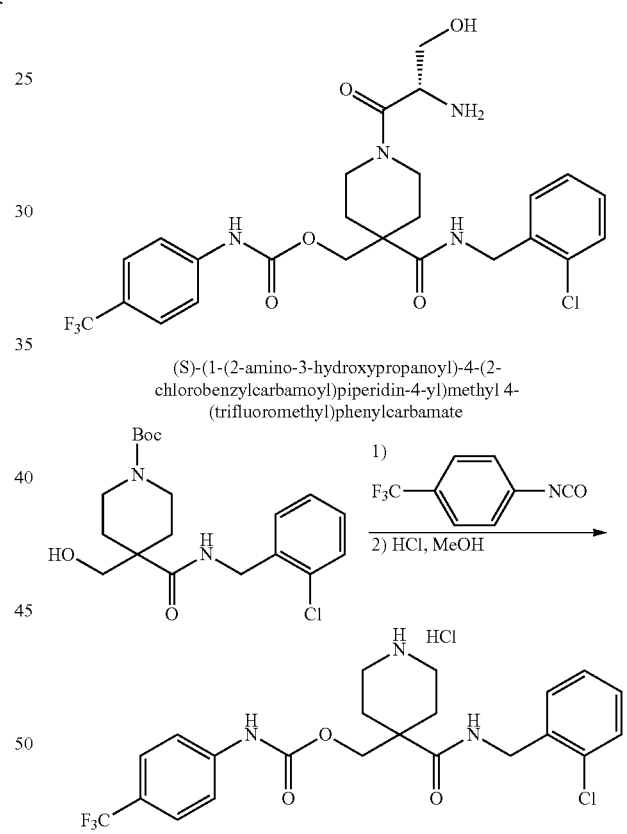

To a solution of tert-butyl 4-(2-chlorobenzylcarbamoyl)-4-(hydroxymethyl)piperidine-1-carboxylate (500 mg, 1.3 mmol), in THF were added DMAP (32 mg, 0.26 mmol, 0.2 equiv.) and 4-trifloromethylphenylisocyanate (0.28 mL, 1.97 mmol, 1.5 equiv.). The reaction mixture was stirred for 1 h. The reaction mixture was concentrated to dryness. To a solution of the above crude mixture in CH$_3$OH (3 mL) was added HCl (4 M in dioxane, 1 mL, 4 mmol, 3 equiv.). The reaction mixture was stirred overnight. The white solid was filtered and dried to give (4-(2-chlorobenzylcarbamoyl)piperidin-4-yl)methyl 4-(trifluoromethyl)phenylcarbamate (615 mg, 93%). LRMS (M-Boc+H$^+$) m/z 470.1.

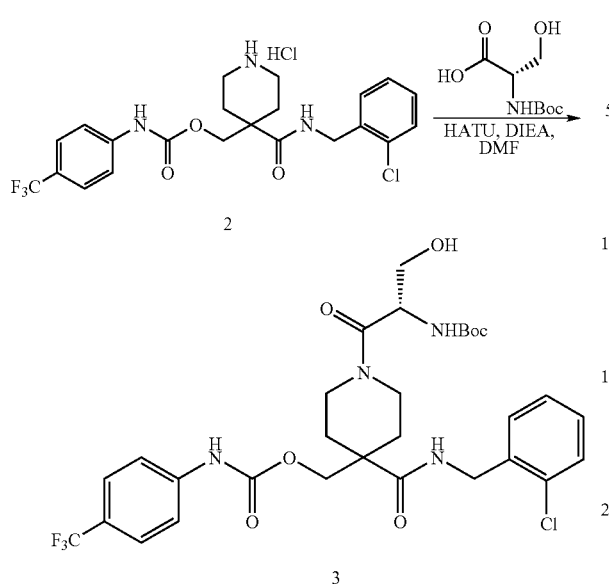

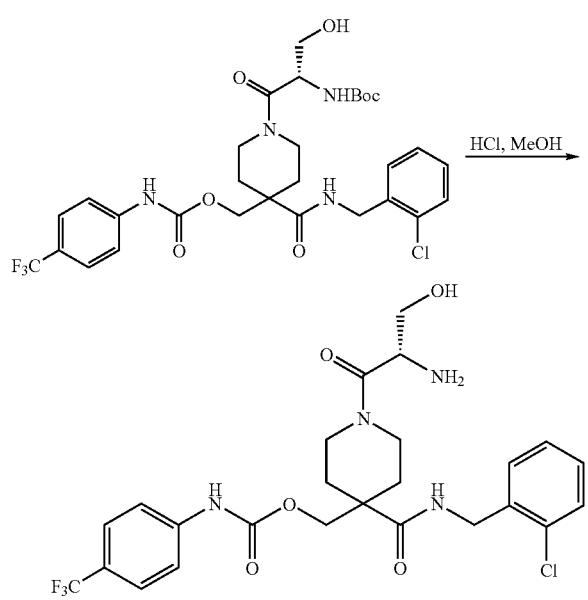

To a solution of Boc-Ser-OH (162 mg, 0.79 mmol, 2 equiv.) in DMF (2 mL) were added HATU (300 mg, 0.79 mmol, 2 equiv.), followed by addition of (4-(2-chlorobenzylcarbamoyl)piperidin-4-yl)methyl 4-(trifluoromethyl)phenylcarbamate (200 mg, 0.39 mmol, 1 equiv.) and DIEA (140 µL, 0.79 mmol, 2 equiv.). The reaction mixture was stirred overnight and purified on RP-HPLC using a mixture of acetonitrile and H₂O to give (S)-(1-(2-(tert-butoxycarbonyl)amino-3-hydroxypropanoyl)-4-(2-chlorobenzylcarbamoyl)piperidin-4-yl)methyl 4-(trifluoromethyl)phenylcarbamate (145 mg, 56%). LRMS (M+H⁺-Boc) m/z 557.1.

To a solution of (S)-(1-(2-(tert-butoxycarbonyl)amino-3-hydroxypropanoyl)-4-(2-chlorobenzylcarbamoyl)piperidin-4-yl)methyl 4-(trifluoromethyl)phenylcarbamate (145 mg, 0.22 mmol) in CH₃OH (1 mL) was added 4M HCl in dioxane (200 µL, 0.8 mmol, 3.6 equiv.), which was stirred for 2 h. The reaction mixture was concentrated to dryness by co-evaporating with toluene to give (S)-(1-(2-amino-3-hydroxypropanoyl)-4-(2-chlorobenzylcarbamoyl)piperidin-4-yl)methyl 4-(trifluoromethyl)phenylcarbamate (130 mg, quant.). LRMS (M+H⁺) m/z 557.1.

Example IV

Preparation of 4-(2-chlorobenzylamino)-3,3-dimethyl-4-oxobutyl 4-ethylphenylcarbamate 4-(2-chlorobenzylamino)-3,3-dimethyl-4-oxobutyl 4-ethylphenylcarbamate

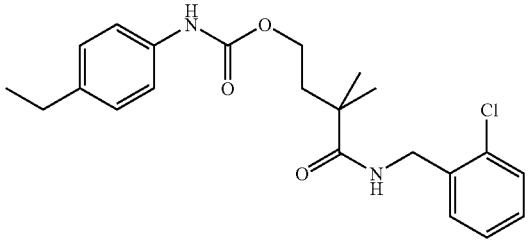

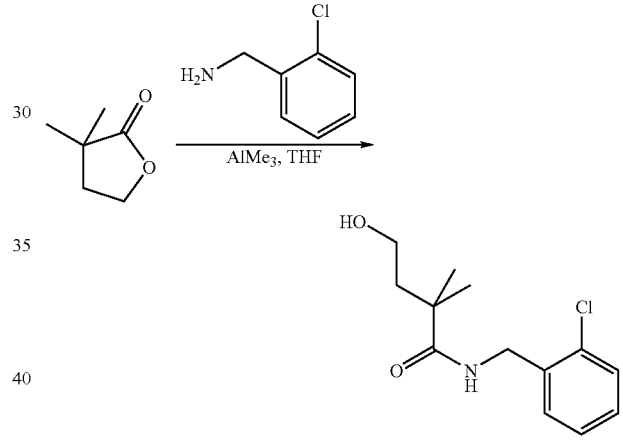

To a solution of 3,3-dimethyl-dihydrofuran-2(3H)-one (2.04 g, 17.9 mmol) in THF (15 mL) were added 2-chlorobenzylamine (2.4 mL, 19.9 mmol, 1.1 equiv.) and AlMe₃ (2M in toluene, 4.5 mL, 9 mmol, 0.5 equiv.). The reaction mixture was stirred for 3 days. The reaction mixture was saturated NaHCO₃ and extracted with EtOAc. The organic layer was washed with saturated NaHCO₃, H₂O and brine, dried over Na₂SO₄, and concentrated to give N-(2-chlorobenzyl)-4-hydroxy-2,2-dimethylbutanamide as a white solid (3.8 g, 83%), which was used without further purification. LRMS (M+H⁺) m/z 256.0.

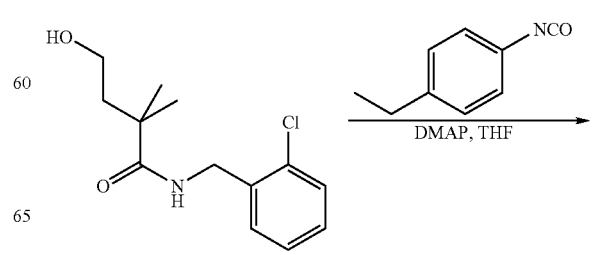

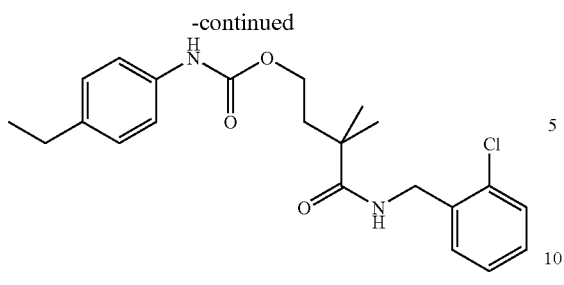

To a solution of N-(2-chlorobenzyl)-4-hydroxy-2,2-dimethylbutanamide (400 mg, 1.6 mmol) in THF (25 mL) were added 4-ethylphenylisocyanate (276 μL, 1.92 mmol, 1.2 equiv.) and DMAP (293 mg, 2.4 mmol, 1.5 equiv.). The reaction mixture was stirred overnight. The reaction mixture was concentrated. The resulting residue was purified on RP-HPLC using a mixture of acetonitrile and H$_2$O, and further purified by flash column chromatography using a mixture of hexanes and EtOAc to give 4-(2-chlorobenzylamino)-3,3-dimethyl-4-oxobutyl 4-ethylphenylcarbamate (160 mg, 25%). LRMS (M+H$^+$) m/z 403.1.

Example V

Preparation of N-(2-chlorobenzyl)-3-(3-(4-ethylphenyl)ureido)-2,2-dimethylpropanamide

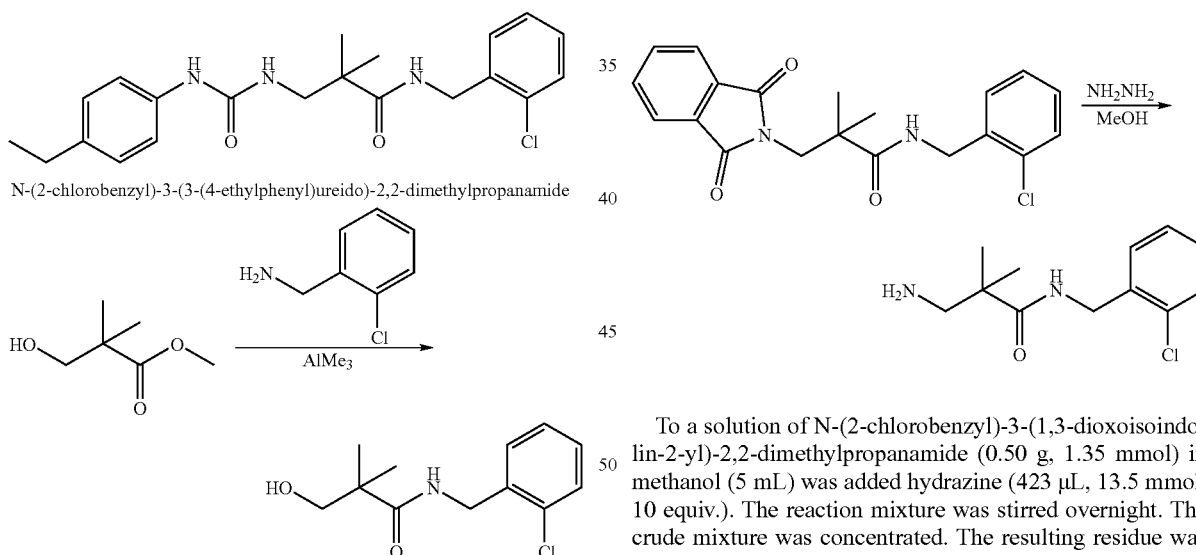

N-(2-chlorobenzyl)-3-(3-(4-ethylphenyl)ureido)-2,2-dimethylpropanamide

To a solution of methyl 3-hydroxy-2,2-dimethylpropanoate (1.0 g, 7.57 mmol) and 2-chlorobenzylamine (1.09 mL, 9.08 mmol, 1.2 equiv.) in toluene (10 mL) was added trimethylaluminum (2M in hexanes, 5.6 mL, 11.4 mmol, 1.5 equiv.). The reaction mixture was stirred at 80° C. for 2 hours. The reaction mixture was concentrated. The resulting residue was dissolved in EtOAc (100 mL). The organic layer was washed with saturated NaHCO$_3$, dried over Na$_2$SO$_4$, and concentrated. The resulting residue was purified on silica gel column using a mixture of hexanes and ethyl acetate to give N-(2-chlorobenzyl)-3-hydroxy-2,2-dimethylpropanamide (1.55 g, 84%). LRMS (M+H$^+$) m/z 242.1.

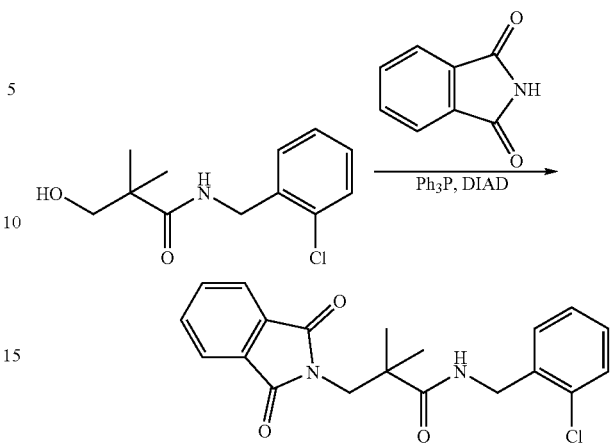

To a solution of N-(2-chlorobenzyl)-3-hydroxy-2,2-dimethylpropanamide (0.50 g, 2.07 mmol) in THF (5 mL) were added phthalimide (0.457 g, 3.10 mmol, 1.5 equiv.) and PPh$_3$ (0.813 g, 3.10 mmol, 1.5 equiv.). DIAD (600 μL, 3.10 mmol, 1.5 equiv.) was added dropwise into the reaction mixture. The resulting mixture was stirred overnight. LC/MS indicated that starting material was consumed. The reaction mixture was concentrated. The resulting residue was purified on silica gel column a mixture of hexanes and ethyl acetate to give N-(2-chlorobenzyl)-3-(1,3-dioxoisoindolin-2-yl)-2,2-dimethylpropanamide (0.50 g, 65%). LRMS (M+H$^+$) m/z 371.1.

To a solution of N-(2-chlorobenzyl)-3-(1,3-dioxoisoindolin-2-yl)-2,2-dimethylpropanamide (0.50 g, 1.35 mmol) in methanol (5 mL) was added hydrazine (423 μL, 13.5 mmol, 10 equiv.). The reaction mixture was stirred overnight. The crude mixture was concentrated. The resulting residue was dried in vacuum to give 3-amino-N-(2-chlorobenzyl)-2,2-dimethylpropanamide, which was used without further purification. LRMS (M+H$^+$) m/z 241.1.

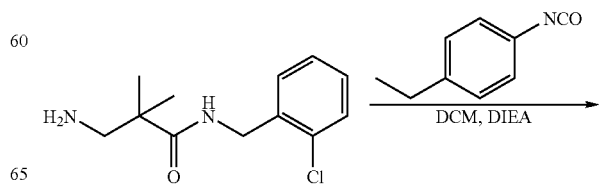

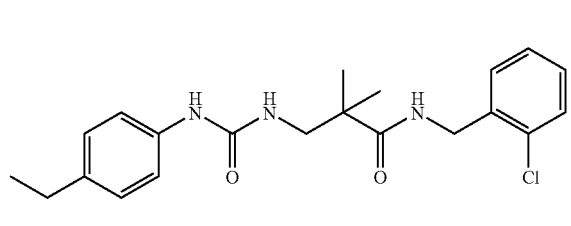

To a solution of 3-amino-N-(2-chlorobenzyl)-2,2-dimethylpropanamide (0.45 mmol) in DCM (5 mL) was added DIEA (157 μL, 0.90 mmol, 2 equiv.) and 4-ethylphenyl isocyanate (97.0 μL, 0.675 mmol, 1.5 equiv.). The reaction mixture was stirred for 30 min. The mixture was concentrated and purified on RP-HPLC using a mixture of acetonitrile and H$_2$O to give N-(2-chlorobenzyl)-3-(3-(4-ethylphenyl)ureido)-2,2-dimethylpropanamide (29.6 mg, 17% for two steps). LRMS (M+H$^+$) m/z 388.1.

Example VI

Preparation of (S)-(1-(2-chlorobenzylcarbamoyl)pyrrolidin-2-yl)methyl 4-ethylphenylcarbamate

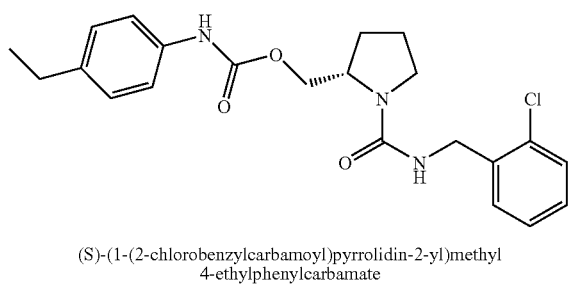

(S)-(1-(2-chlorobenzylcarbamoyl)pyrrolidin-2-yl)methyl 4-ethylphenylcarbamate

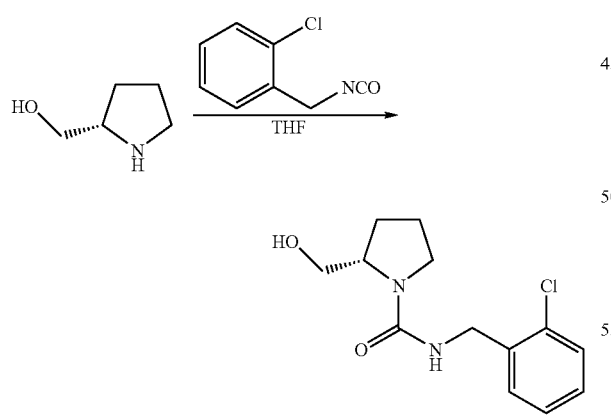

To a solution of (S)-pyrrolidin-2-ylmethanol (110 mg, 1.1 mmol) in THF (2.0 mL) was added 2-chlorobenzyl-isocyanate (167 mg, 1.0 mmol). The reaction mixture was stirred for 1 h and concentrated under reduced pressure to give (S)—N-(2-chlorobenzyl)-2-(hydroxymethyl)pyrrolidine-1-carboxamide as an oil (277 mg), which was used without further purification. LRMS (M+H$^+$) m/z 269.0.

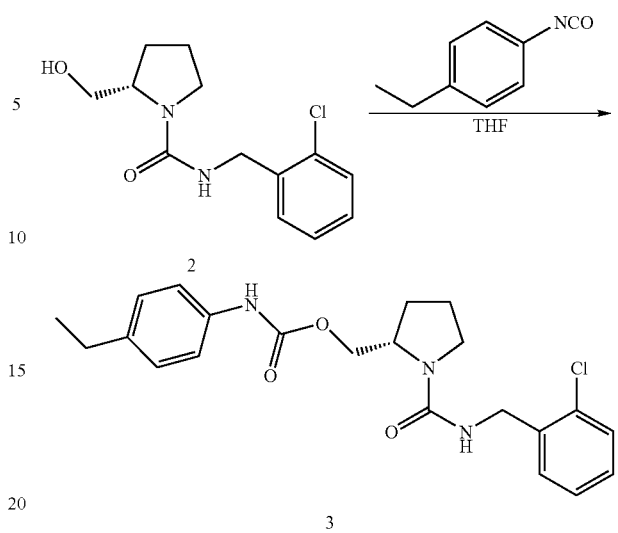

To a solution of (S)—N-(2-chlorobenzyl)-2-(hydroxymethyl)pyrrolidine-1-carboxamide (268 mg, 1.0 mmol) in THF (2.0 mL) was added 4-ethyl-phenyl-isocyanate (220 mg, 1.5 mmol). The reaction mixture was stirred for 1 h. LC/MS indicated the reaction was complete. The reaction was concentrated and the resulting residue was purified on RP-HPLC using a mixture of acetonitrile and H$_2$O to give (S)-(1-(2-chlorobenzylcarbamoyl)pyrrolidin-2-yl)methyl 4-ethylphenylcarbamate (42 mg, 10% for two steps). LRMS (M+H$^+$) m/z 416.0.

Example VII

Preparation of (S)-2-(3-(2-chlorobenzyl)-1-methylureido)propyl 4-ethylphenylcarbamate

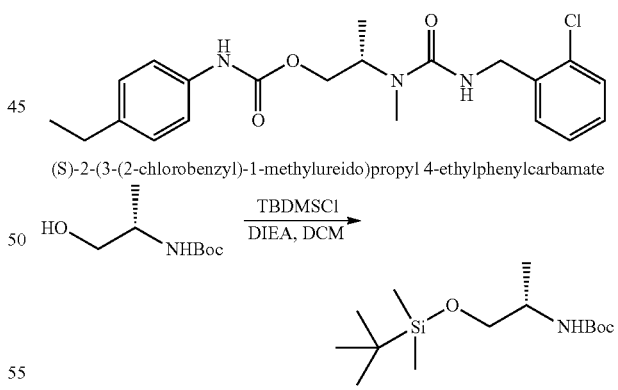

(S)-2-(3-(2-chlorobenzyl)-1-methylureido)propyl 4-ethylphenylcarbamate

To a solution of (S)-tert-butyl 1-hydroxypropan-2-ylcarbamate (3.06 g, 17.46 mmol) in DCM (30 mL) were added TBDMSCl (2.90 g, 19.2 mmol, 1.1 equiv.) and DIEA (4.3 mL, 26.2 mmol, 1.5 equiv.). The reaction was stirred for 1 h. LC/MS indicated the reaction was complete. The reaction mixture was then poured into H$_2$O and diluted with EtOAc. The organic layer was separated, washed with saturated NaHCO$_3$ and brine, dried over Na$_2$SO$_4$, and filtered. The filtrate was concentrated under reduced pressure to give (S)-tert-butyl 1-(tert-butyldimethylsilyloxy)propan-2-ylcarbamate, which was used for the next step without further purification. LRMS (M-Boc+H⁺) m/z 190.1.

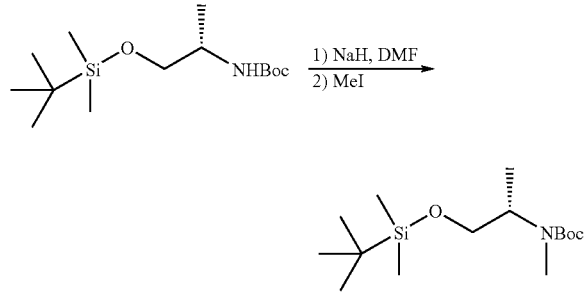

To a solution of NaH (60% dispersed in mineral oil, 60 mg, 1.49 mmol, 1.15 equiv.) in DMF (2.0 mL) was added (S)-tert-butyl 1-(tert-butyldimethylsilyloxy)propan-2-ylcarbamate (360 mg, 1.3 mmol). The reaction mixture was stirred for 30 min followed by addition of methyl iodide (93 μL, 1.49 mmol, 1.15 equiv.) and stirred for 1 h. LC/MS indicated the reaction was complete. The reaction mixture was quenched with saturated NH₄Cl and diluted with EtOAc. The organic layer was separated, washed with brine, dried over Na₂SO₄, and filtered. The filtrate was concentrated under reduced pressure to give (S)-tert-butyl 1-(tert-butyldimethylsilyloxy)propan-2-yl (methyl)carbamate as an oil, which was used in the next step without further purification. LRMS (M-Boc+H⁺) m/z 204.1.

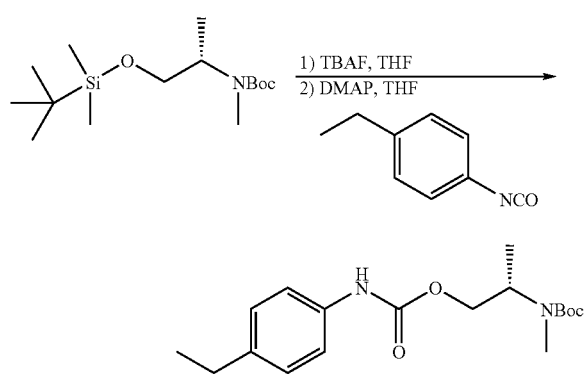

To a solution of (S)-tert-butyl 1-(tert-butyldimethylsilyloxy)propan-2-yl(methyl)carbamate (301 mg, 1.0 mmol) in THF was added TBAF (1M in THF, 1.5 mL, 1.5 mmol, 1.5 equiv.) and the mixture was stirred for 1 h followed by quenched with saturated NaHCO₃ and diluted with EtOAc. The organic layer was separated, washed with brine, dried over Na₂SO₄, and filtered. The filtrate was concentrated under reduced pressure to give a crude oil, which was re-dissolved in THF (2.0 mL). To this THF solution were added DMAP and 4-ethylphenyl isocyanate. The reaction mixture was stirred for 30 min. LC/MS indicated the completion of the reaction and the mixture was filtered and the filtrate was purified on RP-HPLC using a mixture of acetonitrile and H₂O to give (S)-2-(methyl(tert-butoxycarbonyl)amino)propyl 4-ethylphenylcarbamate (118 mg, 30% from 1). LRMS (M-Boc+H⁺) m/z 237.1.

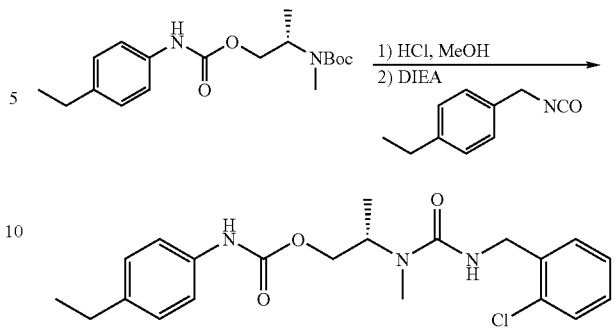

To a solution of (S)-2-(methyl(tert-butoxycarbonyl)amino)propyl 4-ethylphenylcarbamate (105 mg, 0.27 mmol) in MeOH was added HCl (4M in dioxane, 0.2 mL, 0.81 mmol, 3 equiv.) and the mixture was stirred for 2 h. LC/MS indicated the reaction was complete and the mixture was concentrated under reduced pressure to give a crude oil, which was re-dissolved in THF. To this THF solution was added 4-ethylphenyl isocyanate (30 μL, 0.26 mmol) followed by DIEA (0.11 mL, 0.66 mmol, 2.5 equiv.). The reaction mixture was stirred for 2 h. LC/MS indicated the completion of the reaction. The mixture was filtered and the filtrate was purified on RP-HPLC using a mixture of acetonitrile and H₂O to give (S)-2-(3-(2-chlorobenzyl)-1-methylureido)propyl 4-ethylphenylcarbamate (88.6 mg, 81% for two steps). LRMS (M+H⁺) m/z 404.1.

Example VIII

Preparation of (1-(2-aminoacetyl)-4-(3-fluoro-2-methylbenzylcarbamoyl)piperidin-4-yl)methyl 4-ethylphenylcarbamate

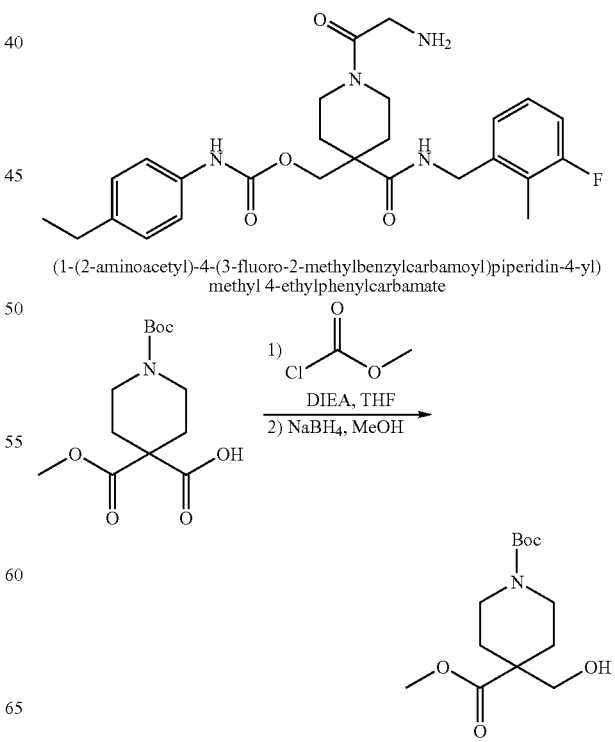

To a solution of 1-(tert-butoxycarbonyl)-4-(methoxycarbonyl)piperidine-4-carboxylic acid (6 g, 21 mmol) and DIEA (7.3 mL, 42 mmol, 2.0 equiv.) in THF (60 mL) was added methyl chloroformate (1.94 mL, 25 mmol, 1.2 equiv.) at 0° C. The mixture was stirred at 0° C. until the reaction was complete. NaBH$_4$ (3.16 g, 84 mmol, 4.0 equiv.) was added at 0° C. MeOH (10 mL) was then added. The mixture was stirred at 0° C. for 90 min. The reaction mixture was then quenched by saturated NaHCO$_3$ and concentrated to dryness. The residue was dissolved in ethyl acetate, washed with saturated NaHCO$_3$, water and brine, dried over Na$_2$SO$_4$, and concentrated. The resulting residue was purified by column chromatography to give 1-tert-butyl 4-methyl 4-(hydroxymethyl)piperidine-1,4-dicarboxylate (2.6 g, 46%). LRMS (M-Boc+H$^+$) m/z 174.1.

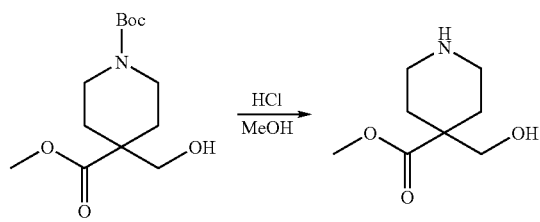

To a solution of 1-tert-butyl 4-methyl 4-(hydroxymethyl)piperidine-1,4-dicarboxylate (470 mg, 1.72 mmol, 1.0 equiv.) in MeOH (1 mL) was added HCl (4 M in dioxane, 1 mL). The mixture was stirred at rt for about 1 h and concentrated to dryness to give methyl 4-(hydroxymethyl)piperidine-4-carboxylate, which was used without further purification. LRMS (M+H$^+$) m/z 174.0.

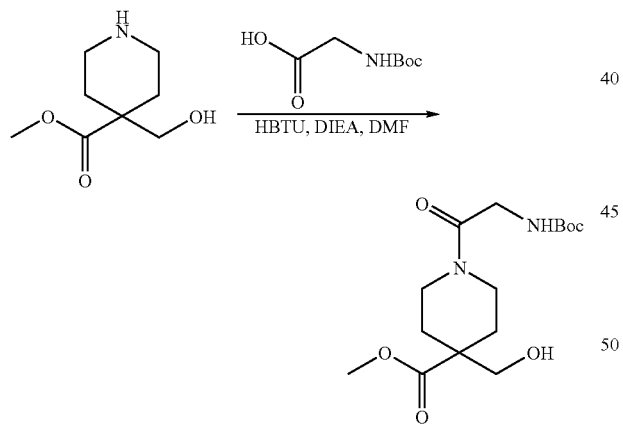

To a solution of Boc-Gly-OH (331 mg, 1.89 mmol, 1.1 equiv.) in DMF (1 mL) was added HBTU (718 mg, 1.89 mmol, 1.1 equiv.), followed by addition of methyl 4-(hydroxymethyl)piperidine-4-carboxylate (1.72 mmol, 1 equiv.) and DIEA (749 μL, 4.30 mmol, 2.5 equiv.) at rt. The reaction mixture was stirred for 1 h. The mixture was partitioned between EtOAc and H$_2$O. The organic layer was washed by saturated NaHCO$_3$, water and brine, dried over Na$_2$SO$_4$, and concentrated. The resulting residue was purified by column chromatography to give methyl 1-(2-(tert-butoxycarbonylamino)acetyl)-4-(hydroxymethyl)piperidine-4-carboxylate (560 mg, 98%, two steps). LRMS (M-Boc+H$^+$) m/z 231.1.

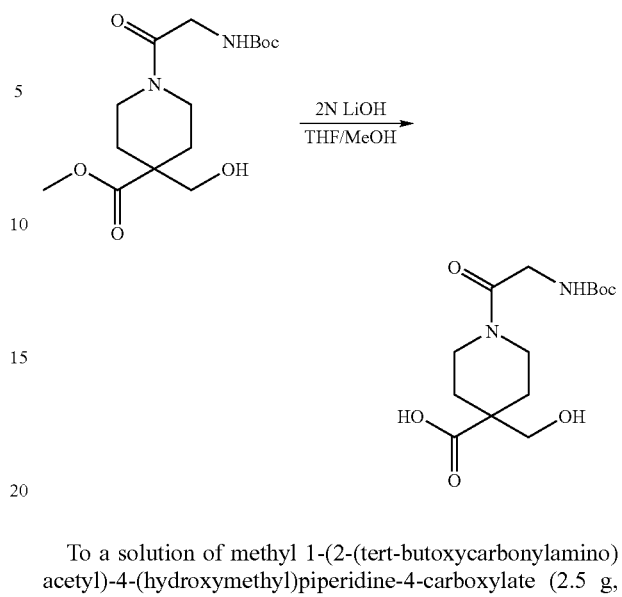

To a solution of methyl 1-(2-(tert-butoxycarbonylamino)acetyl)-4-(hydroxymethyl)piperidine-4-carboxylate (2.5 g, 7.56 mmol, 1.0 equiv.) in THF (10 mL) and CH$_3$OH (10 mL) was added aqueous LiOH (2N, 7.56 mL, 15.13 mmol, 2.0 equiv.). The reaction mixture was stirred at 60° C. for 1 h. The reaction mixture was neutralized with HCl (1 N) and was concentrated to dryness to give 1-(2-(tert-butoxycarbonylamino)acetyl)-4-(hydroxymethyl)piperidine-4-carboxylic acid (3.0 g), which was used without further purification. LRMS (M-Boc+H$^+$) m/z 261.0.

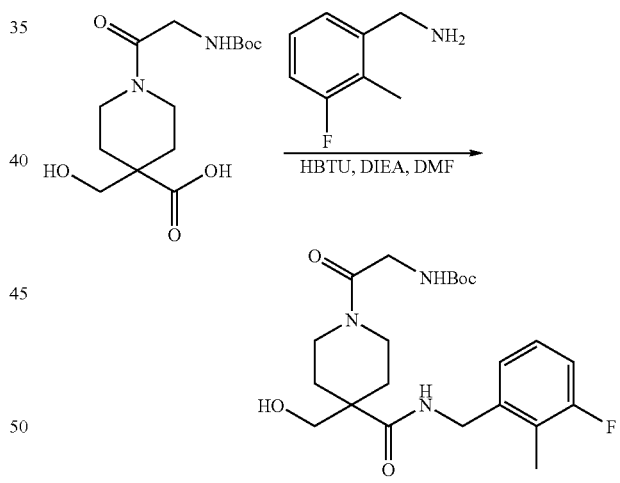

To a solution of crude 1-(2-(tert-butoxycarbonylamino)acetyl)-4-(hydroxymethyl)piperidine-4-carboxylic acid (120 mg, ~0.379 mmol, 1.0 equiv) in DMF (30 mL) were added HBTU (144 mg, 0.379 mmol, 1.0 equiv.), 2-methyl, 3-fluorobenzylamine (53 mg, 0.379 mmol, 1.0 equiv.) and DIEA (132 μL, 0.758 mmol, 2.0 equiv.). The reaction mixture was stirred overnight at rt. The mixture was partitioned between EtOAc and H$_2$O. The organic layer was washed by 1 N HCl, Saturated NaHCO$_3$, water and brine, dried over Na$_2$SO$_4$, and concentrated to dryness to give tert-butyl 2-(4-(3-fluoro-2-methylbenzylcarbamoyl)-4-(hydroxymethyl)piperidin-1-yl)-2-oxoethylcarbamate (185 mg), which was used without further purification. LRMS (M+H$^+$) m/z 439.1.

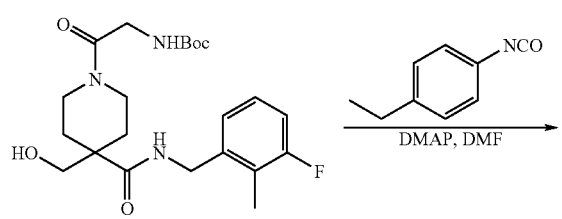

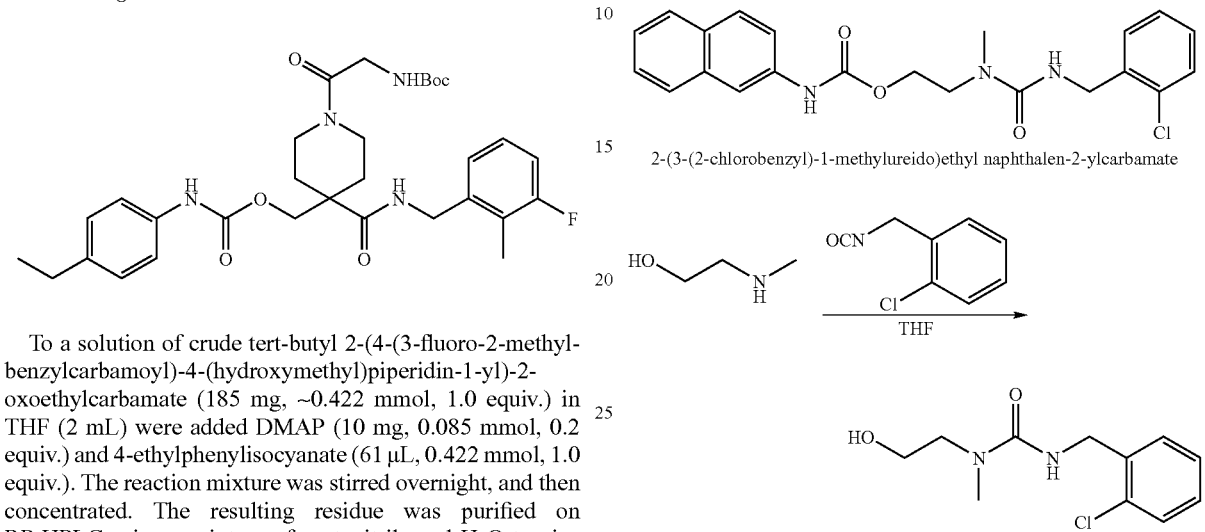

To a solution of crude tert-butyl 2-(4-(3-fluoro-2-methylbenzylcarbamoyl)-4-(hydroxymethyl)piperidin-1-yl)-2-oxoethylcarbamate (185 mg, ~0.422 mmol, 1.0 equiv.) in THF (2 mL) were added DMAP (10 mg, 0.085 mmol, 0.2 equiv.) and 4-ethylphenylisocyanate (61 µL, 0.422 mmol, 1.0 equiv.). The reaction mixture was stirred overnight, and then concentrated. The resulting residue was purified on RP-HPLC using a mixture of acetonitrile and H$_2$O to give (1-(2-(tert-butoxycarbonylamino)acetyl)-4-(3-fluoro-2-methylbenzylcarbamoyl)piperidin-4-yl)methyl 4-ethylphenylcarbamate (12 mg, 5% for three steps). LRMS (M-Boc+H$^+$) m/z 485.2.

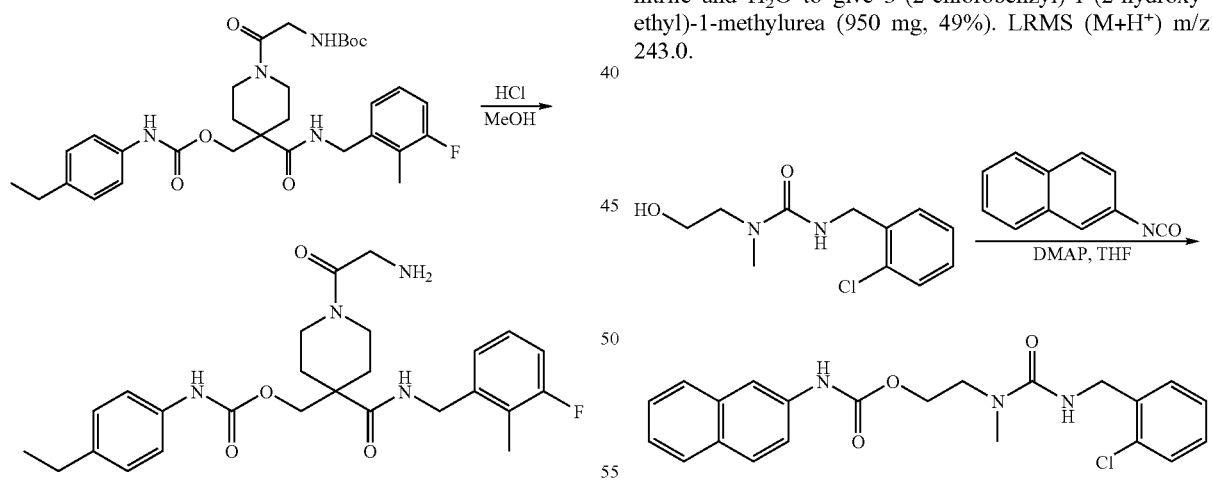

To a solution of give (1-(2-(tert-butoxycarbonylamino)acetyl)-4-(3-fluoro-2-methylbenzylcarbamoyl)piperidin-4-yl)methyl 4-ethylphenylcarbamate (12 mg, 0.021 mmol, 1.0 equiv.) in CH$_2$Cl$_2$ (1 mL) was added 4N HCl (1 mL). The mixture was stirred at rt for about 1 h and concentrated to dryness. The resulting residue was purified on RP-HPLC using a mixture of acetonitrile and H$_2$O to give (1-(2-aminoacetyl)-4-(3-fluoro-2-methylbenzylcarbamoyl)piperidin-4-yl)methyl 4-ethylphenylcarbamate (8 mg, 79%). LRMS (M+H$^+$) m/z 485.1.

Example IX

Preparation of 2-(3-(2-chlorobenzyl)-1-methylureido)ethyl naphthalen-2-ylcarbamate 2-(3-(2-chlorobenzyl)-1-methylureido)ethyl naphthalen-2-ylcarbamate To a solution of 2-(methylamino)ethanol (600 mg, 7.99 mmol) in THF (5.0 mL) was added 2-chlorobenzylisocyanate (0.75 mL, 6.66 mmol). The reaction was stirred at rt for 30 min. The mixture was concentrated, re-dissolved in MeOH, filtered, and purified on RP-HPLC using a mixture of acetonitrile and H$_2$O to give 3-(2-chlorobenzyl)-1-(2-hydroxyethyl)-1-methylurea (950 mg, 49%). LRMS (M+H$^+$) m/z 243.0.

To a solution of 3-(2-chlorobenzyl)-1-(2-hydroxyethyl)-1-methylurea (120 mg, 0.50 mmol) in THF (1.0 mL) were added DMAP (3.0 mg, 0.02) and 2-isocyanatonaphthalene (100 mg, 0.60 mmol). The reaction mixture was stirred for 30 min. LC/MS indicated the completion of the reaction. The mixture was filtered and the filtrate was purified by RP-HPLC using a mixture of acetonitrile and H$_2$O to give 2-(3-(2-chlorobenzyl)-1-methylureido)ethyl naphthalen-2-ylcarbamate (165 mg, 80%). LRMS (M-Boc+H$^+$) m/z 412.1.

Example X

Preparation of 2-(3-(2,3-dichlorobenzyl)-1-methylureido)ethyl 4-ethylphenylcarbamate

Example XI

Preparation of 2-(3-(2-chlorobenzyl)-1-(2-hydroxyethyl)ureido)ethyl 4-ethylphenylcarbamate

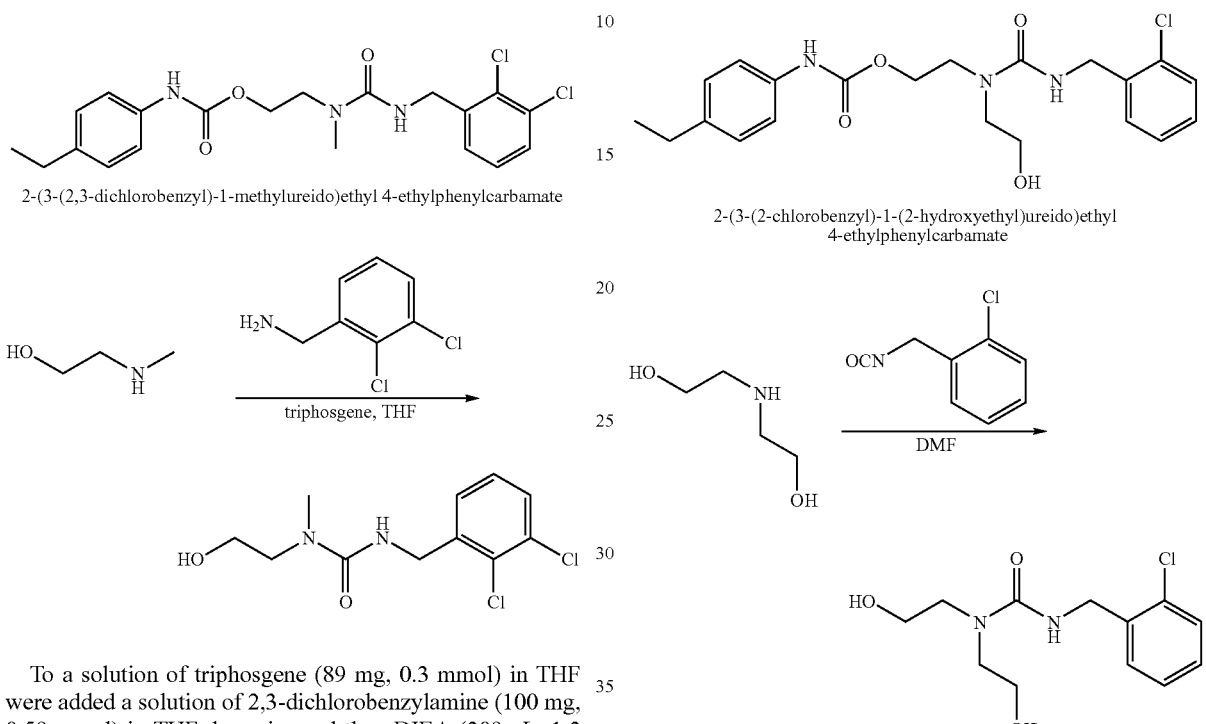

2-(3-(2,3-dichlorobenzyl)-1-methylureido)ethyl 4-ethylphenylcarbamate 2-(3-(2-chlorobenzyl)-1-(2-hydroxyethyl)ureido)ethyl 4-ethylphenylcarbamate To a solution of triphosgene (89 mg, 0.3 mmol) in THF were added a solution of 2,3-dichlorobenzylamine (100 mg, 0.59 mmol) in THF dropwise and then DIEA (209 µL, 1.2 mmol). The reaction mixture was stirred at rt for 10 min, and 2-(methylamino)ethanol (90 mg, 1.2 mmol) was added. The reaction mixture was stirred at rt for 15 min and purified on RP-HPLC using a mixture of acetonitrile and $H_2O$ to give 3-(2,3-dichlorobenzyl)-1-(2-hydroxyethyl)-1-methylurea (70 mg, 44%). LRMS (M+H$^+$) m/z 277.1.

To a solution of 2,2'-azanediyldiethanol (1.58 g, 15 mmol) in DMF (5 mL) was added 2-chlorobenzylisocyanate (1.26 g, 7.5 mmol). The reaction mixture was stirred at rt for 30 min. The mixture was purified on RP-HPLC using a mixture of acetonitrile and $H_2O$ to give 3-(2-chlorobenzyl)-1,1-bis(2-hydroxyethyl)urea (1.3 g, 65%). LRMS (M+H$^+$) m/z 272.1.

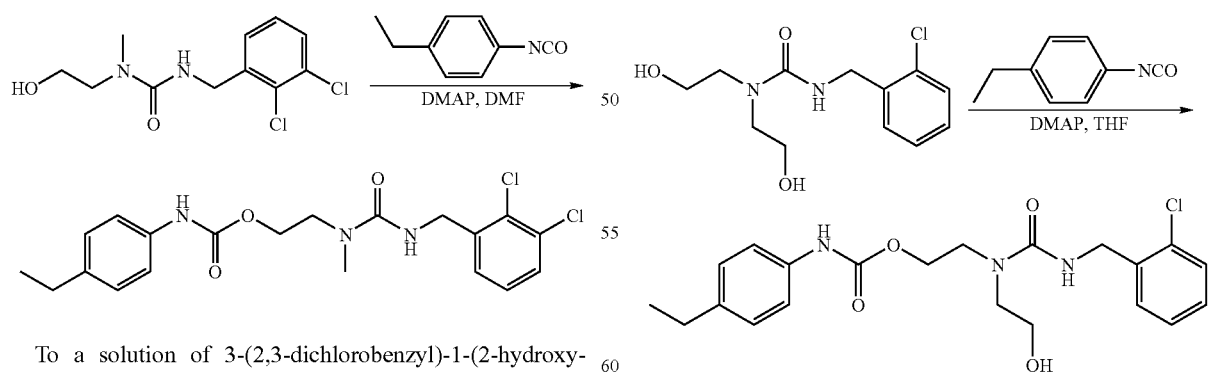

To a solution of 3-(2,3-dichlorobenzyl)-1-(2-hydroxyethyl)-1-methylurea (70 mg, 0.27 mmol) in DMF were added DMAP and 4-ethylphenylisocyanate (80 mg, 0.54 mmol). The reaction mixture was stirred overnight. The reaction mixture was concentrated. The resulting residue was purified on RP-HPLC using a mixture of acetonitrile and $H_2O$ to give 2-(3-(2,3-dichlorobenzyl)-1-methylureido)ethyl 4-ethylphenylcarbamate (7 mg, 6.5%). LRMS (M+H$^+$) m/z 424.1.

To a solution of 3-(2-chlorobenzyl)-1,1-bis(2-hydroxyethyl)urea (2.3 g, 8.46 mmol), in THF were added DMAP and 4-ethylphenylisocyanate (1.24 g, 8.46 mmol). The reaction mixture was stirred for 1 h and concentrated. The resulting residue was purified on RP-HPLC using a mixture of acetonitrile and H₂O to give 2-(3-(2-chlorobenzyl)-1-(2-hydroxyethyl)ureido)ethyl 4-ethylphenylcarbamate (1.7 g, 48%). LRMS (M+H⁺) m/z 420.1.

Example XII

Preparation of ((2S,4R)-4-(2-aminoacetamido)-1-(2-chlorobenzylcarbamoyl)pyrrolidin-2-yl)methyl 4-ethylphenylcarbamate

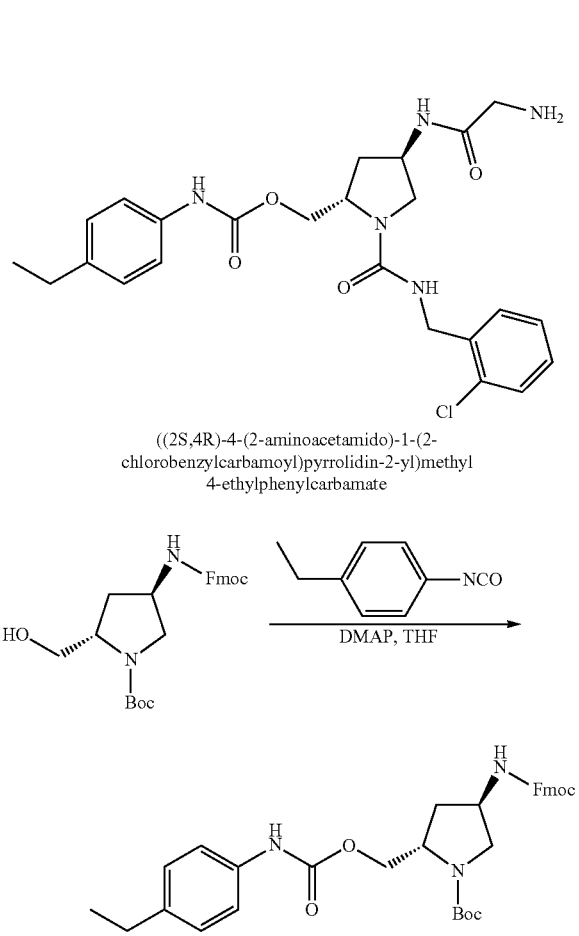

((2S,4R)-4-(2-aminoacetamido)-1-(2-chlorobenzylcarbamoyl)pyrrolidin-2-yl)methyl 4-ethylphenylcarbamate

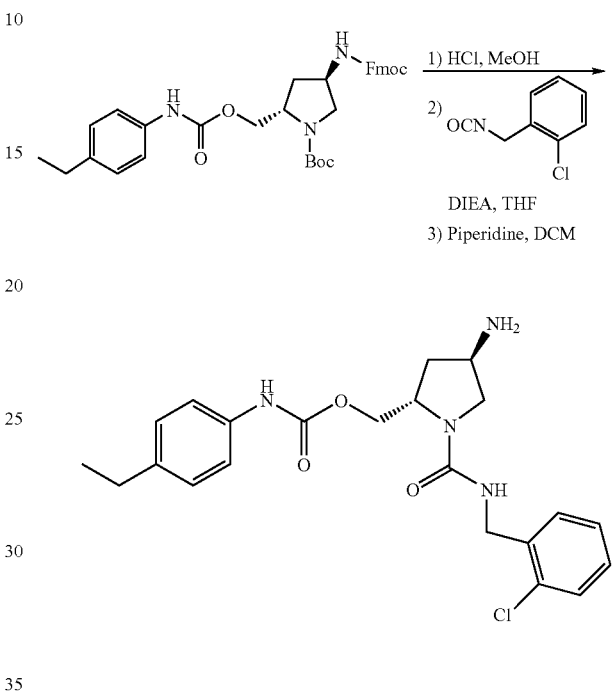

To a solution of (2S,4R)-tert-butyl 4-(((9H-fluoren-9-yl)methoxy)carbonylamino)-2-(hydroxymethyl)pyrrolidine-1-carboxylate (403 mg, 0.92 mmol) and DMAP (134 mg, 1.1 mmol) in THF (10 mL) was added 4-ethylphenyl isocyanate (162 mg, 11 mmol). The reaction mixture was stirred at rt overnight and concentrated to give (2S,4R)-tert-butyl 4-(((9H-fluoren-9-yl)methoxy)carbonylamino)-2-((4-ethylphenylcarbamoyloxy)methyl)pyrrolidine-1-carboxylate, which was used without further purification. LRMS (M+H⁺) m/z 585.1.

To a solution of crude (2S,4R)-tert-butyl 4-(((9H-fluoren-9-yl)methoxy)carbonylamino)-2-((4-ethylphenylcarbamoyloxy)methyl)pyrrolidine-1-carboxylate in MeOH was added HCl (4 N in dioxane). The reaction was stirred at rt for 1 h and concentrated. The residue was dissolved in THF (10 mL). To this solution were added DIEA (469 µL, 2.7 mmol) and 2-chlorobenzylisocyanate. The mixture was stirred at rt for 1 h and concentrated. The residue was dissolved in 10 ml of 20% piperidine in DCM. The reaction mixture was stirred at rt for 15 min, concentrated and purified on RP-HPLC using a mixture of acetonitrile and H₂O to give ((2S,4R)-4-amino-1-(2-chlorobenzylcarbamoyl)pyrrolidin-2-yl)methyl 4-ethylphenylcarbamate (210 mg, 53% for 4 steps). LRMS (M+H⁺) m/z 431.1.

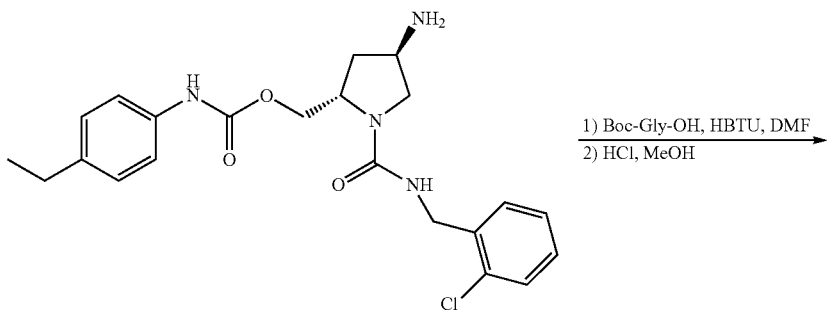

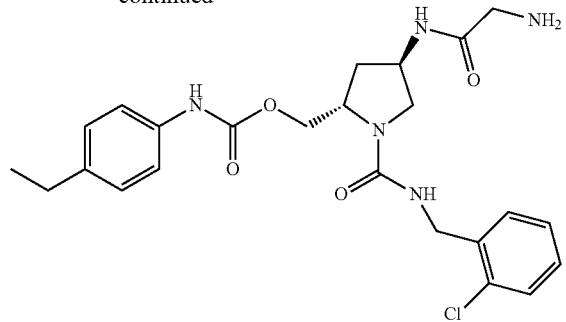

15

To a solution of ((2S,4R)-4-amino-1-(2-chlorobenzylcarbamoyl)pyrrolidin-2-yl)methyl 4-ethylphenylcarbamate (60 mg, 0.14 mmol) in DMF were added Boc-Gly-OH (37 mg, 0.21 mmol) and HBTU (80 mg, 0.21 mmol). The reaction mixture was stirred at rt overnight and purified on RP-HPLC using a mixture of acetonitrile and H$_2$O. The fraction containing the product was combined and concentrated. The residue was dissolved in MeOH and 4N HCl in dioxane. The reaction mixture was stirred at rt for 1 h and concentrated to give ((2S,4R)-4-(2-aminoacetamido)-1-(2-chlorobenzylcarbamoyl)pyrrolidin-2-yl)methyl 4-ethylphenylcarbamate (37 mg, 51%). LRMS (M+H$^+$) m/z 488.1.

Example XIII

Additional Synthesized Compounds

Using procedures similar to those described herein, the compounds in the following table were synthesized and tested.

| IC50 Arithmetic Mean | Ion | m/z | MW | ChemicalName |
|---|---|---|---|---|
| 8.821 | M + H$^+$ | 388.1 | 387.9 | N-[(2-chlorophenyl)methyl]-3-{[(4-ethylphenyl)amino]carbonylamino}-2,2-dimethylpropanamide |
| 4.273 | M + H$^+$ | 445.1 | 444.91 | (4-{[N-(4-acetylphenyl)carbamoyloxy]methyl}(2H-3,4,5,6-tetrahydropyran-4-yl))-N-[(2-chlorophenyl)methyl]carboxamide |
| 17.331 | M + H$^+$ | 437.0 | 437.32 | (4-{[N-(2-chlorophenyl)carbamoyloxy]methyl}(2H-3,4,5,6-tetrahydropyran-4-yl))-N-[(2-chlorophenyl)methyl]carboxamide |
| 19.039 | M + H$^+$ | 433.1 | 432.9 | N-[(2-chlorophenyl)methyl](4-{[N-(3-methoxyphenyl)carbamoyloxy]methyl}(2H-3,4,5,6-tetrahydropyran-4-yl))carboxamide |
| 13.723 | M + H$^+$ | 418.1 | 417.89 | 2-(acetylamino)-N-[(2-chlorophenyl)methyl]-3-[N-(4-ethylphenyl)carbamoyloxy]propanamide |
| 6.388 | M + H$^+$ | 475.1 | 474.93 | ethyl 4-{[(4-{N-[(2-chlorophenyl)methyl]carbamoyl}-2H-3,4,5,6-tetrahydropyran-4-yl)methoxy]carbonylamino}benzoate |
| 0.697 | M + H$^+$ | 417.0 | 416.9 | N-[(2-chlorophenyl)methyl](4-{[N-(4-methylphenyl)carbamoyloxy]methyl}(2H-3,4,5,6-tetrahydropyran-4-yl))carboxamide |
| 1.135 | M + H$^+$ | 471.1 | 470.87 | N-[(2-chlorophenyl)methyl][4-({N-[4-(trifluoromethyl)phenyl]carbamoyloxy}methyl)(2H-3,4,5,6-tetrahydropyran-4-yl)]carboxamide |
| 17.023 | M + H$^+$ | 428.1 | 427.88 | N-[(2-chlorophenyl)methyl](4-{[N-(2-cyanophenyl)carbamoyloxy]methyl}(2H-3,4,5,6-tetrahydropyran-4-yl))carboxamide |
| 7.628 | M + H$^+$ | 445.2 | 444.95 | N-[(2-chlorophenyl)methyl](4-{[N-(4-ethylphenyl)-N-methylcarbamoyloxy]methyl}(2H-3,4,5,6-tetrahydropyran-4-yl))carboxamide |
| 3.555 | M + H$^+$ | 461.1 | 460.91 | methyl 4-{[(4-{N-[(2-chlorophenyl)methyl]carbamoyl}-2H-3,4,5,6-tetrahydropyran-4-yl)methoxy]carbonylamino}benzoate |
| 3.915 | M + H$^+$ | 500.0 | 500.01 | N-[(2-chlorophenyl)methyl][4-({N-[4-(2-methyl(1,3-thiazol-4-yl))phenyl]carbamoyloxy}methyl)(2H-3,4,5,6-tetrahydropyran-4-yl)]carboxamide |
| 2.215 | M + H$^+$ | 435.1 | 434.89 | N-[(2-chlorophenyl)methyl](4-{[N-(3-fluoro-4-methylphenyl)carbamoyloxy]methyl}(2H-3,4,5,6-tetrahydropyran-4-yl))carboxamide |
| 0.361 | M + H$^+$ | 443.1 | 442.94 | N-[(2-chlorophenyl)methyl]{4-[(N-indan-5-ylcarbamoyloxy)methyl](2H-3,4,5,6-tetrahydropyran-4-yl)}carboxamide |
| 14.25 | M + H$^+$ | 435.1 | 434.89 | N-[(2-chlorophenyl)methyl](4-{[N-(6-fluoro-2-methylphenyl)carbamoyloxy]methyl}(2H-3,4,5,6-tetrahydropyran-4-yl))carboxamide |
| 16.159 | M + H$^+$ | 451.0 | 451.34 | (4-{[N-(3-chloro-2-methylphenyl)carbamoyloxy]methyl}(2H-3,4,5,6-tetrahydropyran-4-yl))-N-[(2-chlorophenyl)methyl]carboxamide |

-continued

| IC50 Arithmetic Mean | Ion | m/z | MW | ChemicalName |
|---|---|---|---|---|
| 12.137 | M + H+ | 485.0 | 484.9 | N-[(2-chlorophenyl)methyl][4-({N-[4-methyl-3-(trifluoromethyl)phenyl]carbamoyloxy}methyl)(2H-3,4,5,6-tetrahydropyran-4-yl)]carboxamide |
| 2.335 | M + H+ | 431.1 | 430.92 | (4-{[N-(3,4-dimethylphenyl)carbamoyloxy]methyl}(2H-3,4,5,6-tetrahydropyran-4-yl))-N-[(2-chlorophenyl)methyl]carboxamide |
| 1.961 | M + H+ | 451.0 | 451.34 | (4-{[N-(3-chloro-4-methylphenyl)carbamoyloxy]methyl}(2H-3,4,5,6-tetrahydropyran-4-yl))-N-[(2-chlorophenyl)methyl]carboxamide |
| 0.498 | M + H+ | 445.1 | 444.95 | N-[(2-chlorophenyl)methyl][4-({N-[4-(methylethyl)phenyl]carbamoyloxy}methyl)(2H-3,4,5,6-tetrahydropyran-4-yl)]carboxamide |
| 18.341 | M + H+ | 471.0 | 471.76 | (4-{[N-(3,5-dichlorophenyl)carbamoyloxy]methyl}(2H-3,4,5,6-tetrahydropyran-4-yl))-N-[(2-chlorophenyl)methyl]carboxamide |
| 1.262 | M + H+ | 431.1 | 430.92 | (4-{[N-(2,4-dimethylphenyl)carbamoyloxy]methyl}(2H-3,4,5,6-tetrahydropyran-4-yl))-N-[(2-chlorophenyl)methyl]carboxamide |
| 18.559 | M + H+ | 459.1 | 459.92 | methyl 3-{N-[(2-chlorophenyl)methyl]carbamoyl}-3-{[(4-ethylphenyl)amino]carbonylamino}pyrrolidinecarboxylate |
| 5.229 | M + H+ | 447.1 | 446.92 | N-[(2-chlorophenyl)methyl][4-({N-[4-(hydroxyethyl)phenyl]carbamoyloxy}methyl)(2H-3,4,5,6-tetrahydropyran-4-yl)]carboxamide |
| 15.244 | M + H+ | 403.1 | 402.87 | N-[(2-chlorophenyl)methyl]{4-[(N-phenylcarbamoyloxy)methyl](2H-3,4,5,6-tetrahydropyran-4-yl)}carboxamide |
| 16.101 | M + H+ | 446.1 | 445.9 | 4-{[(4-{N-[(2-chlorophenyl)methyl]carbamoyl}-2H-3,4,5,6-tetrahydropyran-4-yl)methoxy]carbonylamino}benzamide |
| 18.192 | M + H+ | 429.1 | 428.95 | N-[(2-chlorophenyl)methyl][4-({[(4-ethylphenyl)amino]carbonylamino}methyl)(4-piperidyl)]carboxamide |
| 1.879 | M + H+ | 487.1 | 486.99 | N-[(2-chlorophenyl)methyl][4-({[(4-ethylphenyl)amino]carbonylamino}methyl)-1-(2-hydroxyacetyl)(4-piperidyl)]carboxamide |
| 18.738 | M + H+ | 501.1 | 501.02 | N-[(2-chlorophenyl)methyl][4-({[(4-ethylphenyl)amino]-N-methylcarbonylamino}methyl)-1-(2-hydroxyacetyl)(4-piperidyl)]carboxamide |
| 3.138 | M + H+ | 432.0 | 431.91 | 2-(acetylamino)-N-[(2-chlorophenyl)methyl]-3-[N-(4-ethylphenyl)carbamoyloxy]-2-methylpropanamide |
| 4.088 | M + H+ | 448.1 | 447.91 | N-[(2-chlorophenyl)methyl]-3-[N-(4-ethylphenyl)carbamoyloxy]-2-(methoxycarbonylamino)-2-methylpropanamide |
| 9.184 | M + H+ | 448.0 | 447.91 | N-[(2-chlorophenyl)methyl]-3-[N-(4-ethylphenyl)carbamoyloxy]-2-(2-hydroxyacetylamino)-2-methylpropanamide |
| 19.38 | M + H+ | 547.1 | 547.04 | 2-{2-[(tert-butoxy)carbonylamino]acetylamino}-N-[(2-chlorophenyl)methyl]-3-[N-(4-ethylphenyl)carbamoyloxy]-2-methylpropanamide |
| 3.988 | M + H+ | 447.1 | 446.93 | 2-(2-aminoacetylamino)-N-[(2-chlorophenyl)methyl]-3-[N-(4-ethylphenyl)carbamoyloxy]-2-methylpropanamide |
| 11.172 | M + H+ | 477.1 | 476.95 | 2-((2S)-2-amino-3-hydroxypropanoylamino)-N-[(2-chlorophenyl)methyl]-3-[N-(4-ethylphenyl)carbamoyloxy]-2-methylpropanamide |
| 13.086 | M + H+ | 473.3 | 473.01 | {1-(2-aminoacetyl)-4-({[(2-chlorophenyl)methyl]amino}methyl)(4-piperidyl)]methoxy}-N-(4-ethylphenyl)carboxamide |
| 12.353 | M + H+ | 558.1 | 558.11 | N-[(1-(2-aminoacetyl)-4-{N-[(2-chlorophenyl)methyl]carbamoyl}(4-piperidyl))methyl][(4-ethylphenyl)amino]-N-(3-methoxypropyl)carboxamide |
| 16.385 | | | 529.07 | N-[(1-(2-aminoacetyl)-4-{N-[(2-chlorophenyl)methyl]carbamoyl}(4-piperidyl))methyl]-N-(2-aminoethyl)[(4-ethylphenyl)amino]carboxamide |
| 19.481 | M + H+ | 729.3 | 729.31 | (tert-butoxy)-N-(2-{N-[(1-{2-[(tert-butoxy)carbonylamino]acetyl}-4-{N-[(2-chlorophenyl)methyl]carbamoyl}(4-piperidyl))methyl][(4-ethylphenyl)amino]carbonylamino}ethyl)carboxamide |
| 15.319 | | | 464.6 | 3-(1-(2-aminoacetyl)-4-{N-[(2-methylphenyl)methyl]carbamoyl}(4-piperidyl))-N-(4-ethylphenyl)propanamide |
| 1.632 | M + H+ | 390.1 | 389.88 | N-{(1S)-2-[N-(4-ethylphenyl)carbamoyloxy]-isopropyl}{[(2-chlorophenyl)methyl]amino}carboxamide |
| 18.521 | M-tBu + H+ | 448.1 | 504.02 | tert-butyl 2-(N-{(1S)-2-[N-(4-ethylphenyl)carbamoyloxy]-isopropyl}{[(2-chlorophenyl)methyl]amino}carbonylamino)acetate |
| 1.67 | M-H2O + H+ | 430.1 | 447.91 | 2-(N-{(1S)-2-[N-(4-ethylphenyl)carbamoyloxy]-isopropyl}{[(2-chlorophenyl)methyl]amino}carbonylamino)acetic acid |
| 0.148 | M + H+ | 404.1 | 403.9 | N-{(1S)-2-[N-(4-ethylphenyl)carbamoyloxy]-isopropyl}{[(2-chlorophenyl)methyl]amino}-N-methylcarboxamide |
| 6.814 | M + H+ | 404.1 | 403.9 | [(2R)-2-({[(2-chlorophenyl)methyl]amino}-N-methylcarbonylamino)propoxy]-N-(4-ethylphenyl)carboxamide |
| 0.198 | M + H+ | 418.1 | 417.93 | N-{(1S)-3-[N-(4-ethylphenyl)carbamoyloxy]-1-methylpropyl}{[(2-chlorophenyl)methyl]amino}-N-methylcarboxamide |

-continued

| IC50 Arithmetic Mean | Ion | m/z | MW | ChemicalName |
|---|---|---|---|---|
| 6.071 | M + H⁺ | 418.0 | 417.93 | {[(2-chlorophenyl)methyl]amino}-N-{4-[N-(4-ethylphenyl)carbamoyloxy]butyl}-N-methylcarboxamide |
| 1.669 | M + H⁺ | 404.1 | 403.9 | {[(2-chlorophenyl)methyl]amino}-N-{3-[N-(4-ethylphenyl)carbamoyloxy]propyl}-N-methylcarboxamide |
| 18.247 | M + H⁺ | 533.1 | 533.06 | (tert-butoxy)-N-[2-({[(2-chlorophenyl)methyl]amino}-N-{2-[N-(4-ethylphenyl)carbamoyloxy]ethyl}carbonylamino)ethyl]-N-methylcarboxamide |
| 16.325 | M + H⁺ | 433.1 | 432.94 | {[(2-chlorophenyl)methyl]amino}-N-{2-[N-(4-ethylphenyl)carbamoyloxy]ethyl}-N-[2-(methylamino)ethyl]carboxamide |
| 5.856 | M + H⁺ | 490.1 | 489.99 | 2-amino-N-[2-({[(2-chlorophenyl)methyl]amino}-N-{2-[N-(4-ethylphenyl)carbamoyloxy]ethyl}carbonylamino)ethyl]-N-methylacetamide |
| 15.008 | M + H⁺ | 530.1 | 529.94 | 2-amino-N-{2-[{[(2-chlorophenyl)methyl]amino}-N-(2-{N-[4-(trifluoromethyl)phenyl]carbamoyloxy}ethyl)carbonylamino]ethyl}-N-methylacetamide |
| 8.52 | M + H⁺ | 404.3 | 403.9 | [2-({[(2-chlorophenyl)methyl]amino}-N-methylcarbonylamino)-isopropoxy]-N-(4-ethylphenyl)carboxamide |
| 0.248 | M + H⁺ | 438.1 | 437.92 | {[(2-chlorophenyl)methyl]amino}-N-methyl-N-{2-[N-(4-phenylphenyl)carbamoyloxy]ethyl}carboxamide |
| 0.03 | M + H⁺ | 412.1 | 411.88 | {[(2-chlorophenyl)methyl]amino}-N-methyl-N-[2-(N-(2-naphthyl)carbamoyloxy)ethyl]carboxamide |
| 0.875 | M + H⁺ | 389.1 | 388.89 | 3-(2-chlorophenyl)-N-{2-[N-(4-ethylphenyl)carbamoyloxy]ethyl}-N-methylpropanamide |
| 17.505 | M + H⁺ | 439.1 | 438.44 | N-{2-[N-(4-ethylphenyl)carbamoyloxy]ethyl}-2-hydroxy-N-methyl-3-[2-(trifluoromethyl)phenyl]propanamide |
| 1.21 | M + H⁺ | 423.1 | 422.44 | N-{2-[N-(4-ethylphenyl)carbamoyloxy]ethyl}-N-methyl-3-[2-(trifluoromethyl)phenyl]propanamide |
| 2.075 | M + H⁺ | 404.1 | 403.9 | {[(2-chlorophenyl)methyl]methylamino}-N-{2-[N-(4-ethylphenyl)carbamoyloxy]ethyl}-N-methylcarboxamide |
| 3.69 | M + H⁺ | 377.2 | 376.83 | (2-{N-[(2-chlorophenyl)methyl]carbamoyloxy}ethoxy)-N-(4-ethylphenyl)carboxamide |
| 4.732 | M + H⁺ | 402.2 | 401.93 | N-[(2-chlorophenyl)methyl]-4-{[N-(4-ethylphenyl)carbamoyl]amino}-2,2-dimethylbutanamide |
| 13.629 | M + H⁺ | 374.1 | 373.88 | N-[(2-chlorophenyl)methyl]-2-{[(4-ethylphenyl)amino]carbonylamino}-2-methylpropanamide |
| 2.515 | M + H⁺ | 389.1 | 388.89 | N-[(2-chlorophenyl)methyl]-3-[N-(4-ethylphenyl)carbamoyloxy]-2,2-dimethylpropanamide |
| 5.232 | M + H⁺ | 385.1 | 385.89 | N-[({N-[(2-chlorophenyl)methyl]carbamoyl}cyclopropyl)methyl][(4-ethylphenyl)amino]carboxamide |
| 18.156 | M + H⁺ | 385.1 | 384.9 | N-[({N-[(2-chlorophenyl)methyl]carbamoyl}cyclopropyl)methyl]-2-(4-ethylphenyl)acetamide |
| 1.879 | M + H⁺ | 401.2 | 400.9 | [({N-[(2-chlorophenyl)methyl]carbamoyl}cyclobutyl)methoxy]-N-(4-ethylphenyl)carboxamide |
| 0.238 | M + H⁺ | 429.3 | 428.95 | N-[(2-chlorophenyl)methyl]({[N-(4-ethylphenyl)carbamoyloxy]methyl}cyclohexyl)carboxamide |
| 3.211 | M + H⁺ | 430.2 | 530.06 | tert-butyl 4-{N-[(2-chlorophenyl)methyl]carbamoyl}-4-{[N-(4-ethylphenyl)carbamoyloxy]methyl}piperidinecarboxylate |
| 1.663 | M + H⁺ | 430.2 | 429.94 | N-[(2-chlorophenyl)methyl](4-{[N-(4-ethylphenyl)carbamoyloxy]methyl}(4-piperidyl))carboxamide |
| 2.784 | M + H⁺ | 437.0 | 437.32 | (4-{[N-(4-chlorophenyl)carbamoyloxy]methyl}(2H-3,4,5,6-tetrahydropyran-4-yl))-N-[(2-chlorophenyl)methyl]carboxamide |
| 1.362 | M + H⁺ | 413.1 | 412.91 | N-[(2-chlorophenyl)methyl](1-{[N-(4-ethylphenyl)carbamoyloxy]methyl}cyclopent-3-enyl)carboxamide |
| 5.511 | M + H⁺ | 447.1 | 446.92 | N-[(2-chlorophenyl)methyl](1-{[N-(4-ethylphenyl)carbamoyloxy]methyl}-3,4-dihydroxycyclopentyl)carboxamide |
| 0.53 | M + H⁺ | 488.1 | 487.98 | methyl 4-{N-[(2-chlorophenyl)methyl]carbamoyl}-4-{[N-(4-ethylphenyl)carbamoyloxy]methyl}piperidinecarboxylate |
| 16.807 | M + H⁺ | 414.1 | 413.94 | ((1S,2S)-2-{[(4-ethylphenyl)amino]carbonylamino}cyclohexyl)-N-[(2-chlorophenyl)methyl]carboxamide |
| 0.418 | M + H⁺ | 472.1 | 471.97 | (1-acetyl-4-{[N-(4-ethylphenyl)carbamoyloxy]methyl}(4-piperidyl))-N-[(2-chlorophenyl)methyl]carboxamide |
| 0.496 | M + H⁺ | 508.1 | 508.03 | N-[(2-chlorophenyl)methyl](4-{[N-(4-ethylphenyl)carbamoyloxy]methyl}-1-(methylsulfonyl)(4-piperidyl))carboxamide |
| 0.173 | M + H⁺ | 488.1 | 487.98 | N-[(2-chlorophenyl)methyl](4-{[N-(4-ethylphenyl)carbamoyloxy]methyl}-1-(2-hydroxyacetyl)(4-piperidyl))carboxamide |
| 0.919 | M + H⁺ | 487.1 | 587.11 | (tert-butoxy)-N-[2-(4-{N-[(2-chlorophenyl)methyl]carbamoyl}-4-{[N-(4-ethylphenyl)carbamoyloxy]methyl}piperidyl)-2-oxoethyl]carboxamide |
| 0.481 | M + H⁺ | 616.2 | 615.16 | (tert-butoxy)-N-[4-(4-{N-[(2-chlorophenyl)methyl]carbamoyl}-4-{[N-(4-ethylphenyl)carbamoyloxy]methyl}piperidyl)-4-oxobutyl]carboxamide |

-continued

| IC50 Arithmetic Mean | Ion | m/z | MW | ChemicalName |
|---|---|---|---|---|
| 0.175 | M + H⁺ | 487.1 | 486.99 | (1-(2-aminoacetyl)-4-{[N-(4-ethylphenyl)carbamoyloxy]methyl}(4-piperidyl))-N-[(2-chlorophenyl)methyl]carboxamide |
| 0.246 | M + H⁺ | 515.2 | 515.04 | (1-(4-aminobutanoyl)-4-{[N-(4-ethylphenyl)carbamoyloxy]methyl}(4-piperidyl))-N-[(2-chlorophenyl)methyl]carboxamide |
| 1.511 | M + H⁺ | 501.1 | 601.13 | N-[(1S)-2-(4-{N-[(2-chlorophenyl)methyl]carbamoyl}-4-{[N-(4-ethylphenyl)carbamoyloxy]methyl}piperidyl)-1-methyl-2-oxoethyl](tert-butoxy)carboxamide |
| 0.724 | M + H⁺ | 501.1 | 501.02 | (1-((2S)-2-aminopropanoyl)-4-{[N-(4-ethylphenyl)carbamoyloxy]methyl}(4-piperidyl))-N-[(2-chlorophenyl)methyl]carboxamide |
| 0.426 | M + H⁺ | 545.1 | 544.04 | methyl 4-(4-{N-[(2-chlorophenyl)methyl]carbamoyl}-4-{[N-(4-ethylphenyl)carbamoyloxy]methyl}piperidyl)-4-oxobutanoate |
| 0.492 | M + H⁺ | 516.2 | 516.03 | N-[(2-chlorophenyl)methyl](4-{[N-(4-ethylphenyl)carbamoyloxy]methyl}-1-(4-hydroxybutanoyl)(4-piperidyl))carboxamide |
| 2.261 | M + H⁺ | 416.1 | 415.91 | N-[(2-chlorophenyl)methyl]{3-[N-(4-ethylphenyl)carbamoyloxy]piperidyl}carboxamide |
| 5.544 | M + H⁺ | 396.2 | 395.49 | {3-[N-(4-ethylphenyl)carbamoyloxy]piperidyl}-N-[(2-methylphenyl)methyl]carboxamide |
| 0.302 | M + H⁺ | 487.1 | 486.99 | N-[(2-chlorophenyl)methyl](4-{[N-(4-ethylphenyl)carbamoyloxy]methyl}-1-(N-methylcarbamoyl)(4-piperidyl))carboxamide |
| 0.661 | M-Boc + H⁺ | 517.2 | 617.13 | (tert-butoxy)-N-[2-(4-{N-[(2-chlorophenyl)methyl]carbamoyl}-4-{[N-(4-ethylphenyl)carbamoyloxy]methyl}piperidyl)-1-(hydroxymethyl)-2-oxoethyl]carboxamide |
| 0.143 | M + H⁺ | 517.1 | 517.02 | (1-(2-amino-3-hydroxypropanoyl)-4-{[N-(4-ethylphenyl)carbamoyloxy]methyl}(4-piperidyl))-N-[(2-chlorophenyl)methyl]carboxamide |
| 11.978 | M-Boc + H⁺ | 501.2 | 601.13 | N-[(1R)-2-(4-{N-[(2-chlorophenyl)methyl]carbamoyl}-4-{[N-(4-ethylphenyl)carbamoyloxy]methyl}piperidyl)-1-methyl-2-oxoethyl](tert-butoxy)carboxamide |
| 0.255 | M + H⁺ | 501.2 | 501.02 | (1-((2R)-2-aminopropanoyl)-4-{[N-(4-ethylphenyl)carbamoyloxy]methyl}(4-piperidyl))-N-[(2-chlorophenyl)methyl]carboxamide |
| 0.54 | M + H⁺ | 529.2 | 529.07 | (1-(2-amino-3-methylbutanoyl)-4-{[N-(4-ethylphenyl)carbamoyloxy]methyl}(4-piperidyl))-N-[(2-chlorophenyl)methyl]carboxamide |
| 3.549 | M-Boc + H⁺ | 541.1 | 641.2 | tert-butyl 4-[(4-{N-[(2-chlorophenyl)methyl]carbamoyl}-4-{[N-(4-ethylphenyl)carbamoyloxy]methyl}piperidyl)carbonyl]piperidinecarboxylate |
| 0.808 | M + H⁺ | 541.2 | 541.08 | N-[(2-chlorophenyl)methyl](4-{[N-(4-ethylphenyl)carbamoyloxy]methyl}-1-(4-piperidylcarbonyl)(4-piperidyl))carboxamide |
| 1.679 | M + H⁺ | 643.3 | 643.17 | tert-butyl 3-[(4-{N-[(2-chlorophenyl)methyl]carbamoyl}-4-{[N-(4-ethylphenyl)carbamoyloxy]methyl}piperidyl)carbonyl]morpholine-4-carboxylate |
| 0.515 | M + H⁺ | 543.2 | 543.05 | N-[(2-chlorophenyl)methyl](4-{[N-(4-ethylphenyl)carbamoyloxy]methyl}-1-(morpholin-3-ylcarbonyl)(4-piperidyl))carboxamide |
| 14.41 | M + H⁺ | 520.2 | 520.06 | N-[(2-chlorophenyl)methyl](4-{[N-(4-ethylphenyl)carbamoyloxy]methyl}-1-benzyl(4-piperidyl))carboxamide |
| 6.276 | M + H⁺ | 458.1 | 457.99 | N-[(2-chlorophenyl)methyl](1-ethyl-4-{[N-(4-ethylphenyl)carbamoyloxy]methyl}(4-piperidyl))carboxamide |
| 1.52 | M + H⁺ | 503.4 | 502 | methyl 2-(4-{N-[(2-chlorophenyl)methyl]carbamoyl}-4-{[N-(4-ethylphenyl)carbamoyloxy]methyl}piperidyl)acetate |
| 0.275 | M + H⁺ | 546.2 | 546.05 | N-[(2-chlorophenyl)methyl](4-{[N-(4-ethylphenyl)carbamoyloxy]methyl}-1-[3-hydroxy-2-(hydroxymethyl)-2-methylpropanoyl](4-piperidyl))carboxamide |
| 4.036 | M + H⁺ | 474.1 | 473.99 | N-[(2-chlorophenyl)methyl](4-{[N-(4-ethylphenyl)carbamoyloxy]methyl}-1-(2-hydroxyethyl)(4-piperidyl))carboxamide |
| 0.67 | M + H⁺ | 515.2 | 515.04 | (1-(2-amino-2-methylpropanoyl)-4-{[N-(4-ethylphenyl)carbamoyloxy]methyl}(4-piperidyl))-N-[(2-chlorophenyl)methyl]carboxamide |
| 0.213 | M + H⁺ | 501.2 | 501.02 | N-[(2-chlorophenyl)methyl](4-{[N-(4-ethylphenyl)carbamoyloxy]methyl}-1-[2-(methylamino)acetyl](4-piperidyl))carboxamide |
| 4.928 | M + H⁺ | 444.1 | 443.97 | N-[(2-chlorophenyl)methyl](4-{[N-(4-ethylphenyl)carbamoyloxy]methyl}-1-methyl(4-piperidyl))carboxamide |
| 3.502 | M-Boc + H⁺ | 517.1 | 617.13 | N-[(1R)-2-(4-{N-[(2-chlorophenyl)methyl]carbamoyl}-4-{[N-(4-ethylphenyl)carbamoyloxy]methyl}piperidyl)-1-(hydroxymethyl)-2-oxoethyl](tert-butoxy)carboxamide |

-continued

| IC50 Arithmetic Mean | Ion | m/z | MW | ChemicalName |
|---|---|---|---|---|
| 0.164 | M + H$^+$ | 517.2 | 517.02 | (1-((2R)-2-amino-3-hydroxypropanoyl)-4-{[N-(4-ethylphenyl)carbamoyloxy]methyl}(4-piperidyl))-N-[(2-chlorophenyl)methyl]carboxamide |
| 0.416 | M−Boc + H$^+$ | 517.1 | 617.13 | N-[(1S)-2-(4-{N-[(2-chlorophenyl)methyl]carbamoyl}-4-{[N-(4-ethylphenyl)carbamoyloxy]methyl}piperidyl)-1-(hydroxymethyl)-2-oxoethyl](tert-butoxy)carboxamide |
| 0.125 | M + H$^+$ | 518.2 | 517.02 | (1-((2S)-2-amino-3-hydroxypropanoyl)-4-{[N-(4-ethylphenyl)carbamoyloxy]methyl}(4-piperidyl))-N-[(2-chlorophenyl)methyl]carboxamide |
| 1.162 | M + H$^+$ | 474.1 | 473.01 | (1-(2-aminoethyl)-4-{[N-(4-ethylphenyl)carbamoyloxy]methyl}(4-piperidyl))-N-[(2-chlorophenyl)methyl]carboxamide |
| 0.797 | M + H$^+$ | 526.1 | 526.03 | (1-(2-amino-3-cyanopropanoyl)-4-{[N-(4-ethylphenyl)carbamoyloxy]methyl}(4-piperidyl))-N-[(2-chlorophenyl)methyl]carboxamide |
| 5.936 | M + H$^+$ | 470.1 | 469.88 | N-[(2-chlorophenyl)methyl][4-({N-[4-(trifluoromethyl)phenyl]carbamoyloxy}methyl)(4-piperidyl)]carboxamide |
| 0.274 | M + H$^+$ | 537.1 | 537.07 | (1-[(2-aminoethyl)sulfonyl]-4-{[N-(4-ethylphenyl)carbamoyloxy]methyl}(4-piperidyl))-N-[(2-chlorophenyl)methyl]carboxamide |
| 1.023 | M + H$^+$ | 516.1 | 516.03 | (1-(2,3-diaminopropanoyl)-4-{[N-(4-ethylphenyl)carbamoyloxy]methyl}(4-piperidyl))-N-[(2-chlorophenyl)methyl]carboxamide |
| 0.585 | M + H$^+$ | 530.2 | 530.06 | (1-(2,4-diaminobutanoyl)-4-{[N-(4-ethylphenyl)carbamoyloxy]methyl}(4-piperidyl))-N-[(2-chlorophenyl)methyl]carboxamide |
| 0.456 | M + H$^+$ | 528.1 | 527.92 | N-[(2-chlorophenyl)methyl][1-(2-hydroxyacetyl)-4-({N-[4-(trifluoromethyl)phenyl]carbamoyloxy}methyl)(4-piperidyl)]carboxamide |
| 0.285 | M + H$^+$ | 527.1 | 526.94 | [1-(2-aminoacetyl)-4-({N-[4-(trifluoromethyl)phenyl]carbamoyloxy}methyl)(4-piperidyl)]-N-[(2-chlorophenyl)methyl]carboxamide |
| 0.138 | M + H$^+$ | 557.1 | 556.96 | [1-((2S)-2-amino-3-hydroxypropanoyl)-4-({N-[4-(trifluoromethyl)phenyl]carbamoyloxy}methyl)(4-piperidyl)]-N-[(2-chlorophenyl)methyl]carboxamide |
| 0.486 | M + H$^+$ | 502.2 | 502 | N-[(2-chlorophenyl)methyl](4-{[N-(4-ethylphenyl)carbamoyloxy]methyl}-1-(2-methoxyacetyl)(4-piperidyl))carboxamide |
| 4.829 | M + H$^+$ | 513.2 | 613.14 | tert-butyl 2-[4-{N-[(2-chlorophenyl)methyl]carbamoyl}-4-{[N-(4-ethylphenyl)carbamoyloxy]methyl}piperidyl)carbonyl]azetidinecarboxylate |
| 0.221 | M + H$^+$ | 513.2 | 513.03 | (1-(azetidin-2-ylcarbonyl)-4-{[N-(4-ethylphenyl)carbamoyloxy]methyl}(4-piperidyl))-N-[(2-chlorophenyl)methyl]carboxamide |
| 0.606 | M + H$^+$ | 517.2 | 516.03 | N-[(2-chlorophenyl)methyl](4-{[N-(4-ethylphenyl)carbamoyloxy]methyl}-1-(3-methoxypropanoyl)(4-piperidyl))carboxamide |
| 1.495 | M + H$^+$ | 544.1 | 544.09 | (1-(2,5-diaminopentanoyl)-4-{[N-(4-ethylphenyl)carbamoyloxy]methyl}(4-piperidyl))-N-[(2-chlorophenyl)methyl]carboxamide |
| 1.564 | M + H$^+$ | 416.1 | 415.91 | {(3R)-3-[N-(4-ethylphenyl)carbamoyloxy]piperidyl}-N-[(2-chlorophenyl)methyl]carboxamide |
| 0.412 | M + H$^+$ | 535.2 | 534.05 | N-[(2-chlorophenyl)methyl](4-{[N-(4-ethylphenyl)carbamoyloxy]methyl}-1-(phenylcarbonyl)(4-piperidyl))carboxamide |
| 0.695 | M + H$^+$ | 536.2 | 535.03 | N-[(2-chlorophenyl)methyl](4-{[N-(4-ethylphenyl)carbamoyloxy]methyl}-1-(3-pyridylcarbonyl)(4-piperidyl))carboxamide |
| 6.184 | M−Boc + H$^+$ | 515.2 | 615.16 | (tert-butoxy)-N-[2-(4-{N-[(2-chlorophenyl)methyl]carbamoyl}-4-{[N-(4-ethylphenyl)carbamoyloxy]methyl}piperidyl)-1-methyl-2-oxoethyl]-N-methylcarboxamide |
| 1.784 | M + H$^+$ | 516.1 | 515.04 | N-[(2-chlorophenyl)methyl](4-{[N-(4-ethylphenyl)carbamoyloxy]methyl}-1-[2-(methylamino)propanoyl](4-piperidyl))carboxamide |
| 18.544 | M + H$^+$ | 387.1 | 386.91 | N-[(2-chlorophenyl)methyl]-N'-(4-ethylphenyl)-2,2-dimethylpentane-1,5-diamide |
| 1.119 | M−Me + H$^+$ | 545.2 | 559.05 | methyl (3S)-3-amino-4-(4-{N-[(2-chlorophenyl)methyl]carbamoyl}-4-{[N-(4-ethylphenyl)carbamoyloxy]methyl}piperidyl)-4-oxobutanoate |
| 0.12 | M + H$^+$ | 517.2 | 517.02 | (1-(3-amino-2-hydroxypropanoyl)-4-{[N-(4-ethylphenyl)carbamoyloxy]methyl}(4-piperidyl))-N-[(2-chlorophenyl)methyl]carboxamide |
| 0.187 | M + H$^+$ | 532.2 | 531.04 | (1-(4-amino-2-hydroxybutanoyl)-4-{[N-(4-ethylphenyl)carbamoyloxy]methyl}(4-piperidyl))-N-[(2-chlorophenyl)methyl]carboxamide |

-continued

| IC50 Arithmetic Mean | Ion | m/z | MW | ChemicalName |
|---|---|---|---|---|
| 0.123 | M + H⁺ | 518.2 | 518 | (1-(2,3-dihydroxypropanoyl)-4-{[N-(4-ethylphenyl)carbamoyloxy]methyl}(4-piperidyl))-N-[(2-chlorophenyl)methyl]carboxamide |
| 10.197 | M + H⁺ | 416.1 | 415.91 | {(3S)-3-[N-(4-ethylphenyl)carbamoyloxy]piperidyl}-N-[(2-chlorophenyl)methyl]carboxamide |
| 1.526 | M + H⁺ | 545.1 | 545.03 | 3-amino-4-(4-{N-[(2-chlorophenyl)methyl]carbamoyl}-4-{[N-(4-ethylphenyl)carbamoyloxy]methyl}piperidyl)-4-oxobutanoic acid |
| 0.641 | M + H⁺ | 499.3 | 498.01 | N-[(2-chlorophenyl)methyl](1-(cyclopropylcarbonyl)-4-{[N-(4-ethylphenyl)carbamoyloxy]methyl}(4-piperidyl))carboxamide |
| 2.766 | M + H⁺ | 540.2 | 540.09 | N-[(2-chlorophenyl)methyl](1-(cyclohexylcarbonyl)-4-{[N-(4-ethylphenyl)carbamoyloxy]methyl}(4-piperidyl))carboxamide |
| 0.757 | M + H⁺ | 535.1 | 535.03 | N-[(2-chlorophenyl)methyl](4-{[N-(4-ethylphenyl)carbamoyloxy]methyl}-1-(2-pyridylcarbonyl)(4-piperidyl))carboxamide |
| 0.394 | M + H⁺ | 524.1 | 524.01 | N-[(2-chlorophenyl)methyl](4-{[N-(4-ethylphenyl)carbamoyloxy]methyl}-1-(imidazol-2-ylcarbonyl)(4-piperidyl))carboxamide |
| 1.431 | M-Boc + H⁺ | 487.2 | 587.11 | (tert-butoxy)-N-[2-(3-{N-[(2-chlorophenyl)methyl]carbamoyl}-3-{[N-(4-ethylphenyl)carbamoyloxy]methyl}piperidyl)-2-oxoethyl]carboxamide |
| 9.088 | M-Boc + H⁺ | 517.3 | 617.13 | N-[(1S)-2-(3-{N-[(2-chlorophenyl)methyl]carbamoyl}-3-{[N-(4-ethylphenyl)carbamoyloxy]methyl}piperidyl)-1-(hydroxymethyl)-2-oxoethyl](tert-butoxy)carboxamide |
| 0.474 | M + H⁺ | 487.1 | 486.99 | (1-(2-aminoacetyl)-3-{[N-(4-ethylphenyl)carbamoyloxy]methyl}(3-piperidyl))-N-[(2-chlorophenyl)methyl]carboxamide |
| 0.399 | M + H⁺ | 488.1 | 487.98 | N-[(2-chlorophenyl)methyl](3-{[N-(4-ethylphenyl)carbamoyloxy]methyl}-1-(2-hydroxyacetyl)(3-piperidyl))carboxamide |
| 1.483 | M + H⁺ | 517.3 | 517.02 | (1-((2S)-2-amino-3-hydroxypropanoyl)-3-{[N-(4-ethylphenyl)carbamoyloxy]methyl}(3-piperidyl))-N-[(2-chlorophenyl)methyl]carboxamide |
| 0.336 | M + H⁺ | 517.1 | 517.02 | 2-aminoethyl 4-{N-[(2-chlorophenyl)methyl]carbamoyl}-4-{[N-(4-ethylphenyl)carbamoyloxy]methyl}piperidinecarboxylate |
| 0.159 | M + H⁺ | 516.2 | 516.03 | N-(2-aminoethyl)(4-{N-[(2-chlorophenyl)methyl]carbamoyl}-4-{[N-(4-ethylphenyl)carbamoyloxy]methyl}piperidyl)carboxamide |
| 0.474 | M + H⁺ | 488.1 | 487.98 | methyl 3-{N-[(2-chlorophenyl)methyl]carbamoyl}-3-{[N-(4-ethylphenyl)carbamoyloxy]methyl}piperidinecarboxylate |
| 0.526 | M + H⁺ | 472.1 | 472.96 | (1-(2-aminoacetyl)-3-{[N-(4-ethylphenyl)carbamoyloxy]methyl}pyrrolidin-3-yl)-N-[(2-chlorophenyl)methyl]carboxamide |
| 2.44 | M + H⁺ | 501.2 | 501.02 | (1-(2-aminoacetyl)-4-{2-[N-(4-ethylphenyl)carbamoyloxy]ethyl}(4-piperidyl))-N-[(2-chlorophenyl)methyl]carboxamide |
| 0.44 | M + H⁺ | 561.1 | 561.38 | [1-(2-aminoacetyl)-4-({N-[2-chloro-4-(trifluoromethyl)phenyl]carbamoyloxy}methyl)(4-piperidyl)]-N-[(2-chlorophenyl)methyl]carboxamide |
| 1.966 | M + H⁺ | 541.1 | 540.96 | [1-(2-aminoacetyl)-4-({N-[4-methyl-3-(trifluoromethyl)phenyl]carbamoyloxy}methyl)(4-piperidyl)]-N-[(2-chlorophenyl)methyl]carboxamide |
| 0.281 | M + H⁺ | 507.1 | 507.41 | (1-(2-aminoacetyl)-4-{[N-(2-chloro-4-methylphenyl)carbamoyloxy]methyl}(4-piperidyl))-N-[(2-chlorophenyl)methyl]carboxamide |
| 0.126 | M + H⁺ | 499.2 | 499 | {1-(2-aminoacetyl)-4-[(N-indan-5-ylcarbamoyloxy)methyl](4-piperidyl)}-N-[(2-chlorophenyl)methyl]carboxamide |
| 0.569 | M + H⁺ | 493.1 | 493.38 | (1-(2-aminoacetyl)-4-{[N-(4-chlorophenyl)carbamoyloxy]methyl}(4-piperidyl))-N-[(2-chlorophenyl)methyl]carboxamide |
| 1.81 | M + H⁺ | 517.2 | 516.97 | methyl 4-{[(1-(2-aminoacetyl)-4-{N-[(2-chlorophenyl)methyl]carbamoyl}-4-piperidyl)methoxy]carbonylamino}benzoate |
| 0.742 | M + H⁺ | 491.1 | 490.95 | (1-(2-aminoacetyl)-4-{[N-(3-fluoro-4-methylphenyl)carbamoyloxy]methyl}(4-piperidyl))-N-[(2-chlorophenyl)methyl]carboxamide |
| 4.948 | M + H⁺ | 638.1 | 638.15 | N-[(2-chlorophenyl)methyl](4-{[N-(4-ethylphenyl)carbamoyloxy]methyl}-1-{[4-(phenylcarbonyl)phenyl]carbonyl}(4-piperidyl))carboxamide |
| 0.277 | M + H⁺ | 535.1 | 535.03 | (1-(2-aminoacetyl)-4-{[N-(4-phenylphenyl)carbamoyloxy]methyl}(4-piperidyl))-N-[(2-chlorophenyl)methyl]carboxamide |
| 0.083 | M + H⁺ | 509.2 | 509 | {1-(2-aminoacetyl)-4-[(N-(2-naphthyl)carbamoyloxy)methyl](4-piperidyl)}-N-[(2-chlorophenyl)methyl]carboxamide |
| 3.429 | M + H⁺ | 375.1 | 374.86 | N-[(2-chlorophenyl)methyl]-4-[N-(4-ethylphenyl)carbamoyloxy]butanamide |
| 6.808 | M + H⁺ | 390.1 | 389.88 | 2-amino-N-[(2-chlorophenyl)methyl]-4-[N-(4-ethylphenyl)carbamoyloxy]butanamide |

-continued

| IC50 Arithmetic Mean | Ion | m/z | MW | ChemicalName |
|---|---|---|---|---|
| 4.37 | M + H+ | 447.0 | 446.93 | 2-(2-aminoacetylamino)-N-[(2-chlorophenyl)methyl]-4-[N-(4-ethylphenyl)carbamoyloxy]butanamide |
| 3.744 | M + H+ | 501.1 | 501.02 | 2-(1-(2-aminoacetyl)-4-{[N-(4-ethylphenyl)carbamoyloxy]methyl}(4-piperidyl))-N-[(2-chlorophenyl)methyl]acetamide |
| 0.197 | M + H+ | 431.2 | 430.92 | N-[(2-chlorophenyl)methyl](4-{[N-(4-ethylphenyl)carbamoyloxy]methyl}(2H-3,4,5,6-tetrahydropyran-4-yl))carboxamide |
| 17.962 | M + H+ | 378.1 | 377.43 | methyl 1-(2-aminoacetyl)-4-{[N-(4-ethylphenyl)carbamoyloxy]methyl}piperidine-4-carboxylate |
| 0.975 | M + H+ | 567.2 | 566.69 | (tert-butoxy)-N-[2-(4-{[N-(4-ethylphenyl)carbamoyloxy]methyl}-4-{N-[(2-methylphenyl)methyl]carbamoyl}piperidyl)-2-oxoethyl]carboxamide |
| 11.102 | M-Boc + H+ | 453.2 | 552.66 | (tert-butoxy)-N-[2-(4-{[N-(4-ethylphenyl)carbamoyloxy]methyl}-4-[N-benzylcarbamoyl]piperidyl)-2-oxoethyl]carboxamide |
| 3.769 | M + H+ | 471.2 | 570.65 | (tert-butoxy)-N-[2-(4-{[N-(4-ethylphenyl)carbamoyloxy]methyl}-4-{N-[(2-fluorophenyl)methyl]carbamoyl}piperidyl)-2-oxoethyl]carboxamide |
| 0.167 | M + H+ | 467.2 | 466.57 | (1-(2-aminoacetyl)-4-{[N-(4-ethylphenyl)carbamoyloxy]methyl}(4-piperidyl))-N-[(2-methylphenyl)methyl]carboxamide |
| 8.111 | M + H+ | 453.1 | 452.55 | (1-(2-aminoacetyl)-4-{[N-(4-ethylphenyl)carbamoyloxy]methyl}(4-piperidyl))-N-benzylcarboxamide |
| 0.307 | M + H+ | 471.1 | 470.54 | (1-(2-aminoacetyl)-4-{[N-(4-ethylphenyl)carbamoyloxy]methyl}(4-piperidyl))-N-[(2-fluorophenyl)methyl]carboxamide |
| 11.307 | M-Boc + H+ | 483.2 | 582.69 | (1-{2-[(tert-butoxy)carbonylamino]acetyl}-4-{[N-(4-ethylphenyl)carbamoyloxy]methyl}(4-piperidyl))-N-[(2-methoxyphenyl)methyl]carboxamide |
| 14.457 | M-Boc + H+ | 487.1 | 587.11 | [(1-{2-[(tert-butoxy)carbonylamino]acetyl}-4-{N-[(4-chlorophenyl)methyl]carbamoyl}(4-piperidyl))methoxy]-N-(4-ethylphenyl)carboxamide |
| 0.313 | M-Boc + H+ | 521.1 | 621.55 | [(4-{N-[(2,3-dichlorophenyl)methyl]carbamoyl}-1-{2-[(tert-butoxy)carbonylamino]acetyl}(4-piperidyl))methoxy]-N-(4-ethylphenyl)carboxamide |
| 2.164 | M + H+ | 483.2 | 482.57 | (1-(2-aminoacetyl)-4-{[N-(4-ethylphenyl)carbamoyloxy]methyl}(4-piperidyl))-N-[(2-methoxyphenyl)methyl]carboxamide |
| 0.086 | M + H+ | 521.2 | 520.54 | {[1-(2-aminoacetyl)-4-(N-{[2-(trifluoromethyl)phenyl]methyl}carbamoyl)(4-piperidyl)]methoxy}-N-(4-ethylphenyl)carboxamide |
| 1.28 | M + H+ | 487.1 | 486.99 | [(1-(2-aminoacetyl)-4-{N-[(4-chlorophenyl)methyl]carbamoyl}(4-piperidyl))methoxy]-N-(4-ethylphenyl)carboxamide |
| 0.088 | M + H+ | 521.0 | 521.44 | [(1-(2-aminoacetyl)-4-{N-[(2,3-dichlorophenyl)methyl]carbamoyl}(4-piperidyl))methoxy]-N-(4-ethylphenyl)carboxamide |
| 2.98 | M + H+ | 468.2 | 467.56 | [(1-(2-aminoacetyl)-4-{N-[(3-methyl(2-pyridyl))methyl]carbamoyl}(4-piperidyl))methoxy]-N-(4-ethylphenyl)carboxamide |
| 0.146 | M + H+ | 531.1 | 531.44 | [(1-(2-aminoacetyl)-4-{N-[(2-bromophenyl)methyl]carbamoyl}(4-piperidyl))methoxy]-N-(4-ethylphenyl)carboxamide |
| 0.729 | M + H+ | 487.1 | 486.99 | [(1-(2-aminoacetyl)-4-{N-[(3-chlorophenyl)methyl]carbamoyl}(4-piperidyl))methoxy]-N-(4-ethylphenyl)carboxamide |
| 1.593 | M + H+ | 589.2 | 588.64 | [(4-{N-[(2,3-difluorophenyl)methyl]carbamoyl}-1-{2-[(tert-butoxy)carbonylamino]acetyl}(4-piperidyl))methoxy]-N-(4-ethylphenyl)carboxamide |
| 0.164 | M + H+ | 489.1 | 488.53 | [(1-(2-aminoacetyl)-4-{N-[(2,3-difluorophenyl)methyl]carbamoyl}(4-piperidyl))methoxy]-N-(4-ethylphenyl)carboxamide |
| 0.099 | M + H+ | 505.2 | 504.98 | [(1-(2-aminoacetyl)-4-{N-[(3-chloro-2-fluorophenyl)methyl]carbamoyl}(4-piperidyl))methoxy]-N-(4-ethylphenyl)carboxamide |
| 0.081 | M + H+ | 485.2 | 484.56 | [(1-(2-aminoacetyl)-4-{N-[(3-fluoro-2-methylphenyl)methyl]carbamoyl}(4-piperidyl))methoxy]-N-(4-ethylphenyl)carboxamide |
| 0.083 | M + H+ | 501.1 | 501.02 | [(1-(2-aminoacetyl)-4-{N-[(3-chloro-2-methylphenyl)methyl]carbamoyl}(4-piperidyl))methoxy]-N-(4-ethylphenyl)carboxamide |
| 8.238 | M-Boc + H+ | 471.1 | 570.65 | [(1-{2-[(tert-butoxy)carbonylamino]acetyl}-4-{N-[(3-fluorophenyl)methyl]carbamoyl}(4-piperidyl))methoxy]-N-(4-ethylphenyl)carboxamide |
| 10.12 | M-Boc + H+ | 471.1 | 570.65 | [(1-{2-[(tert-butoxy)carbonylamino]acetyl}-4-{N-[(4-fluorophenyl)methyl]carbamoyl}(4-piperidyl))methoxy]-N-(4-ethylphenyl)carboxamide |

-continued

| IC50 Arithmetic Mean | Ion | m/z | MW | ChemicalName |
|---|---|---|---|---|
| 1.03 | M + H+ | 471.1 | 470.54 | [(1-(2-aminoacetyl)-4-{N-[(3-fluorophenyl)methyl]carbamoyl}(4-piperidyl))methoxy]-N-(4-ethylphenyl)carboxamide |
| 1.098 | M + H+ | 471.1 | 470.54 | [(1-(2-aminoacetyl)-4-{N-[(4-fluorophenyl)methyl]carbamoyl}(4-piperidyl))methoxy]-N-(4-ethylphenyl)carboxamide |
| 7.22 | M + H+ | 454.1 | 453.53 | ({1-(2-aminoacetyl)-4-[N-(2-pyridylmethyl)carbamoyl](4-piperidyl)}methoxy)-N-(4-ethylphenyl)carboxamide |
| 1.769 | M + H+ | 543.2 | 542.63 | [(1-{2-[(tert-butoxy)carbonylamino]acetyl}-4-[N-(imidazol-2-ylmethyl)carbamoyl](4-piperidyl))methoxy]-N-(4-ethylphenyl)carboxamide |
| 3.176 | M-Boc + H+ | 525.2 | 624.62 | [(1-{2-[(tert-butoxy)carbonylamino]acetyl}-4-{N-[(3-fluoro-2-methylphenyl)methyl]carbamoyl}(4-piperidyl))methoxy]-N-[4-(trifluoromethyl)phenyl]carboxamide |
| 6.558 | M-Boc + H+ | 545.1 | 645.04 | [(1-{2-[(tert-butoxy)carbonylamino]acetyl}-4-{N-[(3-chloro-2-fluorophenyl)methyl]carbamoyl}(4-piperidyl))methoxy]-N-[4-(trifluoromethyl)phenyl]carboxamide |
| 3.718 | M-Boc + H+ | 560.1 | 661.5 | [(4-{N-[(2,3-dichlorophenyl)methyl]carbamoyl}-1-{2-[(tert-butoxy)carbonylamino]acetyl}(4-piperidyl))methoxy]-N-[4-(trifluoromethyl)phenyl]carboxamide |
| 18.473 | M + H+ | 443.0 | 442.51 | ({1-(2-aminoacetyl)-4-[N-(imidazol-2-ylmethyl)carbamoyl](4-piperidyl)}methoxy)-N-(4-ethylphenyl)carboxamide |
| 7.688 | M-Boc + H+ | 478.2 | 577.67 | (1-{2-[(tert-butoxy)carbonylamino]acetyl}-4-{[N-(4-ethylphenyl)carbamoyloxy]methyl}(4-piperidyl))-N-[(2-cyanophenyl)methyl]carboxamide |
| 0.412 | M + H+ | 525.1 | 524.51 | [(1-(2-aminoacetyl)-4-{N-[(3-fluoro-2-methylphenyl)methyl]carbamoyl}(4-piperidyl))methoxy]-N-[4-(trifluoromethyl)phenyl]carboxamide |
| 0.37 | M + H+ | 545.0 | 544.93 | [(1-(2-aminoacetyl)-4-{N-[(3-chloro-2-fluorophenyl)methyl]carbamoyl}(4-piperidyl))methoxy]-N-[4-(trifluoromethyl)phenyl]carboxamide |
| 0.284 | M + H+ | 561.0 | 561.38 | [(1-(2-aminoacetyl)-4-{N-[(2,3-dichlorophenyl)methyl]carbamoyl}(4-piperidyl))methoxy]-N-[4-(trifluoromethyl)phenyl]carboxamide |
| 5.645 | M + H+ | 541.0 | 641.08 | [(1-{2-[(tert-butoxy)carbonylamino]acetyl}-4-{N-[(3-chloro-2-methylphenyl)methyl]carbamoyl}(4-piperidyl))methoxy]-N-[4-(trifluoromethyl)phenyl]carboxamide |
| 0.904 | M + H+ | 478.2 | 477.56 | (1-(2-aminoacetyl)-4-{[N-(4-ethylphenyl)carbamoyloxy]methyl}(4-piperidyl))-N-[(2-cyanophenyl)methyl]carboxamide |
| 3.238 | M + H+ | 518.1 | 517.5 | [1-(2-aminoacetyl)-4-({N-[4-(trifluoromethyl)phenyl]carbamoyloxy}methyl)(4-piperidyl)]-N-[(2-cyanophenyl)methyl]carboxamide |
| 0.179 | M + H+ | 541.1 | 540.96 | [(1-(2-aminoacetyl)-4-{N-[(3-chloro-2-methylphenyl)methyl]carbamoyl}(4-piperidyl))methoxy]-N-[4-(trifluoromethyl)phenyl]carboxamide |
| 2.288 | M + H+ | 551.2 | 550.53 | methyl 2-({[1-(2-aminoacetyl)-4-({N-[4-(trifluoromethyl)phenyl]carbamoyloxy}methyl)-4-piperidyl]carbonylamino}methyl)benzoate |
| 0.439 | M + H+ | 503.2 | 502.6 | ({1-(2-aminoacetyl)-4-[N-(naphthylmethyl)carbamoyl](4-piperidyl)}methoxy)-N-(4-ethylphenyl)carboxamide |
| 1.081 | M + H+ | 606.2 | 605.1 | [(1-{2-[(tert-butoxy)carbonylamino]acetyl}-4-{N-[(2-chloro-4-fluorophenyl)methyl]carbamoyl}(4-piperidyl))methoxy]-N-(4-ethylphenyl)carboxamide |
| 0.158 | M + H+ | 505.2 | 504.98 | [(1-(2-aminoacetyl)-4-{N-[(2-chloro-4-fluorophenyl)methyl]carbamoyl}(4-piperidyl))methoxy]-N-(4-ethylphenyl)carboxamide |
| 11.841 | M + H+ | 539.1 | 538.53 | {[1-(2-aminoacetyl)-4-(N-{[2-fluoro-4-(trifluoromethyl)phenyl]methyl}carbamoyl)(4-piperidyl)]methoxy}-N-(4-ethylphenyl)carboxamide |
| 0.262 | M + H+ | 505.1 | 504.98 | [(1-(2-aminoacetyl)-4-{N-[(4-chloro-2-fluorophenyl)methyl]carbamoyl}(4-piperidyl))methoxy]-N-(4-ethylphenyl)carboxamide |
| 0.576 | M + H+ | 481.2 | 480.6 | [(1-(2-aminoacetyl)-4-{N-[(2,4-dimethylphenyl)methyl]carbamoyl}(4-piperidyl))methoxy]-N-(4-ethylphenyl)carboxamide |
| 0.145 | M + H+ | 501.1 | 501.02 | [(1-(2-aminoacetyl)-4-{N-[(4-chloro-2-methylphenyl)methyl]carbamoyl}(4-piperidyl))methoxy]-N-(4-ethylphenyl)carboxamide |
| 0.197 | M + H+ | 521.1 | 521.44 | [(1-(2-aminoacetyl)-4-{N-[(2,4-dichlorophenyl)methyl]carbamoyl}(4-piperidyl))methoxy]-N-(4-ethylphenyl)carboxamide |
| 9.436 | M + H+ | 468.1 | 467.56 | [(1-(2-aminoacetyl)-4-{N-[(2-methyl(3-pyridyl))methyl]carbamoyl}(4-piperidyl))methoxy]-N-(4-ethylphenyl)carboxamide |
| 0.949 | M + H+ | 483.2 | 482.57 | (1-(2-aminoacetyl)-4-{[N-(4-ethylphenyl)carbamoyloxy]methyl}(4-piperidyl))-N-{[2-(hydroxymethyl)phenyl]methyl}carboxamide |

-continued

| IC50 Arithmetic Mean | Ion | m/z | MW | ChemicalName |
|---|---|---|---|---|
| 0.951 | M + H+ | 481.2 | 480.6 | [(1-(2-aminoacetyl)-4-{N-[(2-ethylphenyl)methyl]carbamoyl}(4-piperidyl))methoxy]-N-(4-ethylphenyl)carboxamide |
| 15.191 | M + H+ | 458.3 | 457.95 | (4-(2-aminoacetyl)-3-{N-[(2-chlorophenyl)methyl]carbamoyl}piperazinyl)-N-(4-ethylphenyl)carboxamide |
| 2.622 | M + H+ | 415.1 | 414.93 | N-[(2-chlorophenyl)methyl][2-({[(4-ethylphenyl)amino]carbonylamino}methyl)pyrrolidinyl]carboxamide |
| 2.38 | M + H+ | 488.1 | 487.98 | (4-(2-aminoacetyl)-2-{[N-(4-ethylphenyl)carbamoyloxy]methyl}piperazinyl)-N-[(2-chlorophenyl)methyl]carboxamide |
| 0.185 | M + H+ | 416.0 | 415.91 | ((2S)-2-{[N-(4-ethylphenyl)carbamoyloxy]methyl}pyrrolidinyl)-N-[(2-chlorophenyl)methyl]carboxamide |
| 14.906 | M + H+ | 485.1 | 485.02 | N-[(1-(2-aminoacetyl)-4-{N-[(2-chlorophenyl)methyl]carbamoyl}(4-piperidyl))methyl]-2-(4-ethylphenyl)acetamide |
| 7.784 | M + H+ | 484.1 | 483.95 | (1-(2-aminoacetyl)-4-{[N-(4-cyanophenyl)carbamoyloxy]methyl}(4-piperidyl))-N-[(2-chlorophenyl)methyl]carboxamide |
| 0.191 | M + H+ | 473.1 | 472.96 | (1-(2-aminoacetyl)-4-{[N-(4-methylphenyl)carbamoyloxy]methyl}(4-piperidyl))-N-[(2-chlorophenyl)methyl]carboxamide |
| 14.615 | M + H+ | 477.1 | 476.93 | (1-(2-aminoacetyl)-4-{[N-(4-fluorophenyl)carbamoyloxy]methyl}(4-piperidyl))-N-[(2-chlorophenyl)methyl]carboxamide |
| 9.212 | M + H+ | 459.1 | 458.94 | {1-(2-aminoacetyl)-4-[(N-phenylcarbamoyloxy)methyl](4-piperidyl)}-N-[(2-chlorophenyl)methyl]carboxamide |
| 1.186 | M + H+ | 501.1 | 500.97 | (4-{[N-(4-acetylphenyl)carbamoyloxy]methyl}-1-(2-aminoacetyl)(4-piperidyl))-N-[(2-chlorophenyl)methyl]carboxamide |
| 1.443 | M + H+ | 431.1 | 430.93 | ((5S,3R)-3-amino-5-{[N-(4-ethylphenyl)carbamoyloxy]methyl}pyrrolidinyl)-N-[(2-chlorophenyl)methyl]carboxamide |
| 0.234 | M + H+ | 488.1 | 487.98 | N-((5S,3R)-1-{N-[(2-chlorophenyl)methyl]carbamoyl}-5-{[N-(4-ethylphenyl)carbamoyloxy]methyl}pyrrolidin-3-yl)-2-aminoacetamide |
| 1.857 | M + H+ | 473.1 | 472.96 | N-((5S,3R)-1-{N-[(2-chlorophenyl)methyl]carbamoyl}-5-{[N-(4-ethylphenyl)carbamoyloxy]methyl}pyrrolidin-3-yl)acetamide |
| 0.084 | M + H+ | 390.1 | 389.88 | {[(2-chlorophenyl)methyl]amino}-N-{2-[N-(4-ethylphenyl)carbamoyloxy]ethyl}-N-methylcarboxamide |
| 0.059 | M + H+ | 424.1 | 424.32 | {[(2,3-dichlorophenyl)methyl]amino}-N-{2-[N-(4-ethylphenyl)carbamoyloxy]ethyl}-N-methylcarboxamide |
| 0.21 | M + H+ | 420.2 | 419.9 | [2-({[(2-chlorophenyl)methyl]amino}-N-(2-hydroxyethyl)carbonylamino)ethoxy]-N-(4-ethylphenyl)carboxamide |
| 6.754 | M + H+ | 389.1 | 388.89 | N-[2-({[(2-chlorophenyl)methyl]amino}-N-methylcarbonylamino)ethyl][(4-ethylphenyl)amino]carboxamide |
| 11.668 | M + H+ | 432.2 | 431.91 | [(4-{N-[(2-chlorophenyl)methyl]carbamoyl}morpholin-2-yl)methoxy]-N-(4-ethylphenyl)carboxamide |
| 2.543 | M + H+ | 433.2 | 432.94 | N-(3-aminopropyl){[(2-chlorophenyl)methyl]amino}-N-{2-[N-(4-ethylphenyl)carbamoyloxy]ethyl}carboxamide |
| 4.087 | M + H+ | 590.3 | 590.11 | 2-[(tert-butoxy)carbonylamino]-N-[3-({[(2-chlorophenyl)methyl]amino}-N-{2-[N-(4-ethylphenyl)carbamoyloxy]ethyl}carbonylamino)propyl]acetamide |
| 0.188 | M + H+ | 490.2 | 489.99 | 2-amino-N-[3-({[(2-chlorophenyl)methyl]amino}-N-{2-[N-(4-ethylphenyl)carbamoyloxy]ethyl}carbonylamino)propyl]acetamide |
| 2.83 | M + H+ | 419.2 | 418.92 | N-(2-aminoethyl){[(2-chlorophenyl)methyl]amino}-N-{2-[N-(4-ethylphenyl)carbamoyloxy]ethyl}carboxamide |
| 0.896 | M + H+ | 476.2 | 475.97 | 2-amino-N-[2-({[(2-chlorophenyl)methyl]amino}-N-{2-[N-(4-ethylphenyl)carbamoyloxy]ethyl}carbonylamino)ethyl]acetamide |
| 0.346 | M + H+ | 447.2 | 446.97 | [2-(N-(4-aminobutyl){[(2-chlorophenyl)methyl]amino}carbonylamino)ethoxy]-N-(4-ethylphenyl)carboxamide |
| 0.223 | M + H+ | 504.1 | 504.02 | 2-amino-N-[4-({[(2-chlorophenyl)methyl]amino}-N-{2-[N-(4-ethylphenyl)carbamoyloxy]ethyl}carbonylamino)butyl]acetamide |
| 17.394 | M + H+ | 251.1 | 250.29 | N-{2-[N-(4-ethylphenyl)carbamoyloxy]ethyl}acetamide |
| 1.413 | M + H+ | 413.2 | 412.87 | {[(2-chlorophenyl)methyl]amino}-N-methyl-N-[2-(N-(6-quinolyl)carbamoyloxy)ethyl]carboxamide |
| 0.487 | M + H+ | 461.1 | 461 | N-(5-aminopentyl){[(2-chlorophenyl)methyl]amino}-N-{2-[N-(4-ethylphenyl)carbamoyloxy]ethyl}carboxamide |
| 0.355 | M + H+ | 448.2 | 447.95 | {[(2-chlorophenyl)methyl]amino}-N-{2-[N-(4-ethylphenyl)carbamoyloxy]ethyl}-N-(4-hydroxybutyl) carboxamide |
| 2.865 | M + H+ | 646.3 | 645.58 | (tert-butoxy)-N-[2-(4-{N-[(2-bromophenyl)methyl]carbamoyl}-4-{[N-(4-ethylphenyl)carbamoyloxy]methyl}piperidyl)-2-oxoethyl]-N-methylcarboxamide |

| IC50 Arithmetic Mean | Ion | m/z | MW | ChemicalName |
| --- | --- | --- | --- | --- |
| 0.168 | M + H⁺ | 545.2 | 545.47 | [(4-{N-[(2-bromophenyl)methyl]carbamoyl}-1-[2-(methylamino)acetyl](4-piperidyl))methoxy]-N-(4-ethylphenyl)carboxamide |
| 3.052 | M + H⁺ | 387.2 | 386.87 | N-[(2-chlorophenyl)methyl]({[N-(4-ethylphenyl)carbamoyloxy]methyl}cyclopropyl)carboxamide |
| 0.742 | M + H⁺ | 460.1 | 459.97 | 4-(acetylamino)-N-[(2-chlorophenyl)methyl]-2-{[N-(4-ethylphenyl)carbamoyloxy]methyl}-2-methylbutanamide |
| 1.297 | M + H⁺ | 575.2 | 575.1 | 4-{2-[(tert-butoxy)carbonylamino]acetylamino}-N-[(2-chlorophenyl)methyl]-2-{[N-(4-ethylphenyl)carbamoyloxy]methyl}-2-methylbutanamide |
| 1.738 | M + H⁺ | 418.1 | 417.93 | 4-amino-N-[(2-chlorophenyl)methyl]-2-{[N-(4-ethylphenyl)carbamoyloxy]methyl}-2-methylbutanamide |
| 0.283 | M + H⁺ | 475.1 | 474.98 | 4-(2-aminoacetylamino)-N-[(2-chlorophenyl)methyl]-2-{[N-(4-ethylphenyl)carbamoyloxy]methyl}-2-methylbutanamide |
| 0.235 | M + H⁺ | 403.1 | 402.91 | N-[(2-chlorophenyl)methyl]-4-[N-(4-ethylphenyl)carbamoyloxy]-2,2-dimethylbutanamide |
| 0.621 | M + H⁺ | 418.2 | 417.93 | {[(2-chlorophenyl)methyl]amino}-N-{2-[N-(4-ethylphenyl)carbamoyloxy]-tert-butyl}-N-methylcarboxamide |
| 3.526 | M + H⁺ | 416.3 | 415.91 | (2-chlorophenyl)methyl (2S)-2-({[(4-ethylphenyl)amino]carbonylamino}methyl)pyrrolidinecarboxylate |

Screening assays were performed using a pyruvate kinase and lactate dehydrogenase-coupled ATPase assay containing the following reagents: Potassium PIPES (50 mM), MgCl₂ (3 mM), KCl (100 mM), ATP (0.15 mM), DTT (1 mM), BSA (0.1 mg/ml), NADH (0.5 mM), PEP (1.5 mM), pyruvate kinase (4 U/ml), lactate dehydrogenase (8 U/ml), and antifoam (50 ppm) (concentrations expressed are final assay concentrations). The pH was adjusted to 6.80 at 22° C. by addition of potassium hydroxide. Lead optimization assays were performed with a more sensitive pyruvate kinase/horseradish peroxidase/pyruvate oxidase-coupled ATPase assay containing the following reagents: Potassium PIPES (12 mM), MgCl₂ (2 mM), KCl (100 mM), ATP (0.15 mM), BSA (0.05 mg/ml), potassium phosphate (2 mM), amplex red (0.1 mM), PEP (0.1 mM), pyruvate kinase (4 U/ml), horseradish peroxidase (0.5 U/ml), pyruvate oxidase (0.5 U/ml), and antifoam (50 ppm) (concentrations expressed are final assay concentrations). The pH was adjusted to 7.00 at 22° C. by addition of potassium hydroxide.

The protein components specific to this assay are chicken gizzard smooth muscle myosin subfragment-1 that has been chemically crosslinked to either cardiac or skeletal actin using an excess of 1-Ethyl-3-[3-dimethylaminopropyl]carbodiimide hydrochloride and N-hydroxysuccinimide. The exact concentration of the crosslinked smooth muscle myosin in the assay is determined empirically, by titration to achieve a desired rate of ATP hydrolysis. The concentration varies between protein preparations due to variations in the fraction of active molecules in each preparation.

Compound dose response assays are performed by first preparing a dilution series of test compound, each with an assay mixture containing potassium PIPES, MgCl₂, KCl, ATP, BSA, potassium phosphate, amplex red, PEP, crosslinked smooth muscle actomyosin (subfragment-1), antifoam, and water. The assay is started by adding an equal volume of solution containing potassium Pipes, MgCl₂, KCl, BSA, potassium phosphate, pyruvate kinase, horseradish peroxidase, pyruvate oxidase, antifoam, and water. ATP hydrolysis is monitored by measuring the fluorescence of amplex red (excitation at 480 nm, emission at 615 nm). The resulting dose response curve is fit by the 4 parameter equation y=Bottom+((Top-Bottom)/(1+((IC$_{50}$/X)^Hill))). The IC$_{50}$ is defined as the concentration at which ATPase activity is midway between the top and bottom of the dose response curve.

Certain chemical entities described herein have an IC$_{50}$ less than 10 μM; for example, less than 1 μM.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound selected from compounds of Formula I

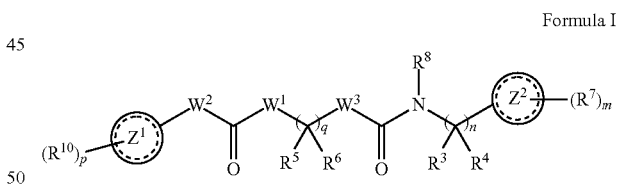

Formula I and pharmaceutically acceptable salts thereof, wherein
W¹ is selected from CR¹¹R¹², NR¹³, and O;
W² is NR¹³;
W³ is CR¹R²;
Z¹ is aryl;
Z² is aryl;
R⁸ is selected from hydrogen and optionally substituted alkyl;
R¹¹ and R¹² are independently selected from hydrogen and optionally substituted alkyl;
R¹ and R² together with the carbon to which they are attached, form a group selected optionally substituted piperidinyl and optionally substituted tetrahydropyranyl;
R¹³ is selected from hydrogen and optionally substituted alkyl;

for each occurrence, $R^3$, $R^4$, $R^5$, and $R^6$ are independently selected from hydrogen, hydroxyl, optionally substituted alkyl, optionally substituted cycloalkyl, optionally substituted alkenyl, optionally substituted alkynyl, optionally substituted alkoxy, optionally substituted aryloxy, optionally substituted heteroaryloxy, optionally substituted heterocycloalkyloxy, optionally substituted aminocarbonyloxy, optionally substituted acyloxy, optionally substituted alkoxycarbonyloxy, optionally substituted acyl, optionally substituted alkoxycarbonyl, optionally substituted amino, optionally substituted aryl, optionally substituted heteroaryl, optionally substituted heterocycloalkyl, optionally substituted aminocarbonyl, and optionally substituted aminosulfonyl;

$R^7$ and $R^{10}$ are independently selected from hydrogen, cyano, halo, hydroxy, carboxy, azido, nitro, sulfonyl, sulfinyl, sulfanyl, optionally substituted alkoxy, optionally substituted aryloxy, optionally substituted heteroaryloxy, optionally substituted heterocycloalkyloxy, optionally substituted alkoxycarbonyl, optionally substituted alkyl, optionally substituted cycloalkyl, optionally substituted alkenyl, optionally substituted alkynyl, optionally substituted aryl, optionally substituted heteroaryl, optionally substituted heterocycloalkyl, optionally substituted amino, optionally substituted acyl, optionally substituted aminocarbonyl, optionally substituted aminosulfonyl, optionally substituted carbaminodoyl;

m is selected from 0, 1, 2 and 3;
n is selected from 0, 1, 2, 3, and 4;
p is selected from 0, 1, 2, and 3; and
q is selected from 0, 1, 2, 3, and 4.

2. The compound of claim 1 wherein $W^1$ is $NR^{13}$.

3. The compound of claim 2 wherein $R^{13}$ is selected from hydrogen and optionally substituted lower alkyl.

4. The compound of claim 3 wherein $R^{13}$ is selected from hydrogen and lower alkyl.

5. The compound of claim 4 wherein $R^{13}$ is hydrogen.

6. The compound of claim 1 wherein $W^1$ is $CR^{11}R^{12}$.

7. The compound of claim 6 wherein $R^{11}$ and $R^{12}$ are each independently selected from hydrogen and optionally substituted lower alkyl.

8. The compound of claim 7 wherein $R^{11}$ and $R^{12}$ are each independently selected from hydrogen and lower alkyl.

9. The compound of claim 8 wherein $R^{11}$ and $R^{12}$ are both hydrogen.

10. The compound of claim 1 wherein $W^1$ is O.

11. The compound of claim 1 wherein the $R^{13}$ of $W^2$ is selected from hydrogen and optionally substituted lower alkyl.

12. The compound of claim 11 wherein $R^{13}$ is selected from hydrogen and lower alkyl.

13. The compound of claim 12 wherein $R^{13}$ is hydrogen.

14. The compound of claim 1 wherein $R^1$ and $R^2$, together with the carbon to which they are attached, form a group selected from piperidine and tetrahydropyran, either of which is optionally substituted with 2-aminoacetyl or 2-(tert-butoxycarbonylamino)acetyl.

15. The compound of claim 14 wherein $R^1$ and $R^2$, together with the carbon to which they are attached, form a group selected from tetrahydropyran, 1-(2-(tert-butoxycarbonylamino)acetyl)piperidin-4-yl, and 1-(2-aminoacetyl)piperidin-4-yl.

16. The compound of claim 1 wherein $R^8$ is selected from hydrogen and optionally substituted lower alkyl.

17. The compound of claim 16 wherein $R^8$ is selected from hydrogen and lower alkyl.

18. The compound of claim 17 wherein $R^8$ is selected from hydrogen and methyl.

19. The compound of claim 18 wherein in $R^8$ is hydrogen.

20. The compound of claim 1 wherein q is 2.

21. The compound of claim 1 wherein q is 1.

22. The compound of claim 21 wherein $R^5$ is selected from hydrogen and optionally substituted lower alkyl.

23. The compound of claim 22 wherein $R^5$ is hydrogen.

24. The compound of claim 21 wherein $R^6$ is selected from hydrogen and optionally substituted lower alkyl.

25. The compound of claim 24 wherein $R^6$ is selected from hydrogen and lower alkyl.

26. The compound of claim 25 wherein $R^6$ is hydrogen.

27. The compound of claim 1 wherein $W^2$ is NH and $W^1$ is O.

28. The compound of claim 1 wherein $W^2$ is NH and $W^1$ is NH.

29. The compound of claim 1 wherein m is 0.

30. The compound of claim 1 wherein m is selected from 1 and 2, and each $R^7$ is selected from halo and optionally substituted alkyl.

31. The compound of claim 30 wherein each $R^7$ is selected from halo and optionally substituted lower alkyl.

32. The compound of claim 31 wherein each $R^7$ is selected from halo and lower alkyl.

33. The compound of claim 32 wherein each $R^7$ is selected from chloro, fluoro, and methyl.

34. The compound of claim 30 wherein —$(R^7)_m$, together with the ring to which it is attached, forms a group selected from 2-chlorophenyl, 2-methylphenyl, 2-chloro-4-fluorophenyl, 2-chloro-3-fluorophenyl, 2,3-dichlorophenyl, 2,3-difluorophenyl, 2,4-dichlorophenyl, 2,4-difluorophenyl, and 3-chloro-2-fluorophenyl.

35. The compound of claim 1 wherein n is selected from 1 and 2.

36. The compound of claim 35 wherein n is 1.

37. The compound of claim 1 wherein each $R^3$ and $R^4$ is independently selected from hydrogen and optionally substituted lower alkyl.

38. The compound of claim 37 wherein each $R^3$ and $R^4$ is independently selected from hydrogen, methyl, ethyl, isopropyl, and hydroxymethyl.

39. The compound of claim 38 wherein each $R^3$ and $R^4$ is hydrogen.

40. The compound of claim 1 wherein p is selected from 0, 1, and 2, and $R^{10}$ is selected from cyano, halo, optionally substituted alkyl, optionally substituted alkenyl, and optionally substituted aryl.

41. The compound of claim 40 wherein p is 0.

42. The compound of claim 40 wherein p is selected from 1 and 2, and each $R^{10}$ is independently selected from cyano, halo, optionally substituted alkyl, optionally substituted alkenyl, and optionally substituted aryl.

43. The compound of claim 42 wherein each $R^{10}$ is independently selected from cyano, halo, optionally substituted lower alkyl, optionally substituted lower alkenyl, and optionally substituted phenyl.

44. The compound of claim 43 wherein each $R^{10}$ is independently selected from cyano, chloro, fluoro, bromo, trifluoromethyl, methyl, ethyl, vinyl, and phenyl.

45. The compound of claim 40 wherein $(R^{10})_p$, together with the ring to which it is attached, forms a group selected from 6-methylphenyl, 5-ethylphenyl, 4-methylphenyl, 5-methylphenyl, 5,6-dichlorophenyl, 5,6-difluorophenyl, 5,6-dimethylphenyl, 5-bromophenyl, 5-phenylphenyl, 5-vinylphenyl, 6-fluorophenyl, 5-fluorophenyl, and 6-trifluoromethylphenyl.

46. The compound of claim 1, wherein $R^1$ and $R^2$, together with the carbon to which they are attached, form tetrahydropyran-4-yl.

47. The compound of claim 1, wherein $R^1$ and $R^2$, together with the carbon to which they are attached, form optionally substituted piperidin-3-yl or optionally substituted piperidin-4-yl.

48. The compound of claim 47 wherein the piperidin-3-yl or piperidin-4-yl is substituted with a group selected from 2-aminoacetyl, 2-(methylamino)acetyl, 2-amino-3-hydroxypropanoyl, (2R)-2-amino-3-hydroxypropanoyl, (2S)-2-amino-3-hydroxypropanoyl, azetidin-2-ylcarbonyl, 2-aminopropanoyl, (2R)-2-aminopropanoyl, (2S)-2-aminopropanoyl, 2-amino-3-methylbutanoyl, 2,4-diaminobutanoyl, 2-amino-2-methylpropanoyl, 2-[(tert-butoxy)carbonylamino]acetyl and 2-(methylamino)propanoyl.

49. The compound of claim 47, wherein $R^1$ and $R^2$, together with the carbon to which they are attached, form 1-(2-aminoacetyl)piperidin-4-yl.

50. The compound of claim 47, wherein $W^1$ is O and $W^2$ is NH.

51. The compound of claim 50, wherein q is 1.

52. The compound of claim 51, wherein n is 1.

53. The compound of claim 52, wherein $Z^1$ is selected from phenyl, naphthyl and indanyl.

54. The compound of claim 53, wherein $Z^1$ is phenyl.

55. The compound of claim 53, wherein $Z^2$ is selected from phenyl and naphthyl.

56. The compound of claim 55, wherein $Z^2$ is phenyl.

57. The compound of claim 1, wherein
$W^1$ is O;
$W^2$ is NH
q is 1;
$R^5$ and $R^6$ are each hydrogen;
$R^1$ and $R^2$, together with the carbon to which they are attached, form optionally substituted tetrahydropyran-4-yl or optionally substituted piperidin-4-yl;
n is 1; and
$R^3$ and $R^4$ are each hydrogen.

58. The compound of claim 57, wherein
$Z^1$ is phenyl;
p is 1 or 2; and
each $R^{10}$ is independently selected from cyano, halo, optionally substituted lower alkyl, optionally substituted lower alkenyl, and optionally substituted phenyl.

59. The compound of claim 58, wherein each $R^{10}$ is independently selected from cyano, chloro, fluoro, bromo, trifluoromethyl, methyl, ethyl, propyl, vinyl, and phenyl.

60. The compound of claim 58 wherein $(R^{10})_p$, together with the ring to which it is attached, forms a group selected from 6-methylphenyl, 5-ethylphenyl, 4-methylphenyl, 5-methylphenyl, 5,6-dichlorophenyl, 5,6-difluorophenyl, 5,6-dimethylphenyl, 5-bromophenyl, 5-phenylphenyl, 5-vinylphenyl, 6-fluorophenyl, 5-fluorophenyl, 6-trifluoromethylphenyl, 2-chlorophenyl, 2-cyanophenyl, 4-ethylphenyl, 4-isopropylphenyl, 4-(trifluoromethyl)phenyl, 4-fluorophenyl, 4-chlorophenyl, 4-cyanophenyl, 4-phenylphenyl, 3,5-dichlorophenyl, 2,4-dimethylphenyl, 3,4-dimethylphenyl, 2-chloro-4-methylphenyl, 2-chloro-4-(trifluoromethyl)phenyl, 3-chloro-2-methylphenyl, 3-chloro-4-methylphenyl, 3-fluoro-4-methylphenyl, 4-methyl-3-(trifluoromethyl)phenyl, 4-ethyl-3-fluorophenyl, 4-ethyl-2-chlorophenyl, and 6-fluoro-2-methylphenyl.

61. The compound of claim 58, wherein
$Z^2$ is phenyl;
m is 1 or 2; and
each $R^7$ is independently selected from cyano, halo, and optionally substituted lower alkyl.

62. The compound of claim 61, wherein each $R^7$ is independently selected from cyano, chloro, fluoro, bromo, trifluoromethyl, methyl, and ethyl.

63. The compound of claim 61 wherein $(R^7)_m$, together with the ring to which it is attached, forms a group selected from 2-cyanophenyl, 2-fluorophenyl, 2-chlorophenyl, 2-bromophenyl, 2-methylphenyl, 2-ethylphenyl, 2-(trifluoromethyl)phenyl, 3-fluorophenyl, 3-chlorophenyl, 4-fluorophenyl, 4-chlorophenyl, 2-chloro-4-fluorophenyl, 2-fluoro-4-(trifluoromethyl)phenyl, 2-chloro-3-fluorophenyl, 2-chloro-4-fluorophenyl, 2,3-dichlorophenyl, 2,3-difluorophenyl, 2,4-dichlorophenyl, 2,4-difluorophenyl, 2,4-dimethylphenyl, 3-chloro-2-fluorophenyl, 3-fluoro-2-methylphenyl, 3-chloro-2-methylphenyl, 4-chloro-2-fluorophenyl, and 4-chloro-2-methylphenyl.

64. The compound of claim 61, wherein $R^1$ and $R^2$, together with the carbon to which they are attached, form 1-(2-aminoacetyl)piperidin-4-yl.

65. A compound selected from
[(1-(2-aminoacetyl)-4-{N-[(3-fluoro-2-methylphenyl)methyl]carbamoyl}(4-piperidyl))methoxy]-N-(4-ethylphenyl)carboxamide,
[(1(2-aminoacetyl)-4-{N-[(3-chloro-2-methylphenyl)methyl]carbamoyl}(4-piperidyl))methoxy]-N-(4-ethylphenyl)carboxamide,
{1(2-aminoacetyl)-4-[(N-2-naphthyl)carbamoyloxy)methyl](4-piperidyl)}-N-[(2-chlorophenyl)methyl]carboxamide,
{[1-(2-aminoacetyl)-4-(N-{[2-(trifluoromethyl)phenyl]methyl}carbamoyl)(4-piperidyl)]methoxy}-N-(4-ethylphenyl)carboxamide,
[(1-(2-aminoacetyl)-4-{N-[(2,3-dichlorophenyl)methyl]carbamoyl}(4-piperidyl))methoxy]-N-(4-ethylphenyl)carboxamide,
[(1-(2-aminoacetyl)-4-{N-[(3-chloro-2-fluorophenyl)methyl]carbamoyl}(4-piperidyl))methoxy]-N-(4-ethylphenyl)carboxamide,
(1-(3-amino-2-hydroxypropanoyl)-4-{[N-(4-ethylphenyl)carbamoyloxy]methyl}(4-piperidyl))-N-[(2-chlorophenyl)methyl]carboxamide,
(1-(2,3-dihydroxypropanoyl)-4-{[N-(4-ethylphenyl)carbamoyloxy]methyl}(4-piperidyl))-N-[(2-chlorophenl)methyl]carboxamide,
(1((2S)-2-amino-3-hydroxypropanoyl)-4-{[N-(4-ethylphenyl)carbamoyloxy]methyl}(4-piperidyl))-N-[(2-chlorophenyl)methyl]carboxamide,
{1-(2-aminoacetyl)-4-[(N-indan-5-ylcarbamoyloxy)methyl](4-piperidyl)}-N-[(2-chlorophenyl)methyl]carboxamide,
[1-((2S)-2-amino-3-hydroxypropanoyl)-4-({N-[4-(trifluoromethyl)phenyl]carbamoyloxy}methyl)(4-piperidyl)]-N-[(2-chlorophenyl)methyl]carboxamide,
(1-(2-amino-3-hydroxypropanoyl)-4-{[N-(4-ethylphenyl)carbamoyloxy]methyl}(4-piperidyl))-N-[(2-chlorophenyl)methyl]carboxamide,
[(1-(2-aminoacetyl)-4-{N-[(4-chloro-2-methylphenyl)methyl]carbamoyl}(4-piperidyl))methoxy]-N-(4-ethylphenyl)carboxamide,
[(1-(2-aminoacetyl)-4-{N-[(2-bromophenyl)methyl]carbamoyl}(4-piperidyl))methoxy]-N-(4-ethylphenyl)carboxamide,
[(1-(2-aminoacetyl)-4{N-[(2-chloro-4-fluorophenyl)methyl]carbamoyl}(4-piperidyl))methoxy]-N-(4-ethylphenyl)carboxamide, N-(2-aminoethyl)(4-{N-[(2-chlorophenyl)methyl]carbamoyl}-4-{[N-(4-ethylphenyl)carbamoyloxy]methyl}piperidyl)carboxamide, (1-((2R)-2-amino-3-hydroxypropanoyl)-4-{[N-(4-ethylphenyl)carbamoyloxy]methyl}(4-piperidyl))-N-[(2-chlorophenyl)methyl]carboxamide,

[(1-(2-aminoacetyl)-4-{N-[(2,3-difluorophenyl)methyl]carbamoyl}(4-piperidyl))methoxy]-N-(4-ethylphenyl)carboxamide, (1-(2-aminoacetyl)-4-{[N-(4-ethylphenyl)carbamoyloxy]methyl}(4-piperidyl))-N-[(2-methylphenyl)methyl]carboxamide,

[(4-{N-[(2-bromophenyl)methyl]carbamoyl}-1-[2-(methylamino)acetyl](4-piperidyl))methoxy]-N-(4-ethylphenyl)carboxamide, N-[(2-chlorophenyl)methyl](4-{[N-(4-ethylphenyl)carbamoyloxy]methyl}-1-(2-hydroxyacetyl)(4-piperidyl))carboxamide, (1-(2-aminoacetyl)-4-{[N-(4-ethylphenyl)carbamoyloxy]methyl}(4-piperidyl))-N-[(2-chlorophenyl)methyl]carboxamide,

[(1-(2-aminoacetyl)-4-{N-[(3-chloro-2-methylphenyl)methyl]carbamoyl}(4-piperidyl))methoxy]-N-[4-(trifluoromethyl)phenyl]carboxamide, (1-(4-amino-2-hydroxybutanoyl)-4-{[N-(4-ethylphenyl)carbamoyloxy]methyl}(4-piperidyl))-N-[(2-chlorophenyl)methyl]carboxamide, (1-(2-aminoacetyl)-4-{[N-(4-methylphenyl)carbamoyloxy]methyl}(4-piperidyl))-N-[(2-chlorophenyl)methyl]carboxamide, N-[(2-chlorophenyl)methyl](4-{[N-(4-ethylphenyl)carbamoyloxy]methyl}(2H-3,4,5,6-tetrahydropyran-4-yl))carboxamide,

[(1-(2-aminoacetyl)-4-{N-[(2,4-dichlorophenyl)methyl]carbamoyl}(4-piperidyl))methoxy]-N-(4-ethylphenyl)carboxamide, N-[(2-chlorophenyl)methyl](4-{[N-(4-ethylphenyl)carbamoyloxy]methyl}-1-[2-(methylamino)acetyl](4-piperidyl))carboxamide, (1-(azetidin-2-ylcarbonyl)-4-{[N-(4-ethylphenyl)carbamoyloxy]methyl}(4-piperidyl))-N-[(2-chlorophenyl)methyl]carboxamide, (1-(4-aminobutanoyl)-4-{[N-(4-ethylphenyl)carbamoyloxy]methyl}(4-piperidyl))-N-[(2-chlorophenyl)methyl]carboxamide, (1-((2R)-2-aminopropanoyl)-4-{[N-(4-ethylphenyl)carbamoyloxy]methyl}(4-piperidyl))-N-[(2-chlorophenyl)methyl]carboxamide,

[(1-(2-aminoacetyl)-4{N-[(4-chloro-2-fluorophenyl)methyl]carbamoyl}(4-piperidyl))methoxy]-N-(4-ethylphenyl)carboxamide, (1-[(2-aminoethyl)sulfonyl]-4-{[N-(4-ethylphenyl)carbamoyloxy]methyl}(4-piperidyl))-N-[(2-chlorophenyl)methyl]carboxamide, N-[(2-chlorophenyl)methyl](4-{[N-(4-ethylphenyl)carbamoyloxy]methyl}-1-3-hydroxy-2-(hydroxymethyl)-2-methylpropanoyl](4-piperidyl))carboxamide, (1-(2-aminoacetyl)-4-{[N-(4-phenylphenyl)carbamoyloxy]methyl}(4-piperidyl))-N-[(2-chlorophenyl)methyl]carboxamide, (1-(2-aminoacetyl)-4-{[N-(2-chloro-4-methylphenyl)carbamoyloxy]methyl}(4-piperidyl))-N-[(2-chlorophenyl)methyl]carboxamide,

[(1-(2-aminoacetyl)-4-{N-[(2,3-dichlorophenyl)methyl]carbamoyl}(4-piperidyl))methoxy]-N-[4-(trifluoromethyl)phenyl]carboxamide,

[1-(2-aminoacetyl)-4-({N-[4-(trifluoromethyl)phenyl]carbamoyloxy}methyl)(4-piperidyl)]-N-[(2-chlorophenyl)methyl]carboxamide, N-[(2-chlorophenyl)methyl](4-{[N-(4-ethylphenyl)carbamoyloxy]methyl}-1-(N-methylcarbamoyl)(4-piperidyl))carboxamide, (1-(2-aminoacetyl)-4-{[N-(4-ethylphenyl)carbamoyloxy]methyl}(4-piperidyl))-N-[(2-fluorophenyl)methyl]carboxamide,

[(4-{N-[(2,3-dichlorophenyl)methyl]carbamoyl}-1-{2-[(tert-butoxy)carbonylamino]acetyl}(4-piperidyl))methoxy]-N-(4-ethylphenyl)carboxamide, 2-aminoethyl 4-{N-[(2-chlorophenyl)methyl]carbamoyl}-4-{[N-(4-ethylphenyl)carbamoyloxy]methyl}piperidinecarboxylate, N-[(2-chlorophenyl)methyl]{4-[(N-indan-5-ylcarbamoyloxy)methyl](2H-3,4,5,6-tetrahydropyran-4-yl)}carboxamide,

[(1-(2-aminoacetyl)-4-{N-[(3-chloro-2-fluorophenyl)methyl]carbamoyl}(4-piperidyl))methoxy]-N-[4-(trifluoromethyl)phenyl]carboxamide, N-[(2-chlorophenyl)methyl](4-{[N-(4-ethylphenyl)carbamoyloxy]methyl}-1-(imidazol-2-ylcarbonyl)(4-piperidyl))carboxamide, N-[(2-chlorophenyl)methyl](3-{[N-(4-ethylphenyl)carbamoyloxy]methyl}-1-(2-hydroxyacetyl)(3-piperidyl))carboxamide, N-[(2-chlorophenyl)methyl](4-{[N-(4-ethylphenyl)carbamoyloxy]methyl}-1-(phenylcarbonyl)(4-piperidyl))carboxamide,

[(1-(2-aminoacetyl)-4-{N-[(3-fluoro-2-methylphenyl)methyl]carbamoyl}(4-piperidyl))methoxy]-N-[4-(trifluoromethyl)phenyl]carboxamide, N-[(1S)-2-(4-{N-[(2-chlorophenyl)methyl]carbamoyl}-4-{[N-(4-ethylphenyl)carbamoyloxy]methyl}piperidyl)-1-(hydroxymethyl)-2-oxoethyl](tert-butoxy)carboxamide, (1-acetyl-4-{[N-(4-ethylphenyl)carbamoyloxy]methyl}(4-piperidyl))-N-[(2-chlorophenyl)methyl]carboxamide, methyl 4-(4-{N-[(2-chlorophenyl)methyl]carbamoyl}-4-{[N-(4-ethylphenyl)carbamoyloxy]methyl}piperidyl)-4-oxobutanoate, ({1-(2-aminoacetyl)-4[N-(naphthylmethyl)carbamoyl](4-piperidyl)}methoxy)-N-(4-ethylphenyl)carboxamide,

[1-(2-aminoacetyl)-4-({N-[2-chloro-4-(trifluoromethyl)phenyl]carbamoyloxy}methyl)(4-piperidyl)]-N-[(2-chlorophenyl)methyl]carboxamide, N-[(2-chlorophenyl)methyl][]1-(2-hydroxyacetyl)-4-({N-[4-(trifluoromethyl)phenyl]carbamoyloxy}methyl)(4-piperidyl)]carboxamide, (1-(2-aminoacetyl)-3-{[N-(4-ethylphenyl)carbamoyloxy]methyl}(3-piperidyl))-N-[(2-chlorophenyl)methyl]carboxamide, methyl 3-{N-[(2-chlorophenyl)methyl]carbamoyl}-3-{[N-(4-ethylphenyl)carbamoyloxy]methyl}piperidinecarboxylate, (tert-butoxy)-N-[4-(4-{N-[(2-chlorophenyl)methyl]carbamoyl}-4-{[N-(4-ethylphenyl)carbamoyloxy]methyl}piperidyl)-4-oxobutyl]carboxamide, N-[(2-chlorophenyl)methyl](4-{[N-(4-ethylphenyl)carbamoyloxy]methyl}-1-(2-methoxyacetyl)(4-piperidyl))carboxamide, N-[(2-chlorophenyl)methyl](4-{[N-(4-ethylphenyl)carbamoyloxy]methyl}-1-(4-hydroxybutanoyl)(4-piperidyl))carboxamide, N-[(2-chlorophenyl)methyl](4-{[N-(4-ethylphenyl)carbamoyloxy]methyl}-1-(methylsulfonyl)(4-piperidyl))carboxamide, N-[(2-chlorophenyl)methyl][4-({N-[4-(methylethyl)phenyl]carbamoyloxy}methyl)(2H-3,4,5,6-tetrahydropyran-4-yl)]carboxamide, N-[(2-chlorophenyl)methyl](4-{[N-(4-ethylphenyl)carbamoyloxy]methyl}-1-(morpholin-3-ylcarbonyl)(4-piperidyl))carboxamide, methyl 4-{N-[(2-chlorophenyl)methyl]carbamoyl}-4-{[N-(4-ethylphenyl)carbamoyloxy]methyl}piperidinecarboxylate, (1-(2-amino-3-methylbutanoyl)-4-{[N-(4-ethylphenyl)carbamoyloxy]methyl}(4-piperidyl))-N-[(2-chlorophenyl)methyl]carboxamide, (1-(2-aminoacetyl)-4-{[N-(4-chlorophenyl)carbamoyloxy]methyl}(4-piperidyl))-N-[(2-chlorophenyl)methyl]carboxamide,

[(1-(2-aminoacetyl)-4-{N-[(2,4-dimethylphenyl)methyl]carbamoyl}(4-piperidyl))methoxy]-N-(4-ethylphenyl)carboxamide, (1-(2,4-diaminobutanoyl)-4-{[N-(4-ethylphenyl)carbamoyloxy]methyl}(4-piperidyl))-N-[(2-chlorophenyl)methyl]carboxamide, N-[(2-chlorophenyl)methyl](4-{[N-(4-ethylphenyl)carbamoyloxy]methyl}-1-(3-methoxypropanoyl)(4-piperidyl))carboxamide, N-[(2-chlorophenyl)methyl](1-(cyclopropylcarbonyl)-4-{[N-(4-ethylphenyl)carbamoyloxy]methyl}(4-piperidyl))carboxamide, (tert-butoxy)-N-[2-(4-{N-[(2-chlorophenyl)methyl]carbamoyl}-4-{[N-(4-ethylphenyl)carbamoyloxy]methyl}piperidyl)-1-(hydroxymethyl)-2-oxoethyl]carboxamide, (1-(2-amino-2-methylpropanoyl)-4-{[N-(4-ethylphenyl)carbamoyloxy]methyl}(4-piperidyl))-N-[(2-chlorophenyl)methyl]carboxamide, N-[(2-chlorophenyl)methyl](4-{[N-(4-ethylphenyl)carbamoyloxy]methyl}-1-(3-pyridylcarbonyl)(4-piperidyl))carboxamide, N-[(2-chlorophenyl)methyl](4-{[N-(4-methylphenyl)carbamoyloxy]methyl}(2H-3,4,5,6-tetrahydropyran-4-yl))carboxamide, (1((2S)-2-aminopropanoyl)-4-{[N-(4-ethylphenyl)carbamoyloxy]methyl}(4-piperidyl))-N-[(2-chlorophenyl)methyl]carboxamide,

[(1-(2-aminoacetyl)-4-{N-[(3-chlorophenyl)methyl]carbamoyl}(4-piperidyl))methoxy]-N-(4-ethylphenyl)carboxamide, (1-(2-aminoacetyl)-4-{[N-(3-fluoro-4-methylphenyl)carbamoyloxy]methyl}(4-piperidyl))-N-[(2-chlorophenyl)methyl]carboxamide, N-[(2-chlorophenyl)methyl](4-{[N-(4-ethylphenyl)carbamoyloxy]methyl}-1-(2-pyridylcarbonyl)(4-piperidyl))carboxamide, (1-(2-amino-3-cyanopropanoyl)-4-{[N-(4-ethylphenyl)carbamoyloxy]methyl}(4-piperidyl))-N-[(2-chlorophenyl)methyl]carboxamide, N-[(2-chlorophenyl)methyl](4-{[N-(4-ethylphenyl)carbamoyloxy]methyl}-1-(4-piperidylcarbonyl)(4-piperidyl))carboxamide, (1-(2-aminoacetyl)-4-{[N-(4-ethylphenyl)carbamoyloxy]methyl}(4-piperidyl))-N-[(2-cyanophenyl)methyl]carboxamide, (tert-butoxy)-N-[2-(4-{N-[(2-chlorophenyl)methyl]carbamoyl}-4-{[N-(4-ethylphenyl)carbamoyloxy]methyl}piperidyl)-2-oxoethyl]carboxamide, (1-(2-aminoacetyl)-4-{[N-(4-ethylphenyl)carbamoyloxy]methyl}(4-piperidyl))-N-{[2-(hydroxymethyl)phenyl]methyl}carboxamide,

[(1-(2-aminoacetyl)-4-{N-[(2-ethylphenyl)methyl]carbamoyl}(4-piperidyl))methoxy]-N-(4-ethylphenyl)carboxamide, (tert-butoxy)-N-[2-(4-{[N-(4-ethylphenyl)carbamoyloxy]methyl}-4-{N-[(2-methylphenyl)methyl]carbamoyl}piperidyl)-2-oxoethyl]carboxamide, (1-(2,3-diaminopropanoyl)-4-{[N-(4-ethylphenyl)carbamoyloxy]methyl}(4-piperidyl))-N-[(2-chlorophenyl)methyl]carboxamide,

[(1-(2-aminoacetyl)-4-{N-[(3-fluorophenyl)methyl]carbamoyl}(4-piperidyl))methoxy]-N-(4-ethylphenyl)carboxamide,

[(1-{2-[(tert-butoxy)carbonylamino]acetyl}-4-{N-[(2-chloro-4-fluorophenyl)methyl]carbamoyl}(4-piperidyl))methoxy]-N-(4-ethylphenyl)carboxamide,

[(1-(2-aminoacetyl)-4-{N-[(4-fluorophenyl)methyl]carbamoyl}(4-piperidyl))methoxy]-N-(4-ethylphenyl)carboxamide, methyl (3S)-3-amino-4-(4-{N-[(2-chlorophenyl)methyl]carbamoyl}-4-{[N-(4-ethylphenyl)carbamoyloxy]methyl}piperidyl)-4-oxobutanoate, N-[(2-chlorophenyl)methyl][4-({N[4-(trifluoromethyl)phenyl]carbamoyloxy}methyl)(2H-3,4,5,6-tetrahydropyran-4-yl)]carboxamide, (1-(2-aminoethyl)-4-{[N-(4-ethylphenyl)carbamoyloxy]methyl}(4-piperidyl))-N-[(2-chlorophenyl)methyl]carboxamide, (4-{[N-(4-acetylphenyl)carbamoyloxy]methyl}-1-(2-aminoacetyl)(4-piperidyl))-N-[(2-chlorophenyl)methyl]carboxamide, (4-{[N-(2,4-dimethylphenyl)carbamoyloxy]methyl}(2H-3,4,5,6-tetrahydropyran-4-yl))-N-[(2-chlorophenyl)methyl]carboxamide,

[(1-(2-aminoacetyl)-4-{N-[(4-chlorophenyl)methyl]carbamoyl}(4-piperidyl))methoxy]-N-(4-ethylphenyl)carboxamide, (1(2S)-2,5-diaminopentanoyl)-4-{[N-(4-ethylphenyl)carbamoyloxy]methyl}(4-piperidyl))-N-[(2-chlorophenyl)methyl]carboxamide, (tert-butoxy)-N-[2-(3-{N-[(2-chlorophenyl)methyl]carbamoyl}-3-{[N-(4-ethylphenyl)carbamoyloxy]methyl}piperidyl)-2-oxoethyl]carboxamide, (1((2S)-2-amino-3-hydroxypropanoyl)-3-{[N-(4-ethylphenyl)carbamoyloxy]methyl}(3-piperidyl))-N-[(2-chlorophenyl)methyl]carboxamide, (1-(2,5-diaminopentanoyl)-4-{[N-(4-ethylphenyl)carbamoyloxy]methyl}(4-piperidyl))-N-[(2-chlorophenyl)methyl]carboxamide, N-[(1S)-2-(4-{N-[(2-chlorophenyl)methyl]carbamoyl}-4-{[N-(4-ethylphenyl)carbamoyloxy]methyl}piperidyl)-1-methyl-2-oxoethyl(tert-butoxy)carboxamide, methyl 2-(4-{N-[(2-chlorophenyl)methyl]carbamoyl}-4-{[N-(4-ethylphenyl)carbamoyloxy]methyl}piperidyl)acetate, 3-amino-4-(4-{N-[(2-chlorophenyl)methyl]carbamoyl}-4-{[N-(4-ethylphenyl)carbamoyloxy]methyl}piperidyl)-4-oxobutanoic acid, N-[2-(N-benzothiazol-6-ylcarbamoyloxy)ethyl]{[(2-chlorophenyl)methyl]amino}-N-methylcarbamoyl,

[(4-{N-[(2,3-difluorophenyl)methyl]carbamoyl}-1-{2-[(tert-butoxy)carbonylamino]acetyl}(4-piperidyl))methoxy]-N-(4-ethylphenyl)carboxamide, N-[(2-chlorophenyl)methyl](4-{[N-(4-ethylphenyl)carbamoyloxy]methyl}(4-piperidyl))carboxamide,
tert-butyl 3-[(4-{N-[(2-chlorophenyl)methyl]carbamoyl}-4-{[N-(4-ethylphenyl)carbamoyloxy]methyl}piperidyl)carbonyl]morpholine-4-carboxylate,
N-[(2-chlorophenyl)methyl](4-{[N-(4-ethylphenyl)carbamoyloxy]methyl}-1-[2-(methylamino)propanoyl]4-piperidyl))carboxamide,
methyl 4-{[(1-(2-aminoacetyl)-4-{N-[(2-chlorophenyl)methyl]carbamoyl}-4-piperidyl)methoxy]carbonylamino}benzoate,
N-[(2-chlorophenyl)methyl][4-({[(4-ethylphenyl)amino]carbonylamino}methyl)-1-(2-hydroxyacetyl)(4-piperidyl)]carboxamide,
(4-{[N-(3-chloro-4-methylphenyl)carbamoyloxy]methyl}(2H-3,4,5,6-tetrahydropyran-4-yl))-N-[(2-chlorophenyl)methyl]carboxamide,
[1-(2-aminoacetyl)-4-({N-[4-methyl-3-(trifluoromethyl)phenyl]carbamoyloxy}methyl)(4-piperidyl)]-N-[(2-chlorophenyOmethyl]carboxamide,
(1-(2-aminoacetyl)-4-{[N-(4-ethylphenyl)carbamoyloxy]methyl}(4-piperidyl))-N-[(2-methoxyphenyl)methyl]carboxamide,
N-[(2-chlorophenyl)methyl](4-{[N-(3-fluoro-4-methylphenyl)carbamoyloxy]methyl}(2H-3,4,5,6-tetrahydropyran-4-yl))carboxamide,
methyl 2-({[1-(2-aminoacetyl)-4-({N-[4-(trifluoromethyl)phenyl]carbamoyloxy}methyl)-4-piperidyl]carbonylamino}methyl)benzoate,
(4-{[N-(3,4-dimethylphenyl)carbamoyloxy]methyl}(2H-3,4,5,6-tetrahydropyran-4-yl))-N-[(2-chlorophenyl)methyl]carboxamide,
(1-(2-aminoacetyl)-4-{2]N-(4-ethylphenyl)carbamoyloxy]ethyl}(4-piperidyl))-N-[(2-chlorophenyl)methyl]carboxamide,
N-[(2-chlorophenyl)methyl](1-(cyclohexylcarbonyl)-4-{[N-(4-ethylphenyl)carbamoyloxy]methyl}(4-piperidyl))carboxamide,
(4-{[N-(4-chlorophenyl)carbamoyloxy]methyl}(2H-3,4,5,6-tetrahydropyran-4-yl))-N-[(2-chlorophenyl)methyl]carboxamide,
(tert-butoxy)-N-[2-(4-{N-[(2-bromophenyl)methyl]carbamoyl}-4-{[N-(4-ethylphenyl)carbamoyloxy]methyl}piperidyl)-2-oxoethyl]-N-methylcarboxamide,
[(1-{2-[(tert-butoxy)carbonylamino]acetyl}-4-{N-[(3-fluoro-2-methylphenyl)methyl]carbamoyl}(4-piperidyl))methoxy]-N-[4-(trifluoromethyl)phenyl]carboxamide,
tort-butyl 4-{N-[(2-chlorophenyl)methyl]carbamoyl}-4-{[N-(4-ethylphenyl)carbamoyloxy]methyl}piperidinecarboxylate,
[1-(2-aminoacetyl)-4-({N-[4-(trifluoromethyl)phenyl]carbamoyloxy}methyl)(4-piperidyl)]-N-[(2-cyanophenyl)methyl]carboxamide,
N-[(1R)-2-(4-{N-[(2-chlorophenyl)methyl]carbamoyl}-4-{[N-(4-ethylphenyl)carbamoyloxy]methyl}piperidyl)-1-(hydroxymethyl)-2-oxoethyl](tert-butoxy)carboxamide,
tert-butyl 4-[(4-{N-[(2-chlorophenyl)methyl]carbamoyl}-4-{[N-(4-ethylphenyl)carbamoyloxy]methyl}piperidyl)carbonyl]piperidinecarboxylate,
methyl 4-{[(4-{N-[(2-chlorophenyl)methyl]carbamoyl}-2H-3,4,5,6-tetrahydropyran-4-yl)methoxy]carbonylamino}benzoate,
[(4-{N-[(2,3-dichlorophenyl)methyl]carbamoyl}-1-{2-[(tert-butoxy)carbonylamino]acetyl}(4-piperidy))methoxy]-N-[4-(trifluoromethyl)phenyl]carboxamide,
2-(1-(2-aminoacetyl)-4-{[N-(4-ethylphenyl)carbamoyloxy]methyl}(4-piperidyl))-N-[(2-chlorophenyl)methyl]acetamide,
(tert-butoxy)-N-]2-(4-{[N-(4-ethylphenyl)carbamoyloxy]methyl}-4-{N-[(2-fluorophenyl)methyl]carbamoyl}piperidyl)-2-oxoethyl]carboxamide,
N-[(2-chlorophenyl)methyl][4-({N-[4-(2-methyl(1,3-thiazol-4-yl))phenyl]carbamoyloxy}methyl)(2H-3,4,5,6-tetrahydropyran-4-yl)]carboxamide,
N-[(2-chlorophenyl)methyl](4-{[N-(4-ethylphenyl)carbamoyloxy]methyl}-1-(2-hydroxyethyl)(4-piperidyl))carboxamide,
(4-{[N-(4-acetylphenyl)carbamoyloxy]methyl}(2H-3,4,5,6-tetrahydropyran-4-yl))-N-[(2-chlorophenyl)methyl]carboxamide,
tert-butyl 2-[(4-{N-[(2-chlorophenyl)methyl]carbamoyl}-4-{[N-(4-ethylphenyl)carbamoyloxy]methyl}piperidyl)carbonyl]azetidinecarboxylate,
N-[(2-chlorophenyl)methyl]4-{[N-(4-ethylphenyl)carbamoyloxy]methyl}-1-methyl(4-piperidyl))carboxamide,
N-[(2-chlorophenyl)methyl](4-{[N-(4-ethylphenyl)carbamoyloxy]methyl}-1-{[4-(phenylcarbonyl)phenyl]carbonyl}(4-piperidyl))carboxamide,
N-[(2-chlorophenyl)methyl][4-({N-[4-(hydroxyethyl)phenyl]carbamoyloxy}methyl)(2H-3,4,5,6-tetrahydropyran-4-yl)]carboxamide,
[(1-{2-[(tert-butoxy)carbonylamino]acetyl}-4-{N-[(3-chloro-2-methylphenyl)methyl]carbamoyl}(4-piperidyl))methoxy]-N-[4-(trifluoromethyl)phenyl]carboxamide,
N-[(2-chlorophenyl)methyl][4-({N-[4-(trifluoromethyl)phenyl]carbamoyloxy}methyl)(4-piperidyl)]carboxamide,
(tert-butoxy)-N-[2-(4-{N-[(2-chlorophenyl)methyl]carbamoyl}-4-{[N-(4-ethylphenyl)carbamoyloxy]methyl}piperidyl)-1-methyl-2-oxoethyl]-N-methylcarboxamide,
N-[(2-chlorophenyl)methyl](1-ethyl-4-{[N-(4-ethylphenyl)carbamoyloxy]methyl}(4-piperidyl))carboxamide,
ethyl 4-[[(4-{N-[(2-chlorophenyl)methyl]carbamoyl}-2H-3,4,5,6-tetrahydropyran-4-yl)methoxy]carbonylamino]benzoate,
[(1-{2-[(tert-butoxy)carbonylamino]acetyl}-4-{N-[(3-chloro-2-fluorophenyl)methyl]carbamoyl{(4-piperidyl))methoxy]-N-[4-(trifluoromethyl)phenyl]carboxamide,
N-[(2-chlorophenyl)methyl](4-{[N-(4-ethylphenyl)-N-methylcarbamoyloxy]methyl}(2H-3,4,5,6-tetrahydropyran-4-yl))carboxamide,
(1-{2-[(tert-butoxy)carbonylamino]acetyl}-4-{[N-(4-ethylphenyl)carbamoyloxy]methyl}(4-piperidyl))-N-[(2-cyanophenyl)methyl]carboxamide,
(1-(2-aminoacetyl)-4-{[N-(4-cyanophenyl)carbamoyloxy]methyl}(4-piperidyl))-N-[(2-chlorophenyl)methyl]carboxamide,
(1-(2-aminoacetyl)-4-{[N-(4-ethylphenyl)carbamoyloxy]methyl}(4-piperidyl))-N-benzylcarboxamide,
[(1-{2-[(tert-butoxy)carbonylamino]acetyl}-4-{N-[(3-fluorophenyl)methyl]carbamoyl}(4-piperidyl))methoxy]-N-(4-ethylphenyl)carboxamide,
N-[(1S)-2-(3-{N-[(2-chlorophenyl)methyl]carbamoyl}-3-{[N-(4-ethylphenyl)carbamoyloxy]methyl}piperidyl)-1-(hydroxymethyl)-2-oxoethyl](tert-butoxy)carboxamide, {1-(2-aminoacetyl)-4-[(N-phenylcarbamoyloxy)methyl](4-piperidyl)}-N-[(2-chlorophenyl)methyl]carboxamide,
[(1-{2-[(tert-butoxy)carbonylamino]acetyl}-4-{N-[(4-fluorophenyl)methyl]carbamoyl}(4-piperidyl))methoxy]-N-(4-ethylphenyl)carboxamide,
(tert-butoxy)-N-[2-(4-{[N-(4-ethylphenyl)carbamoyloxy]methyl}-4[N-benzylcarbamoyl]piperidyl)-2-oxoethyl]carboxamide,
(1-{2-[(tert-butoxy)carbonylamino]acetyl}-4-{[N-(4-ethylphenyl)carbamoyloxy]methyl}(4-piperidyl))-N-[(2-methoxyphenyl)methyl]carboxamide,
{1-(2-aminoacetyl)-4-(N-{[2-fluoro-4-(trifluoromethyl)phenyl]methyl}carbamoyl)(4-piperidyl)]methoxy}-N-(4-ethylphenyl)carboxamide,
N-[(1R)-2-(4-{N-[(2-chlorophenyl)methyl]carbamoyl}-4-{[N-(4-ethylphenyl)carbamoyloxy]methyl}piperidyl)-1-methyl-2-oxoethyl]tert-butoxy)carboxamide,
N-[(2-chlorophenyl)methyl][4-({N-[4-methyl-3-(trifluoromethyl)phenyl]carbamoyloxy}methyl)(2H-3,4,5,6-tetrahydropyran-4-yl)]carboxamide,
N-[(1-(2-aminoacetyl)-4-{N-[(2-chlorophenyl)methyl]carbamoyl}(4-piperidyl))methyl][(4-ethylphenyl)amino]-N-(3-methoxypropyl)carboxamide,
N-[(2-chlorophenyl)methyl](4-{[N-(6-fluoro-2-methylphenyl)carbamoyloxy]methyl}(2H-3,4,5,6-tetrahydropyran-4-yl))carboxamide,
N-[(2-chlorophenyl)methyl](4-{[N-(4-ethylphenyl)carbamoyloxy]methyl}-1-benzyl(4-piperidyl))carboxamide,
[(1-{2-[(tert-butoxy)carbonylamino]acetyl}-4-{N-[(4-chlorophenyl)methyl]carbamoyl}(4-piperidyl))methoxy]-N-(4-ethylphenyl)carboxamide,
(1-(2-aminoacetyl)-4-{[N-(4-fluorophenyl)carbamoyloxy]methyl}(4-piperidyl))-N-[(2-chlorophenyl)methyl]carboxamide,
N-[(1-(2-aminoacetyl)-4-{N-[(2-chlorophenyl)methyl]carbamoyl}(4-piperidyl))methyl]-2-(4-ethylphenyl)acetamide,
N-[(2-chlorophenyl)methyl]{4-[(N-phenylcarbamoyloxy)methyl](2H-3,4,5,6-tetrahydropyran-4-yl)}carboxamide,
3-(1-(2-aminoacetyl)-4-{N-[(2-methylphenyl)methyl]carbamoyl}(4-piperidyl))-N-(4-ethylphenyl)propanamide,
4-{[(4-{N-[(2-chlorophenyl)methyl]carbamoyl}-2H-3,4,5,6-tetrahydropyran-4-yl)methoxy]carbonylamino}benzamide,
(4-{[N-(3-chloro-2-methylphenyl)carbamoyloxy]methyl}(2H-3,4,5,6-tetrahydropyran-4-yl))-N-[(2-chlorophenyl)methyl]carboxamide,
N-[(1-(2-aminoacetyl)-4-{N-[(2-chlorophenyl)methyl]carbamoyl}(4-piperidyl))methyl]-N-(2-aminoethyl)[(4-ethylphenyl)amino]carboxamide,
N-[(2-chlorophenyl)methyl](4-{[N-(2-cyanophenyl)carbamoyloxy]methyl} (2H-3,4,5,6-tetrahydropyran-4-yl))carboxamide,
(4-{[N-(2-chlorophenyl)carbamoyloxy]methyl}(2H-3,4,5,6-tetrahydropyran-4-yl))-N-[(2-chlorophenyl)methyl]carboxamide,
N-[(2-chlorophenyl)methyl][4-({[(4-ethylphenyl)amino]carbonylamino}methyl)(4-piperidyl)]carboxamide,
(4-{[N-(3,5-dichlorophenyl)carbamoyloxy]methyl}(2H-3,4,5,6-tetrahydropyran-4-yl))-N-[(2-chlorophenyl)methyl]carboxamide,
N-[(2-chlorophenyl)methyl][4-({[(4-ethylphenyl)amino]-N-methylcarbonylamino}methyl)-1-(2-hydroxyacetyl)(4-piperidyl)]carboxamide,
N-[(2-chlorophenyl)methyl](4-{[N-(3-methoxyphenyl)carbamoyloxy]methyl}(2H-3,4,5,6-tetrahydropyran-4-yl))carboxamide and
(tert-butoxy)-N-(2-{N-[(1-{2-[(tert-butoxy)carbonylamino]acetyl}-4-{N-[(2-chlorophenyl)methyl]carbamoyl}(4-piperidyl))methyl][(4-ethylphenyl)amino]carbonylamino}ethyl)carboxamide,
or a pharmaceutically acceptable salt thereof.

66. A pharmaceutical composition comprising a pharmaceutically acceptable carrier and a compound of claim 1.

67. The pharmaceutical composition of claim 66 wherein the composition is formulated in a form selected from tablet, capsule, powder, liquid, suspension, suppository, and aerosol.

* * * * *